United States Patent
Lawrence et al.

(10) Patent No.: US 9,616,064 B2
(45) Date of Patent: Apr. 11, 2017

(54) RHO KINASE INHIBITORS AND METHODS OF USE

(75) Inventors: Nicholas J. Lawrence, Tampa, FL (US); Said M. Sebti, Tampa, FL (US); Roberta Pireddu, Tampa, FL (US)

(73) Assignee: H. LEE MOFFITT CANCER CENTER AND RESEARCH INSTITUTE, INC., Tampa, FL (US)

(*) Notice: Subject to any disclaimer, the term of this patent is extended or adjusted under 35 U.S.C. 154(b) by 165 days.

(21) Appl. No.: 14/008,678

(22) PCT Filed: Mar. 30, 2012

(86) PCT No.: PCT/US2012/031575
§ 371 (c)(1),
(2), (4) Date: Nov. 12, 2013

(87) PCT Pub. No.: WO2012/135697
PCT Pub. Date: Oct. 4, 2012

(65) Prior Publication Data
US 2014/0179689 A1 Jun. 26, 2014

Related U.S. Application Data

(62) Division of application No. 61/469,482, filed on Mar. 30, 2011.

(51) Int. Cl.
| | | |
|---|---|---|
| *A61K 31/52* | (2006.01) | |
| *A61K 31/505* | (2006.01) | |
| *A61K 31/506* | (2006.01) | |
| *A61K 45/06* | (2006.01) | |
| *C07D 417/12* | (2006.01) | |
| *C07D 473/34* | (2006.01) | |
| *C07D 403/12* | (2006.01) | |
| *C07D 403/14* | (2006.01) | |
| *C07D 239/48* | (2006.01) | |
| *C07D 401/04* | (2006.01) | |
| *C07D 403/04* | (2006.01) | |

(52) U.S. Cl.
CPC ............ *A61K 31/52* (2013.01); *A61K 31/505* (2013.01); *A61K 31/506* (2013.01); *A61K 45/06* (2013.01); *C07D 239/48* (2013.01); *C07D 401/04* (2013.01); *C07D 403/04* (2013.01); *C07D 403/12* (2013.01); *C07D 403/14* (2013.01); *C07D 417/12* (2013.01); *C07D 473/34* (2013.01)

(58) Field of Classification Search
CPC .... A61K 31/52; A61K 31/505; A61K 31/506; A61K 45/06; C07D 417/12; C07D 473/34; C07D 403/12; C07D 403/14; C07D 239/48
USPC ......... 514/218, 275, 252.14, 263.4; 544/323, 544/295, 277; 435/375
See application file for complete search history.

(56) References Cited

U.S. PATENT DOCUMENTS

| | | |
|---|---|---|
| 3,478,030 A | 11/1969 | Short |
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,167,649 A | 12/1992 | Zook |
| 5,223,505 A | 6/1993 | Hargreaves et al. |
| 6,924,290 B2 | 8/2005 | Nagarathnam et al. |
| 6,960,648 B2 | 11/2005 | Bonny |
| 2002/0035243 A1 | 3/2002 | Imfeld et al. |
| 2002/0120100 A1 | 8/2002 | Bonny |
| 2003/0032594 A1 | 2/2003 | Bonny |

FOREIGN PATENT DOCUMENTS

WO WO 2009/158011 12/2009

OTHER PUBLICATIONS

Adams PD et al., "PHENIX: a comprehensive Python-based system for macromolecular structure solution" *Acta Crystallographica D Biological Crystallography*, 2010, D66(Pt 2):213-221.
Belgiovine C et al., "Reduced Expression of the ROCK Inhibitor Rnd3 Is Associated with Increased Invasiveness and Metastatic Potential in Mesenchymal Tumor Cells" *PLoS One*, 2010, 5(11):e14154.
De Sütö-Nagy G and Johnson TB "(ρ-Sulfamylphenylamino-)-pyrimidines" Journal of the American Chemical Society CLXXV, 1941, 63:3234-3235.

(Continued)

*Primary Examiner* — Alexander R Pagano
*Assistant Examiner* — Ebenezer O Sackey
(74) *Attorney, Agent, or Firm* — Saliwanchik, Lloyd & Eisenschenk

(57) ABSTRACT

The subject invention concerns materials and methods for treating diseases and disorders associated with expression of Rho associated kinases (ROCKs). Examples of diseases and disorders contemplated within the scope of the invention include, but are not limited to, oncological disorders, cardiovascular diseases, CNS disorders, and inflammatory disorders. In one embodiment, a method of the invention comprises administering a therapeutically effective amount of one or more compounds of the present invention, or a composition comprising the compounds, to a person or animal in need of treatment. The subject invention also concerns compounds that inhibit ROCKs, and compositions that comprise the inhibitor compounds of the invention. Compounds contemplated within the scope of the invention include, but are not limited to, those compounds shown in Table 5.

9 Claims, 4 Drawing Sheets

(56) References Cited

OTHER PUBLICATIONS

Dong M et al., "Current Status of Rho-Associated Kinases (ROCKs) in Coronary Atherosclerosis and Vasospasm" *Cardiovascular & Hematological Agents in Medicinal Chemistry*, 2009,7:322-330.
Emsley P. and Cowtan K, "*Coot: model-building tools for molecular graphics*" Acta Crystallographica D Biological Crystallography, 2004, D60:2126-2132.
Fritz G and Kaina B, "Rho GTPasses: Promising Cellular Targets for Novel Anticancer Drugs" *Current Cancer Drug Targets*, 2006, 6:1-14.
Hampson L et al., "Analogues of Y27632 increase gap junction communication and suppress the formation of transformed NIH3T3 colonies" *British Journal of Cancer*, 2009, 101:829-839.
Hu E and Lee D, "Rho kinase as potential therapeutic target for cardiovascular diseases: opportunities and challenges" *Expert Opinion on Therapeutic Targets*, 2005, 9:715-736.
Huryn DM "Medicinal Chemistry in the Pilot Phase of the Molecular Libraries Screening Center Network" *Current Topics in Medicinal Chemistry*, 2009, 9:1158-9.
Huryn DM and Cosford NDP, "The Molecular Libraries Screening Center Network (MLSCN): Identifying Chemical Probes of Biological Systems" *Annual Reports in Medicinal Chemistry*, 2007, 42:401-416.
Igishi T et al., "Enhancement of cisplatin-induced cytotoxicity by ROCK inhibitor through suppression of focal adhesion kinaseindependent mechanism in lung carcinoma cells" *International Journal of Oncology*, 2003, 23:1079-1085.
Imamura F et al., "Y-27632, an Inhibitor of Rho-associated Protein Kinase, Suppresses Tumor Cell Invasion via Regulation of Focal Adhesion and Focal Adhesion Kinase" *Japanese Journal of Cancer Research*, 2000, 91:811-816.
Ishizaki T et al., "Pharmacological Properties of Y-27632, a Specific Inhibitor of Rho-Associated Kinases" *Molecular Pharmacology*, 2000, 57:976-983.
Itoh K et al., "An essential part for Rho-associated kinase in the transcellular invasion of tumor cells" Nature Medicine, 1999, 5:221-225.
Kabsch W, "Automatic Processing of Rotation Diffraction Data from Crystals of Initially Unknown Symmetry and Cell Constants" *Journal of Applied Crystallography*, 1993, 26(6):795-800.
Kamai T et al., "Overexpression of RhoA, Rac1, and Cdc42 GTPases Is Associated with Progression in Testicular Cancer" *Clinical Cancer Research*, 2004, 10:4799-4805.
Kang NS et al., "Identification of small molecules that inhibit GSK-3b through virtual screening" Bioorganic & Medicinal Chemistry Letters, 2009, 19:533-537.
Koresawa M and Okabe T, "High-Throughput Screening with Quantitation of ATP Consumption: A Universal Non-Radioisotope, Homogeneous Assay for Protein Kinase" *Assay and Drug Development Technologies*, 2004, 2(2):153-160.
Kubo T et al., "The therapeutic effects of Rho-ROCK inhibitors on CNS disorders" *Therapeutics and Clinical Risk Management*, 2008, 4(3):605-615.
Kubo T and Yamashita T, "Rho-ROCK inhibitors for the treatment of CNS injury" *Recent patents on CNS drug discovery*, 2007, 2:173-9.
Liao JK et al., "Rho Linase (ROCK) inhibitors" *Journal of Cardiovascular Pharmacology*, 2007, 50(1):17-24.
Liu S et al., "Inhibition of Rho-Associated Kinase Signaling Prevents Breast Cancer Metastasis to Human Bone" *Cancer Research*, 2009, 69(22):8742-8751.
Lograsso P and Yangbo F, "Rho Kinase (ROCK) Inhibitors and Their Application to Inflammatory Disorders" *Current Topics in Medicinal Chemistry*, 2009, 9:704-23.
Lu Q et al., "Signaling Through Rho GTPase Pathway as Viable Drug Target" *Current Medicinal Chemistry*, 2009, 16:1355-1365.
Matssui T et al., "Rho-associated kinase, a novel serine/threonine kinase, as a putative target for the small GTP binding protein Rho" *The EMBO Journal*, 1996, 15(9):2208-2216.
Micuda S et al., "ROCK Inhibitors as Emerging Therapeutic candidates for Ssarcomas" *Current Cancer Drug Targets*, 2010, 10:127-134.
Nakabayashi H and Shimizu K, "HA1077, a Rho kinase inhibitor, suppresses glioma-induced angiogenesis by targeting the Rho-ROCK and the mitogen-activated protein kinase kinase/extracellular signal-regulated kinase (MEK/ERK) signal pathways" *Cancer Science*, 2011, 102(2):393-399.
Nakajima M et al., "Effect of Wf-536, a novel ROCK inhibitor, against metastasis of B16 melanoma" *Cancer Chemotherapy and Pharmacology*, 2003, 52:319-24.
Nakajima M et al., "WF-536 prevents tumor metastasis by inhibiting both tumor motility and angiogenic actions" *European Journal of Pharmacology*, 2003, 459:113-120.
Narumiya S et al., "Use and properties of ROCK-specific inhibitor Y-27632" *Methods in Enzymology*, 2000, 325:373-284.
Ogata S et al., "Fasudil Inhibits Lysophosphatidic Acid-Induced Invasiveness of Human Ovarian Cancer Cells" *International Journal of Gynecological Cancer*, 2009, 19(9):1473-80.
PubChemCompounds, Datasheet [online compound summary] Retrieved from the Internet: URL://pubchem.ncbi.nlm.nih.gov/search/search.cgi; See CID 459822, CID 437671, CID 31036, CID 355750, CID 459823.
Schmitz AAP et al., "Rho GTPases: Signaling, Migration, and Invasion" *Experimental Cell Research*, 2000, 261:1-12.
Shimokawah and Rashid M, "Development of Rho-kinase inhibitors for cardiovascular medicine" *Trends in Pharmacological Science*, 2007, 28:296-302.
Shimokawa H and Takeshita A, "Rho-Kinase Is an Important Therapeutic Target in Cardiovascular Medicine" *Arteriosclerosis, Thrombosis, and Vascular Biology*, 2005, 25:1767-1775.
Somlyo AV et al., "Rho-Kinase Inhibitor Retards Migration and in Vivo Dissemination of Human Prostate Cancer Cells" *Biochemical and Biophysical Research Communications*, 2000, 269:652-659.
Somlyo AV et al., "Rho kinase and matrix metalloproteinase inhibitors cooperate to inhibit angiogenesis and growth of human prostate cancer xenotransplants" *The FASEB Journal*, 2003, 17:223-234.
Suwa H et al., "Overexpression of the rhoC gene correlates with progression of ductal adenocarcinoma of the pancreas" *British Journal of Cancer*, 1998, 77:147-152.
Collaborative Computational Project, No. 4, "The CCP4 Suite: Programs for Protein Crystallography" *Acta Crystallographica Section D Biological Crystallography*, 1994, 50:760-763.
Toyoizumi T et al., "Combined Therapy with Chemotherapeutic Agents and Herpes Simplex Virus Type I ICP34.5 Mutant (HSV-1716) in Human Non-Small Cell Lung Cancer" *Human Gene Therapy*, 1999, 10(18):3013-3029.
Uchida S et al., "The Suppression of Small GTPase Rho Signal Transduction Pathway Inhibits Angiogenesis in Vitro and in Vivo" *Biochemical and Biophysical Research Communications*, 2000, 269:633-640.
Uehata M et al., "Calcium sensitization of smooth muscle mediated by a Rho-associated protein kinase in hypertension" *Nature*, 1997, 389:990-994.
Wu J et al., "Screening of a PKC ζ-specific kinase inhibitor PKCzI257.3 which inhibits EGF-induced breast cancer cell chemotaxis" *Invest New Drugs*, 2010, 28:268-275.
Xing XQ et al., "Rho-kinase as a Potential Therapeutic Target for the Treatment of Pulmonary Hypertension" *Drug News & Perspectives*, 2006, 19(9):517-522.
Yin L et al., "Fasudil inhibits vascular endothelial growth factor-induced angiogenesis in vitro and in vivo" *Molecular Cancer Therapeutics*, 2007, 6:1517-1525.
Ying H "The Rho kinase inhibitor fasudil inhibits tumor progression in human and rat tumor models" *Molecular Cancer Therapeutics*, 2006, 5:2158-2164.
Zohrabian VM et al., "Rho/ROCK and MAPK Signaling Pathways Are Involved in Glioblastoma Cell Migration and Proliferation" *Anticancer Research*, 2009, 29:119-123.

RHO KINASE INHIBITORS AND METHODS OF USE

CROSS-REFERENCE TO RELATED APPLICATIONS

The present application is the National Stage of International Application Number PCT/US2012/031575, filed Mar. 30, 2012, which claims the benefit of U.S. Provisional Application Serial No. 61/469,482, filed Mar. 30, 2011, which is hereby incorporated by reference herein in its entirety, including any figures, tables, nucleic acid sequences, amino acid sequences, or drawings.

GOVERNMENT SUPPORT

This invention was made with government support under grant number CA067771 awarded by the National Institutes of Health. The government has certain rights in the invention.

BACKGROUND OF THE INVENTION

Rho associated protein kinases (ROCKs) are Ser/Thr protein kinases, activated by small GTPases of the Rho family that act as molecular switches to mediate cell signaling. The Rho/ROCK signaling pathway (Lu et al. 2009) is known to participate in the regulation of numerous cellular functions such as actin cytoskeleton organization, contraction, cell adhesion, motility, and morphology, proliferation, cytokinesis, gene expression, and angiogenesis.

Rho kinases are important drug targets involved in several therapeutic areas including cardiovascular diseases (Shimokawa et al. (2007); Xing et al. (2006); Liao et al. (2007); Shimokawa et al. (2005); Dong et al. (2009); Hu et al. (2005)), CNS disorders (Kubo et al. (2008); Kubo et al. (2007)), inflammation (LoGrasso et al. (2009)), and cancer (Suwa et al. (1998); Kamai et al. (2004); Schmitz et al. (2000); Imamura et al. (2000); Somlyo et al. (2000); Uchida et al. (2000); Itoh et al. (1999); Uehata et al. (1997); Ishizaki et al. (2000); Narumiya et al. (2000); Nakajima et al. (2003a); Nakajima et al. (2003b); Ying et al. (2006); Somlyo et al. (2003); Hampson et al. (2009); Igishi et al. (2003); Liu et al. (2009); Ogata et al. (2009); Zohrabian et al. (2009); Micuda et al. (2010)). Rho kinases and the effects of ROCK inhibitors upon several hallmarks of cancer, including invasion (Imamura et al. (2000); Somlyo et al. (2000)), metastasis (Itoh et al. (1999); Belgiovine et al. (2010)), proliferation and angiogenesis (Uchida et al. (2000); Nakabayashi et al. (2011); Yin et al. (2007)) have been reported.

Co-overexpression of Rho and ROCK proteins in cancer cells has been reported in ovarian cancer, pancreatic, testicular, and bladder cancer (Suwa et al. (1998); Kamai et al. (2004)). The Rho/ROCK pathway plays an important role in the development and progression of cancer by modulating the changes (required for malignant transformation and for the process of metastasis) in the migratory, invasive and adhesive properties of tumor cells, and changes in the regulation cellular processes depending on the proper assembly/disassembly of actin-cytoskeleton (Schmitz et al. (2000)). The involvement of the Rho/ROCK signalling pathway in tumor cell invasion, angiogenesis, and metastasis has been well documented. In light of these findings inhibition of ROCKs has been proposed as a promising strategy in the prevention of cell invasion, a central event in the process of metastasis (Itoh et al. (1999); Uehata et al. (1997); Ishizaki et al. (2000); Narumiya et al. (2000)).

The potential of ROCK inhibitors as anticancer drugs was demonstrated by the identification of ATP competitive inhibitors, Y27632, and Wf536 (FIG. 1) (Itoh et al. (1999); Nakajima et al. (2003a); Nakajima et al. (2003b); Somlyo et al. (2003)), displaying high inhibitory potency for ROCKs. Specifically, Y27632 was reported to reduce metastasis in animal model systems (Itoh et al. (1999)), while Wf-536 has shown efficacy in preventing tumor metastasis in vivo models by inhibiting tumor-induced angiogenesis as well as tumor motility (Nakajima et al. (2003a); Nakajima et al. (2003b); Somlyo et al. (2003)). Han and coworkers have also investigated the ability of Fasudil, currently the only ROCK inhibitor clinically approved (in Japan for the treatment of cerebral vasospasm) to inhibit tumor progression in human and rat tumor models (Ying et al. (2006)).

BRIEF SUMMARY OF THE INVENTION

The subject invention concerns materials and methods for treating diseases and disorders associated with expression of Rho associated kinases (ROCKs). Examples of diseases and disorders contemplated within the scope of the invention include, but are not limited to, oncological disorders, cardiovascular diseases, CNS disorders, and inflammatory disorders. In one embodiment, a method of the invention comprises administering a therapeutically effective amount of one or more compounds of the present invention, or a composition comprising the compounds, to a person or animal in need of treatment.

The subject invention also concerns compounds that inhibit ROCKs, and compositions that comprise the inhibitor compounds of the invention. Compounds contemplated within the scope of the invention include, but are not limited to, those compounds shown in Table 5.

BRIEF DESCRIPTION OF THE DRAWINGS

(FIG. 6a) Surface presentation of the ROCK1 dimer in complex with RPM1510 determined by X-ray crystallography at 3.25 Å resolution. Exploded view detailing the binding interactions of RPM1510 (yellow) within the ATP site; the hinge and DFG regions are indicated in orange and cyan, respectively. Displayed in blue is the 2Fo-Fc electron density, contoured at 1a around the inhibitor. (FIG. 6b) Schematic presentation of the binding interactions between RPM1510 and the ATP site. (FIG. 6c) The mFo-Fc electron density map (red) contoured at 3σ around the inhibitor after RPM1510 was omitted during refinement. Potential hydrogen bonding and van der Waal interactions are shown as black and green dotted lines, respectively.

DETAILED DESCRIPTION OF THE INVENTION

Figure 1:
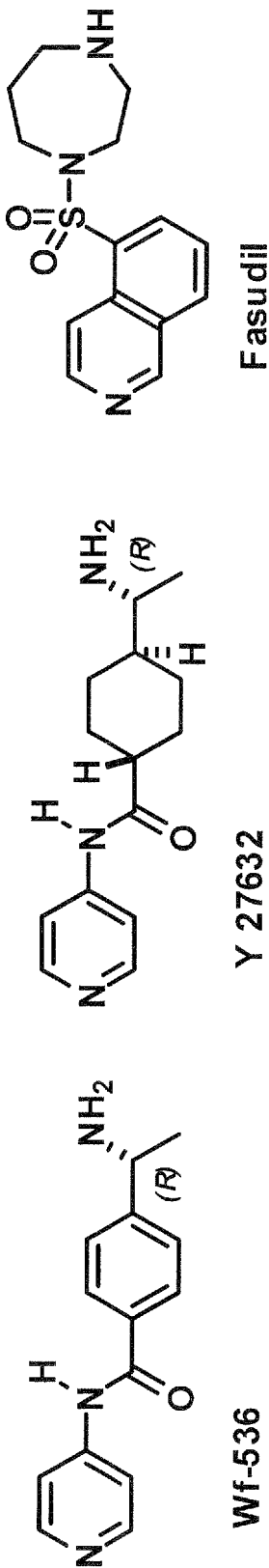
FIG. 1 shows the ROCK inhibitors Wf536, Y27632, and Fasudil.

The subject invention concerns materials and methods for treating diseases and disorders associated with expression of Rho associated kinases (ROCKs). Examples of diseases and disorders contemplated within the scope of the invention include, but are not limited to, oncological disorders, cardiovascular diseases, CNS disorders, and inflammatory disorders. In one embodiment, a method of the invention comprises administering a therapeutically effective amount of one or more compounds of the present invention, or a composition comprising the compounds, to a person or animal in need of treatment.

The subject invention also concerns compounds that inhibit ROCKs, and compositions that comprise the inhibitor compounds of the invention. Compounds contemplated within the scope of the invention include, but are not limited to, those compounds shown in Table 5. In one embodiment, a compound of the invention has the structure shown in formula I:

formula I

$R^1$ is H, OH, S-alkyl, $SO_2NR^2R^3$, $NO_2$, $CONH_2$, $SO_2$-alkyl, NHC(O)-alkyl, $CO_2H$, alkyl, cycloalkyl, alkoxy, cycloalkoxl, heterocycloalkyl, alkoxycarbonyl, heteroaryl, aryl aryloxy or a halogen;

$R^2$ is H, CO, alkoxy, alkyl, aryl, heteroalkyl, heteroaryl, heterocycloalkyl, alkylcarbonyl, arylcarbonyl, or alkoxycarbonyl;

$R^3$ is H, CO, alkoxy, alkyl, aryl, heteroalkyl, heteroaryl, heterocycloalkyl, alkylcarbonyl, arylcarbonyl, or alkoxycarbonyl;

any of which of $R^1$, $R^2$, and $R^3$ can be optionally substituted with one or more of halogen, alkyl, alkoxy, or aryl optionally substituted with alkoxy;

or a pharmaceutically acceptable salt or hydrate thereof.

Compounds of formula I can comprise one or more R substituents.

In one embodiment, a compound of the invention has the structure of formula I wherein:

TABLE 1

$R^1$ can be:

—$SO_2NH_2$

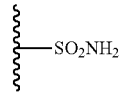

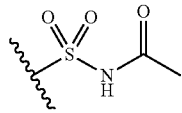 [SMILES: *S(=O)(=O)NC(C)=O]

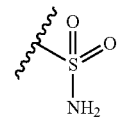

TABLE 1-continued $R^1$ can be:

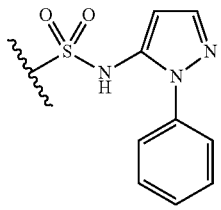 [SMILES: *S(=O)(=O)Nc1ccnn1-c1ccccc1]

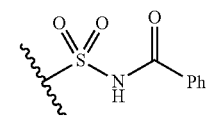 [SMILES: *S(=O)(=O)NC(=O)c1ccccc1]

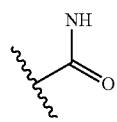 [SMILES: *C(N)=O]

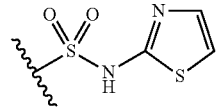 [SMILES: *S(=O)(=O)Nc1nccs1]

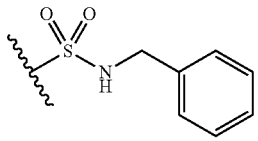 [SMILES: *S(=O)(=O)NCc1ccccc1]

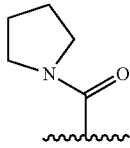

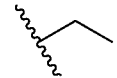 [SMILES: *CC]

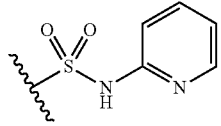 [SMILES: *S(=O)(=O)Nc1ccccn1]

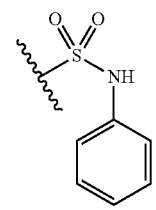 [SMILES: *S(=O)(=O)Nc1ccccc1]

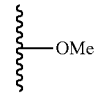

—OMe

TABLE 1-continued

R¹ can be:

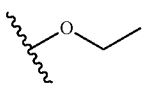 [SMILES: *OCC]

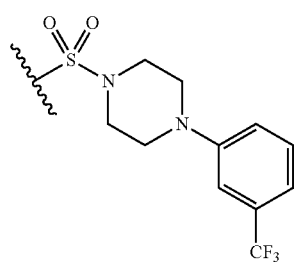 [SMILES: *S(=O)(=O)N1CCN(c2cccc(C(F)(F)F)c2)CC1]

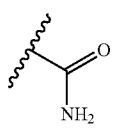

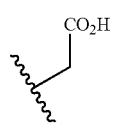 [SMILES: *CC(=O)O]

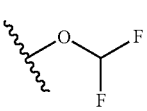

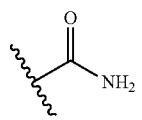

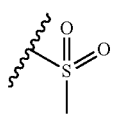

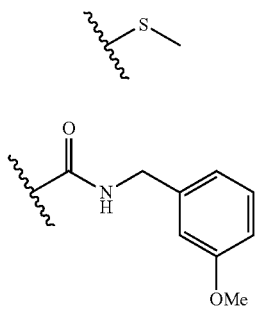

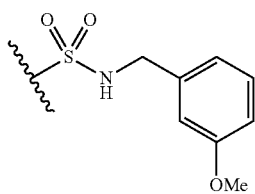 [SMILES: *S(=O)(=O)NCc1cccc(OC)c1]

TABLE 1-continued

R¹ can be:

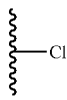

( ⸍ = point of attachment; Me = methyl group)

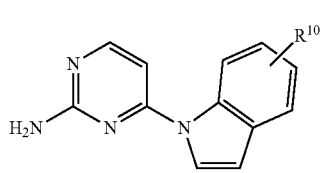

formula IIa

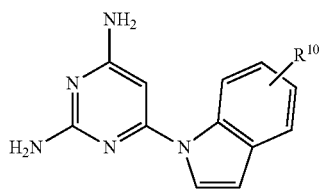

formula IIb wherein $R^{10}$ is H, $NO_2$, halogen, —$CH_3$, —$SO_2$-alkyl, —$OCH_3$, alkoxy, —C(O)NH-alkyl, —C(O)NH-aryl, —NHC(O)-alkyl, —NHC(O)-aryl, or aryloxy, any of which can be substituted with one or more of aryl or alkoxy, any of which can be optionally substituted with halogen, —OH, alkoxy, or aryl optionally substituted with alkoxy;

or a pharmaceutically acceptable salt or hydrate thereof.

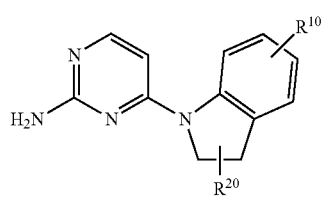

formula III wherein $R^{10}$ is H, $NO_2$, halogen, —$CH_3$, —$SO_2$-alkyl, —$OCH_3$, alkoxy, —C(O)NH-alkyl, —C(O)NH-aryl, —NHC(O)-alkyl, —NHC(O)-aryl, or aryloxy, any of which can be substituted with one or more of aryl or alkoxy, any of which can be optionally substituted with halogen, —OH, alkoxy, or aryl optionally substituted with alkoxy;

$R^{20}$ is —$CH_3$, —$CO_2H$, heteroalkyl, aryl, or alkyl;

or a pharmaceutically acceptable salt or hydrate thereof.

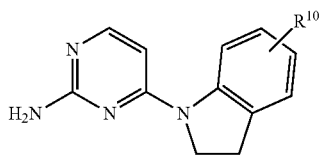

formula IV wherein

R[10] is H, NO$_2$, halogen, —CH$_3$, —SO$_2$-alkyl, —OCH$_3$, alkoxy, —C(O)NH-alkyl, —C(O)NH-aryl, —NHC(O)-alkyl, —NHC(O)-aryl, or aryloxy, any of which can be substituted with one or more of aryl or alkoxy, any of which can be optionally substituted with halogen, —OH, alkoxy, or aryl optionally substituted with alkoxy;

or a pharmaceutically acceptable salt or hydrate thereof.

Compounds of Formula IIa, IIb, III, and IV can comprise one or more R[10] and/or R[20].

In one embodiment, a compound of the invention has the structure shown in formula IIa, formula IIb, formula III, or formula IV wherein:

TABLE 2

R[10] can be:

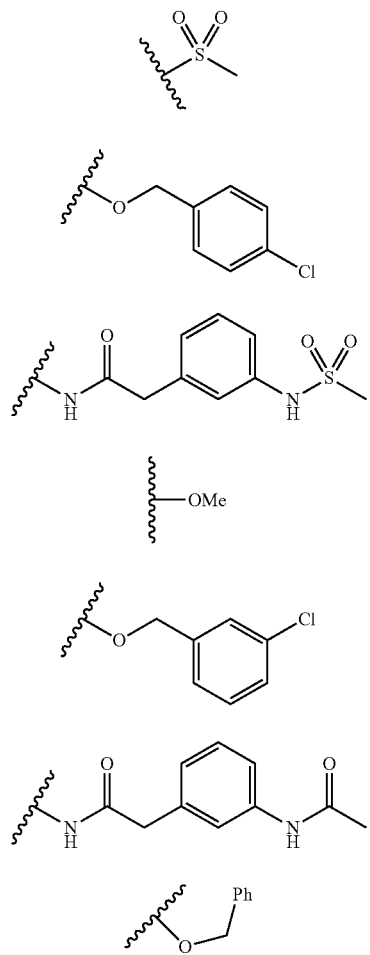

TABLE 2-continued

R[10] can be:

TABLE 2-continued

R¹⁰ can be:

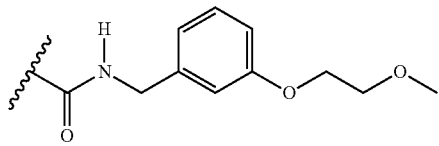 [SMILES: *C(=O)NCc1cccc(OCCOC)c1]

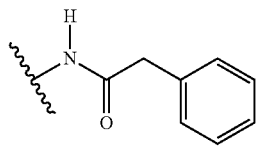 [SMILES: *NC(=O)Cc1ccccc1]

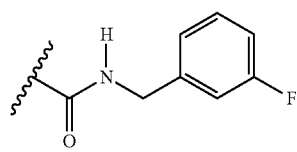 [SMILES: *C(=O)NCc1cccc(F)c1]

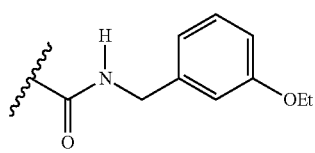 [SMILES: *C(=O)NCc1cccc(OCC)c1]

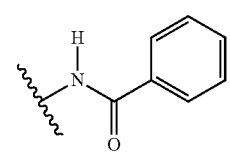 [SMILES: *NC(=O)c1ccccc1]

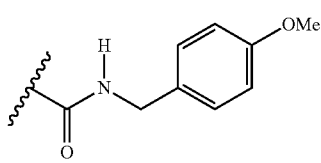 [SMILES: *C(=O)NCc1ccc(OC)cc1]

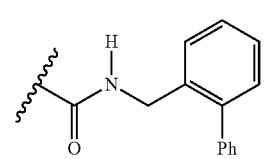 [SMILES: *C(=O)NCc1ccccc1-c1ccccc1]

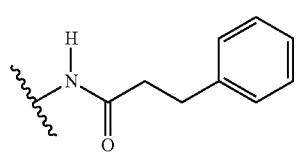 [SMILES: *NC(=O)CCc1ccccc1]

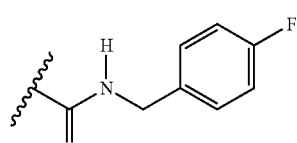

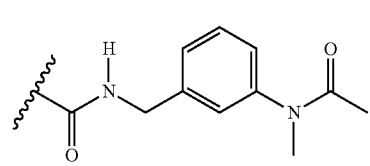 [SMILES: *C(=O)NCc1cccc(N(C)C(C)=O)c1]

TABLE 2-continued

R¹⁰ can be:

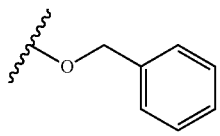 [SMILES: *OCc1ccccc1]

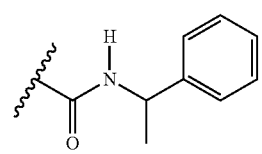 [SMILES: *C(=O)NC(C)c1ccccc1]

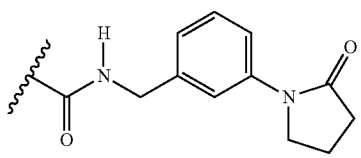 [SMILES: *C(=O)NCc1cccc(N2CCCC2=O)c1]

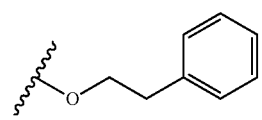 [SMILES: *OCCc1ccccc1]

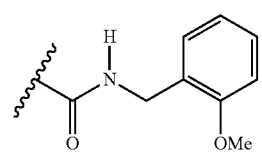 [SMILES: *C(=O)NCc1ccccc1OC]

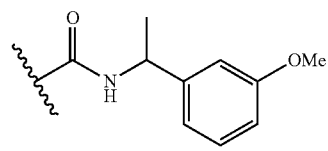 [SMILES: *C(=O)NC(C)c1cccc(OC)c1]

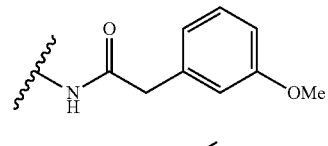

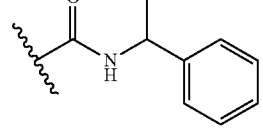

( ⸗ = point of attachment; Me = methyl group; Et = ethyl group)

As used herein, alkyl means straight or branched chain, saturated or mono- or polyunsaturated hydrocarbon groups having from 1 to 20 carbon atoms and $C_{1-X}$ alkyl means straight or branched chain alkyl groups containing from one up to X carbon atoms. For example, $C_{1-6}$ alkyl means straight or branched chain alkyl groups containing from one up to 6 carbon atoms. Alkoxy means an alkyl-O— group in which the alkyl group is as previously described. Cycloalkyl includes a nonaromatic monocyclic or multicyclic ring system, including fused and spiro rings, of from about three to about 10 carbon atoms. A cyclic alkyl may optionally be partially unsaturated. Cycloalkoxy means a cycloalkyl-O— group in which cycloalkyl is as defined herein. Aryl means an aromatic monocyclic or multicyclic carbocyclic ring system, including fused and spiro rings, containing from about six to about 14 carbon atoms. Aryloxy means an aryl-O— group in which the aryl group is as described herein. Alkylcarbonyl means a RC(O)— group where R is an alkyl group as previously described. Alkoxycarbonyl means an ROC(O)— group where R is an alkyl group as previously described. Cycloalkylcarbonyl means an RC(O)— group where R is a cycloalkyl group as previously described. Cycloalkoxycarbonyl means an ROC(O)— group where R is a cycloalkyl group as previously described.

Heteroalkyl means a straight or branched-chain having from one to 20 carbon atoms and one or more heteroatoms selected from nitrogen, oxygen, or sulphur, wherein the nitrogen and sulphur atoms may optionally be oxidized, i.e., in the form of an N-oxide or an S-oxide. Heterocycloalkyl means a monocyclic or multicyclic ring system (which may be saturated or partially unsaturated), including fused and spiro rings, of about five to about 10 elements wherein one or more of the elements in the ring system is an element other than carbon and is selected from nitrogen, oxygen, silicon, or sulphur atoms. Heteroaryl means a five to about a 14-membered aromatic monocyclic or multicyclic hydrocarbon ring system, including fused and spiro rings, in which one or more of the elements in the ring system is an element other than carbon and is selected from nitrogen, oxygen, silicon, or sulphur and wherein an N atom may be in the form of an N-oxide. Arylcarbonyl means an aryl-CO— group in which the aryl group is as described herein. Heteroarylcarbonyl means a heteroaryl-CO— group in which the heteroaryl group is as described herein and heterocycloalkylcarbonyl means a heterocycloalkyl-CO— group in which the heterocycloalkyl group is as described herein. Aryloxycarbonyl means an ROC(O)— group where R is an aryl group as previously described. Heteroaryloxycarbonyl means an ROC(O)— group where R is a heteroaryl group as previously described. Heteroaryloxy means a heteroaryl-O— group in which the heteroaryl group is as previously described. Heterocycloalkoxy means a heterocycloalkyl-O— group in which the heterocycloalkyl group is as previously described. Heterocycloalkoxycarbonyl means an ROC(O)— group where R is a heterocycloalkyl group as previously described.

Examples of saturated alkyl groups include, but are not limited to, methyl, ethyl, N-propyl, isopropyl, N-butyl, tert-butyl, isobutyl, sec-butyl, N-pentyl, N-hexyl, N-heptyl, and N-octyl. An unsaturated alkyl group is one having one or more double or triple bonds. Unsaturated alkyl groups include, for example, ethenyl, propenyl, butenyl, hexenyl, vinyl, 2-propynyl, 2-isopentenyl, 2-butadienyl, ethynyl, 1-propynyl, 3-propynyl, and 3-butynyl. Cycloalkyl groups include, for example, cyclopentyl, cyclohexyl, 1-cyclohexenyl, 3-cyclohexenyl, and cycloheptyl. Heterocycloalkyl groups include, for example, 1-piperidinyl, 2-piperidinyl, 3-piperidinyl, 3-morpholinyl, 4-morpholinyl, tetrahydrofuran-2-yl, tetrahydrofuran-3-yl, tetrahydrothien-2-yl, tetrahydrothien-3-yl, 1-piperazinyl, 2-piperazinyl, and 1,4-diazabicyclooctane. Aryl groups include, for example, phenyl, indenyl, biphenyl, 1-naphthyl, 2-naphthyl, anthracenyl, and phenanthracenyl. Heteroaryl groups include, for example, 1-pyrrolyl, 2-pyrrolyl, 3-pyrrolyl, furyl, thienyl, imidazolyl, oxazolyl, thiazolyl, pyrazolyl, pyridyl, indolyl, quinolinyl, isoquinolinyl, benzoquinolinyl, carbazolyl, and diazaphenanthrenyl.

As used herein, halogen means the elements fluorine (F), chlorine (Cl), Bromine (Br), and iodine (I).

Compounds of the subject invention also include physiologically-acceptable salts and hydrates of the subject compounds. Physiologically-acceptable salts include salts of the compounds of the invention which are prepared with acids or bases, depending on the particular substituents found on the subject complexes described herein. Examples of physiologically-acceptable base addition salts include sodium, potassium, calcium, ammonium, or magnesium salt. Examples of physiologically-acceptable acid addition salts include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Physiologically-acceptable salts of compounds of the invention can be prepared using conventional techniques.

It will be appreciated by those skilled in the art that certain of the compounds of the invention may contain one or more asymmetrically substituted carbon atoms which can give rise to stereoisomers. It is understood that the invention extends to all such stereoisomers, including enantiomers, and diastereoisomers and mixtures, including racemic mixtures thereof.

The subject invention also concerns methods for treating a person or animal having a disorder or condition associated with aberrant or excessive ROCK activity or expression in a cell. In one embodiment, the disorder or condition is an oncological disorder or condition. In another embodiment, the disorder or condition is a cardiovascular-related disorder or condition. Examples of cardiovascular disorders and conditions that can be treated using the compounds and/or compositions of the invention include, but are not limited to, cerebral and coronary vasospasm, angina, hypertension, pulmonary hypertension, arteriosclerosis, ischemia/reperfusion injury, restenosis, stroke, and heart failure. In a further embodiment, the disorder or condition is a central nervous system (CNS) disorder or condition. Examples of CNS disorders and conditions that can be treated using the compounds and/or compositions of the invention include, but are not limited to, spinal cord injury, stroke, and Alzheimer's disease (AD). In one embodiment, a person or animal in need of treatment is administered an effective amount of one or more inhibitor compounds or compositions of this invention. In a specific embodiment, the compound is the compound designated herein as 30b. In another embodiment, the compound is the compound designated herein as 30h. In a specific embodiment, the 30h compound is the (R) stereoisomer. In one embodiment, compounds and compositions of the invention can be used in the methods of treatment in combination with other ROCK inhibitors, including, but not limited to, Y27632, Wf536, Fasudil, H-1152P, and/or CID5056270.

The subject invention also concerns methods of inhibiting migratory or invasive capacity of a cell, or inhibiting metastatic potential of a cell. In one embodiment, a cell is contacted with an effective amount of one or more inhibitor compounds or compositions of this invention. In a specific embodiment, the compound is the compound designated herein as 30b. In another embodiment, the compound is the compound designated herein as 30h. In a specific embodiment, the 30h compound is the (R) stereoisomer. Cells can be any animal cell, such as a mammalian cell. Cells can be any mammalian cell, such as a human cell, canine cell, feline cell, or equine cell. In one embodiment the cell is a tumor cell, a cancer cell or a transformed cell. In one embodiment, compounds and compositions of the invention can be used in combination with other ROCK inhibitors, including, but not limited to, Y27632, Wf536, Fasudil, H-1152P, and/or CID5056270.

The subject invention also concerns methods for inhibiting ROCK activity in a cell. In one embodiment, a cell is contacted with an effective amount of one or more inhibitor compounds or compositions of this invention. In a specific embodiment, the compound is the compound designated herein as 30b. In another embodiment, the compound is the compound designated herein as 30h. In a specific embodiment, the 30h compound is the (R) stereoisomer. Cells can be any animal cell, such as a mammalian cell. Cells can be any mammalian cell, such as a human cell, canine cell, feline cell, or equine cell. In one embodiment the cell is a tumor cell, a cancer cell or a transformed cell. In one embodiment, compounds and compositions of the invention can be used in combination with other ROCK inhibitors, including, but not limited to, Y27632, Wf536, Fasudil, H-1152P, and/or CID5056270.

The subject invention also concerns a packaged dosage formulation comprising in one or more containers at least one inhibitor compound or composition of the invention. In one embodiment, a packaged dosage formulation comprises a compound designated herein as 30b. In another embodiment, the compound is the compound designated herein as 30h. In a specific embodiment, the 30h compound is the (R) stereoisomer. A packaged dosage formulation can optionally comprise in one or more containers a pharmaceutically acceptable carrier or diluent. A packaged dosage formulation can also optionally comprise, in addition to an inhibitor compound or composition of the invention, other ROCK inhibitors, including, but not limited to, Y27632, Wf536, Fasudil, H-1152P, and/or CID5056270.

In vivo application of the subject compounds, and compositions containing them, can be accomplished by any suitable method and technique presently or prospectively known to those skilled in the art. The subject compounds can be formulated in a physiologically- or pharmaceutically-acceptable form and administered by any suitable route known in the art including, for example, oral, nasal, rectal, and parenteral routes of administration. As used herein, the term parenteral includes subcutaneous, intradermal, intravenous, intramuscular, intraperitoneal, and intrasternal administration, such as by injection. Administration of the subject compounds of the invention can be a single administration, or at continuous or distinct intervals as can be readily determined by a person skilled in the art.

The compounds of the subject invention, and compositions comprising them, can also be administered utilizing liposome technology, slow release capsules, implantable pumps, and biodegradable containers. These delivery methods can, advantageously, provide a uniform dosage over an extended period of time. The compounds of the invention can also be administered in their salt derivative forms or crystalline forms.

Compounds of the subject invention can be formulated according to known methods for preparing physiologically acceptable compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the compound is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional physiologically-acceptable carriers and diluents which are known to those skilled in the art. Examples of carriers or diluents for use with the subject compounds include ethanol, dimethyl sulfoxide, glycerol, alumina, starch, saline, and equivalent carriers and diluents. To provide for the administration of such dosages for the desired therapeutic treatment, compositions of the invention will advantageously comprise between about 0.1% and 99%, and especially, 1 and 15% by weight of the total of one or more of the subject compounds based on the weight of the total composition including carrier or diluent.

Compounds of the invention, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions of the invention to a cell comprises attaching the compounds to a protein or nucleic acid that is targeted for delivery to the target cell. U.S. Pat. No. 6,960,648 and Published U.S. Patent Application Nos. 20030032594 and 20020120100 disclose amino acid sequences that can be coupled to another composition and that allows the composition to be translocated across biological membranes. Published U.S. Patent Application No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a 20:80 molar ratio (as used in GLIADEL); chondroitin; chitin; and chitosan.

The subject invention also concerns methods for treating oncological disorders in a patient. In one embodiment, an effective amount of one or more compounds or compositions of the present invention is administered to a patient having an oncological disorder and who is in need of treatment thereof. Methods of the invention can optionally include identifying a patient who is or may be in need of treatment of an oncological disorder. The patient can be a human or other mammal, such as a primate (monkey, chimpanzee, ape, etc.), dog, cat, cow, pig, or horse, or other animals having an oncological disorder. Means for administering and formulating compounds for administration to a patient are known in the art, examples of which are described herein. Oncological disorders within the scope of the invention include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment with the present invention include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Examples of cancers that can be treated according to the present invention are listed in Table 3.

TABLE 3

| Examples of Cancer Types | |
|---|---|
| Acute Lymphoblastic Leukemia, Adult | Hairy Cell Leukemia |
| Acute Lymphoblastic Leukemia, Childhood | Head and Neck Cancer |
| Acute Myeloid Leukemia, Adult | Hepatocellular (Liver) Cancer, Adult (Primary) |
| Acute Myeloid Leukemia, Childhood | Hepatocellular (Liver) Cancer, Childhood (Primary) |
| Adrenocortical Carcinoma | |
| Adrenocortical Carcinoma, Childhood | Hodgkin's Lymphoma, Adult |
| AIDS-Related Cancers | Hodgkin's Lymphoma, Childhood |
| AIDS-Related Lymphoma | Hodgkin's Lymphoma During Pregnancy |
| Anal Cancer | Hypopharyngeal Cancer |
| Astrocytoma, Childhood Cerebellar | Hypothalamic and Visual Pathway Glioma, Childhood |
| Astrocytoma, Childhood Cerebral | |
| Basal Cell Carcinoma | Intraocular Melanoma |
| Bile Duct Cancer, Extrahepatic | Islet Cell Carcinoma (Endocrine Pancreas) |
| Bladder Cancer | Kaposi's Sarcoma |
| Bladder Cancer, Childhood | Kidney (Renal Cell) Cancer |
| Bone Cancer, Osteosarcoma/Malignant Fibrous Histiocytoma | Kidney Cancer, Childhood |
| | Laryngeal Cancer |
| Brain Stem Glioma, Childhood | Laryngeal Cancer, Childhood |
| Brain Tumor, Adult | Leukemia, Acute Lymphoblastic, Adult |
| Brain Tumor, Brain Stem Glioma, Childhood | Leukemia, Acute Lymphoblastic, Childhood |
| | Leukemia, Acute Myeloid, Adult |
| Brain Tumor, Cerebellar Astrocytoma, Childhood | Leukemia, Acute Myeloid, Childhood |
| | Leukemia, Chronic Lymphocytic |
| Brain Tumor, Cerebral Astrocytoma/Malignant Glioma, Childhood | Leukemia, Chronic Myelogenous |
| | Leukemia, Hairy Cell |
| | Lip and Oral Cavity Cancer |
| Brain Tumor, Ependymoma, Childhood | Liver Cancer, Adult (Primary) |
| Brain Tumor, Medulloblastoma, Childhood | Liver Cancer, Childhood (Primary) |
| | Lung Cancer, Non-Small Cell |
| Brain Tumor, Supratentorial Primitive Neuroectodermal Tumors, Childhood | Lung Cancer, Small Cell |
| | Lymphoma, AIDS-Related |
| Brain Tumor, Visual Pathway and Hypothalamic Glioma, Childhood | Lymphoma, Burkitt's |
| | Lymphoma, Cutaneous T-Cell, see Mycosis Fungoides and Sézary Syndrome |
| Brain Tumor, Childhood | |
| Breast Cancer | Lymphoma, Hodgkin's, Adult |
| Breast Cancer, Childhood | Lymphoma, Hodgkin's, Childhood |
| Breast Cancer, Male | Lymphoma, Hodgkin's During Pregnancy |
| Bronchial Adenomas/Carcinoids, Childhood | Lymphoma, Non-Hodgkin's, Adult |
| | Lymphoma, Non-Hodgkin's, Childhood |
| Burkitt's Lymphoma | Lymphoma, Non-Hodgkin's During Pregnancy |
| Carcinoid Tumor, Childhood | |
| Carcinoid Tumor, Gastrointestinal | Lymphoma, Primary Central Nervous System |
| Carcinoma of Unknown Primary | Macroglobulinemia, Waldenström's |
| Central Nervous System Lymphoma, Primary | Malignant Fibrous Histiocytoma of Bone/Osteosarcoma |
| Cerebellar Astrocytoma, Childhood | Medulloblastoma, Childhood |
| Cerebral Astrocytoma/Malignant Glioma, Childhood | Melanoma |
| | Melanoma, Intraocular (Eye) |
| Cervical Cancer | Merkel Cell Carcinoma |
| Childhood Cancers | Mesothelioma, Adult Malignant |
| Chronic Lymphocytic Leukemia | Mesothelioma, Childhood |
| Chronic Myelogenous Leukemia | Metastatic Squamous Neck Cancer with Occult Primary |
| Chronic Myeloproliferative Disorders | |
| Colon Cancer | Multiple Endocrine Neoplasia Syndrome, Childhood |
| Colorectal Cancer, Childhood | |
| Cutaneous T-Cell Lymphoma, see Mycosis Fungoides and Sézary Syndrome | Multiple Myeloma/Plasma Cell Neoplasm |
| | Mycosis Fungoides |
| | Myelodysplastic Syndromes |
| Endometrial Cancer | Myelodysplastic/Myeloproliferative Diseases |
| Ependymoma, Childhood | Myelogenous Leukemia, Chronic |
| Esophageal Cancer | Myeloid Leukemia, Adult Acute |
| Esophageal Cancer, Childhood | Myeloid Leukemia, Childhood Acute |
| Ewing's Family of Tumors | Myeloma, Multiple |
| Extracranial Germ Cell Tumor, Childhood | Myeloproliferative Disorders, Chronic |
| | Nasal Cavity and Paranasal Sinus Cancer |
| Extragonadal Germ Cell Tumor | Nasopharyngeal Cancer |
| Extrahepatic Bile Duct Cancer | Nasopharyngeal Cancer, Childhood |
| Eye Cancer, Intraocular Melanoma | Neuroblastoma |
| Eye Cancer, Retinoblastoma | Non-Hodgkin's Lymphoma, Adult |
| Gallbladder Cancer | Non-Hodgkin's Lymphoma, Childhood |
| Gastric (Stomach) Cancer | Non-Hodgkin's Lymphoma During Pregnancy |
| Gastric (Stomach) Cancer, Childhood | Non-Small Cell Lung Cancer |
| Gastrointestinal Carcinoid Tumor | Oral Cancer, Childhood |
| Germ Cell Tumor, Extracranial, | Oral Cavity Cancer, Lip and |

TABLE 3-continued

Examples of Cancer Types

| | |
|---|---|
| Childhood | Oropharyngeal Cancer |
| Germ Cell Tumor, Extragonadal | Osteosarcoma/Malignant Fibrous |
| Germ Cell Tumor, Ovarian | Histiocytoma of Bone |
| Gestational Trophoblastic Tumor | Ovarian Cancer, Childhood |
| Glioma, Adult | Ovarian Epithelial Cancer |
| Glioma, Childhood Brain Stem | Ovarian Germ Cell Tumor |
| Glioma, Childhood Cerebral | Ovarian Low Malignant Potential Tumor |
| Astrocytoma | Pancreatic Cancer |
| Glioma, Childhood Visual Pathway and | Pancreatic Cancer, Childhood |
| Hypothalamic | Pancreatic Cancer, Islet Cell |
| Skin Cancer (Melanoma) | Paranasal Sinus and Nasal Cavity Cancer |
| Skin Carcinoma, Merkel Cell | Parathyroid Cancer |
| Small Cell Lung Cancer | Penile Cancer |
| Small Intestine Cancer | Pheochromocytoma |
| Soft Tissue Sarcoma, Adult | Pineoblastoma and Supratentorial Primitive |
| Soft Tissue Sarcoma, Childhood | Neuroectodermal Tumors, Childhood |
| Squamous Cell Carcinoma, see Skin | Pituitary Tumor |
| Cancer (non-Melanoma) | Plasma Cell Neoplasm/Multiple Myeloma |
| Squamous Neck Cancer with Occult | Pleuropulmonary Blastoma |
| Primary, Metastatic | Pregnancy and Breast Cancer |
| Stomach (Gastric) Cancer | Pregnancy and Hodgkin's Lymphoma |
| Stomach (Gastric) Cancer, Childhood | Pregnancy and Non-Hodgkin's Lymphoma |
| Supratentorial Primitive | Primary Central Nervous System Lymphoma |
| Neuroectodermal Tumors, Childhood | Prostate Cancer |
| T-Cell Lymphoma, Cutaneous, see | Rectal Cancer |
| Mycosis Fungoides and Sézary | Renal Cell (Kidney) Cancer |
| Syndrome | Renal Cell (Kidney) Cancer, Childhood |
| Testicular Cancer | Renal Pelvis and Ureter, Transitional Cell |
| Thymoma, Childhood | Cancer |
| Thymoma and Thymic Carcinoma | Retinoblastoma |
| Thyroid Cancer | Rhabdomyosarcoma, Childhood |
| Thyroid Cancer, Childhood | Salivary Gland Cancer |
| Transitional Cell Cancer of the Renal | Salivary Gland Cancer, Childhood |
| Pelvis and Ureter | Sarcoma, Ewing's Family of Tumors |
| Trophoblastic Tumor, Gestational | Sarcoma, Kaposi's |
| Unknown Primary Site, Carcinoma of, | Sarcoma, Soft Tissue, Adult |
| Adult | Sarcoma, Soft Tissue, Childhood |
| Unknown Primary Site, Cancer of, | Sarcoma, Uterine |
| Childhood | Sezary Syndrome |
| Unusual Cancers of Childhood | Skin Cancer (non-Melanoma) |
| Ureter and Renal Pelvis, Transitional | Skin Cancer, Childhood |
| Cell Cancer | |
| Urethral Cancer | |
| Uterine Cancer, Endometrial | |
| Uterine Sarcoma | |
| Vaginal Cancer | |
| Visual Pathway and Hypothalamic | |
| Glioma, Childhood | |
| Vulvar Cancer | |
| Waldenström's Macroglobulinemia | |
| Wilms' Tumor | |

For the treatment of oncological disorders, the compounds of this invention can be administered to a patient in need of treatment in combination with other antitumor or anticancer substances and/or with radiation and/or photodynamic therapy and/or with surgical treatment to remove a tumor. These other substances or treatments may be given at the same as or at different times from the compounds of this invention. For example, the compounds of the present invention can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. In one embodiment, compounds and compositions of the invention can be used in combination with other ROCK inhibitors, including, but not limited to, Y27632, Wf536, Fasudil, H-1152P, and CID5056270.

Many tumors and cancers have viral genome present in the tumor or cancer cells. For example, Epstein-Barr Virus (EBV) is associated with a number of mammalian malignancies. The compounds of the subject invention can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds of the subject invention can also be used in combination with viral based treatments of oncologic disease. For example, compounds of the invention can be used with mutant herpes simplex virus in the treatment of non-small cell lung cancer (Toyoizumi et al., 1999).

The methods of the present invention can be used with humans and other animals. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses.

While inhibitor compounds or agents of the invention can be administered as isolated compounds or agents, these compounds can also be administered as part of a pharmaceutical composition. The subject invention thus further provides compositions comprising one or more compounds or agents in association with at least one pharmaceutically acceptable carrier. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

The inhibitor compounds or agents of the invention can be formulated according to known methods for preparing pharmaceutically useful compositions. Formulations are described in a number of sources which are well known and readily available to those skilled in the art. For example, *Remington's Pharmaceutical Science* (Martin 1995) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

The compounds and agents of the present invention include all hydrates and salts that can be prepared by those of skill in the art. Under conditions where the compounds and agents of the present invention are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of a compound or agent may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Therapeutic application of compounds and/or agents and compositions containing them can be accomplished by any suitable therapeutic method and technique presently or prospectively known to those skilled in the art. Further, compounds and agents of the invention have use as starting materials or intermediates for the preparation of other useful compounds and compositions.

Compounds and agents of the invention, and compositions thereof, may be locally administered at one or more anatomical sites, such as sites of unwanted cell growth (such as a tumor site or benign skin growth, e.g., injected or topically applied to the tumor or skin growth) or sites of fungal infection, optionally in combination with a pharmaceutically acceptable carrier such as an inert diluent. Compounds and agents of the invention, and compositions thereof, may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Compounds and agents and compositions of the invention, including pharmaceutically acceptable salts or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents of the invention may be applied in as a liquid or solid. However, it will generally be desirable to administer them topically to the skin as compositions, in combination with a dermatologically acceptable carrier, which may be a solid or a liquid. Compounds and agents and compositions of the subject invention can be applied topically to a subject's skin to reduce the size (and may include complete removal) of malignant or benign growths, or to treat an infection site. Compounds and agents of the invention can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The present invention also concerns pharmaceutical compositions comprising a compound and/or agent of the invention in combination with a pharmaceutically acceptable carrier. Pharmaceutical compositions adapted for oral, topical or parenteral administration, comprising an amount of a compound constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions contemplated by the present invention can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions of the present invention can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments may be given at the same as or at different times from the compounds of this invention. Examples of other chemotherapeutic agents contemplated within the scope of the invention include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of immunotherapeutic agents contemplated within the scope of the invention include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) The subject invention also concerns methods for treating an oncological disorder comprising administering an effective amount of a compound and/or agent of the invention prior to, subsequent to, and/or in combination with administration of a chemotherapeutic agent, an immunotherapeutic agent, a radiotherapeutic agent, or radiotherapy.

Examples of some chemotherapeutic agents that can be used according to the present invention are listed in Table 4.

TABLE 4

Examples of Chemotherapeutic Agents

| | |
|---|---|
| 13-cis-Retinoic Acid | Mylocel |
| 2-Amino-6-Mercaptopurine | Letrozole |
| | Neosar |
| 2-CdA | Neulasta |
| 2-Chlorodeoxyadenosine | Neumega |
| 5-fluorouracil | Neupogen |
| 5-FU | Nilandron |
| 6-TG | Nilutamide |
| 6-Thioguanine | Nitrogen Mustard |
| 6-Mercaptopurine | Novaldex |
| 6-MP | Novantrone |
| Accutane | Octreotide |
| Actinomycin-D | Octreotide acetate |
| Adriamycin | Oncospar |
| Adrucil | Oncovin |
| Agrylin | Ontak |
| Ala-Cort | Onxal |
| Aldesleukin | Oprevelkin |
| Alemtuzumab | Orapred |
| Alitretinoin | Orasone |
| Alkaban-AQ | Oxaliplatin |
| Alkeran | Paclitaxel |
| All-transretinoic acid | Pamidronate |
| Alpha interferon | Panretin |
| Altretamine | Paraplatin |
| Amethopterin | Pediapred |
| Amifostine | PEG Interferon |
| Aminoglutethimide | Pegaspargase |
| Anagrelide | Pegfilgrastim |
| Anandron | PEG-INTRON |
| Anastrozole | PEG-L-asparaginase |
| Arabinosylcytosine | Phenylalanine Mustard |
| Ara-C | Platinol |
| Aranesp | Platinol-AQ |
| Aredia | Prednisolone |
| Arimidex | Prednisone |
| Aromasin | Prelone |
| Arsenic trioxide | Procarbazine |
| Asparaginase | PROCRIT |
| ATRA | Proleukin |
| Avastin | Prolifeprospan 20 with Carmustine implant |
| BCG | Purinethol |
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | Rubex |
| Bleomycin | Rubidomycin hydrochloride |
| Bortezomib | Sandostatin |
| Busulfan | Sandostatin LAR |
| Busulfex | Sargramostim |
| C225 | Solu-Cortef |
| Calcium Leucovorin | Solu-Medrol |
| Campath | STI-571 |
| Camptosar | Streptozocin |
| Camptothecin-11 | Tamoxifen |
| Capecitabine | Targretin |
| Carac | Taxol |
| Carboplatin | Taxotere |
| Carmustine | Temodar |
| Carmustine wafer | Temozolomide |
| Casodex | Teniposide |
| CCNU | TESPA |
| CDDP | Thalidomide |
| CeeNU | Thalomid |
| Cerubidine | TheraCys |

TABLE 4-continued

Examples of Chemotherapeutic Agents

| | |
|---|---|
| cetuximab | Thioguanine |
| Chlorambucil | Thioguanine Tabloid |
| Cisplatin | Thiophosphoamide |
| Citrovorum Factor | Thioplex |
| Cladribine | Thiotepa |
| Cortisone | TICE |
| Cosmegen | Toposar |
| CPT-11 | Topotecan |
| Cyclophosphamide | Toremifene |
| Cytadren | Trastuzumab |
| Cytarabine | Tretinoin |
| Cytarabine liposomal | Trexall |
| Cytosar-U | Trisenox |
| Cytoxan | TSPA |
| Dacarbazine | VCR |
| Dactinomycin | Velban |
| Darbepoetin alfa | Velcade |
| Daunomycin | VePesid |
| Daunorubicin | Vesanoid |
| Daunorubicin hydrochloride | Viadur |
| | Vinblastine |
| Daunorubicin liposomal | Vinblastine Sulfate |
| DaunoXome | Vincasar Pfs |
| Decadron | Vincristine |
| Delta-Cortef | Vinorelbine |
| Deltasone | Vinorelbine tartrate |
| Denileukin diftitox | VLB |
| DepoCyt | VP-16 |
| Dexamethasone | Vumon |
| Dexamethasone acetate | Xeloda |
| dexamethasone sodium phosphate | Zanosar |
| | Zevalin |
| Dexasone | Zinecard |
| Dexrazoxane | Zoladex |
| DHAD | Zoledronic acid |
| DIC | Zometa |
| Diodex | Gliadel wafer |
| Docetaxel | Glivec |
| Doxil | GM-CSF |
| Doxorubicin | Goserelin |
| Doxorubicin liposomal | granulocyte - colony stimulating factor |
| Droxia | Granulocyte macrophage colony stimulating factor |
| DTIC | |
| DTIC-Dome | Halotestin |
| Duralone | Herceptin |
| Efudex | Hexadrol |
| Eligard | Hexalen |
| Ellence | Hexamethylmelamine |
| Eloxatin | HMM |
| Elspar | Hycamtin |
| Emcyt | Hydrea |
| Epirubicin | Hydrocort Acetate |
| Epoctin alfa | Hydrocortisone |
| Erbitux | Hydrocortisone sodium phosphate |
| *Erwinia* L-asparaginase | Hydrocortisone sodium succinate |
| Estramustine | Hydrocortone phosphate |
| Ethyol | Hydroxyurea |
| Etopophos | Ibritumomab |
| Etoposide | Ibritumomab Tiuxetan |
| Etoposide phosphate | Idamycin |
| Eulexin | Idarubicin |
| Evista | Ifex |
| Exemestane | IFN-alpha |
| Fareston | Ifosfamide |
| Faslodex | IL-2 |
| Femara | IL-11 |
| Filgrastim | Imatinib mesylate |
| Floxuridine | Imidazole Carboxamide |
| Fludara | Interferon alfa |
| Fludarabine | Interferon Alfa-2b (PEG conjugate) |
| Fluoroplex | Interleukin-2 |
| Fluorouracil | Interleukin-11 |
| Fluorouracil (cream) | Intron A (interferon alfa-2b) |
| Fluoxymesterone | Leucovorin |
| Flutamide | Leukeran |
| Folinic Acid | Leukine |
| FUDR | Leuprolide |
| Fulvestrant | Leurocristine |

TABLE 4-continued

Examples of Chemotherapeutic Agents

| | |
|---|---|
| G-CSF | Leustatin |
| Gefitinib | Liposomal Ara-C |
| Gemcitabine | Liquid Pred |
| Gemtuzumab ozogamicin | Lomustine |
| Gemzar | L-PAM |
| Gleevec | L-Sarcolysin |
| Lupron | Meticorten |
| Lupron Depot | Mitomycin |
| Matulane | Mitomycin-C |
| Maxidex | Mitoxantrone |
| Mechlorethamine | M-Prednisol |
| Mechlorethamine Hydrochlorine | MTC |
| | MTX |
| Medralone | Mustargen |
| Medrol | Mustine |
| Megace | Mutamycin |
| Megestrol | Myleran |
| Megestrol Acetate | Iressa |
| Melphalan | Irinotecan |
| Mercaptopurine | Isotretinoin |
| Mesna | Kidrolase |
| Mesnex | Lanacort |
| Methotrexate | L-asparaginase |
| Methotrexate Sodium | LCR |
| Methylprednisolone | |

The subject invention also concerns methods for inhibiting a ROCK protein in a cell by contacting the cell with an effective amount of a compound, agent, or composition of the invention. In one embodiment, the cell is a human or mammalian cell, and can be a cancer or tumor cell or other cell that exhibits abnormal proliferation, survival, migration or differentiation. In one embodiment, the cell constitutively expresses or expresses elevated or abnormal levels of a ROCK protein. In a specific embodiment, the compound is the compound designated herein as 30b. In another embodiment, the compound is the compound designated herein as 30h. In a specific embodiment, the 30h compound is the (R) stereoisomer.

The subject invention also concerns methods for treating a person or animal having a disorder associated with constitutive, abnormal, or elevated expression of a ROCK protein in a cell, wherein a therapeutically effective amount of a compound, agent, or composition of the invention is administered to the person or animal. The disorder can be one characterized, for example, by abnormal cell proliferation, cell survival, cell migration, and/or cell differentiation. In a specific embodiment, the compound is the compound designated herein as 30b. In another embodiment, the compound is the compound designated herein as 30h. In a specific embodiment, the 30h compound is the (R) stereoisomer.

Depending upon the disorder or disease condition to be treated, a suitable dose(s) may be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound and/or agent can be continuous or at distinct intervals, as can be determined by a person of ordinary skill in the art.

To provide for the administration of such dosages for the desired therapeutic treatment, in some embodiments, pharmaceutical compositions of the invention can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The subject invention also concerns kits comprising a composition comprising an inhibitor compound and/or agent of the invention in one or more containers. Kits of the invention can optionally include pharmaceutically acceptable carriers and/or diluents. In one embodiment, a kit of the invention includes one or more other components, adjuncts, or adjuvants as described herein. In another embodiment, a kit includes one or more anti-cancer agents, such as those agents described herein. In one embodiment, a kit of the invention includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent of the invention is provided in the kit as a solid, such as a tablet, pill, or powder form. In another embodiment, a compound and/or agent of the invention is provided in the kit as a liquid or solution. In one embodiment, the kit comprises an ampoule or syringe containing a compound and/or agent of the invention in liquid or solution form. A kit of the invention can also optionally comprise, in addition to an inhibitor compound or composition of the invention, other ROCK inhibitors, including, but not limited to, Y27632, Wf536, Fasudil, H-1152P, and/or CID5056270.

Mammalian species which benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient" and "subject" are used interchangeably and are intended to include such human and non-human species. Likewise, in vitro methods of the present invention can be carried out on cells of such human and non-human species.

The inventors have established a program to develop potent and selective ROCK1 inhibitors to provide in vitro and in vivo tools to probe the pharmacological inhibition of ROCK1 and to further establish its role in cancer and metastasis. The inventors undertook a screen of the NCI Diversity set using a Z-lyte FRET assay (Kang et al. (2009); Wu et al. (2010)) to measure kinase inhibition. NSC-135784 (de Suto-Nagy et al. (1941)) was identified as a weak inhibitor ($IC_{50}$ 92 µM). Active in only 1 screen from 127 assessed in the Molecular Libraries Screening Centers Network (MLSCN) (Huryn et al. (2007); Huryn (2009)), NSC-135784 appeared to be a good hit for library development and was synthesized to confirm the identity of the NCI sample and the ROCK inhibition [1aa (in house NSC-135784): ROCK1: $IC_{50}$=38 µM; ROCK2: $IC_{50}$=25 µM].

NSC-135784 was chosen as a starting point for the development of novel ROCK inhibitors.

Materials and Methods

Chemistry

The inventors prepared the hit 1aa following the synthetic routes depicted in Scheme 1 (EtOH, microwave heating, 120° C., 10 min). To establish a preliminary structure activity relationship the library of 4-anilino-2-aminopyrimidines 1 was rapidly synthesized via microwave-assisted reaction of anilines 2 with 4-chloropyrimidin-2-amine (3) (Scheme 1). The use of microwave-assisted heating was successfully applied to the synthesis of analogs 6-8 that possess different A-rings (Scheme 2). The nitrogen atom linking the two rings of NSC-135784 was replaced by an oxygen atom as shown in Scheme 3. This library of 4-(2-aminopyrimidyl) phenyl ethers 10 was prepared by reacting with 4-chloropyrimidin-2-amine (3) with commercially available phenols 9 (microwave heating, 165° C., 10 min).

The hit optimization process initially directed us towards the generation of a small library of indoline 13 and indoles 15 (Scheme 4, conditions b, c, d or c). The indoline building blocks 12 were either commercially available or prepared in-house via reduction of the corresponding commercially available indoles 11 (Scheme 4, conditions a). To further explore the structure activity relationships, additional analogs 16-18 were synthesized according to the route illustrated in Scheme 5.

The series of indoles 21 was prepared as illustrated in Scheme 6. The synthesis involves the alkylation of available phenols with benzyl halides 19 to afford the indole building blocks 20, which were subsequently reacted with 4-chloropyrimidin-2-amine (3) to afford the desired library 21. The synthesis of amide building blocks 23 was achieved via coupling of various commercially indole carboxylic acids with inexpensive and readily available amines 22 (benzylamines, anilines, and phenethylamines) using EDC as coupling reagent in presence of catalytic amount of DMAP (Scheme 6). These conditions were also successfully applied to the preparation of reverse-amide building blocks 26 and the alpha-substituted benzylamides 29 from 25 and 28 respectively. Alternatively, EDC/HOBt coupling reagents were utilized for the synthesis of the alpha-substituted benzylamides 29 (Scheme 6, condition c). Finally, microwave heating provided an efficient and convenient method for the rapid generation of the desired libraries 24, 27 and 30 (Scheme 6) using the same conditions described for library 21 (DMF, $Cs_2CO_3$, 150° C., microwave, 30 min). As seen in our preliminary SAR (compounds 6, 7, 8), one aspect of the SAR focused on the effect of the modifications of the 2-amino-pyrimidyl position on selected compounds of interest. The synthesis of N-phenylpyrimidine 33 was successfully carried out via microwave-assisted heating under acidic conditions (aq. 0.1 M HCl) (Scheme 7). The pyrrolo containing pyrimidine 35 was prepared as under the conditions described in Scheme 8. Treatment of 30b with acetic anhydride afforded the N-acyl derivative 36 (Scheme 9). Finally, reaction of 29a and 37 afforded the target compound 38.

The synthesis of analogs 46 and 47 is illustrated in Scheme 11 and 12. The synthesis of amide and sulfonamide building blocks 41 and 44 was achieved via coupling of commercially available para-nitrobenzoyl chloride and para-nitrosulfonyl chloride with 3-methoxybenzylamine 40 (Scheme 11). Tin chloride was utilized for the reduction of 41 and 44 to the corresponding aniline 42 and 45. Finally, microwave heating provided an efficient and convenient method for the rapid generation of 46 and 47 (Scheme 12) (EtOH, 150° C., microwave, 20 min).

The structures of all final compounds were confirmed by their spectroscopy data. In addition, HPLC methods were also developed to assess the purity (generally>96%) of the most potent compounds.

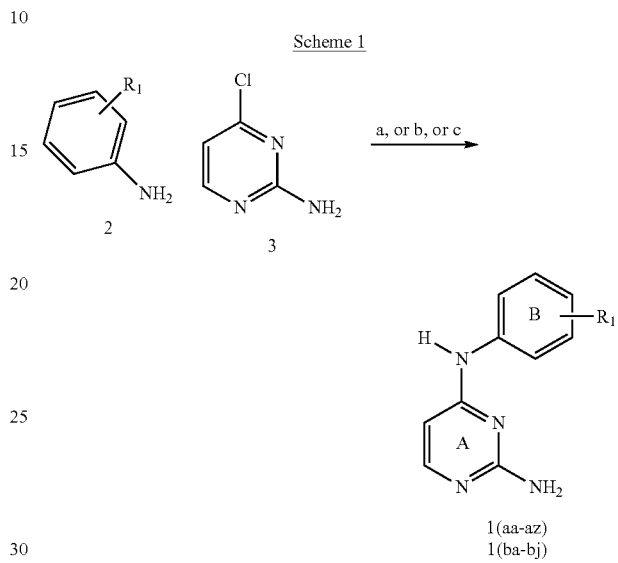

Scheme 1

Conditions: a) EtOH, 10-20 min, microwave, 120° C.; EtOH, 15-20 min, microwave, 150° C. Product 1 was isolated as the HCl salt from methods a and c, and as the freebase from method b.

Scheme 2

-continued
7, R = NH₂, 72%
8, R = H, 80%
Conditions: a) AcOH NaCNBH₃, rt, 3 h; b) 3, EtOH, 20-30 min, microwave, 120° C.; c) 3, EtOH, 15 min, microwave, 150° C.; d) 3, DMF, Cs₂CO₃, microwave, 110° C., 1 h; e) 3, NMP, Cs₂CO₃, microwave, 150° C., 30 min.
Scheme 3
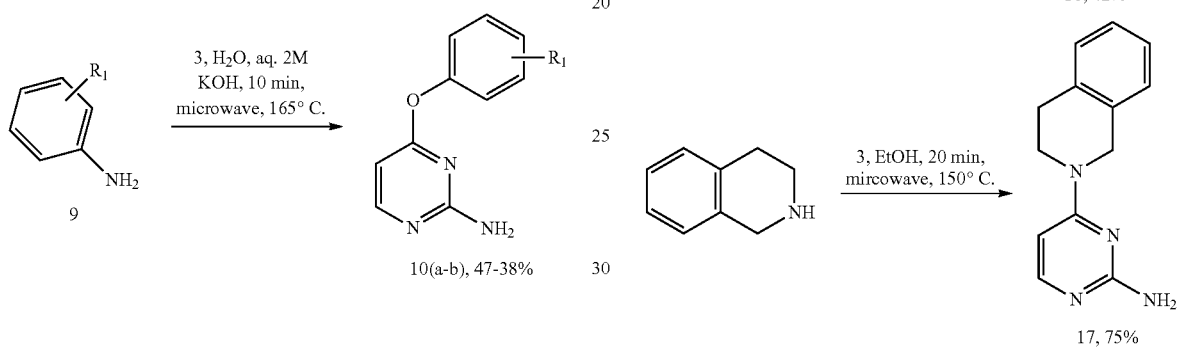
Scheme 4
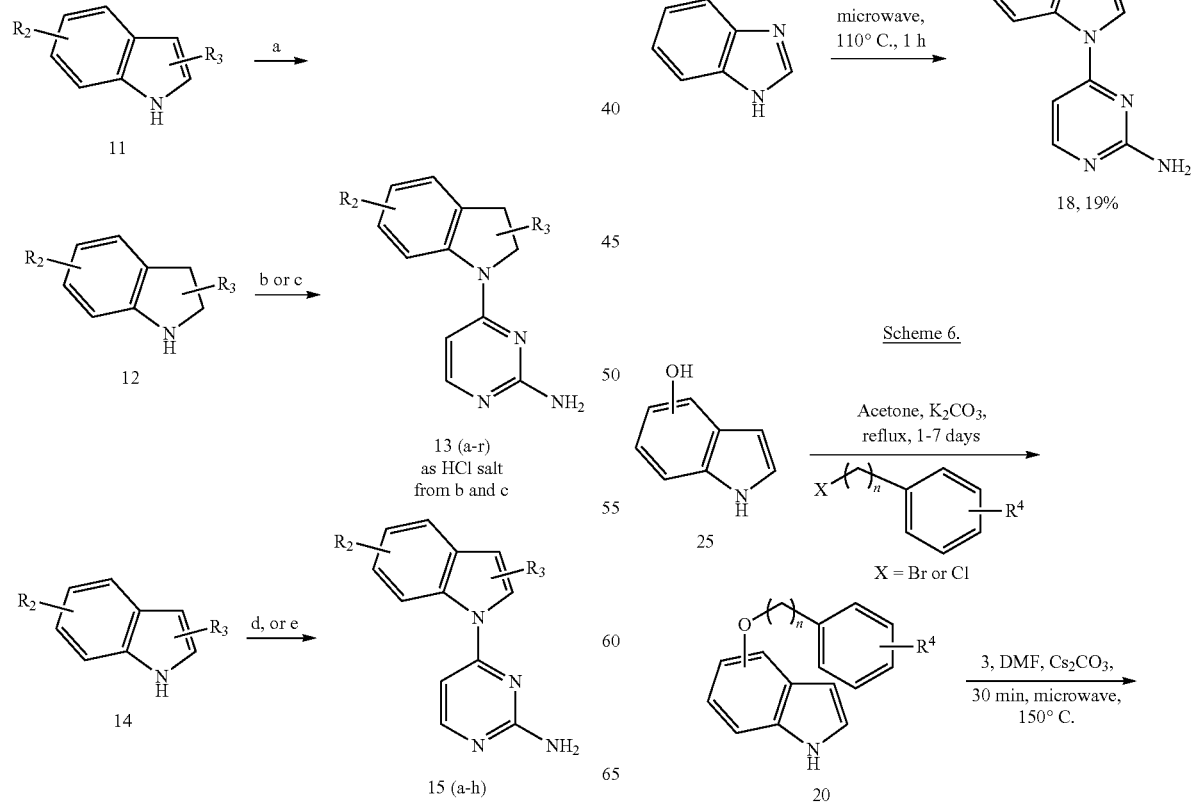

31
-continued
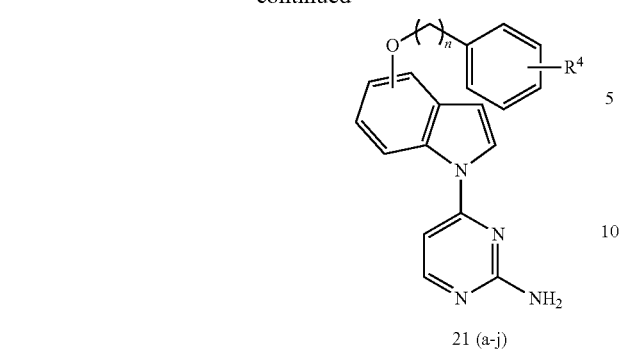
21 (a-j)
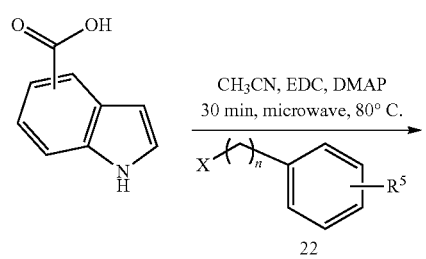
22
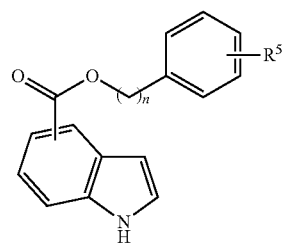
23
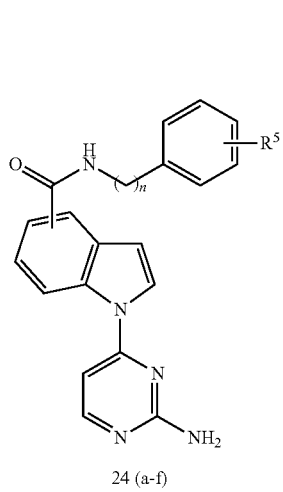
24 (a-f)
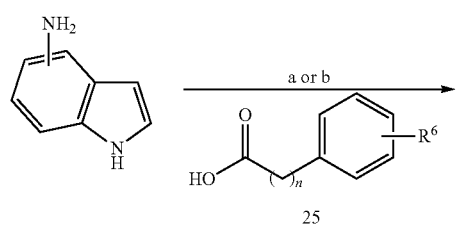
25
32
-continued
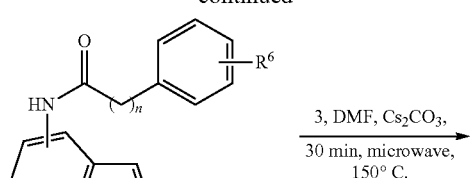
26
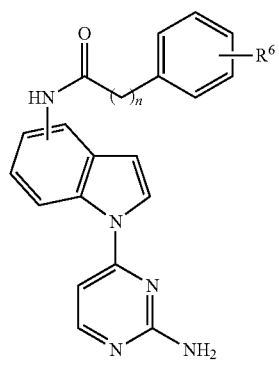
27 (a-d)
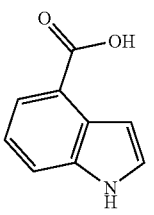 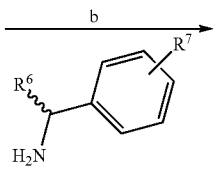
28
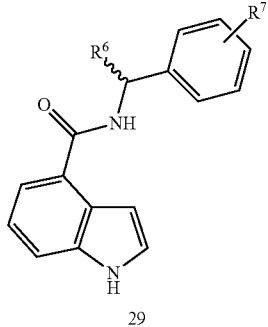
29

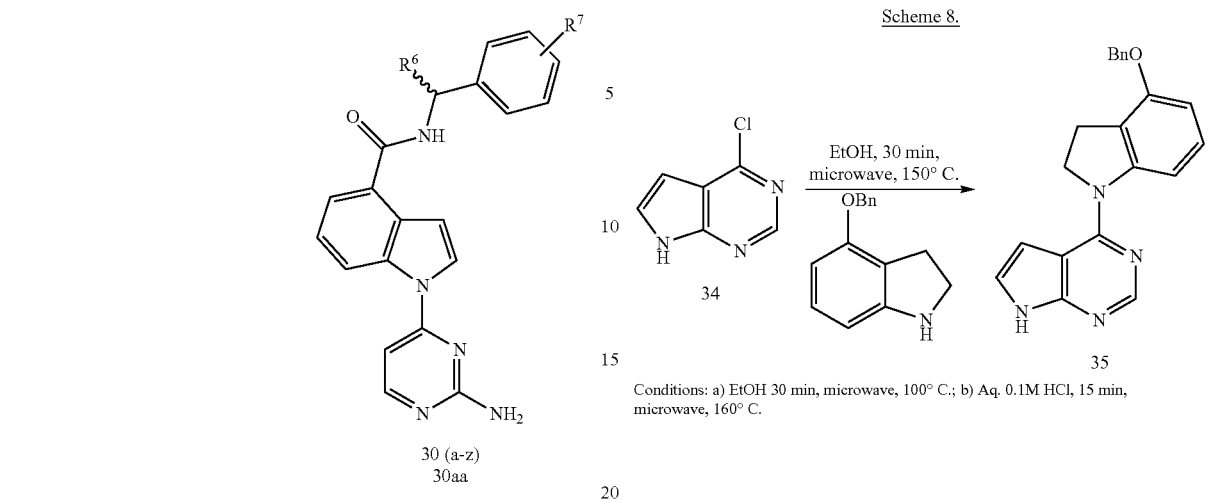

Scheme 11
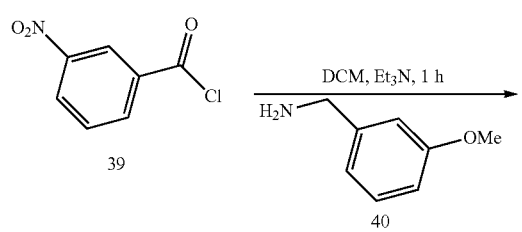
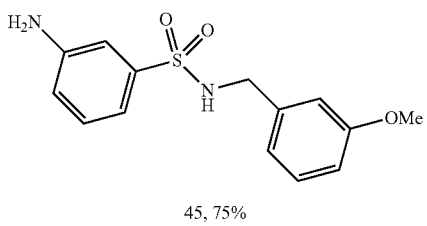
Scheme 12
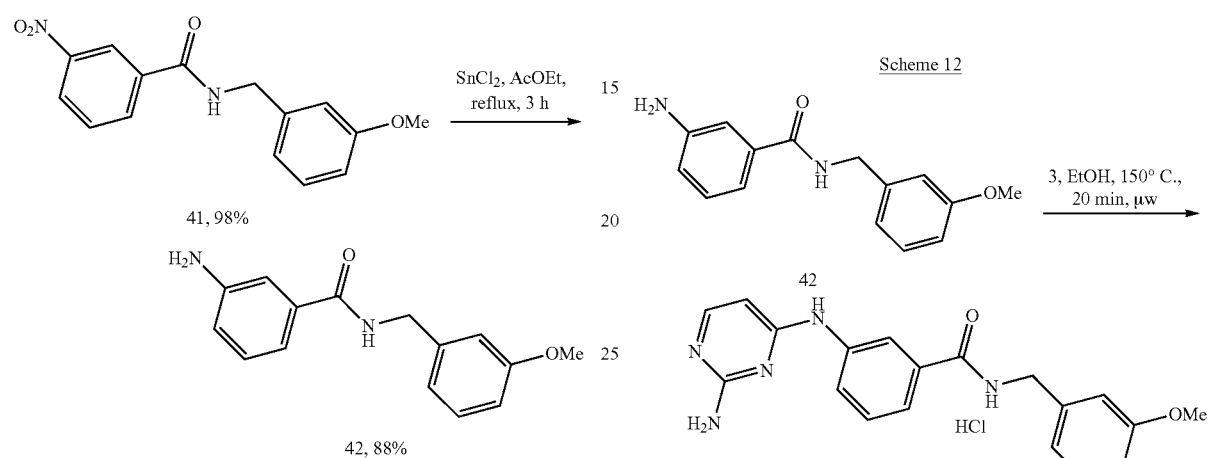
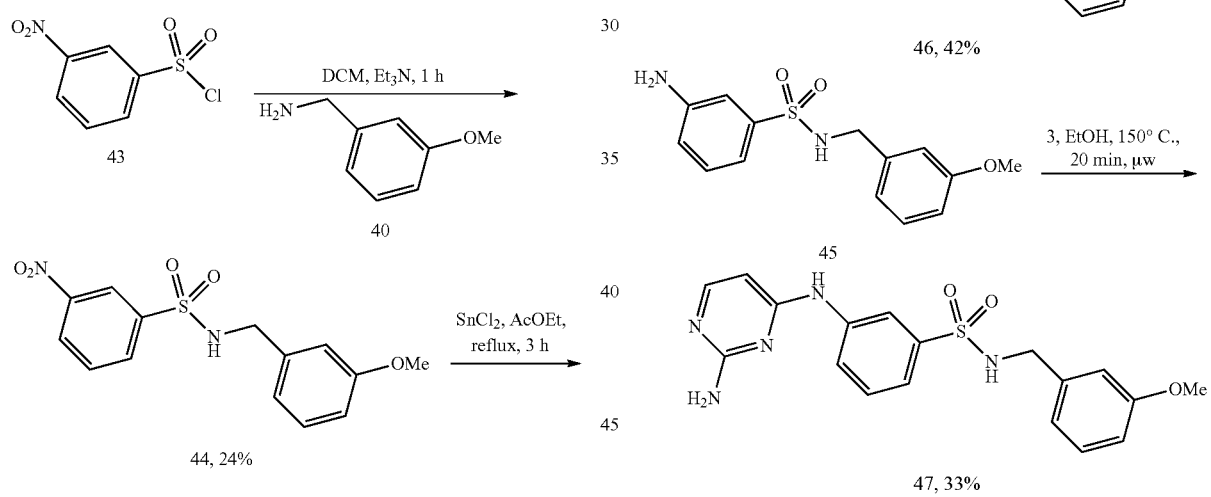
TABLE 5
Examples of compounds, structures and ROCK1&2 IC$_{50}$ (μM)
| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| (1aa)(in house NSC135784) C$_{10}$H$_{12}$ClN$_5$O$_2$S; MW, 301.75 | 60 ± 3 | 38.5 ± 3.4 | 25.5 ± 5.8 |

TABLE 5-continued

Examples of compounds, structures and ROCK1&2 IC$_{50}$ (μM)

| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| 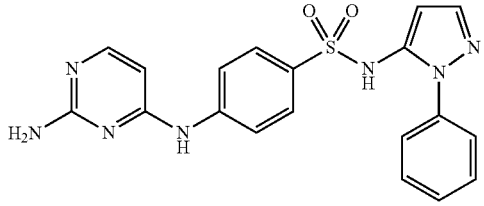<br>(1ab)<br>C$_{19}$H$_{17}$N$_7$O$_2$S; MW, 407.45 | 1.8 ± 0.8 | nd | nd |
| 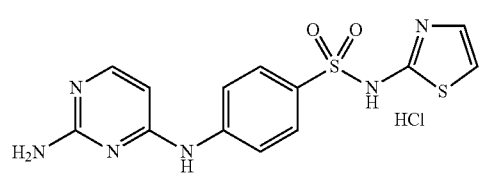<br>(1ac)<br>C$_{13}$H$_{13}$ClN$_6$O$_2$S$_2$; MW, 384.86 | 21 ± 10 | nd | nd |
| 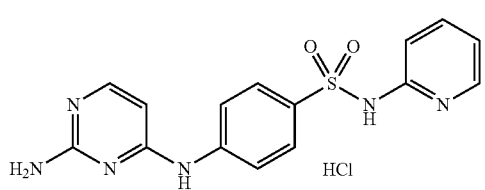<br>(1ad)<br>C$_{15}$H$_{15}$ClN$_6$O$_2$S; MW, 378.84 | 2.8 ± 2.3 | nd | nd |
| 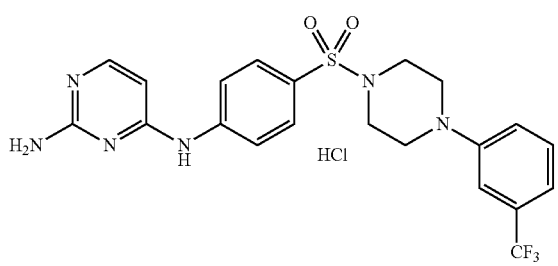<br>(1ae)<br>C$_{21}$H$_{22}$ClF$_3$N$_6$O$_2$; MW, 514.95 | −0.3 ± 0.7 | nd | nd |
| 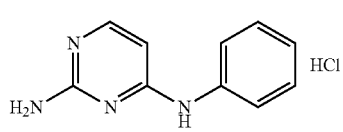<br>(1af)<br>C$_{10}$H$_{11}$ClN$_4$; MW, 222.67 | 47 ± 6 | 55.3 ± 13.4 | >50 |
| 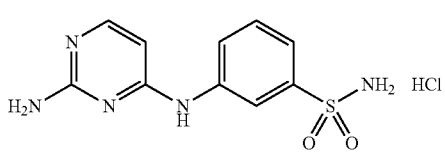<br>(1ag)<br>C$_{10}$H$_{12}$ClN$_5$O$_2$S; MW, 301.75 | 90 ± 2 | 6.1 ± 0.6 | 6.1 ± 1.1 |

TABLE 5-continued

Examples of compounds, structures and ROCK1&2 IC$_{50}$ (μM)

| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| 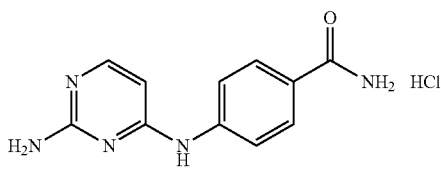<br>(1ah)<br>C$_{11}$H$_{12}$ClN$_5$O; MW, 265.70 | 82 ± 2 | 13.3 ± 1.7 | 11.5 ± 1.2 |
| 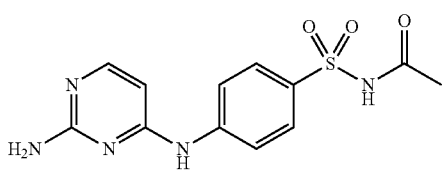<br>(1ai)<br>C$_{12}$H$_{13}$N$_5$O$_3$S; MW, 307.33 | 9 ± 1.5 | nd | nd |
| 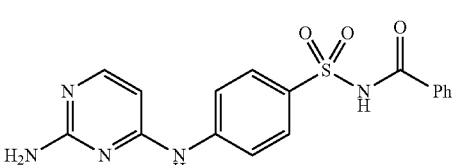<br>(1aj)<br>C$_{17}$H$_{15}$N$_5$O$_3$S; MW, 369.40 | 2.1 ± 1.9 | nd | nd |
| 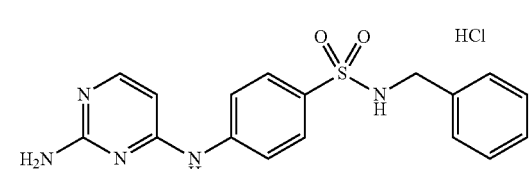<br>(1ak)<br>C$_{17}$H$_{18}$ClN$_5$O$_2$S; MW, 391.88 | 30 ± 1 | nd | nd |
| 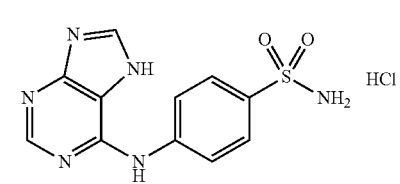<br>(8)<br>C$_{11}$H$_{11}$ClN$_6$O$_2$S; MW, 326.76 | 54 ± 4 | 42.7 ± 0.9 | nd |
| 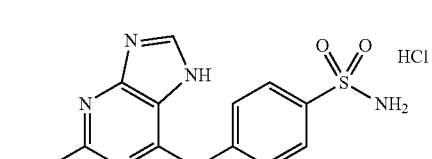<br>(7)<br>C$_{11}$H$_{12}$ClN$_7$O$_2$S; MW, 341.78 | 9 ± 2 | nd | nd |

TABLE 5-continued

Examples of compounds, structures and ROCK1&2 IC$_{50}$ (μM)

| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| 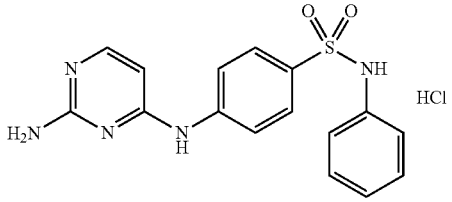<br>(1al)<br>C$_{16}$H$_{16}$ClN$_5$O$_2$S; MW, 377.85 | 46 ± 4 | >100 | nd |
| 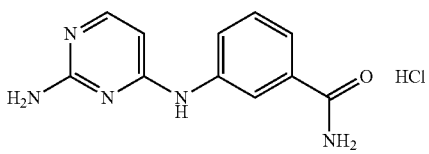<br>(1am)<br>C$_{11}$H$_{12}$ClN$_5$O; MW, 265.70 | 54 ± 4 | 38.9 ± 0.9 | 33.3 ± 2.8 |
| 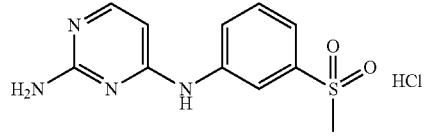<br>(1an)<br>C$_{11}$H$_{13}$ClN$_4$O$_2$S; MW, 300.76 | 90 ± 1 | 6.7 ± 1.3 | 7.3 ± 2.0 |
| 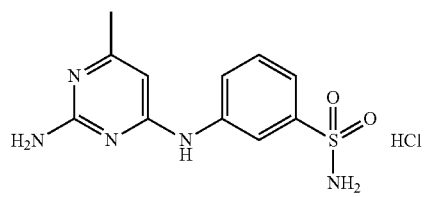<br>(6)<br>C$_{11}$H$_{14}$ClN$_5$O$_2$S; MW, 315.78 | 0.8 ± 1.2 | nd | nd |
| 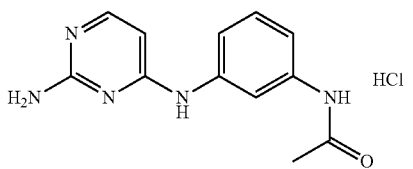<br>(1ao)<br>C$_{12}$H$_{14}$ClN$_5$O; MW, 279.73 | 42 ± 6 | nd | nd |
| 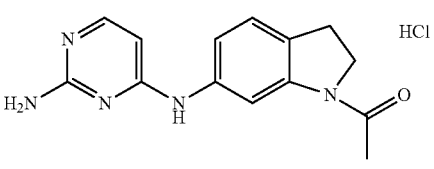<br>(1ap)<br>C$_{14}$H$_{16}$ClN$_5$O; MW, 305.76 | 10 ± 12 | nd | nd |

TABLE 5-continued

Examples of compounds, structures and ROCK1&2 IC$_{50}$ (μM)

| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| 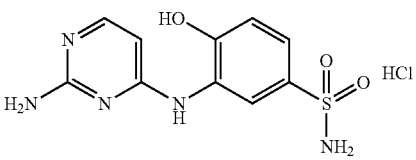<br>(1aq)<br>C$_{10}$H$_{12}$ClN$_5$O$_3$S; MW, 317.75 | 36 ± 5 | nd | nd |
| 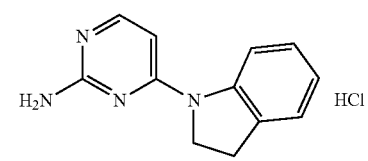<br>(13a)<br>C$_{12}$H$_{13}$ClN$_4$; MW, 248.71 | 85 ± 4 | 6.6 ± 0.5 | 3.4 ± 0.3 |
| 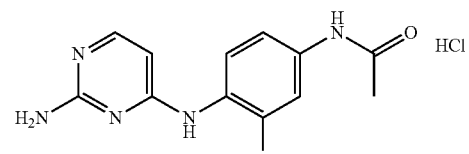<br>(1ar)<br>C$_{13}$H$_{16}$ClN$_5$O$_2$; MW, 309.75 | 2 ± 1 | nd | nd |
| 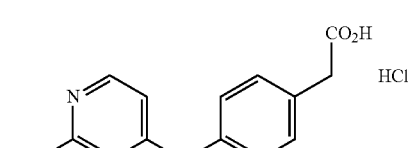<br>(1as)<br>C$_{12}$H$_{13}$ClN$_4$O$_2$; MW, 280.71 | 2 ± 1 | nd | nd |
| 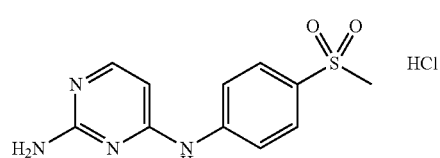<br>(1at)<br>C$_{11}$H$_{13}$ClN$_4$O$_2$S; MW, 300.76 | 38 ± 1 | nd | nd |
| 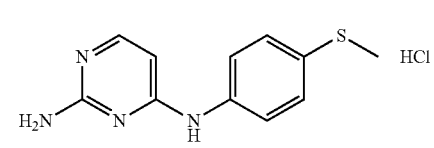<br>(1au)<br>C$_{11}$H$_{13}$ClN$_4$S; MW, 268.77 | 76 ± 2 | 21.0 ± 8.8 | 17.1 ± 2.8 |

TABLE 5-continued

Examples of compounds, structures and ROCK1&2 IC$_{50}$ (μM)

| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| 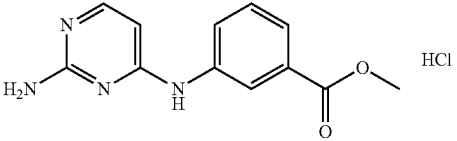<br>(1av)<br>C$_{12}$H$_{13}$ClN$_4$O$_2$; MW, 280.71 | 63 ± 5 | 37.0 ± 8.8 | 39.6 ± 6.2 |
| 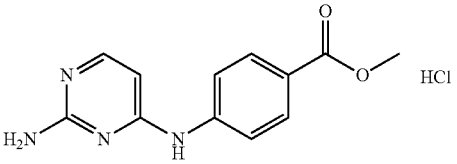<br>(1aw)<br>Chemical Formula: C$_{12}$H$_{13}$ClN$_4$O$_2$; MW, 280.71 | 77 ± 3 | 20.5 ± 8.0 | 13.9 ± 1.7 |
| 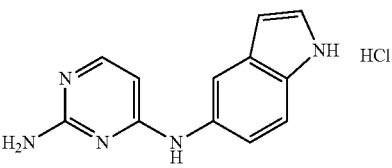<br>(1az)<br>C$_{12}$H$_{12}$ClN$_5$; MW, 261.71 | 37 ± 1 | nd | nd |
| 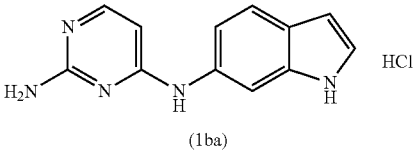<br>(1ba)<br>C$_{12}$H$_{12}$ClN$_5$; MW, 261.71 | 23 ± 1 | nd | nd |
| 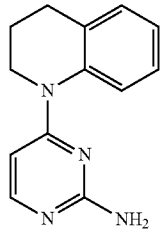<br>(16)<br>C$_{13}$H$_{14}$N$_4$; MW, 226.28 | 69 ± 1 | 19.8 ± 4.3 | 35.3 ± 5.1 |
| 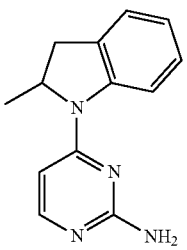<br>(13b)<br>C$_{13}$H$_{14}$N$_4$; MW, 226.28 | 97 ± 1 | 1.7 ± 0.2 | 1.9 ± 0.4 |

TABLE 5-continued
Examples of compounds, structures and ROCK1&2 IC$_{50}$ (μM)
| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| 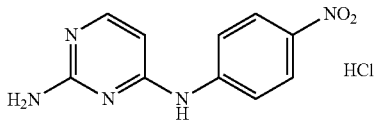<br>(1bb)<br>C$_{10}$H$_{10}$ClN$_5$O$_2$; MW, 267.67 | 89 ± 2 | 3.9 ± 0.3 | 3.7 ± 0.8 |
| 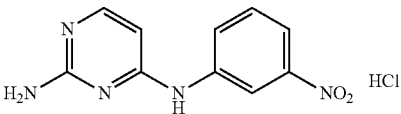<br>(6)<br>C$_{10}$H$_{10}$ClN$_5$O$_2$; MW, 267.67 | 91 ± 2 | 4.86 ± 0.6 | 7.82 ± 2.3 |
| 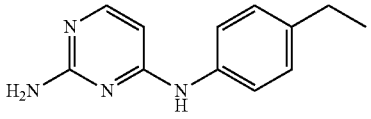<br>(1bd)<br>C$_{12}$H$_{14}$N$_4$; MW, 214.27 | 36 ± 6 | nd | nd |
| 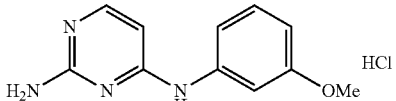<br>(1be)<br>C$_{11}$H$_{13}$ClN$_4$O; MW, 252.70 | 63 ± 5 | 30.2 ± 2.5 | 42.5 ± 6.7 |
| 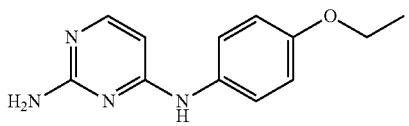<br>(1bf)<br>C$_{12}$H$_{14}$N$_4$O; MW, 230.27 | 31 ± 4 | nd | nd |
| 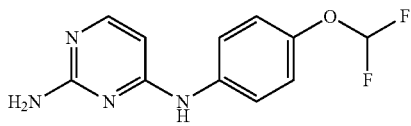<br>(1bg)<br>C$_{11}$H$_{10}$F$_2$N$_4$O; MW, 252.22 | 64 ± 7 | 30.0 ± 3.2 | 23.4 ± 5.5 |

TABLE 5-continued

Examples of compounds, structures and ROCK1&2 IC$_{50}$ (μM)

| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| (13c) C$_{12}$H$_{12}$Cl$_2$N$_4$; MW, 283.16 | 73 ± 3 | 1.5 ± 0.2 | 1.2 ± 0.2 |
| (10a) C$_{10}$H$_9$N$_3$O; MW, 187.20 | −0.5 ± 1 | nd | nd |
| (10b) C$_{10}$H$_{10}$N$_4$O$_3$S; MW, 266.28 | −0.3 ± 1 | nd | nd |
| (10c) C$_{11}$H$_{10}$N$_4$O$_2$; MW, 230.22 | 2 ± 1 | nd | nd |
| (32) C$_{12}$H$_{11}$Cl$_2$N$_3$; MW, 268.14 | −3 ± 1 | nd | nd |
| (18) C$_{11}$H$_9$N$_5$; MW, 211.22 | 50 ± 1 | 38.7 ± 1.6 | 37.4 ± 4.0 |

TABLE 5-continued
Examples of compounds, structures and ROCK1&2 IC$_{50}$ (μM)
| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| 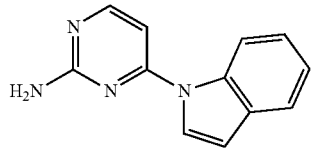<br>(15a)<br>C$_{12}$H$_{10}$N$_4$; MW, 210.23 | 88 ± 4 | 4.8 ± 0.3 | 4.0 ± 0.3 |
| 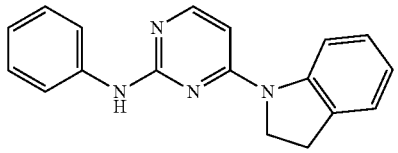<br>(33)<br>C$_{18}$H$_{16}$N$_4$; MW, 288.35 | −1 ± 2 | nd | nd |
| 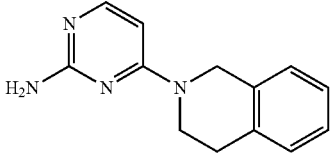<br>(17)<br>C$_{13}$H$_{14}$N$_4$; MW, 226.28 | 6 ± 1 | nd | nd |
| 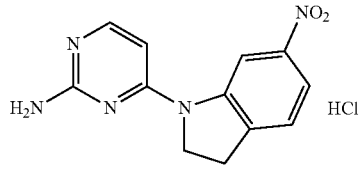<br>(13d)<br>C$_{12}$H$_{12}$ClN$_5$O$_2$; MW, 293.71 | 51 ± 1 | 2.2 ± 0.3 | 1.8 ± 0.3 |
| 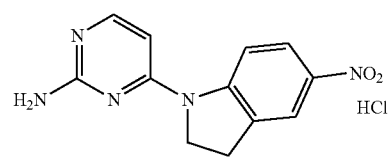<br>(13e)<br>C$_{12}$H$_{12}$ClN$_5$O$_2$; MW, 293.71 | 24 ± 2 | nd | nd |
| 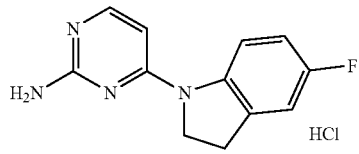<br>(13f)<br>C$_{12}$H$_{12}$ClFN$_4$; MW, 266.70 | 89 ± 7 | 1.2 ± 0.2 | 0.7 ± 0.1 |

TABLE 5-continued

Examples of compounds, structures and ROCK1&2 IC$_{50}$ (μM)

| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| (13g) C$_{13}$H$_{15}$ClN$_4$O$_2$S; MW, 326.80 | 49 ± 4 | 41.0 ± 2.3 | 37.9 ± 2.0 |
| (13h) C$_{18}$H$_{17}$ClN$_4$; MW, 324.81 | 18 ± 1 | nd | nd |
| (13i) C$_{13}$H$_{14}$ClN$_5$O$_2$; MW, 307.74 | 98 ± 2 | 0.5 ± 0.1 | 0.4 ± 0.1 |
| (13j) C$_{12}$H$_{12}$BrClN$_4$; MW, 327.61 | 83 ± 5 | 1.7 ± 0.3 | 1.2 ± 0.1 |
| (13k) C$_{13}$H$_{13}$ClN$_4$O$_2$; MW, 292.72 | 6 ± 0.4 | nd | nd |

TABLE 5-continued
Examples of compounds, structures and ROCK1&2 $IC_{50}$ (μM)
| Compound ID, Structure, formula and MW | ROCK1 % inhibition @ 50 μM otherwise specified | ROCK1 $IC_{50}$ (μM) | ROCK2 $IC_{50}$ (μM) |
|---|---|---|---|
| 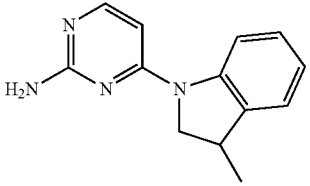<br>(13l)<br>$C_{13}H_{15}ClN_4$; MW, 262.74 | 93 ± 2 | 4.8 ± 0.5 | 2.6 ± 0.1 |
| 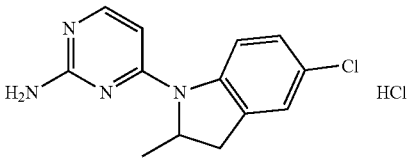<br>(13m)<br>$C_{13}H_{14}Cl_2N_4$; MW, 297.18 | 87 ± 10 | 1.2 ± 0.1 | 0.5 ± 0.03 |
| 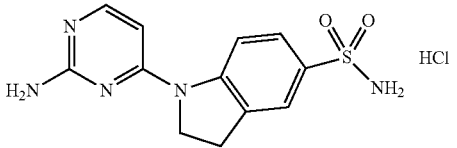<br>(13n)<br>$C_{12}H_{14}ClN_5O_2S$; MW, 327.79 | 73 ± 4 | 25.8 ± 2.6 | 10.3 ± 0.9 |
| 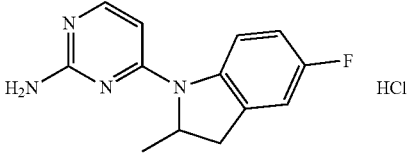<br>(13o)<br>$C_{13}H_{14}ClFN_4$; MW, 280.73 | 97 ± 4 | 0.4 ± 0.1 | 0.2 ± 0.01 |
| 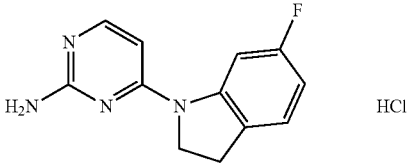<br>(13p)<br>$C_{12}H_{12}ClFN_4$; MW, 266.70 | 89 ± 4 | 3.7 ± 0.4 | 1.34 ± 0.09 |
| 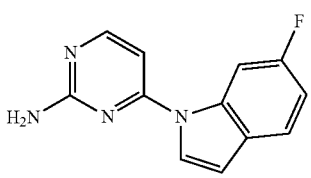<br>(15b)<br>$C_{12}H_9FN_4$; MW, 228.23 | 86 ± 5 | 4.9 ± 0.5 | 1.7 ± 0.1 |

TABLE 5-continued
Examples of compounds, structures and ROCK1&2 IC$_{50}$ (μM)
| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| 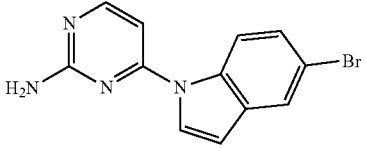<br>(15c)<br>C$_{12}$H$_9$BrN$_4$; MW, 289.13 | 89 ± 1 | 2.1 ± 0.3 | 1.7 ± 0.3 |
| 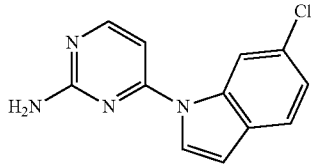<br>(15d)<br>C$_{12}$H$_9$ClN$_4$; MW, 244.68 | 88 ± 0.3 | 1.2 ± 0.2 | 1.0 ± 0.3 |
| 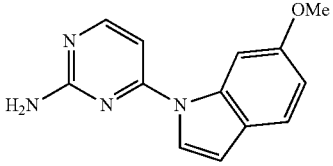<br>(15e)<br>C$_{13}$H$_{12}$N$_4$O; MW, 240.26 | 88 ± 2 | 4.9 ± 0.5 | 4.9 ± 1.0 |
| 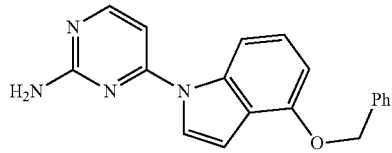<br>(21a)<br>C$_{19}$H$_{16}$N$_4$O; MW, 316.36 | 80 ± 3 | 0.8 ± 0.5 | 0.4 ± 0.1 |
| 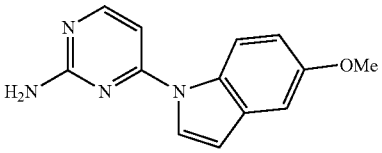<br>(15f)<br>C$_{13}$H$_{12}$N$_4$O; MW, 240.26 | 96 ± 3 | 0.4 ± 0.1 | 0.25 ± 0.13 |
| 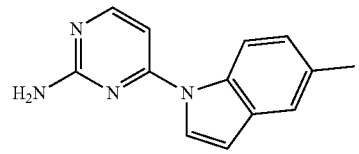<br>(15g)<br>C$_{13}$H$_{12}$N$_4$; MW, 224.26 | 82 ± 5 | 8.3 ± 0.9 | 7.1 ± 2.1 |

TABLE 5-continued
Examples of compounds, structures and ROCK1&2 IC$_{50}$ (μM)
| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| 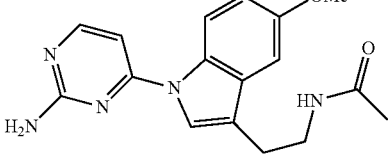<br>(15h)<br>C$_{17}$H$_{19}$N$_5$O$_2$; MW, 325.37 | 89 ± 1 | 4.9 ± 0.8 | 5.3 ± 1.2 |
| 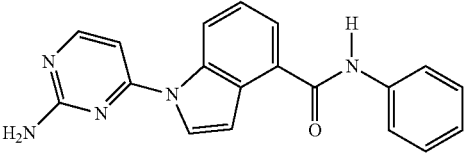<br>(24a)<br>C$_{19}$H$_{15}$N$_5$O; MW, 329.36 | 9 ± 1 | nd | nd |
| 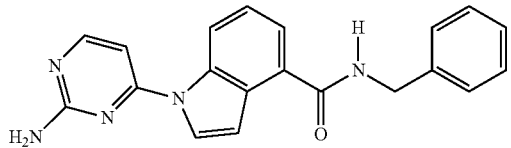<br>(24b)<br>C$_{20}$H$_{17}$N$_5$O; MW, 343.38 | 92 ± 1 | 1.0 ± 0.5 | 0.2 ± 0.1 |
| 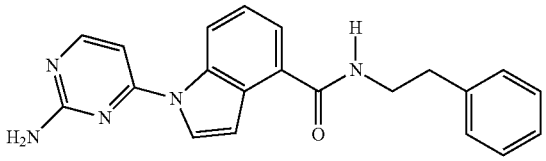<br>(24c)<br>C$_{21}$H$_{19}$N$_5$O; MW, 357.41 | 91 ± 1 | 2.0 ± 0.5 | 0.5 ± 0.1 |
| 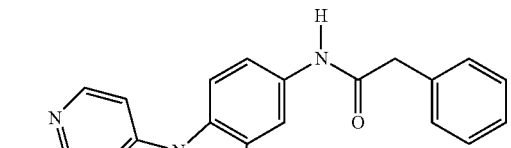<br>(27a)<br>C$_{20}$H$_{17}$N$_5$O; MW, 343.38 | 53 ± 1 | 20.8 ± 6.3 | 5.8 ± 1.4 |
| 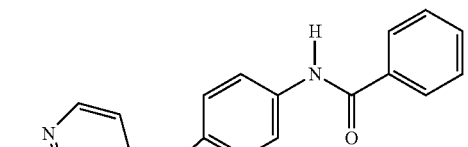<br>(27b)<br>C$_{19}$H$_{15}$N$_5$O; MW, 329.36 | 8 ± 3 | nd | nd |

TABLE 5-continued
Examples of compounds, structures and ROCK1&2 IC$_{50}$ (μM)
| Compound ID, Structure, formula and MW | ROCK1 % inhibition @ 50 μM otherwise specified | ROCK1 IC$_{50}$ (μM) | ROCK2 IC$_{50}$ (μM) |
| --- | --- | --- | --- |
| 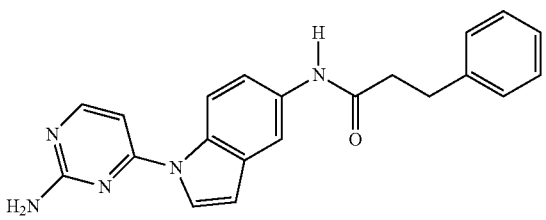<br>(27c)<br>C$_{21}$H$_{19}$N$_5$O; MW, 357.41 | 60 ± 2 | 54.1 ± 1.1 | 8.4 ± 2.0 |
| 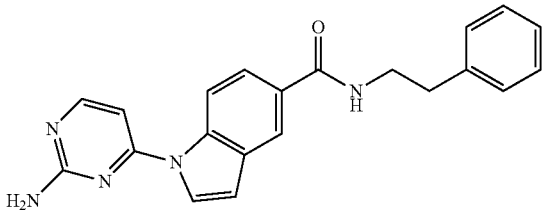<br>(24d)<br>C$_{21}$H$_{19}$N$_5$O; MW, 357.41 | 96 ± 1 | 2.8 ± 0.3 | 0.7 ± 0.3 |
| 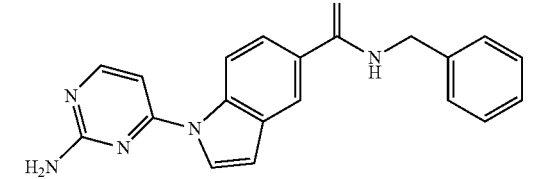<br>(24e)<br>C$_{20}$H$_{17}$N$_5$O; MW, 343.38 | 96 ± 1 | 2.4 ± 1.6 | 0.3 ± 0.1 |
| 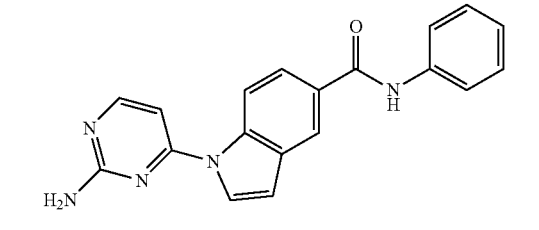<br>(24f)<br>C$_{19}$H$_{15}$N$_5$O; MW, 329.36 | 17 ± 2 | nd | nd |
| 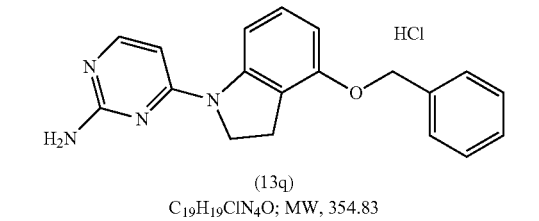 [SMILES: Nc1nccc(N2CCc3c(OCc4ccccc4)cccc32)n1 ; Cl]<br>(13q)<br>C$_{19}$H$_{19}$ClN$_4$O; MW, 354.83 | 90 ± 1 | 0.48 ± 0.099 | 0.25 ± 0.07 |

TABLE 5-continued

Examples of compounds, structures and ROCK1&2 IC$_{50}$ (μM)

| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| (21b) C$_{19}$H$_{16}$N$_4$O; MW, 316.36 | 76 ± 2 | 39.0 ± 6.9 | 16.3 ± 5.5 |
| (21c) C$_{20}$H$_{18}$N$_4$O; MW, 330.38 | 63 ± 5 | 53.6 ± 4.1 | 17.0 ± 1.7 |
| (1ah) | 22 ± 4 | nd | nd |
| (21d) C$_{19}$H$_{14}$ClFN$_4$O; MW, 368.79 | 10 ± 2 | nd | nd |
| (21e) C$_{19}$H$_{15}$ClN$_4$O; MW, 350.80 | 71 ± 2 | 1.90 ± 0.42 | 0.46 ± 0.08 |

TABLE 5-continued
Examples of compounds, structures and ROCK1&2 IC$_{50}$ (μM)
| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| 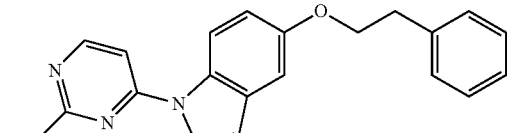<br>(21f)<br>C$_{20}$H$_{18}$N$_4$O; MW, 330.38 | 21 ± 14 | nd | nd |
| 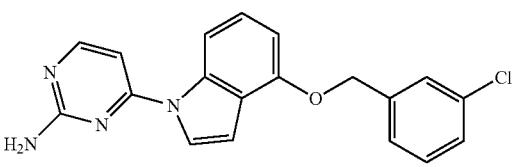<br>(21g)<br>C$_{19}$H$_{15}$ClN$_4$O; MW, 350.80 | 44 ± 9 | 34.6 ± 8.2 | 32.7 ± 8.1 |
| 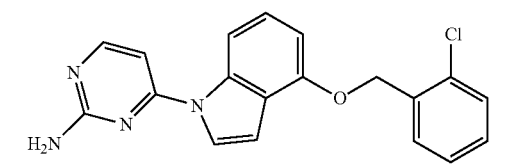<br>(21h)<br>C$_{19}$H$_{15}$ClN$_4$O; MW, 350.80 | 62 ± 6 | 29.1 ± 8.2 | 19.0 ± 5.9 |
| 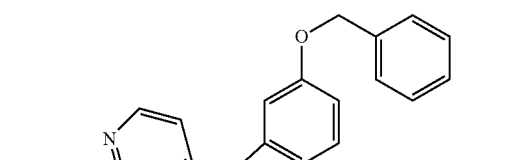<br>(21i)<br>C$_{19}$H$_{16}$N$_4$O; MW, 316.36 | −5 ± 2 | nd | nd |
| 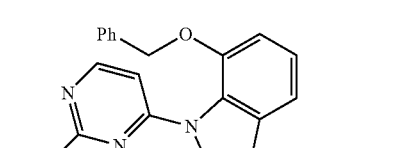<br>(21j)<br>C$_{19}$H$_{16}$N$_4$O; MW, 316.36 | −5 ± 0.5 | nd | nd |
| 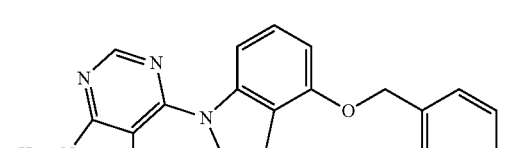<br>(35)<br>C$_{21}$H$_{18}$N$_4$O; MW, 342.39 | 33 ± 4 | nd | nd |

TABLE 5-continued
Examples of compounds, structures and ROCK1&2 IC$_{50}$ (μM)
| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| 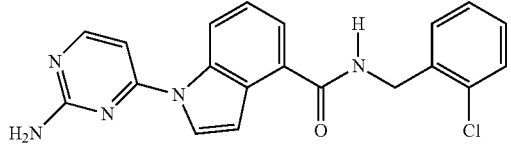<br>(30a)<br>C$_{20}$H$_{16}$ClN$_5$O; MW, 377.83 | 39.22 ± 4.19 | nd | nd |
| 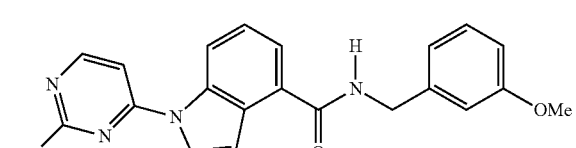<br>(30b)<br>C$_{21}$H$_{19}$N$_5$O$_2$; MW, 373.41 | 93 ± 7 | 0.15 ± 0.02 | 0.04 ± 0.03 |
| 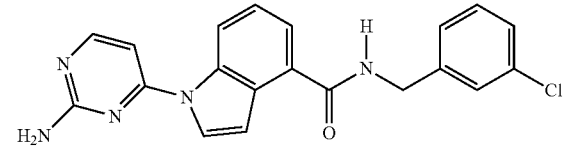<br>(30c)<br>C$_{20}$H$_{16}$ClN$_5$O; MW, 377.83 | 86 ± 4 | 6.8 ± 3.0 | 0.72 ± 0.13 |
| 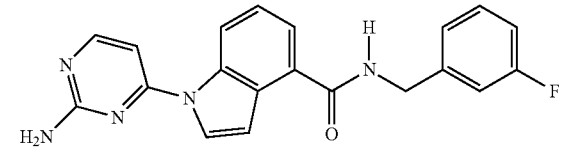<br>(30d)<br>C$_{20}$H$_{16}$FN$_5$O; MW, 361.37 | 72 ± 10 | 2.7 ± 1.78 | 0.26 ± 0.09 |
| 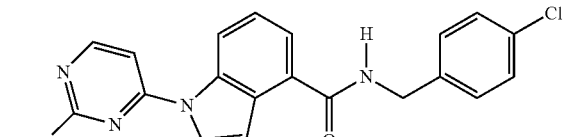<br>(30e)<br>C$_{20}$H$_{16}$ClN$_5$O MW = 377.8269 | 31 ± 10 | nd | nd |
| 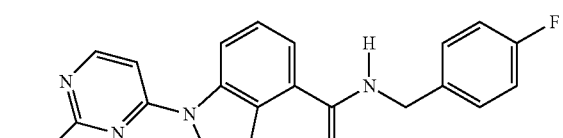<br>(=30f)<br>C$_{20}$H$_{16}$FN$_5$O; MW, 361.37 | 70 ± 3 | 10.5 ± 1.0 | 1.10 ± 0.49 |

TABLE 5-continued

Examples of compounds, structures and ROCK1&2 IC$_{50}$ (μM)

| Compound ID, Structure, formula and MW | ROCK1 % inhibition @ 50 μM otherwise specified | ROCK1 IC$_{50}$ (μM) | ROCK2 IC$_{50}$ (μM) |
| --- | --- | --- | --- |
| (30g) C$_{21}$H$_{19}$N$_5$O; MW, 357.41 | 85 ± 6 | 1.7 ± 0.5 | 0.21 ± 0.15 |
| (30h) C$_{21}$H$_{19}$N$_5$O; MW, 357.41 | 105 ± 1 | 0.12 ± 0.02 | 0.06 ± 0.02 |
| (30i) C$_{21}$H$_{19}$N$_5$O$_2$; MW, 373.41 | 69 ± 3 | 6.0 ± 2.0 | 1.80 ± 0.68 |
| (30j) C$_{21}$H$_{19}$N$_5$O; MW, 357.41 | 102.2 ± 0.2 | 3.43 ± 0.44 | 1.20 ± 0.32 |
| (30k) C$_{20}$H$_{16}$FN$_5$O; MW 361.1339 | 88.71 ± 5.96 | 5.67 ± 0.32 | 0.92 ± 0.48 |
| (30l) C$_{21}$H$_{19}$N$_5$O$_2$; MW 373.1539 | 19.44 ± 13.73 | nd | nd |

TABLE 5-continued

Examples of compounds, structures and ROCK1&2 IC$_{50}$ (μM)

| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| (27d) C$_{21}$H$_{19}$N$_5$O$_2$; MW, 373.41 | ROCK1 % inhibition @ 100 μM 62 ± 12 | 13.03 ± 6.81 | nd |
| (30m) C$_{21}$H$_{20}$N$_6$O$_3$S; MW, 436.49 | ROCK1 % inhibition @ 100 μM 100 ± 8 | 3.26 ± 0.57 | nd |
| (30n) C$_{22}$H$_{20}$N$_6$O$_2$; MW, 400.43 | ROCK1 % inhibition @ 100 μM 117 ± 3 | 1.39 ± 0.26 | nd |
| (30o) C$_{22}$H$_{21}$N$_5$O; MW, 371.44 | ROCK1 % inhibition @ 100 μM 122 ± 1 | 1.77 ± 0.24 | nd |
| (30p) C$_{22}$H$_{21}$N$_5$O$_2$; MW, 387.43 | ROCK1 % inhibition @ 100 μM 91 ± 9 | 15.43 ± 6.04 | nd |
| (30q) C$_{22}$H$_{21}$N$_5$O$_2$; MW, 387.43 | ROCK1 % inhibition @ 100 μM 89 ± 6 | 15.25 ± 3.74 | nd |

TABLE 5-continued

Examples of compounds, structures and ROCK1&2 IC$_{50}$ (μM)

| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| 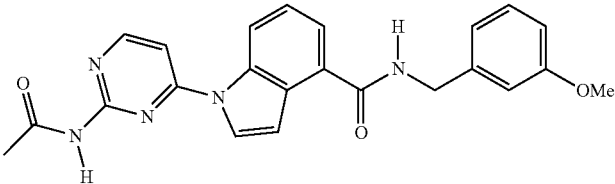<br>(36)<br>C$_{23}$H$_{21}$N$_5$O$_3$; MW, 415.44 | ROCK1 % inhibition @ 100 μM 80 ± 0.5 | 15.42 ± 4.02 | nd |
| 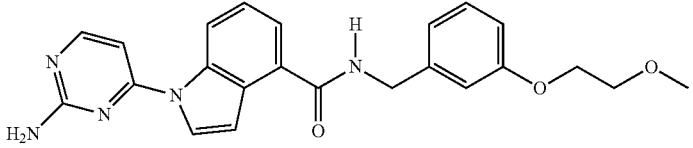<br>(30r)<br>C$_{23}$H$_{23}$N$_5$O$_3$; MW, 417.46 | ROCK1 % inhibition @ 100 μM 86 ± 10 | 9.31 ± 8.68 | nd |
| 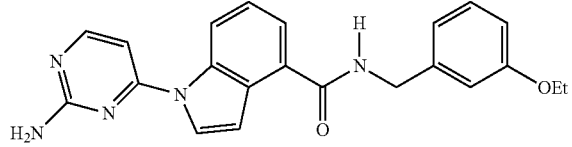<br>(3s)<br>C$_{22}$H$_{21}$N$_5$O$_2$; MW, 387.43 | ROCK1 % inhibition @ 100 μM 61 ± 1.2 | 3.37 ± 0.53 | nd |
| 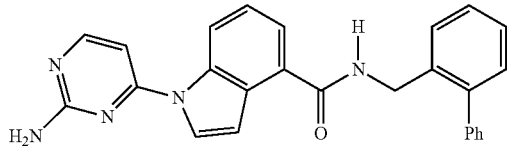<br>(30t)<br>C$_{26}$H$_{21}$N$_5$O; MW, 419.48 | ROCK1 % inhibition @ 100 μM 7 ± 1.1 | nd | nd |
| 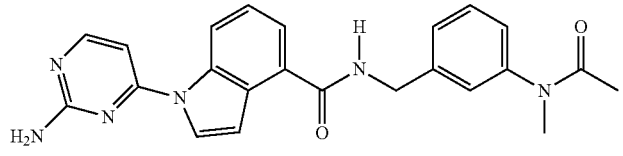<br>(30u)<br>C$_{23}$H$_{22}$N$_6$O$_2$; MW, 414.46 | ROCK1 % inhibition @ 100 μM 47 ± 1 | 40.33 ± 11.03 | nd |
| 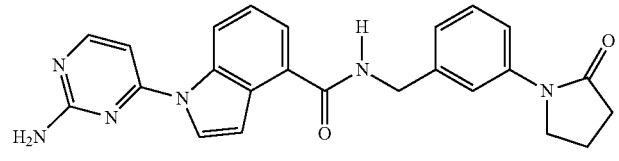<br>(30v)<br>C$_{24}$H$_{22}$N$_6$O$_2$; MW, 426.47 | ROCK1 % inhibition @ 100 μM 99 ± 7 | 8.31 ± 7.39 | nd |

TABLE 5-continued

Examples of compounds, structures and ROCK1&2 IC$_{50}$ (μM)

| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
| 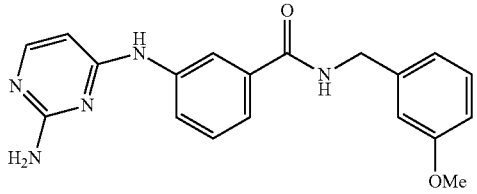<br>(46)<br>C$_{19}$H$_{20}$ClN$_5$O$_2$; MW: 385.8474 | ROCK1 % inhibition @ 100 μM<br>97 ± 6 | 7.30 ± 1.29 | nd |
| 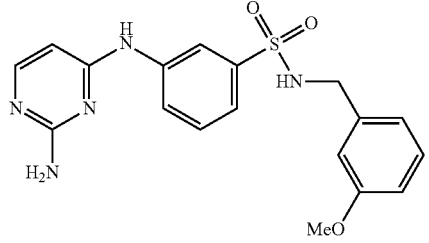<br>(47)<br>C$_{18}$H$_{19}$N$_5$O$_3$S MW: 385.4402 | ROCK1 % inhibition @ 100 μM<br>70 ± 4 | 33.38 ± 8.52 | nd |
| 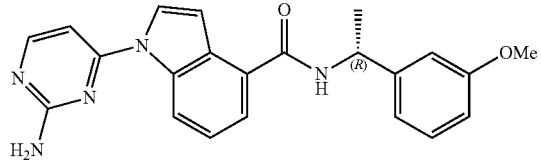<br>(=30w)<br>C$_{22}$H$_{21}$N$_5$O$_2$; MW 387.4344 | ROCK1 % inhibition @ 100 μM<br>92 ± 1.3 | 0.213 ± 0.025 | nd |
| 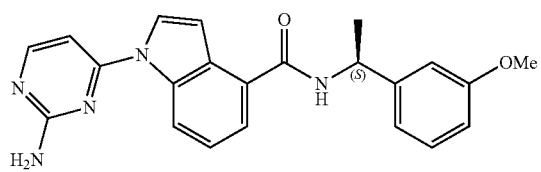<br>(30z)<br>C$_{22}$H$_{21}$N$_5$O$_2$ MW 387.4344 | ROCK1 % inhibition @ 100 μM<br>97 ± 1 | 1.38 ± 0.63 | nd |
| 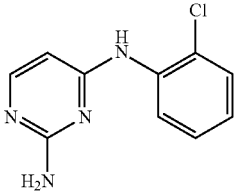<br>(ibi)<br>C$_{10}$H$_9$ClN$_4$ MW: 220.6583 | ROCK1 % inhibition @ 100 μM<br>39 ± 1.5 | nd | nd |

TABLE 5-continued

Examples of compounds, structures and ROCK1&2 IC$_{50}$ (μM)

| Compound ID, Structure, formula and MW | ROCK1 % inhibition @ 50 μM otherwise specified | ROCK1 IC$_{50}$ (μM) | ROCK2 IC$_{50}$ (μM) |
|---|---|---|---|
|  (ibj) C$_{10}$H$_9$ClN$_4$ MW: 220.6583 | ROCK1 % inhibition @ 100 μM 89 ± 9 | 5.71 ± 1.44 | nd |
| 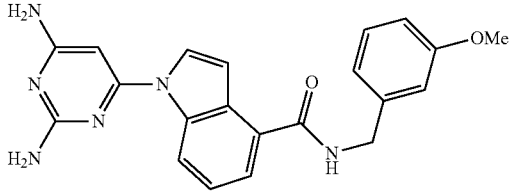 (38) Molecular Weight: 388.4225 | 1.26 ± 0.79 | nd | nd |
| 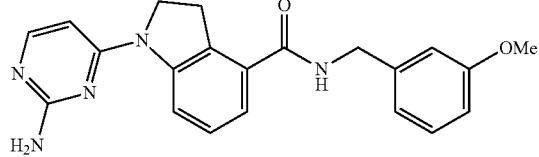 (=13r) Molecular Weight: 375.4237 | 92.75 ± 3.64 | 1.62 ± 0.86 | 0.25 ± 0.02 |
| 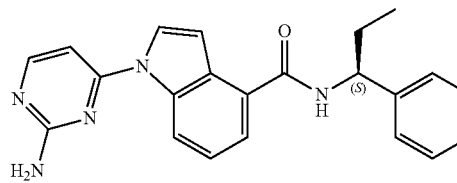 (30aa) C$_{22}$H$_{21}$N$_5$O MW 371.4350 | ROCK1 % inhibition @ 100 μM 88 ± 1.4 | 9.76 ± 0.86'' | nd |

EXPERIMENTAL PART

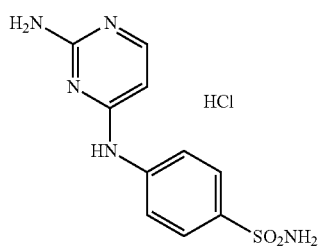 [SMILES: Nc1nccc(Nc2ccc(S(N)(=O)=O)cc2)n1 ; Cl]

4-(2-Aminopyrimidin-4-ylamino)benzenesulfonamide hydrochloride 1aa. A mixture of 2-amino-4-chloropyrimidine (0.078 g, 0.602 mmol), 4-aminobenzenesulfonamide (0.103 g, 0.602 mmol) in anhydrous ethanol (0.6 ml) was stirred in a Biotage microwave reactor for 10 min at 120° C. After cooling to room temperature, the solid precipitate was filtered and dried under vacuum to afford 1aa (0.137 g, 0.516 mmol, 86%) as an off-white solid. $^1$H NMR (400 MHz, CD$_3$OD) δ 7.97 (d, J=9.0 Hz, 2H), 7.90 (d, J=8.9 Hz, 2H), 7.79 (d, J=7.2 Hz, 1H), 6.36 (d, J=7.2 Hz, 1H). HRMS (ESI+ve) calculated for C$_{10}$H$_{12}$N$_4$O$_2$S (M+H—Cl)$^+$ 266.0706, found 266.0703.

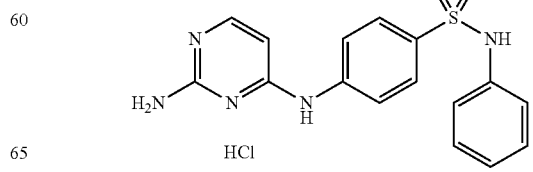

4-(2-Aminopyrimidin-4-ylamino)-N-phenylbenzenesulfonamide hydrochloride (1al). This was prepared from 2-amino-4-chloropyrimidine (0.072 g, 0.556 mmol), and 4-amino-N-phenylbenzenesulfonamide (0.138 g, 0.556 mmol) in a similar manner as described for 1aa. After cooling to room temperature, the solid precipitate was filtered and dried under vacuum to afford 1al (0.071 g, 0.207 mmol, 37%) as an off-white solid. $^1$H NMR (400 MHz, DMSO-$d_6$) δ 12.45 (s, 1H), 11.08 (s, 1H), 10.28 (s, 1H), 7.97 (d, J=8.7 Hz, 2H), 7.89 (d, J=7.1 Hz, 1H), 7.70 (d, J=8.8 Hz, 2H), 7.21 (t, J=7.9 Hz, 2H), 7.08 (d, J=8.3 Hz, 2H), 7.00 (t, J=7.9 Hz, 1H), 6.41 (d, J=7.1 Hz, 1H). HRMS (ESI+ve) calculated for $C_{16}H_{17}N_5O_2S$ (M+H—Cl)$^+$ 342.1019, found 342.1039.

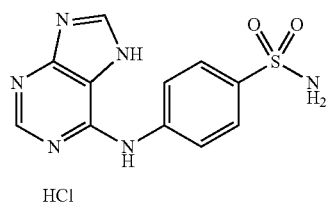 [SMILES: NS(=O)(=O)c1ccc(Nc2ncnc3nc[nH]c23)cc1 ; Cl]

HCl 4-(7H-Purin-6-ylamino)benzenesulfonamide hydrochloride (8). A mixture of 6-chloro-7H-purine (0.286 g, 1.66 mmol), and 4-aminobenzenesulfonamide (0.257 g, 1.66 mmol) was stirred in a Biotage microwave reactor for 20 min at 120° C. and 10 min at 160° C. After cooling to room temperature, the solid precipitate was filtered, washed with methanol, ether, further triturated with methanol, filtered and dried under vacuum. Pure 8 (0.434 g, 1.33 mmol, 80%) was obtained as a green solid. $^1$H NMR (400 MHz, CD$_3$OD) δ 8.71 (s, 1H), 8.59 (s, 1H), 7.99 (s, 4H). HRMS (ESI+ve) calculated for $C_{11}H_{11}N_6O_2S$ (M+H—Cl)$^+$ 291.0658, found 291.0659.

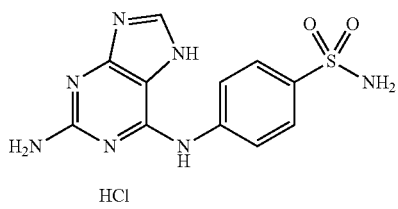 [SMILES: Nc1nc(Nc2ccc(S(N)(=O)=O)cc2)c2[nH]cnc2n1 ; Cl]

HCl 4-(2-amino-7H-purin-6-ylamino)benzenesulfonamide hydrochloride (7). A mixture of 6-chloro-7H-purin-2-amine (0.143 g, 0.8444 mmol), and 4-aminobenzenesulfonamide (0.145 g, 0.843 mmol) was stirred in a Biotage microwave reactor for 20 min at 120° C. and 20 min at 160° C. After cooling to room temperature, the solid precipitate was filtered, washed with methanol, ether, further and dried under vacuum. Pure 7 (0.186 g, 0.609 mmol, 72%) was obtained as an off white solid. $^1$H NMR (400 MHz, DMSO-$d_6$) δ 8.30 (s, 1H), 8.12 (d, J=8.4 Hz, 2H), 8.08 (s, 1H), 7.79 (d, J=8.4 Hz, 2H), 7.31 (s, 2H), 6.73 (s, 2H). HRMS (ESI+ve) calculated for $C_{11}H_{12}N_7O_2S$ (M+H—Cl)$^+$ 306.0767, found 306.0779.

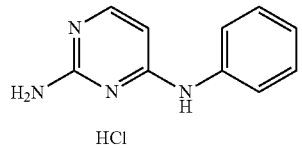 [SMILES: Nc1nccc(Nc2ccccc2)n1 ; Cl]

HCl

N$^4$-phenylpyrimidine-2,4-diamine hydrochloride (1af). This was prepared from 2-amino-4-chloropyrimidine (0.084 g, 0.648 mmol), aniline (0.060 g, 0.648 mmol) in a similar manner as described for 1aa. After cooling to room temperature, the solvent was removed under reduced pressure. The remaining solid was solid triturated with ethyl acetate, filtered and dried under vacuum to afford 1af (0.136 g, 0.610 mmol, 94%) as an off-white solid. $^1$H NMR (400 MHz, CD$_3$OD) δ 7.71-7.69 (m, 3H), 7.39 (t, J=7.8 Hz, 2H), 7.20 (t, J=7.3 Hz, 1H), 6.30 (d, J=7.3 Hz, 1H). HRMS (ESI+ve) calculated for $C_{10}H_{11}N_4$ (M+H—Cl)$^+$ 187.0978, found 187.0979.

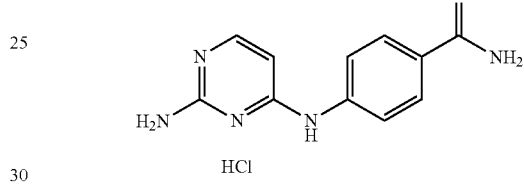

HCl 4-(2-aminopyrimidin-4-ylamino)benzamide hydrochloride (1ah). This was prepared from 2-amino-4-chloropyrimidine (0.096 g, 0.741 mmol), 4-aminobenzamide (0.100 g, 0.741 mmol) in a similar manner as described for 1aa. After cooling to room temperature, the solvent was removed under reduced pressure. The remaining solid was solid triturated with ethyl acetate, filtered and dried under vacuum to afford 1ah (0.161 g, 0.606 mmol, 82%) as a yellow solid. $^1$H NMR (400 MHz, DMSO-$d_6$) δ 12.30 (s, 1H), 10.90 (s, 1H), 7.95-7.85 (m, 6H), 7.33 (s, 1H), 6.39 (d, J=6.6 Hz, 1H). HRMS (ESI+ve) calculated for $C_{11}H_{12}N_5O$ (M+H—Cl)$^+$ 230.1036, found 230.1041.

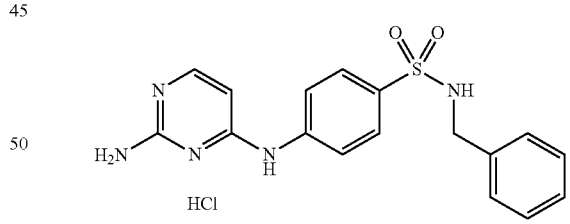

HCl 4-(2-aminopyrimidin-4-ylamino)-N-benzylbenzenesulfonamide hydrochloride (1ak). This was prepared from 2-amino-4-chloropyrimidine (0.076 g, 0.586 mmol), and 4-amino-N-benzylbenzenesulfonamide (0.153 g, 0.586 mmol) in a similar manner as described for 1aa. After cooling to room temperature, the solvent was removed under reduced pressure and the remaining solid was triturated with DCM, filtered and dried under vacuum. Pure 1ak (0.203 g, 0.518 mmol, 88%) was obtained as an off-white solid. $^1$H NMR (400 MHz, CD$_3$OD) δ 7.96 (d, J=8.5 Hz, 2H), 7.83-7.89 (m, 3H), 7.25-7.17 (m, 5H), 6.37 (dd, J=7.3, 1.2 Hz, 1H), 4.07 (s, 2H). HRMS (ESI+ve) calculated for $C_{17}H_{18}N_5O_2S$ (M+H—Cl)$^+$ 356.1175, found 356.1188.

3-(2-aminopyrimidin-4-ylamino)benzenesulfonamide hydrochloride (1ag). This was prepared from 2-amino-4-chloropyrimidine (0.077 g, 0.594 mmol), and 3-aminobenzenesulfonamide (0.102 g, 0.594 mmol) in a similar manner as described for 1aa. After cooling to room temperature, the solid precipitate was filtered, washed with methanol and dried under vacuum. Pure 1ag (0.159 g, 0.527 mmol, 89%) was obtained as an off-white solid. $^1$H NMR (400 MHz, CD$_3$OD) δ 8.41 (s, 1H), 7.88 (d, J=6.2 Hz, 1H), 7.77 (d, J=7.2 Hz, 1H), 7.72 (d, J=7.8 Hz, 1H), 7.57 (t, J=8.0 Hz, 1H), 6.35 (d, J=7.3 Hz, 1H). HRMS (ESI+ve) calculated for C$_{10}$H$_{12}$N$_5$O$_2$S (M+H—Cl)$^+$ 266.0706, found 266.0718.

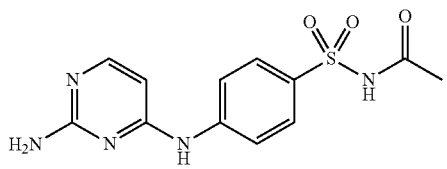

N-(4-(2-aminopyrimidin-4-ylamino)phenylsulfonyl)acetamide (1ai). This was prepared from 2-amino-4-chloropyrimidine (0.076 g, 0.586 mmol), and N-(4-aminophenylsulfonyl)acetamide (0.125 g, 0.586 mmol) in a similar manner as described for 1aa. After cooling to room temperature, DIPEA (0.2 ml) was added and the solvent was removed under reduced pressure. The remaining solid was triturated with water, filtered, washed with acetonitrile, and dried under vacuum. Pure 1ai (0.137 g, 0.445 mmol, 76%) was obtained as a yellow solid. $^1$H NMR (400 MHz, CD$_3$OD) δ 7.93 (d, J=9.0 Hz, 2H), 7.89 (d, J=9.2 Hz, 2H), 7.82 (d, J=7.5 Hz, 1H), 6.16 (d, J=6.2 Hz, 1H), 1.93 (s, 3H). HRMS (ESI+ve) calculated for C$_{12}$H$_{14}$N$_5$O$_3$S (M+H)$^+$ 308.0811, found 308.0818.

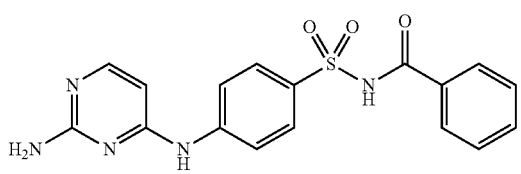 [SMILES: Nc1nccc(Nc2ccc(S(=O)(=O)NC(=O)c3ccccc3)cc2)n1]

N-(4-(2-aminopyrimidin-4-ylamino)phenylsulfonyl)benzamide (1aj). This was prepared from 2-amino-4-chloropyrimidine (0.082 g, 0.632 mmol), and N-(4-aminophenylsulfonyl)benzamide (0.174 g, 0.632 mmol) in a similar manner as described for 1aa. After cooling to room temperature, DIPEA (0.5 ml) was added and the solvent was removed under reduced pressure. The remaining solid was triturated with water, filtered, washed with acetonitrile, and dried under vacuum. Pure 1aj (0.145 g, 0.392 mmol, 62%) was obtained as a yellow solid. $^1$H NMR (400 MHz, DMSO-d$_6$) δ 10.07 (s, 1H), 7.85-7.81 (m, 7H), 7.46 (t, J=7.3 Hz, 1H), 7.36 (t, J=7.5 Hz, 2H), 7.14 (s, 2H), 6.16 (d, J=6.4 Hz, 1H). HRMS (ESI+ve) calculated for C$_{17}$H$_{16}$N$_5$O$_3$S (M+H)$^+$ 370.0968, found 370.0979.

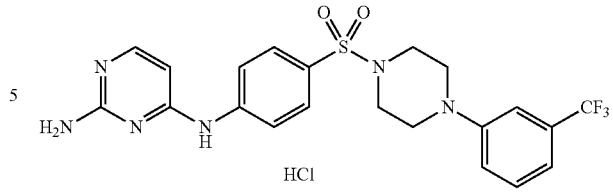

N-(4-(4-(3-(trifluoromethyl)phenyl)piperazin-1-ylsulfonyl)phenyl)pyrimidine-2,4-diamine hydrochloride (1ae). A mixture of 2-amino-4-chloropyrimidine (0.031 g, 0.241 mmol), 4-(4-(3-(trifluoromethyl)phenyl)piperazin-1-ylsulfonyl)aniline (0.093 g, 0.241 mmol) in anhydrous ethanol (0.4 ml) was stirred in a Biotage microwave reactor for 20 min at 150° C. After cooling to room temperature, the solid precipitate was filtered, washed with Et$_2$O, and dried under vacuum to afford 1ae (0.050 g, 0.104 mmol, 43%) as a white solid. $^1$H NMR (400 MHz, DMSO-d$_6$) δ 11.06 (s, 1H), 8.08 (d, J=8.5 Hz, 1H), 7.91 (d, J=7.0 Hz, 1H), 7.73 (d, J=8.7 Hz, 1H), 7.39 (t, J=8.1 Hz, 1H), 7.18-7.13 (m, 2H), 7.08 (d, J=7.3 Hz, 1H), 6.41 (d, J=7.1 Hz, 1H), 3.00 (s, 4H). HRMS (ESI+ve) calculated for C$_{21}$H$_{22}$N$_6$F$_3$O$_2$S (M+H—Cl)$^+$ 479.1471, found 479.1474.

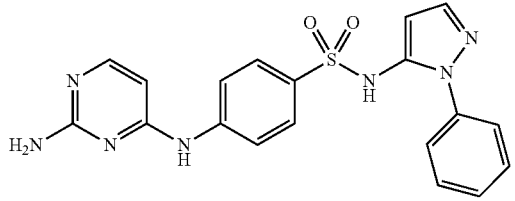 [SMILES: Nc1nccc(Nc2ccc(S(=O)(=O)Nc3ccnn3-c3ccccc3)cc2)n1]

4-(2-aminopyrimidin-4-ylamino)-N-(1-phenyl-1H-pyrazol-5-yl)benzenesulfonamide (1ab). This was prepared from 2-amino-4-chloropyrimidine (0.093 g, 0.717 mmol), and 44-amino-N-(1-phenyl-1H-pyrazol-5-yl)benzenesulfonamide (0.255 g, 0.717 mmol) in a similar manner as described for 1ae. After cooling to room temperature, the solvent was removed under reduced pressure. The crude material was redissolved in MeOH, followed by the addition of DIPEA (0.3 ml). The solvent was removed under reduced pressure. The obtained solid was slurried with water, filtered, washed with acetone, ether, dried under vacuum, dried under vacuum. Pure 1ab was obtained as a white solid (0.093 g, 0.228 mmol, 31%). $^1$H NMR (400 MHz, CD$_3$OD) δ 7.91 (d, J=8.6 Hz, 2H), 7.83-7.79 (m, 1H), 7.64 (d, J=8.7 Hz, 2H), 7.57 (dd, J=1.9, 0.6 Hz, 1H), 7.40 (dd, J=8.0, 3.1 Hz, 3H), 7.29-7.22 (m, 2H), 6.43-6.34 (m, 1H), 6.13 (dd, J=1.9, 0.6 Hz, 1H). HRMS (ESI+ve) calculated for C$_{19}$H$_{18}$N$_7$O$_2$S (M+H)$^+$ 408.1237, found 408.1246.

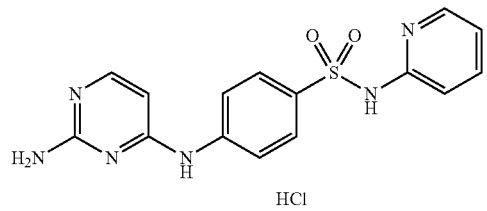 [SMILES: Nc1nccc(Nc2ccc(S(=O)(=O)Nc3ccccn3)cc2)n1 ; Cl]

4-(2-aminopyrimidin-4-ylamino)-N-(pyridin-2-yl)benzenesulfonamide hydrochloride (1ad). This was obtained as a white solid (0.052 g, 0.155 mmol, 20%) from 2-amino-4-chloropyrimidine (0.095 g, 0.733 mmol), and 4-amino-N-(pyridin-2-yl)benzenesulfonamide (0.183 g, 0.733 mmol) in a similar manner as described for 1ae. $^1$H NMR (400 MHz, CD$_3$OD) δ 7.97-7.93 (m, 5H), 7.77 (d, J=7.2 Hz, 1H), 7.71-7.69 (m, 1H), 7.24 (d, J=8.7 Hz, 1H), 6.90-6.87 (m, 1H), 6.35 (d, J=7.3 Hz, 1H), HRMS (ESI+ve) calculated for C$_{15}$H$_{15}$N$_6$O$_2$S (M+H—Cl)$^+$ 343.0971, found 343.0974.

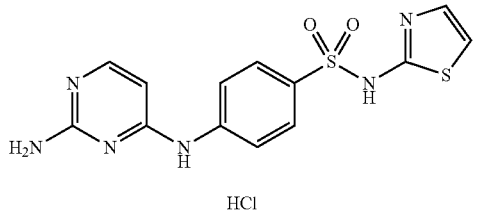 [SMILES: Nc1nccc(Nc2ccc(S(=O)(=O)Nc3nccs3)cc2)n1 ; Cl]

4-(2-aminopyrimidin-4-ylamino)-N-(thiazol-2-yl)benzenesulfonamide hydrochloride (1ac). This was obtained as a white solid (0.208 g, 0.540 mmol, 67%) from 2-amino-4-chloropyrimidine (0.105 g, 0.810 mmol), and 4-amino-N-(thiazol-2-yl)benzenesulfonamide (0.206 g, 0.810 mmol) in a similar manner as described for 1ae. $^1$H NMR (400 MHz, CD$_3$OD) δ 7.94-7.87 (m, 4H), 7.78 (d, J=7.2 Hz, 1H), 7.10 (d, J=4.7 Hz, 1H), 6.73 (d, J=4.7 Hz, 1H), 6.35 (d, J=7.3 Hz, 1H). HRMS (ESI+ve) calculated for C$_{13}$H$_{13}$N$_6$O$_2$S$_2$ (M+H—Cl)$^+$ 349.0535, found 349.0542.

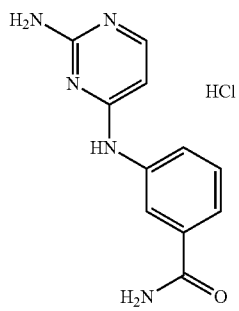 [SMILES: NC(=O)c1cccc(Nc2ccnc(N)n2)c1 ; Cl]

3-(2-aminopyrimidin-4-ylamino)benzamide hydrochloride (1am. A mixture of 2-amino-4-chloropyrimidine (0.099 g, 0.764 mmol), 3-aminobenzamide (0.104 g, 0.764 mmol) in anhydrous ethanol (0.8 ml) was stirred in a Biotage microwave reactor for 15 min at 120° C. After cooling to room temperature, the solid precipitate was filtered, washed with MeOH, and dried under vacuum to afford 1am (0.137 g, 0.515 mmol, 67%) as an off-white solid. $^1$H NMR (400 MHz, CD$_3$OD) δ 8.44 (s, 1H), 7.76-7.74 (m, 2H), 7.68 (d, J=7.9 Hz, 1H), 7.48 (t, J=7.9 Hz, 1H), 6.32 (d, J=7.2 Hz, 1H). HRMS (ESI+ve) calculated for C$_{11}$H$_{12}$N$_5$O (M+H—Cl)$^+$ 230.1036, found 230.1037.

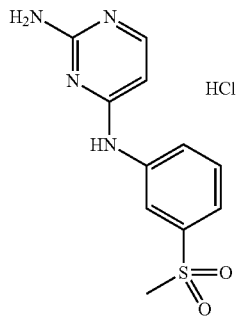 [SMILES: CS(=O)(=O)c1cccc(Nc2ccnc(N)n2)c1 ; Cl]

N-(3-(methylsulfonyl)phenyl)pyrimidine-2,4-diamine hydrochloride (1an). This was obtained as an off-white solid (0.162 g, 0.482 mmol, 54%) from of 2-amino-4-chloropyrimidine (0.166 g, 0.895 mmol), 3-(methylsulfonyl)aniline (0.185 g, 0.895 mmol) in a similar manner as described for 1am. After cooling to room temperature, the solid precipitate was filtered, washed with MeOH, and dried under vacuum to afford 1an. $^1$H NMR (400 MHz, CD$_3$OD) δ 8.42 (s, 1H), 8.05 (d, J=8.8 Hz, 1H), 7.80-7.76 (m, 2H), 6.36 (d, J=7.2 Hz, 1H), 3.18 (s, 3H). HRMS (ESI+ve) calculated for C$_{11}$H$_{12}$N$_4$O$_2$S (M+H—Cl)$^+$ 265.0753, found 265.0757.

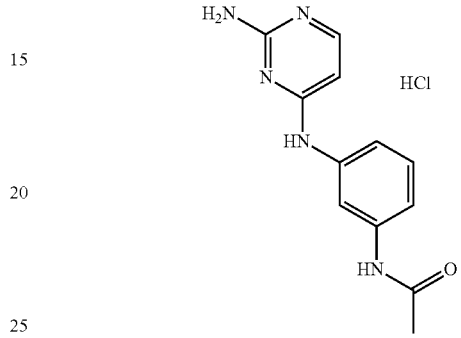

N-(3-(2-aminopyrimidin-4-ylamino)phenyl)acetamide hydrochloride (1ao). This was obtained as a white solid (0.216 g, 0.771 mmol, 92%) from 2-amino-4-chloropyrimidine (0.106 g, 0.837 mmol), and N-(3-aminophenyl)acetamide (0.150 g, 1.00 mmol) in a similar manner as described for 1ae. After cooling to room temperature, the solid precipitate was filtered, washed with MeOH, and dried under vacuum to afford 1ao. $^1$H NMR (400 MHz, CD$_3$OD) δ 8.10 (s, 1H), 7.70 (d, J=7.3 Hz, 1H), 7.48 (s, 1H), 7.32 (t, J=8.1 Hz, 1H), 7.21 (d, J=8.7 Hz, 1H), 6.30 (d, J=7.3 Hz, 1H), 2.14 (s, 3H). HRMS (ESI+ve) calculated for C$_{12}$H$_{14}$N$_5$O (M+H—Cl)$^+$ 244.1192, found 244.1198.

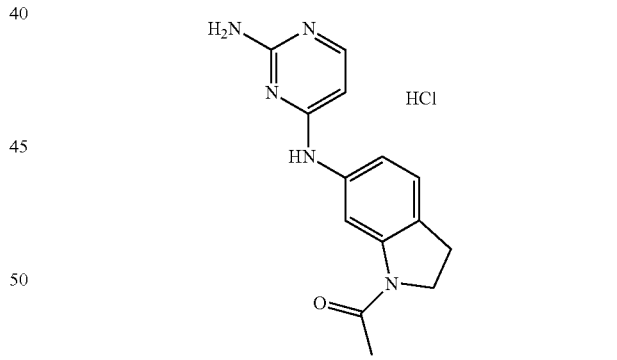

1-(6-(2-aminopyrimidin-4-ylamino)indolin-1-yl)ethanone hydrochloride (1ap). This was obtained as a white solid (0.130 g, 0.430 mmol, 57%) from 2-amino-4-chloropyrimidine (0.097 g, 0.748 mmol), and 1-(6-aminoindolin-1-yl)ethanone (0.131 g, 0.748 mmol) in a similar manner as described for 1am. After cooling to room temperature, the solid precipitate was filtered, washed with MeOH, and dried under vacuum to afford 1ap. $^1$H NMR (400 MHz, DMSO-d$_6$) δ 12.19 (s, 1H), 10.57 (s, 1H), 8.03 (s, 1H), 7.80 (d, J=7.2 Hz, 1H), 7.20 (d, J=8.1 Hz, 1H), 6.27 (d, J=6.7 Hz, 1H), 4.10 (t, J=8.5 Hz, 2H), 3.11 (t, J=8.4 Hz, 2H), 2.15 (s, 3H). HRMS (ESI+ve) calculated for C$_{14}$H$_{15}$N$_5$O (M+H—Cl)$^+$ 270.1349, found 270.1357.

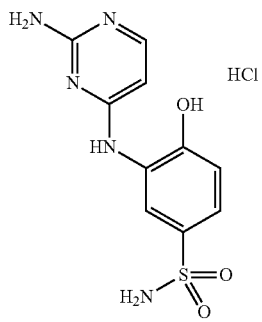 [SMILES: Nc1nccc(Nc2cc(S(N)(=O)=O)ccc2O)n1 ; Cl]

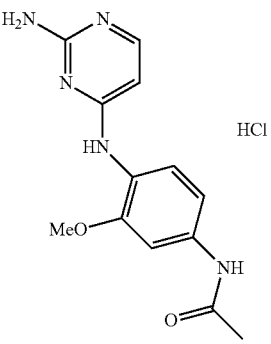

3-(2-aminopyrimidin-4-ylamino)-4-hydroxybenzenesulfonamide hydrochloride (1aq). This was obtained as a white solid (0.150 g, 0.472 mmol, 72%) from 2-amino-4-chloropyrimidine (0.085 g, 0.656 mmol), and 3-amino-4-hydroxybenzenesulfonamide (0.123 g, 656 mmol) in a similar manner as described for 1am. After cooling to room temperature, the solid precipitate was filtered, washed with MeOH, and dried under vacuum to afford 1aq. $^1$H NMR (400 MHz, DMSO-d6) δ 12.16 (s, 1H), 10.57 (s, 1H), 8.03 (s, 1H), 7.90 (bs, 2H), 7.80 (d, J=7.2 Hz, 2H), 7.21 (d, J=8.2 Hz, 1H), 6.27 (d, J=7.1 Hz, 1H), 4.10 (t, J=8.6 Hz, 1H), 3.11 (t, J=8.5 Hz, 1H), 2.15 (s, 1H). HRMS (ESI+ve) calculated for $C_{o2}H_{12}N_5O_3S$ (M+H—Cl)$^+$ 282.0655, found 282.0658.

N-(4-(2-aminopyrimidin-4-ylamino)-3-methoxyphenyl)acetamide hydrochloride (1ar). This was obtained from 2-amino-4-chloropyrimidine (0.087 g, 0.671 mmol), and N-(4-amino-3-methoxyphenyl)acetamide (0.121 g, 0.671 mmol) in a similar manner as described for 1am. After cooling to room temperature, the solid precipitate was filtered, washed with methanol, ether, further triturated with methanol, filtered and dried under vacuum (0.082 g). The methanolic solution was concentrated to dryness. The obtained solid was slurried with methanol, filtered and dried under vacuum (0.019 g). The two batches were combined to provide pure 1ar (0.101 g, 0.326 mmol, 49%) as a yellow solid. $^1$H NMR (400 MHz, CD$_3$OD) δ 8.18 (s, 1H), 7.69 (d, J=7.3 Hz, 1H), 7.30 (dd, J=2.5, 9.0 Hz, 1H), 7.04 (d, J=8.9 Hz, 1H), 6.37 (s, 1H), 3.87 (s, 3H), 2.11 (s, 4H). HRMS (ESI+ve) calculated for $C_{13}H_{16}N_5O_2$ (M+H—Cl)$^+$ 274.1298, found 274.1301.

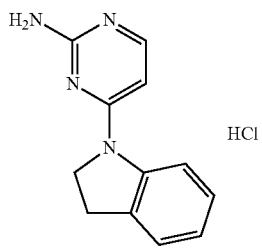 [SMILES: Nc1nccc(N2CCc3ccccc32)n1 ; Cl]

4-(indolin-1-yl)pyrimidin-2-amine hydrochloride (13a). A mixture of 2-amino-4-chloropyrimidine (0.097 g g, 0.748 mmol), and indoline (0.098 g, 0.823 mmol) was stirred in a Biotage microwave reactor for 15 min at 120° C. and 10 min at 160° C. After cooling to room temperature, the solid precipitate was filtered, washed with methanol, ether, further triturated with methanol, filtered and dried under vacuum (0.106 g). The methanolic solution was concentrated to dryness. The obtained solid was slurried with methanol, filtered and dried under vacuum (0.043 g). The two batches were combined to provide pure 13a (0.149 g, 0.587 mmol, 78%) as a pale yellow solid. $^1$H NMR (400 MHz, CD$_3$OD) δ 8.66 (m, 1H), 7.83 (d, J=7.5 Hz, 1H), 7.31 (d, J=7.4 Hz, 1H), 7.25 (d, J=7.9 Hz, 1H), 7.13 (t, J=7.4 Hz, 1H), 6.46 (s, 1H), 4.21 (t, J=8.3 Hz, 3H). HRMS (ESI+ve) calculated for $C_{12}H_{12}N_4$ (M+H—Cl)$^+$ 213.1134, found 213.1139.

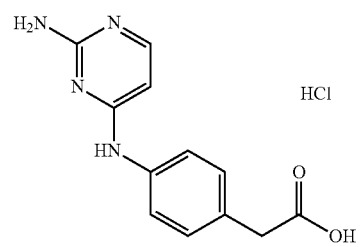 [SMILES: Nc1nccc(Nc2ccc(CC(=O)O)cc2)n1 ; Cl]

2-(4-(2-aminopyrimidin-4-ylamino)phenyl)acetic acid hydrochloride (1as). This was obtained from 2-amino-4-chloropyrimidine (0.092 g, 0.710 mmol), and 2-(4-aminophenyl)acetic acid (0.107 g, 0.710 mmol) in a similar manner as described for 1am. After cooling to room temperature, the solvent was removed under reduced pressure. The obtained the solid was filtered, slurried with acetone, filtered and dried under vacuum to provide pure 1as (0.149 g, 0.530 g, 75%)—as a yellow solid. $^1$H NMR (400 MHz, CD$_3$OD) δ 7.69 (d, J=7.3 Hz, 2H), 7.65 (s, 1H), 7.31 (d, J=8.4 Hz, 2H), 6.28 (d, J=7.3 Hz, 1H), 3.60 (s, 2H).

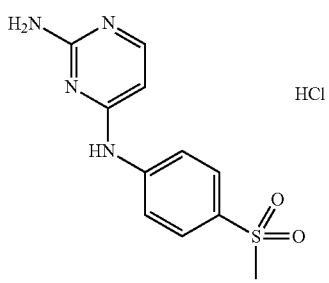 [SMILES: CS(=O)(=O)c1ccc(Nc2ccnc(N)n2)cc1 ; Cl]

N-(4-(methylsulfonyl)phenyl)pyrimidine-2,4-diamine hydrochloride (1at). This was obtained from 2-amino-4-chloropyrimidine (0.104 g, 0.802 mmol), and 4-(methylsulfonyl)aniline (0.143 g, 827 mmol) in a similar manner as described for 1am. After cooling to room temperature, the solid precipitate was filtered, slurried with MeOH, filtered, and dried under vacuum Pure 1at (0.165 g, 0.534 mmol, 67%) as a yellow solid. $^1$H NMR (400 MHz, CD$_3$OD) δ 8.08 (d, J=8.7 Hz, 2H), 7.96 (d, J=8.8 Hz, 2H), 7.82 (d, J=7.2 Hz, 1H), 6.39 (d, J=7.2 Hz, 1H), 3.12 (s, 3H). MS (M+H)$^+$ 265.07.

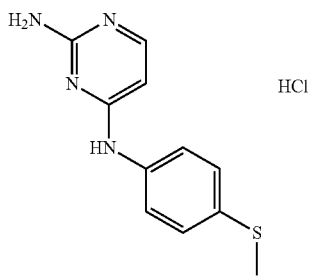 [SMILES: CSc1ccc(Nc2ccnc(N)n2)cc1 ; Cl]

N-(4-(methylthio)phenyl)pyrimidine-2,4-diamine hydrochloride (1au). This was obtained from 2-amino-4-chloropyrimidine (0.099 g, 0.764 mmol), and 4-(methylthio)aniline (0.106 g, 764 mmol) in a similar manner as described for 1am. After cooling to room temperature, the solid precipitate was filtered, washed with DCM, and dried under vacuum Pure 1au (0.085 g, 0.316 mmol, 41%) as a yellow solid $^1$H NMR (400 MHz, CD$_3$OD) δ 7.69 (d, J=7.3 Hz, 2H), 7.66 (s, 1H), 7.29 (d, J=8.7 Hz, 2H), 6.28 (d, J=7.3 Hz, 1H), 2.48 (s, 3H). HRMS (ESI+ve) calculated for C$_{11}$H$_{13}$N$_4$S (M+H—Cl)$^+$ 232.0855, found 232.0864.

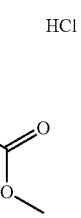

Methyl 4-(2-aminopyrimidin-4-ylamino)benzoate hydrochloride (1aw). A mixture of 2-amino-4-chloropyrimidine (0.140 g g, 1.08 mmol), and methyl-4-aminobenzoic acid (0.163 g, 1.08 mmol) was stirred in a Biotage microwave reactor for 15 min at 150° C. After cooling to room temperature, the solid precipitate was filtered, washed with methanol, DCM, dried under vacuum. Pure 1aw (0.189 g, 0.908 mmol, 84%) as a pale yellow solid. $^1$H NMR (400 MHz, CD$_3$OD) δ 8.03 (d, J=8.62 Hz, 2H), 7.93 (d, J=8.6 Hz, 2H), 7.78 (d, J=7.2 Hz, 1H), 6.37 (d, J=7.2 Hz, 1H), 3.90 (s, 3H). HRMS (ESI+ve) calculated for C$_{12}$H$_{13}$N$_4$O$_2$ (M+H)$^+$ 245.1033, found 245.1043.

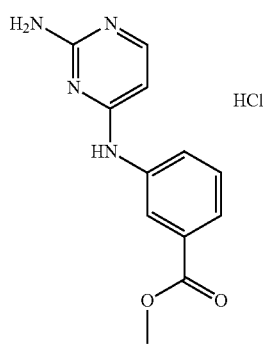 [SMILES: COC(=O)c1cccc(Nc2ccnc(N)n2)c1 ; Cl]

Methyl 3-(2-aminopyrimidin-4-ylamino)benzoate hydrochloride (1ay). A mixture of 2-amino-4-chloropyrimidine (0.097 g, 0.748 mmol), and methyl-3-aminobenzoic acid (0.113 g, 0.748 mmol) was stirred in a Biotage microwave reactor for 15 min at 120° C. After cooling to room temperature, the solvent was removed under reduced pressure and the obtained solid was slurried with DCM, filtered, dried under vacuum to provide pure 1ay (0.136 g, 0.485 mmol, 65%) as a pale yellow solid. $^1$H NMR (400 MHz, CD$_3$OD) δ 8.34 (s, 1H), 8.10 (s, 1H), 7.84 (d, J=7.9 Hz, 1H), 7.74 (d, J=7.2 Hz, 1H), 7.51 (t, J=7.9 Hz, 1H), 6.32 (d, J=7.2 Hz, 1H), 3.93 (s, 3H). HRMS (ESI+ve) calculated for C$_{12}$H$_{13}$N$_4$O$_2$ (M+H)$^+$ 245.1033, found 245.1042.

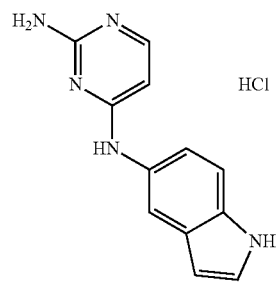

N-(1H-indol-5-yl)pyrimidine-2,4-diamine hydrochloride (1az). This was obtained as a white solid from 2-amino-4-chloropyrimidine (0.115 g, 0.887 mmol), and 1H-indol-5-amine (0.117 g, 887 mmol) in a similar manner as described for 1am. After cooling to room temperature, the solid precipitate was filtered, washed with DCM, and dried under vacuum Pure 1az (0.161 g, 0.612 mmol, 69%) was obtained as a brown solid. $^1$H NMR (400 MHz, CD$_3$OD) δ 7.85 (s, 1H), 7.64 (d, 1H, J=7.6 Hz, 1H), 7.55 (d, J=8.4 Hz, 1H), 7.27 (d, J=2.9 Hz, 1H), 7.14 (s, 1H), 6.45 (d, J=2.8 Hz, 1H), 6.27 (d, J=6.8 Hz, 1H), HRMS (ESI+ve) calculated for C$_{12}$H$_{12}$N$_5$ (M+H—Cl)$^+$ 226.1087, found 226.1092

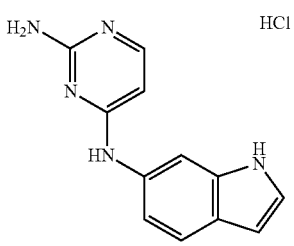 [SMILES: Cl ; Nc1nccc(Nc2ccc3cc[nH]c3c2)n1]

N⁴-(1H-indol-6-yl)pyrimidine-2,4-diamine hydrochloride

N-(1H-indol-6-yl)pyrimidine-2,4-diamine hydrochloride (1ba). This was obtained from 2-amino-4-chloropyrimidine (0.131 g, 1.01 mmol), and 1H-indol-6-amine (0.133 g, 1.01 mmol) in a similar manner as described for 1am. After cooling to room temperature, the solvent was removed under reduced pressure. The remaining solid was slurried with ether, DCM, filtered and dried under vacuum. Pure 1ba (0.136 g, 0.519 mmol, 51%) as a brown solid $^1$H NMR (400 MHz, CD$_3$OD) δ 7.96 (s, 1H), 7.62 (d, J=7.3 Hz, 1H), 7.39 (s, 1H), 7.28 (s, 2H), 6.46 (s, d, J=2.3 Hz, 1H), 6.25 (s, 1H), HRMS (ESI+ve) calculated for C$_{12}$H$_{12}$N$_5$ (M+H—Cl)⁺ 226.1087 found 226.1095.

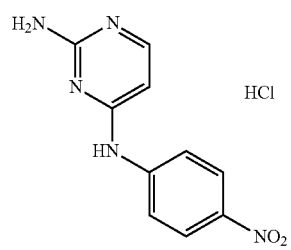

N 4-(3,4-dihydroquinolin-1(2H)-yl)pyrimidin-2-amine (16). This was obtained from 2-amino-4-chloropyrimidine (0.120 g, 0.926 mmol), and 1,2,3,4-tetrahydroquinoline (0.185 g, 1.389 mmol), in a similar manner as described for 1aw. After cooling to room temperature, Et$_3$N (1 ml) was added. The solvent was removed under reduced pressure. The remaining solid was slurried with water, filtered, washed with ether, dried under vacuum. Pure 16 (0.089 g, 0.392 mmol, 42%) was obtained as an off-white solid. $^1$H NMR (400 MHz, CD$_3$OD) δ 7.73 (d, J=6.2 Hz, 1H), 7.32 (d, J=8.1 Hz, 1H), 7.19 (d, J=7.5 Hz, 1H), 7.14 (d, J=7.6 Hz, 1H), 7.05 (t, J=7.4 Hz, 1H), 6.35 (d, J=6.2 Hz, 1H), 3.91 (t, J=6.3 Hz, 2H), 2.74 (t, J=6.5 Hz, 2H), 1.94 (p, 2H, J=6.5 Hz, 2H). HRMS (ESI+ve) calculated for C$_{13}$H$_{15}$N$_4$ (M+H)⁺ 227.1291, found 227.1294.

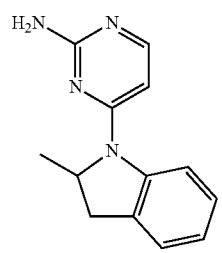 [SMILES: CC1Cc2ccccc2N1c1ccnc(N)n1]

4-(2-methylindolin-1-yl)pyrimidin-2-amine (13b). This was obtained from 2-amino-4-chloropyrimidine (0.091 g, 0.702 mmol) and 2-methylindoline (0.093 g, 0.702 mmol),) in a similar manner as described for 1aw. After cooling to room temperature, Et$_3$N (1 ml) was added. The solvent was removed under reduced pressure. The remaining solid was slurried with water, filtered, washed with ether, dried under vacuum. Pure 13b (0.090 g, 0.396 mmol, 56%) was obtained as an off-white solid $^1$H NMR (400 MHz, CD$_3$OD) δ 8.31 (d, J=8.1 Hz, 1H), 7.87 (d, J=6.2 Hz, 1H), 7.21 (d, J=8.0 Hz, 1H), 7.16 (d, J=7.9 Hz, 1H), 6.97-6.91 (m, 1H), 6.24 (d, J=6.2 Hz, 1H), 4.69-4.61 (m, 1H), 3.40 (dd, J=15.8, 9.1 Hz, 1H), 2.69 (d, J=15.8 Hz, 1H), 1.26 (d, J=6.3 Hz, 3H). HRMS (ESI+ve) calculated for C$_{13}$H$_{15}$N$_4$ (M+H)⁺ 227.1291, found 227.1292

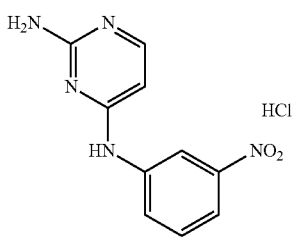 [SMILES: Nc1nccc(Nc2cccc([N+](=O)[O-])c2)n1 ; Cl]

N-(4-nitrophenyl)pyrimidine-2,4-diamine hydrochloride (1bb). This was obtained from 2-amino-4-chloropyrimidine (0.109 g, 0.841 mmol) p-nitroaniline (0.116 g, 0.841 mmol), in a similar manner as described for 1aw. After cooling to room temperature, the solid precipitate was filtered, washed with methanol, and dried under vacuum (0.116 g). The methanolic solution was concentrated to dryness. The obtained solid was slurried with methanol, filtered and dried under vacuum (0.029 g). The two batches were combined to provide pure 1bb (0.145 g, 0.541 mmol, 64%) as a yellow solid. $^1$H NMR (400 MHz, CD$_3$OD) δ 8.27 (d, J=9.2 Hz, 2H), 8.07 (d, J=8.9 Hz, 2H), 7.84 (d, J=7.2 Hz, 1H), 6.41 (d, J=7.2 Hz, 1H). HRMS (ESI+ve) calculated for C$_{10}$H$_{10}$N$_5$O$_2$ (M+H—Cl)⁺ 232.0829, found 232.0836

N-(3-nitrophenyl)pyrimidine-2,4-diamine hydrochloride (1bc). This was obtained from 2-amino-4-chloropyrimidine (0.133 g, 1.02 mmol) m-nitroaniline (0.141 g, 1.02 mmol), in a similar manner as described for 1aw. After cooling to room temperature, the solid precipitate was filtered, washed with methanol, and dried under vacuum. Pure 1bc (0.213 g, 0.795 mmol, 76%) as a yellow solid. $^1$H NMR (400 MHz, CD$_3$OD) δ 8.63 (s, 1H), 8.19 (d, J=9.8 Hz, 1H), 8.05 (d, J=8.3 Hz, 1H), 7.81 (d, J=5.8 Hz, 1H), 7.64 (t, J=8.2 Hz, 1H), 6.37 (d, J=7.2 Hz, 1H). HRMS (ESI+ve) calculated for C$_{10}$H$_{10}$N$_5$O$_2$ (M+H—Cl)⁺ 232.0829, found 232.0838

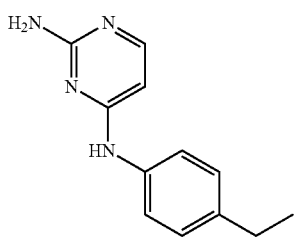 [SMILES: CCc1ccc(Nc2ccnc(N)n2)cc1]

N⁴-(4-ethylphenyl)pyrimidine-2,4-diamine

N-(4-ethylphenyl)pyrimidine-2,4-diamine (1bd). This was obtained from 2-amino-4-chloropyrimidine (0.091 g, 0.702 mmol), and p-ethylaniline (0.085 g, 0.702 mmol) in a similar manner as described for 1aw. After cooling to room temperature, Et₃N (1 ml) was added. The solvent was removed under reduced pressure. The remaining solid was slurried with water, filtered, washed with ether, dried under vacuum. Pure 1bd (0.064 g, 0.299 mmol, 43%) was obtained as an off-white solid. $^1$H NMR (400 MHz, CD₃OD) δ 7.72 (d, J=6.4 Hz, 1H), 7.45 (d, J=8.4 Hz, 2H), 7.14 (d, J=8.2 Hz, 2H), 6.02 (d, J=6.0 Hz, 1H), 2.61 (q, J=7.6 Hz, 2H), 1.21 (t, J=7.6 Hz, 3H). HRMS (ESI+ve) calculated for $C_{12}H_{15}N_4$ (M+H—Cl)⁺ 215.1291, found 215.1308

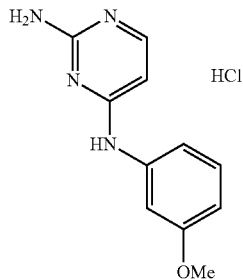 [SMILES: COc1cccc(Nc2ccnc(N)n2)c1 ; Cl]

N-(3-methoxyphenyl)pyrimidine-2,4-diamine hydrochloride (1be). This was obtained from 2-amino-4-chloropyrimidine (0.090 g, 0.694 mmol), and 3-methoxyaniline (0.085 g, 0.694 mmol) in a similar manner as described for 1aw. After cooling to room temperature, the solid precipitate was filtered, washed with methanol, ether, further triturated with methanol, filtered and dried under vacuum (0.015 g). The methanolic solution was concentrated to dryness. The obtained solid was slurried with methanol, filtered and dried under vacuum (0.033 g). The methanolic solution was concentrated to dryness. The obtained solid was slurried with DCM, filtered and dried under vacuum (0.077 g). The three batches were combined to provide pure 1be (0.125 g, 0.494 mmol, 71%) as a yellow solid. $^1$H NMR (400 MHz, CD₃OD) δ 7.70 (d, J=7.3 Hz, 1H), 7.35-7.24 (m, 3H), 6.78 (d, J=7.2 Hz, 1H), 6.29 (d, J=7.3 Hz, 1H), 3.81 (s, 3H). HRMS (ESI+ve) calculated for $C_{11}H_{13}N_4O$ (M+H—Cl)⁺ 217.1083, found 217.1098.

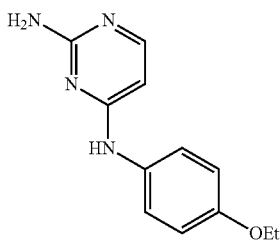 [SMILES: CCOc1ccc(Nc2ccnc(N)n2)cc1]

N-(4-ethoxyphenyl)pyrimidine-2,4-diamine (1bf). This was obtained from 2-amino-4-chloropyrimidine (0.118 g, 0.910 mmol), and p-ethoxyaniline (0.124 g, 0.910 mmol) in a similar manner as described for 1aw. After cooling to room temperature, Et₃N (1 ml) was added. The solvent was removed under reduced pressure. The remaining solid was slurried with water, filtered, washed with ether, dried under vacuum. Pure 1bf (0.137 g, 0.593 mmol, 65%) was obtained as an off-white solid. $^1$H NMR (400 MHz, CD₃OD) δ 7.70 (d, J=6.1 Hz, 1H), 7.40 (d, J=8.9 Hz, 2H), 6.87 (d, J=8.9 Hz, 2H), 5.96 (d, J=4.5 Hz, 1H), 4.01 (q, J=7.0 Hz, 2H), 1.37 (t, J=7.0 Hz, 3H). HRMS (ESI+ve) calculated for $C_{12}H_{15}N_4O$ (M+H)⁺ 231.1240, found 231.1253

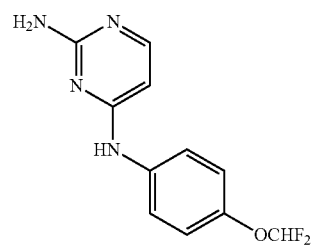 [SMILES: Nc1nccc(Nc2ccc(OC(F)F)cc2)n1]

N-(4-(difluoromethoxy)phenyl)pyrimidine-2,4-diamine (1bg). This was obtained from 2-amino-4-chloropyrimidine (0.098 g, 0.756 mmol), and 4-(difluoromethoxy)aniline (0.120 g, 0.756 mmol) in a similar manner as described for 1aw. After cooling to room temperature, Et₃N (1 ml) was added. The solvent was removed under reduced pressure. The remaining solid was slurried with water, filtered, washed with ether/hexane solution (1/1), dried under vacuum. Pure 1bg (0.155 g, 0.613 mmol, 81%) was obtained as a brown solid. $^1$H NMR (400 MHz, CD₃OD) δ 7.75 (d, J=6.0 Hz, 1H), 7.66 (d, J=9.0 Hz, 2H), 7.08 (d, J=9.0 Hz, 2H), 6.73 (t, J=74.5 Hz, 1H), 6.03 (d, J=6.0 Hz, 1H). HRMS (ESI+ve) calculated for $C_{11}H_{11}F_2N_4O$ (M+H)⁺ 253.0895, found 253.0904.

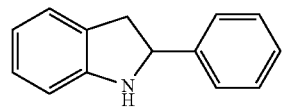

2-phenylindoline (12a). NaBH₃CN (2.11 g, 33.62 mmol) was added to a suspension of 2-phenylindole (1.083 g, 5.60 mml) in acetic acid (glacial, 24 mL) at 0° C. under Argon. The reaction mixture was then stirred at room temperature for 3 h. An aq. sat. solution of NaHCO₃ was then added slowly to pH 8-9. The mixture was then extracted with AcOEt, the organic phase separated, dried (Na₂SO₄), filtered and the solvent removed under reduced pressure. Chromatography on silica gel using the FlashMaster 3 purification station (AcOEt/Hexane) afforded 12a (0.174 g, 0.892 mmol, 16%) as a yellow oil. $^1$H NMR (400 MHz, CDCl₃) δ 744-7.30 (m, 5H), 7.10-7.-4 (m, 2H), 6.74 (td, J=7.5, 0.9 Hz, 1H), 6.68 (d, J=7.7 Hz, 1H), 4.96 (t, J=9.0 Hz, 1H), 3.45 (dd, J=15.7, 9.1 Hz, 1H), 2.99 (dd, J=15.6, 9.0 Hz, 1H).

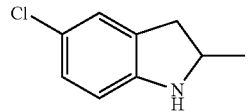

5-chloro-2-methylindoline (12b). This was obtained from 5-chloro-2-methylindole (0.372 g, 2.25 mmol), in a similar manner as described for 12a. Chromatography on silica gel using the FlashMaster 3 purification station (AcOEt/Hexane) afforded 12b (0.256 g, 1.532 mmol, 68%) as a brown oil. $^1$H NMR (400 MHz, CDCl$_3$) δ 7.06-6.98 (m, 1H), 6.96-6.92 (m, 1H), 6.49 (d, J=8.2 Hz, 1H), 4.08-3.92 (m, 1H), 3.12 (dd, J=15.7, 8.5 Hz, 1H), 2.61 (dd, J=15.7, 7.6 Hz, 1H), 1.27 (d, J=6.3 Hz, 3H).

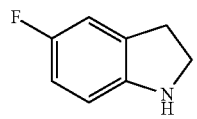

5-fluoro-indoline (12c). This was obtained from 5-fluoroindole (0.316 g, 2.33 mmol), in a similar manner as described for 12a. Chromatography on silica gel using the FlashMaster 3 purification station (AcOEt/Hexane) afforded 12c (0.041 g, 0.299 mmol, 13%) as a colourless oil. $^1$H NMR (400 MHz, CDCl$_3$) δ 7.00-6.96 (m, 1H), 6.37-6.30 (m, 2H), 3.59 (t, J=8.4 Hz, 2H), 2.97 (t, J=8.4 Hz, 2H).

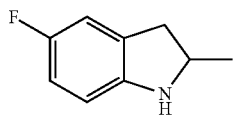

5-fluoro-2-methylindoline (12d). This was obtained from 5-fluoro-2-methylindole (0.426 g, 2.85 mmol), in a similar manner as described for 12a. Chromatography on silica gel using the FlashMaster 3 purification station (AcOEt/Hexane) afforded 12d (0.144 g, 0.953 mmol, 33%) as a colourless oil. $^1$H NMR (400 MHz, CDCl$_3$) δ 6.80-6.77 (m, 1H), 6.71-6.67 (m, 1H), 6.49 (dd, J=8.4, 4.4 Hz, 1H), 4.07-3.84 (m, 1H), 3.12 (dd, J=15.7, 8.4 Hz, 1H), 2.62 (dd, J=15.7, 7.9 Hz, 1H), 1.28 (d, J=6.2 Hz, 3H).

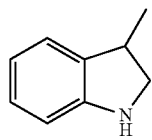

3-methylindoline (12e). This was obtained from 3-methylindole (0.414 g, 3.15 mmol), in a similar manner as described for 12a. Chromatography on silica gel using the FlashMaster 3 purification station (AcOEt/Hexane) afforded 12e (0.123 g, 0.924 mmol, 29%) as a colourless oil. $^1$H NMR (400 MHz, CDCl$_3$) δ 7.09-7.08 (m, 1H), 7.04-7.01 (m, 1H), 6.74 (t, J=7.2 Hz, 1H), 6.65 (d, J=7.8 Hz, 1H), 3.70 (t, J=8.6 Hz, 1H), 3.41-3.18 (m, 1H), 3.11 (t, J=8.6 Hz, 1H), 1.33 (d, J=6.7 Hz, 3H).

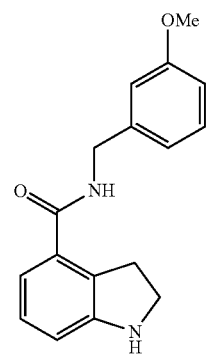 [SMILES: COc1cccc(CNC(=O)c2cccc3c2CCN3)c1]

N-(3-methoxybenzyl)indoline-4-carboxamide (12f). This was obtained from 29a (0.186 g, 0.663 mmol), in a similar manner as described for 12a. The crude material (0.163 g, 0.578 mmol, 87%) was used in the next step without further purification. $^1$H NMR (400 MHz, CDCl$_3$) δ δ 7.24 (t, J=7.8 Hz, 1H), 6.99 (t, J=7.7 Hz, 1H), 690-6.85 (m, 3H), 6.81 (dd, J=8.2, 2.0 Hz, 1H), 6.66 (d, J=7.7 Hz, 1H), 6.47 (s, 1H), 4.54 (d, J=5.7 Hz, 2H), 3.77 (s, 3H), 3.51 (t, J=8.4 Hz, 2H), 3.25 (t, J=8.4 Hz, 2H).

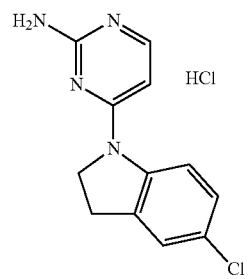 [SMILES: Nc1nccc(N2CCc3cc(Cl)ccc32)n1 ; Cl]

N-(5-chloroindolin-1-yl)pyrimidin-2-amine hydrochloride (13c). This was obtained from 2-amino-4-chloropyrimidine (0.100 g, 0.771 mmol), and 5-chloroindoline (0.118 g, 0.771 mmol) in a similar manner as described for 1aw. After cooling to room temperature, the solid precipitate was filtered, washed with DCM and dried under vacuum. Pure 13c (0.166 g, 0.586 mmol, 76%) was obtained as an off-white solid $^1$H NMR (400 MHz, CD$_3$OD) δ 8.63 (s, 1H), 7.85 (d, J=7.4 Hz, 1H), 7.31 (s, 1H), 7.23 (d, J=8.5 Hz, 1H), 6.43 (t, J=4.0 Hz, 1H), 4.23 (t, J=8.2 Hz, 2H). HRMS (ESI+ve) calculated for C$_{12}$H$_{12}$N$_4$Cl (M+H)$^+$ 247.0745, found 247.0753.

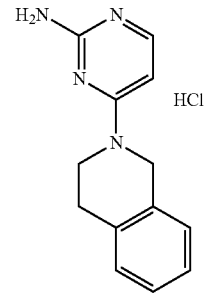 [SMILES: Nc1nccc(N2CCc3ccccc3C2)n1 ; Cl]

4-(3,4-dihydroisoquinolin-2(1H)-yl)pyrimidin-2-amine hydrochloride (17). This was obtained from 2-amino-4- chloropyrimidine (0.116 g, 0.895 mmol), and 1,2,3,4-tetrahydroisoquinoline (0.262 g, 1.97 mmol) in a similar manner as described for 1aw. After cooling to room temperature, the solid precipitate was filtered, washed with methanol, dried under vacuum. Pure 17 (0.154 g, 0.679 mmol, 76%) as a white solid. $^1$H NMR (400 MHz, CD$_3$OD) δ 7.75 (d, J=6.4 Hz, 1H), 7.18-7.16 (m, 4H), 6.16 (d, J=6.4 Hz, 1H), 4.72 (s, 2H), 3.83 (t, J=5.9 Hz, 2H), 2.91 (t, J=5.9 Hz, 2H). HRMS (ESI+ve) calculated for C$_{13}$H$_{15}$N$_4$ (M+H—Cl)$^+$ 227.1291, found 227.1293.

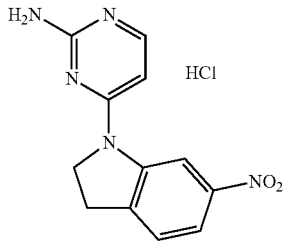 [SMILES: Nc1nccc(N2CCc3ccc([N+](=O)[O-])cc32)n1 ; Cl]

4-(6-nitroindolin-1-yl)pyrimidin-2-amine hydrochloride (13d). This w obtained from 2-amino-4-chloropyrimidine (0.106 g, 0.818 mmol), and 6-nitroindoline (0.134 g, 0.818 mmol) in a similar manner as described for 1aw. After cooling to room temperature, the solid precipitate was filtered, washed with methanol, dried under vacuum. Pure 13d (0.200 g, 0.680 mmol, 83%) as a yellow solid $^1$H NMR (400 MHz, CD$_3$OD) δ 9.32 (s, 1H), 8.04 (dd, J=1.9, 8.4 Hz, 1H), 7.94 (d, J=7.4 Hz, 1H), 7.52 (d, 1H, J=8.2 Hz, 1H), 6.52 (d, J=6.9 Hz, 1H), 4.34 (t, J=8.5 Hz, 2H), 3.42 (t, J=8.1 Hz, 2H). HRMS (ESI+ve) calculated for C$_{12}$H$_{12}$N$_5$O$_2$ (M+H—Cl)$^+$ 258.0985, found 258.0988.

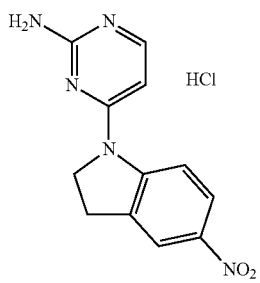 [SMILES: Nc1nccc(N2CCc3cc([N+](=O)[O-])ccc32)n1 ; Cl]

4-(5-nitroindolin-1-yl)pyrimidin-2-amine hydrochloride (13e). This was obtained from 2-amino-4-chloropyrimidine (0.103 g, 0.795 mmol), and 5-nitroindoline (0.130 g, 0.795 mmol) in a similar manner as described for 1aw. After cooling to room temperature, the solid precipitate was filtered, washed with methanol, dried under vacuum. Pure 13e (0.174 g, 0.592 mmol, 75%) as a yellow solid. $^1$H NMR (400 MHz, CD$_3$OD) δ 8.84 (d, J=7.6 Hz, 1H), 8.24-8.17 (m, 2H,), 7.97 (d, J=7.4 Hz, 1H), 6.56 (d, 1H, J=7.5 Hz, 1H), 4.35 (t, J=8.5 Hz, 2H), 3.41 (t, J=8.5 Hz, 2H).). HRMS (ESI+ve) calculated for C$_{12}$H$_{12}$N$_5$O$_2$ (M+H—Cl)$^+$ 258.0985, found 258.0990.

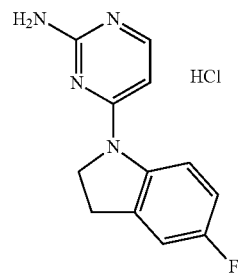 [SMILES: Nc1nccc(N2CCc3cc(F)ccc32)n1 ; Cl]

4-(5-fluoroindolin-1-yl)pyrimidin-2-amine hydrochloride (13f). This was obtained from 2-amino-4-chloropyrimidine (0.143 g, 1.10 mmol), and 5-fluoroindoline (0.151 g, 1.10 mmol) in a similar manner as described for 1aw. After cooling to room temperature, the solid precipitate was filtered, washed with methanol, dried under vacuum. Pure 13f (0.220 g, 0.592 mmol, 75%) as an off white solid. $^1$H NMR (400 MHz, CD$_3$OD) δ 8.66 (s, 1H), 7.83 (d, J=7.5 Hz, 1H), 7.08 (d, J=6.9 Hz, 1H), 7.00-6.95 (m, 1H), 6.44 (d, J=6.3 Hz, 1H), 4.25 (t, J=8.4 Hz, 2H). HRMS (ESI+ve) calculated for C$_{12}$H$_{12}$FN$_5$ (M+H—Cl)$^+$ 231.1040, found 231.1045.

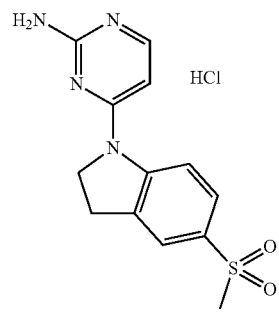 [SMILES: CS(=O)(=O)c1ccc2c(c1)CCN2c1ccnc(N)n1 ; Cl]

4-(5-(methylsulfonyl)indolin-1-yl)pyrimidin-2-amine hydrochloride (13g). This was obtained from 2-amino-4-chloropyrimidine (0.110 g, 0.849 mmol), and 5-(methylsulfonyl)indoline (0.167 g, 0.849 mmol) in a similar manner as described for 1aw. After cooling to room temperature, the solid precipitate was filtered, washed with methanol, dried under vacuum. Pure 13g (0.214 g, 0.654 mmol, 77%) as an off white solid. $^1$H NMR (400 MHz, CD$_3$OD) δ 8.87 (s, 1H), 7.95 (dd, J=0.8, 7.4 Hz, 1H), 7.87 (s, 1H), 7.85-7.83 (m, 1H), 6.54 (d, J=7.4 Hz, 1H), 4.32 (t, J=8.5 Hz, 2H), 3.40 (t, J=8.6 Hz, 2H), 3.12 (s, 3H). HRMS (ESI+ve) calculated for C$_{13}$H$_{14}$N$_4$O$_2$S (M+H—Cl)$^+$ 291.0910, found 291.0915.

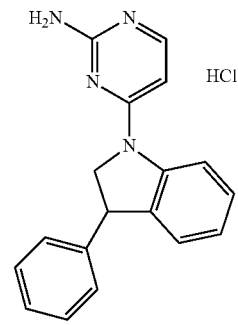 [SMILES: Nc1nccc(N2CC(c3ccccc3)c3ccccc32)n1 ; Cl]

4-(3-phenylindolin-1-yl)pyrimidin-2-amine hydrochloride (13h). This was obtained from 2-amino-4-chloropyrimidine (0.077 g, 0.594 mmol), and 12a (0.116 g, 0.594 mmol) in a similar manner as described for 1aw. After cooling to room temperature, the solid precipitate was filtered, washed with methanol, and dried under vacuum (0.036 g). The methanolic solution was concentrated to dryness. The obtained solid was slurried with acetone, filtered and dried under vacuum (0.107 g). The two batches were combined to provide pure 13h (0.143 g, 0.440 mmol, 74%) as a yellow solid. $^1$H NMR (400 MHz, CD$_3$OD) δ 8.75 (s, 1H), 7.67 (d, J=7.6 Hz, 1H), 7.37-7.24 (m, 5H), 7.19 (t, J=7.4 Hz, 3H), 6.22 (s, 1H), 5.78 (d, J=10.0 Hz, 1H), 3.91 (dd, J=9.8, 16.5 Hz, 1H), 3.04 (d, J=16.3 Hz, 2H). HRMS (ESI+ve) calculated for C$_{18}$H$_{17}$N$_4$ (M+H—Cl)$^+$ 289.1447, found 289.1447

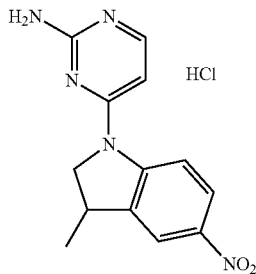 [SMILES: CC1CN(c2ccnc(N)n2)c2ccc([N+](=O)[O-])cc21 ; Cl]

4-(3-methyl-5-nitroindolin-1-yl)pyrimidin-2-amine hydrochloride (13i). This was obtained from 2-amino-4-chloropyrimidine (0.115 g, 0.887 mmol), and 3-methyl-5-nitroindoline (0.158 g, 0.887 mmol) in a similar manner as described for 1aw. After cooling to room temperature, the solid precipitate was filtered, washed with methanol, and dried under vacuum Pure 13i (0.094 g, 0.304 mmol, 34%) as a yellow solid. $^1$H NMR (400 MHz, CD$_3$OD) δ 9.21 (s, 1H), 8.06 (dd, J=2.1, 8.2 Hz, 1H), 7.94 (d, J=7.5 Hz, 1H), 7.55 (d, J=8.3 Hz, 1H), 6.65 (d, J=7.5 Hz, 1H), 4.99-4.94 (m 1H), 3.60 (dd, J=9.0, 17.0 Hz, 1H), 2.97 (d, J=17.0 Hz, 2H), 1.36 (d, J=6.5 Hz, 3H). HRMS (ESI+ve) calculated for C$_{13}$H$_{14}$N$_5$O$_2$ (M+H—Cl)$^+$ 272.1142, found 272.1141.

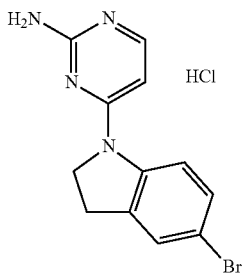 [SMILES: Nc1nccc(N2CCc3cc(Br)ccc32)n1 ; Cl]

4-(5-bromoindolin-1-yl)pyrimidin-2-amine hydrochloride (13j). This was obtained from 2-amino-4-chloropyrimidine (0.081 g, 0.625 mmol), and 5-bromoindoline (0.123 g, 0.625 mmol) in a similar manner as described for 1aw. After cooling to room temperature, the solid precipitate was filtered, washed with methanol, and dried under vacuum. Pure 13j (0.149 g, 0.455 mmol, 73%) as a yellow solid. $^1$H NMR (400 MHz, CD$_3$OD) δ 8.59 (s, 1H), 7.86 (d, J=7.5 Hz, 1H), 7.47 (s, 1H), 7.39 (d, J=7.6 Hz, 1H), 6.45 (d, J=5.7 Hz, 1H), 4.23 (t, J=8.5 Hz, 2H). HRMS (ESI+ve) calculated for C$_{12}$H$_{12}$BrN$_4$ (M+H—Cl)$^+$ 291.0239, found 291.0240.

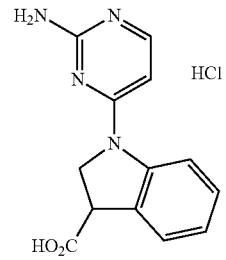 [SMILES: Nc1nccc(N2CC(C(=O)O)c3ccccc32)n1 ; Cl]

1-(2-aminopyrimidin-4-yl)indoline-3-carboxylic acid hydrochloride (13k). This was obtained from 2-amino-4-chloropyrimidine (0.070 g, 0.540 mmol), and indoline-3-carboxylic acid (0.088 g, 0.540 mmol) in a similar manner as described for 1aw. After cooling to room temperature, the solid precipitate was filtered, washed with methanol, and dried under vacuum. Pure 13k (0.079 g, 0.269 mmol, 50%) as a yellow solid. $^1$H NMR (400 MHz, CD$_3$OD) δ 8.70 (s, 1H), 7.85 (s, 1H), 7.32-7.28 (m, 3H), 7.16 (t, J=7.3 Hz, 1H), 6.32 (s, 1H), 5.32 (s, 1H), 3.75-3.68 (m, 1H). HRMS (ESI+ve) calculated for C$_{13}$H$_{13}$O$_2$N$_4$ (M+H—Cl)$^+$ 257.1033, found 257.1034

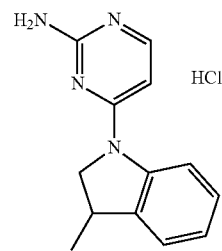 [SMILES: CC1CN(c2ccnc(N)n2)c2ccccc21 ; Cl]

4-(3-methylindolin-1-yl)pyrimidin-2-amine hydrochloride (13l). This was obtained from 2-amino-4-chloropyrimidine (0.070 g, 0.540 mmol), and 12e (0.072 g, 0.540 mmol) in a similar manner as described for 1aw. After cooling to room temperature, the solid precipitate was filtered, washed with methanol, and dried under vacuum (0.058 g). The methanolic solution was concentrated to dryness. The obtained solid was slurried with acetone, filtered and dried under vacuum (0.050 g). The two batches were combined to provide pure 13l (0.108 g, 0.411 mmol, 76%) as a yellow solid. $^1$H NMR (400 MHz, CD$_3$OD) δ 8.62 (s, 1H), 7.83 (d, J=7.5 Hz, 1H), 7.33 (d, J=7.4 Hz, 1H), 7.28 (t, J=7.2 Hz, 1H), 7.17 (t, J=7.3 Hz, 1H), 6.47 (d, J=6.1 Hz, 1H). 4.40 (t, 1H, J=9.9 Hz, 1H), 3.75 (dd, J=6.3, 10.9 Hz, 1H), 3.61 (m, 1H), 1.40 (d, J=6.9 Hz, 3H). HRMS (ESI+ve) calculated for C$_{13}$H$_{15}$N$_4$ (M+H—Cl)$^+$ 227.1291, found 227.1290

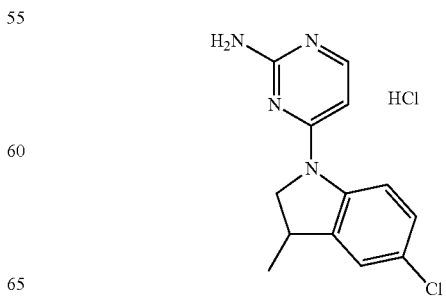

4-(5-chloro-3-methylindolin-1-yl)pyrimidin-2-amine hydrochloride (13m). This was obtained from 2-amino-4-chloropyrimidine (0.055 g, 0.431 mmol), and 12b (0.072 g, 0.341 mmol) in a similar manner as described for 1aw. After cooling to room temperature, the solvent was removed under reduced pressure. The obtained solid was slurried DCM, filtered and dried under vacuum. Pure 13m (0.082 g, 0.276 mmol, 64%) was obtained as an off white solid. $^1$H NMR (400 MHz, CD$_3$OD) δ 8.52 (s, 1H), 7.85 (d, J=7.5 Hz, 1H), 7.35 (s, 1H), 7.26 (dd, J=8.5, 1.5 Hz, 1H), 6.58 (d, J=7.4 Hz, 1H), 3.50 (dd, J=8.9, 16.3 Hz, 1H), 2.84 (d, J=16.3 Hz, 1H), 1.32 (d, J=6.4 Hz, 3H). HRMS (ESI+ve) calculated for C$_{13}$H$_{14}$ClN$_4$ (M+H—Cl)$^+$ 261.0901, found 261.0904

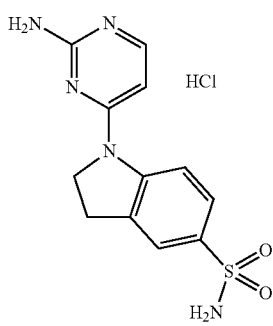 [SMILES: Nc1nccc(N2CCc3cc(S(N)(=O)=O)ccc32)n1 ; Cl]

1-(2-aminopyrimidin-4-yl)indoline-5-sulfonamide hydrochloride (13n). This was obtained from 2-amino-4-chloropyrimidine (0.076 g, 0.586 mmol), and indoline-5-sulfonamide (0.116 g, 0.586 mmol) in a similar manner as described for 1aw. After cooling to room temperature, the solid precipitate was filtered, washed with methanol, and dried under vacuum. Pure 13n (0.170 g, 0.518 mmol, 88%) was obtained as a yellow solid. $^1$H NMR (400 MHz, DMSO-d$_6$) δ 8.72 (d, J=8.6 Hz, 1H), 8.06 (d, J=7.2 Hz, 1H), 7.70 (s, 1H), 7.64 (d, J=10.0 Hz, 1H), 7.33 (s, 2H), 6.53 (s, 1H), 6.46 (d, J=7.2 Hz, 1H), 4.21 (t, J=8.4 Hz, 2H), 3.27 (t, J=8.3 Hz, 2H). HRMS (ESI+ve) calculated for C$_{12}$H$_{14}$ClN$_5$O$_2$S (M+H—Cl)$^+$ 292.0862, found 292.0863.

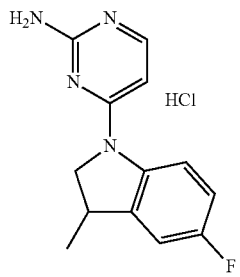 [SMILES: CC1CN(c2ccnc(N)n2)c2ccc(F)cc21 ; Cl]

4-(5-fluoro-3-methylindolin-1-yl)pyrimidin-2-amine hydrochloride (13o). This was obtained from 2-amino-4-chloropyrimidine (0.042 g, 0.324 mmol), and 12d (0.049 g, 0.324 mmol) in a similar manner as described for 1aw. After cooling to room temperature, Et$_3$N was added. The solvent was removed under reduced pressure. The remaining solid was slurried with water, filtered, washed with ether, dried under vacuum. Pure 13o (0.043 g, 0.171 mmol, 53%) was obtained as an off white solid. $^1$H NMR (400 MHz, CD$_3$OD) δ 8.39 (dd, J=4.9, 8.8 Hz, 1H), 7.87 (d, J=6.1 Hz, 1H), 6.97 (d, J=8.1 Hz, 1H), 6.89 (td, J=9.1, 2.7 Hz, 1H), 6.19 (d, J=6.2 Hz, 1H), 4.69-4.62 (m, 1H), 3.42 (dd, J=9.4, 16.5 Hz, 1H), 2.71 (d, J=16.4 Hz, 1H), 1.26 (d, J=6.3 Hz, 3H). HRMS (ESI+ve) calculated for C$_{13}$H$_{14}$FN$_4$ (M+H—Cl)$^+$ 245.1197, found 245.1211

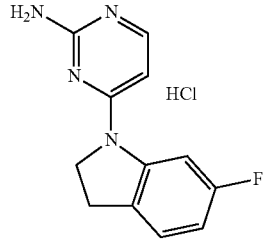 [SMILES: Nc1nccc(N2CCc3ccc(F)cc32)n1 ; Cl]

4-(6-fluoroindolin-1-yl)pyrimidin-2-amine hydrochloride (13p). This was obtained from 2-amino-4-chloropyrimidine (0.026 g, 0.204 mmol), and 12c (0.028 g, 0.204 mmol) in a similar manner as described for 1aw. After cooling to room temperature, the solid precipitate was filtered, washed with methanol, and dried under vacuum. Pure 13p (0.032 g, 0.120 mmol, 59%) was obtained as an off white solid $^1$H NMR (400 MHz, CD$_3$OD) δ 8.44 (d, J=10.8 Hz, 1H), 7.88 (d, J=7.2 Hz, 1H), 7.26-7.22 (m, 1H), 6.83-6.79 (m, 1H), 6.37 (dd, J=7.1, 1.1 Hz, 1H), 4.22 (t, 2H, J=8.3 Hz, 2H), 3.24 (t, J=9.2 Hz, 2H), HRMS (ESI+ve) calculated for C$_{12}$H$_{12}$FN$_4$ (M+H—Cl)$^+$ 231.1040, found 231.1038

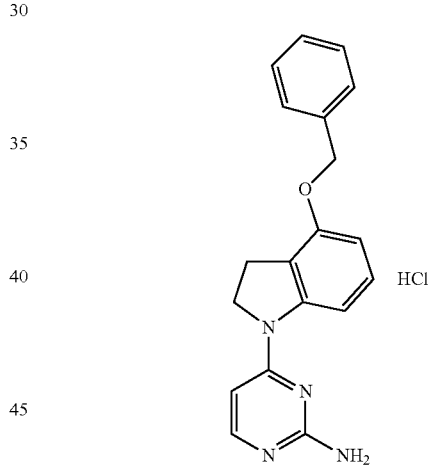

4-(4-(benzyloxy)indolin-1-yl)pyrimidin-2-amine hydrochloride (13q). This was obtained from 2-amino-4-chloropyrimidine (0.090 g, 0.694 mmol), and 4-(benzyloxy)indoline (0.156 g, 0.694 mmol) in a similar manner as described for 1aw. After cooling to room temperature, the solid precipitate was filtered, washed with methanol, and dried under vacuum. Pure 13q (0.119 g, 0.336 mmol, 48%) was obtained as an off white solid. $^1$H NMR (400 MHz, CD$_3$OD) δ 8.30 (s, 1H), 7.82 (d, J=7.5 Hz, 1H), 7.45-7.43 (m, 2H), 7.39-7.35 (m, 2H), 7.33-7.28 (m, 1H), 7.22 (t, J=8.3 Hz, 1H), 6.84 (d, J=8.3 Hz, 1H), 6.39 (s, 1H), 5.15 (s, 2H), 4.21 (t, J=8.2 Hz, 2H), 3.22 (t, J=8.1 Hz, 2H). HPLC: Purity 99.53%, MeOH 60%, (0.1% TFA in H$_2$O) 40%, 20 min, Flow 1 ml/min, R$_t$ 10.067 min. HRMS (ESI-ve) calculated for C$_{19}$H$_{19}$N$_4$O (M+H)$^+$ 319.1553, found 319.1563

101

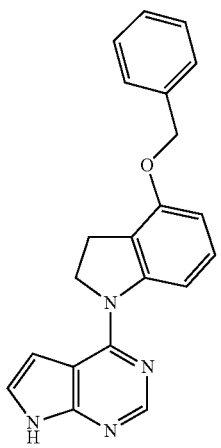 [SMILES: c1ccc(COc2cccc3c2CCN3c2ncnc3[nH]ccc23)cc1]

4-(4-(benzyloxy)indolin-1-yl)-7H-pyrrolo[2,3-d]pyrimidine (35). A mixture of -(benzyloxy) indoline (0.060 g, 0.266 mmol), 4-chloro-7H-pyrrolo[2,3-d]pyrimidine (0.039 g, 0.253 mmol) in anhydrous ethanol (0.6 ml) was stirred in a Biotage microwave reactor for 30 min at 150° C. After cooling to room temperature, Et$_3$N was added. The solvent was removed under reduced pressure. The remaining solid was slurried with water, filtered, washed with methanol, dried under vacuum. Pure 35 (0.046 g, 0.134 mmol, 53%) was obtained as an off white solid. $^1$H NMR (400 MHz, DMSO-d$_6$) δ 11.86 (s, 1H), 8.29 (s, 1H), 8.18 (d, J=8.2 Hz, 1H), 7.46 (d, J=7.0 Hz, 2H), 7.39 (t, J=7.4 Hz, 2H), 7.33-7.25 (m, 2H), 7.12 (t, J=8.3 Hz, 1H), 6.69-6.67 (m, 2H), 5.16 (s, 2H), 4.53 (t, J=9.5 Hz, 2H), 3.17 (t, J=9.4 Hz, 2H). HRMS (ESI–ve) calculated for C$_{21}$H$_{19}$N$_4$O (M+H)$^+$ 343.1553, found 343.1562

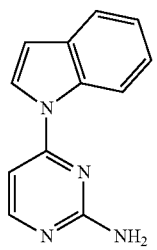 [SMILES: Nc1nccc(-n2ccc3ccccc32)n1]

4-(1H-indol-1-yl)pyrimidin-2-amine (15a). A mixture of 2-amino-4-chloropyrimidine (0.206 g, 1.590 mmol), indole (0.372 g, 3.180 mmol) and Cs$_2$CO$_3$ (1.550 g, 4.77 mmol) in anhydrous DMF (1.6 ml) was stirred in a Biotage microwave reactor for 1 h at 110° C. After cooling to room temperature, the reaction mixture diluted with water (5 ml) and extracted with ethyl acetate (2×10 ml). The combined organic extracts were dried over Na$_2$SO$_4$ and the solvent removed under reduced pressure. Chromatography on silica gel using the FlashMaster 3 purification station (AcOEt/Hexane) afforded 15a (0.125 g, 0.593 mmol, 37%) as an off-white solid. $^1$H NMR (400 MHz, DMSO-d$_6$) δ 8.78 (d, 1H, J=8.28 Hz), 8.23 (d, J=5.64 Hz, 1H), 8.03 (d, J=3.64 Hz, 1H), 7.59 (d, J=7.76 Hz, 1H), 7.27-7.22 (m, 1H), 7.17 (t, J=7.36 Hz, 1H), 6.93 (d, J=5.92 Hz, 1H), (bs, 2H), 6.74 (d, J=3.60 Hz, 1H); HRMS (ESI–ve) calculated for C$_{12}$H$_{11}$N$_4$ (M+H)$^+$ 211.0978, found 211.0979.

102

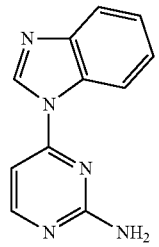 [SMILES: Nc1nccc(-n2cnc3ccccc32)n1]

4-(1H-benzo[d]imidazol-1-yl)pyrimidin-2-amine (18). A mixture of 2-amino-4-chloropyrimidine (0.120 g, 0.926 mmol), imidazole (0.109 g, 0.926 mmol) and Cs$_2$CO$_3$ (0.603 g, 1.852 mmol) in anhydrous DMF (0.9 ml) was stirred in a Biotage microwave reactor for 1 h at 110° C. After cooling to room temperature, water was added to the reaction mixture. The solid precipitate was filtered and dried under vacuum. The obtained solid was slurried with methanol, filtered, further slurried with ethyl acetate, filtered and dried under vacuum. Pure 18 (0.038 g, 0.178 mmol, 19%) was obtained as an off-white solid. $^1$H NMR (400 MHz, DMSO-d$_6$) δ 9.02 (s, 1H), 8.62 (d, J=7.0 Hz, 1H), 8.34 (d, J=5.5 Hz, 1H), 7.73 (d, J=8.5 Hz, 1H), 7.38-7.30 (m, 2H), 7.12 (d, J=5.6 Hz, 1H), 7.06 (s, 2H); HRMS (ESI–ve) calculated for C$_{11}$H$_{10}$N$_5$ (M+H)$^+$ 212.0930, found 212.0929.

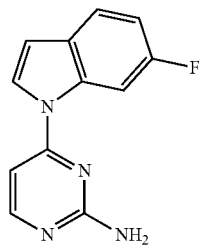 [SMILES: Nc1nccc(-n2ccc3ccc(F)cc32)n1]

4-(6-fluoro-1H-indol-1-yl)pyrimidin-2-amine (15b) A mixture of 2-amino-4-chloropyrimidine (0.062 g, 0.478 mmol), 6-fluoroindole (0.083 g, 0.621 mmol) and Cs$_2$CO$_3$ (0.467 g, 1.43 mmol) in anhydrous NMP (0.5 ml) was stirred in a Biotage microwave reactor for 30 min at 180° C. After cooling to room temperature, the reaction mixture diluted with water (5 ml) and extracted with ethyl acetate (2×10 ml). The combined organic extracts were dried over Na$_2$SO$_4$ and the solvent removed under reduced pressure. Chromatography on silica gel using the FlashMaster 3 purification station (AcOEt/Hexane) afforded 15b as a brown solid which was triturated with methanol, filtered, dried in vacuo. Pure 15b was obtained (0.013 g, 0.057 mmol, 25%) as an off-white solid. $^1$H NMR (400 MHz, DMSO-d$_6$) δ 8.66 (dd, J=2.5, 11.4 Hz, 1H), 8.24 (d, J=5.6 Hz, 1H), 8.06 (d, J=3.7 Hz, 1H), 7.60 (dd, J=5.8, 8.6 Hz, 1H), 7.05 (td, J=2.0, 8.8 Hz, 1H), 6.95 (s, 2H) 6.93 (d, J=5.7 Hz, 1H), 6.76 (d, J=3.7 Hz, 1H); HPLC: Purity 97.73%, MeOH 40%, (0.1% TFA in H$_2$O) 60%, 20 min, Flow 1 ml/min, R$_t$11.533 min, HRMS (ESI–ve) calculated for C$_{12}$H$_{10}$N$_4$ (M+H)$^+$ 229.0884, found 229.0895

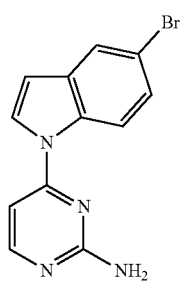 [SMILES: Nc1nccc(-n2ccc3cc(Br)ccc32)n1]

4-(5-bromo-1H-indol-1-yl)pyrimidin-2-amine (15c). A mixture of 2-amino-4-chloropyrimidine (0.091 g, 0.702 mmol), 5-bromoindole (0.083 g, 0.621 mmol) and Cs$_2$CO$_3$ (0.686 g) in anhydrous NMP (0.8 ml) was stirred in a Biotage microwave reactor for 30 min at 150° C. After cooling to room temperature, the reaction mixture diluted with water and extracted with DCM. The organic extract was dried over Na$_2$SO$_4$ and the solvent removed under reduced pressure. Chromatography on silica gel using the FlashMaster 3 purification station (AcOEt/Hexane) afforded 15c as an off white solid which was triturated with water, filtered, dried in vacuo. Pure 15c was obtained (0.100 g, 0.345 mmol, 49%) as an off-white solid. $^1$H NMR (400 MHz, DMSO-d$_6$) δ 8.77 (d, J=8.9 Hz, 1H), 8.25 (d, J=5.6 Hz, 1H), 8.11 (d, J=3.7 Hz, 1H), 7.82 (d, J=2.0 Hz, 1H), 7.35 (dd, J=8.9, 2.1 Hz, 1H), 6.94-6.92 (m, 3H), 6.75 (d, J=3.6 Hz, 1H). HPLC: Purity 99.02%, CH$_3$CN 30%, (0.1% TFA in H$_2$O) 70%, 20 min, Flow 1 ml/min, R$_t$ 11.533 min, Purity 98.18%, MeOH 50%, (0.1% TFA in H$_2$O) 50%, 20 min, Flow 1 ml/min, R$_t$ 16.240 min, HRMS (ESI–ve) calculated for C$_{12}$H$_{10}$BrN$_4$ (M+H)$^+$ 289.0083, found 289.0077

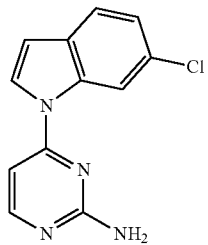 [SMILES: Nc1nccc(-n2ccc3ccc(Cl)cc32)n1]

4-(6-chloro-1H-indol-1-yl)pyrimidin-2-amine (15d). This was obtained from 2-amino-4-chloropyrimidine (0.088 g, 0.689 mmol), and 6-chloroindole (0.154 g, 1.01 mmol) in a similar manner as described for 15c. After cooling to room temperature, the reaction mixture diluted with water and extracted with DCM. The organic extract was dried over Na$_2$SO$_4$ and the solvent removed under reduced pressure. Chromatography on silica gel using the FlashMaster 3 purification station (AcOEt/Hexane) afforded 15d as an orange oil. Water was added to the obtained oil and the solid precipitate was filtered, washed with water and dried in vacuo. Pure 15d was obtained (0.089 g, 0.363 mmol, 49%) as an off-white solid $^1$H NMR (400 MHz, DMSO-d$_6$) δ 8.84 (d, 1H, J=1.92 Hz), 8.25 (d, J=5.64 Hz, 1H), 8.08 (d, J=3.68 Hz, 1H), 7.61 (d, J=8.36 Hz, 1H), 7.21 (dd, J=8.38, 1.98 Hz, 1H), 6.98 (bs, 2H, disappeared on D$_2$O shake), 6.93 (d, J=5.68 Hz, 1H), 6.78 (dd, J=3.68, 0.8 Hz, 1H), HPLC: Purity 99.02%, CH$_3$CN 30%, (0.1% TFA in H$_2$O) 70%, 20 min, Flow 1 ml/min, R$_t$ 8.360 min, Purity 99.44 2%, MeOH 50%, (0.1% TFA in H$_2$O) 50%, 20 min, Flow 1 ml/min, R$_t$ 10.933 min; HRMS (ESI–ve) calculated for C$_{12}$H$_{10}$ClN$_4$ (M+H)$^+$ 245.0588, found 245.0589

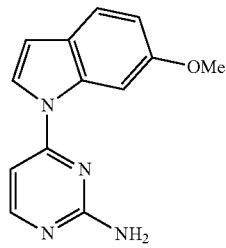 [SMILES: COc1ccc2ccn(-c3ccnc(N)n3)c2c1]

4-(6-methoxy-1H-indol-1-yl)pyrimidin-2-amine (15e). This was obtained from 2-amino-4-chloropyrimidine (0.089 g, 0.686 mmol), and 6-methoxyindole (0.151 g, 1.02 mmol) in a similar manner as described for 15c. After cooling to room temperature, the reaction mixture diluted with water and extracted with DCM. The organic extract was dried over Na$_2$SO$_4$ and the solvent removed under reduced pressure. Chromatography on silica gel using the FlashMaster 3 purification station (AcOEt/Hexane) afforded pure 15e (0.081 g, 0.336 mmol, 49%). $^1$H NMR (400 MHz, DMSO-d$_6$) δ 8.32 (d, 1H, J=2.24 Hz), 8.22 (d, J=5.64 Hz, 1H), 7.87 (d, J=3.68 Hz, 1H), 7.46 (d, J=8.52 Hz, 1H), 6.89 (d, J=5.72 Hz, 1H), 6.87 (bs, 2H), 6.82 (dd, J=8.58, 2.38 Hz, 1H), 6.65 (d, J=3.12 Hz, 1H), 3.83 (m, 3H). HPLC: Purity 99.02%, CH$_3$CN 30%, (0.1% TFA in H$_2$O) 70%, 20 min, Flow 1 ml/min: R$_t$ 5.613 min; Purity 99.51%, MeOH 50%, (0.1% TFA in H$_2$O) 50%, 20 min, Flow 1 ml/min, R$_t$ 6.600 min. HRMS (ESI–ve) calculated for C$_{13}$H$_{13}$ON$_4$ (M+H)$^+$ 241.1083, found 241.1083

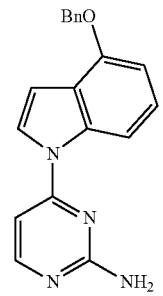 [SMILES: Nc1nccc(-n2ccc3c(OCc4ccccc4)cccc32)n1]

4-(4-(benzyloxy)-1H-indol-1-yl)pyrimidin-2-amine (21a). This was obtained from 2-amino-4-chloropyrimidine (0.087 g, 0.671 mmol), and 4-benzyloxyindole (0.224 g, 1.00 mmol) in a similar manner as described for 15c. After cooling to room temperature, the reaction mixture diluted with water and extracted with DCM. The organic extract was dried over Na$_2$SO$_4$ and the solvent removed under reduced pressure. Chromatography on silica gel using the FlashMaster 3 purification station (AcOEt/Hexane) afforded 21a as an off white solid. Water was added to the obtained solid and the solid precipitate was filtered, washed with water and dried in vacuo. Pure 21a was obtained (0.107 g, 0.337 mmol, 50%) as an off-white solid. $^1$H NMR (400 MHz, DMSO-d$_6$) δ 8.35 (d, J=8.4 Hz, 1H), 8.23 (d, J=5.6 Hz, 1H), 7.94 (d, J=3.7 Hz, 1H), 7.50 (d, J=7.1 Hz, 2H), 7.39 (t, J=7.4, Hz, 2H), 7.32 (t, J=7.3 Hz, 1H), 7.16 (t, J=8.2 Hz, 1H), 6.92 (d, J=5.7 Hz, 1H), 6.87 (s, 2H), 6.81 (d, J=7.9 Hz, 1H), 6.78 (d, J=3.4 Hz, 1H), 5.24 (s, 2H). HPLC: Purity 99.46%, CH$_3$CN 50%, (0.1% TFA in H$_2$O) 50%, 20 min, Flow 1 ml/min: R$_t$ 3.413 min, Purity 98.48%, MeOH 60%, (0.1% TFA in H$_2$O) 40%, 20 min, Flow 1 ml/min, R$_t$ 12.600 min, HRMS (ESI–ve) calculated for C$_{19}$H$_{17}$ON$_4$ (M+H)$^+$ 317.1396, found 317.1399.

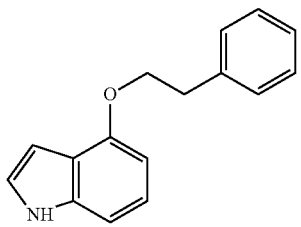 [SMILES: c1ccc(CCOc2cccc3[nH]ccc23)cc1]

4-phenethoxy-1H-indole (20a). A mixture of 4-hydroxyindole (1) (0.400 g, 3.00 mmol), (2-bromoethyl)benzene (0.557 g, 3.00 mmol) and $K_2CO_3$ (1.243 g, 9.0 mmol) in acetone (3 mL) was refluxed under argon for 4 days. After cooling to room temperature, the solid precipitate was filtered and washed with acetone. The filtrates were combined and the solvent was removed under reduced pressure to afford 20a as a black oil (0.714 g, 3.00 mmol, quantitative). The crude material was used in the next step without purification. $^1$H NMR (400 MHz, CDCl$_3$) δ 8.08 (s, 1H), 7.30-7.21 (m, 5H), 7.06-7.03 (m, 1H), 7.01 (d, J=7.8 Hz, 1H), 6.95 (d, J=8.1 Hz, 1H), 6.59 (t, J=1.6 Hz, 1H), 6.45 (d, J=7.6 Hz, 1H), 4.26 (t, J=7.1 Hz, 2H), 3.13 (t, J=7.1 Hz, 2H).

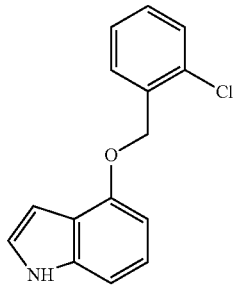 [SMILES: Clc1ccccc1COc1cccc2[nH]ccc12]

4-(2-chlorobenzyloxy)-1H-indole (20b). A mixture of 4-hydroxyindole (0.133 g, 2.00 mmol), 3-chlorobenzylchloride (0.381 g, 2.4 mmol), and $K_2CO_3$ (0.829 g, 6.0 mmol) in acetone (15 mL) was refluxed under argon for 9 days in presence of tetrabutylammonium bromide (0.038 g, 0.118 mmol). After cooling to room temperature, the solid precipitate was filtered and washed with acetone. The organic solutions were combined and the solvent removed under reduced pressure. Chromatography on silica gel, performed using a FlashMaster 3 purification station (AcOEt/Hexane), afforded 20b (0.080 g, 0.311 mmol, 16%) as a brown oil. $^1$H NMR (400 MHz, CDCl$_3$) δ 8.10 (bs, 1H), 7.61 (dd, J=1.4, 7.2 Hz, 1H), 7.33 (dd, J=1.6, 7.6 Hz, 1H), 7.24-7.16 (m, 2H), 7.07-6.96 (m, 3H), 6.68 (m, 1H), 6.51 (d, J=7.5 Hz, 1H).

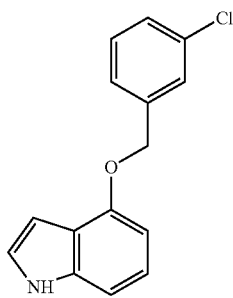 [SMILES: Clc1cccc(COc2cccc3[nH]ccc23)c1]

4-(3-chlorobenzyloxy)-1H-indole (20c). This was prepared from 4-hydroxyindole (0.133 g, 2.0 mmol) and 3-chlorobenzylbromide (0.205 g, 2.4 mmol) in the same manner as described for 20a. Reaction time: 22 hrs. Chromatography on silica gel performed twice using a FlashMaster 3 purification station (AcOEt/Hexane), afforded 20c (0.267 g, 1.04 mmol, 52%) as a brown oil, Analysis of $^1$H NMR revealed that a mixture of the desired product and an unknown impurity was isolated. The mixture was used as obtained in the next step. $^1$H NMR (400 MHz, CDCl$_3$) δ 8.19 (s, 1H), 7.52 (s, 1H), 7.4-7.28 (m, 3H), 7.16-7.05 (m, 3H), 6.78-6.71 (m, 1H), 6.56 (dd, J=7.3, 1.0 Hz, 1H), 5.21 (s, 2H).

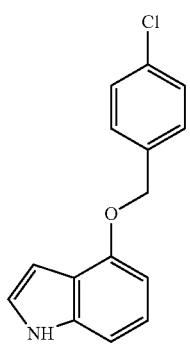 [SMILES: Clc1ccc(COc2cccc3[nH]ccc23)cc1]

4-(4-chlorobenzyloxy)-1H-indole (20d). This was prepared from 4-hydroxyindole (0.266 g, 2.0 mmol) and 4-chlorobenzylbromide (0.493 g, 2.4 mmol) in a similar manner as described for preparation of 20a. Reaction time: 96 hours. Chromatography on silica gel, performed using the Flash Master purification station (AcOEt/Hexane), afforded an off white solid 20d (0.372 g, 1.44 mmol, 72%). Analysis of $^1$H NMR revealed that a mixture of the desired product and an unknown impurity was isolated. The mixture was used as obtained in the next step. $^1$H NMR (400 MHz, CDCl$_3$) δ 8.13 (s, 1H), 7.37 (d, J=8.3 Hz, 2H), 7.30-7.25 (m, 3H), 7.07 (t, J=3.0 Hz, 1H), 7.03-6.94 (m, 1H), 6.63 (t, J=2.7 Hz, 1H), 6.48 (d, J=7.4 Hz, 1H), 5.13 (s, 2H).

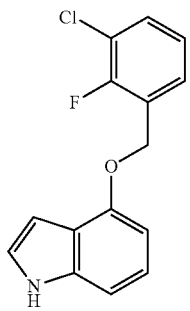 [SMILES: Fc1c(Cl)cccc1COc1cccc2[nH]ccc12]

4-(3-chloro-2-fluorobenzyloxy)-1H-indole (20e). This was prepared from 4-hydroxyindole (0.100 g, 0.751 mmol) and 2-fluorobenzylbromide (0.201 g, 0.901 mmol) in a similar manner as described for preparation of 20a. Reaction time: 34 hrs. Chromatography on silica gel, performed using the Flash Master purification station (AcOEt/Hexane), afforded an off-white solid, 20e (0.372 g, 1.44 mmol, 72%) as an off white solid. Analysis of $^1$H NMR revealed that a mixture of the desired product and an unknown impurity was isolated. The mixture was used as obtained in the next step. ¹H NMR (400 MHz, CDCl₃) δ 8.32 (s, 1H), 7.53 (t, J=7.0 Hz, 1H), 7.41-7.34 (m, 1H), 7.14-7.01 (m, 4H), 6.72 (t, J=2.7 Hz, 1H), 6.60 (d, J=7.6 Hz, 1H), 5.32 (s, 2H).

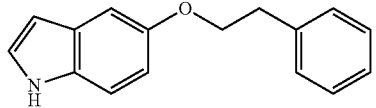 [SMILES: c1ccc(CCOc2ccc3[nH]ccc3c2)cc1]

5-phenethoxy-1H-indole (20f). This was prepared from (2-bromoethyl)benzene (0.557 g, 3.00 mmol) and 5-hydroxyindole (0.400 g, 3.00 mmol) in a similar manner as described for preparation of 20a. Reaction tim1: 24 hrs. Chromatography on silica gel, performed using the Flash Master purification station (AcOEt/Hexane), afforded 20f (0.090 g, 0.378 mmol, 13%) as a brown oil. ¹H NMR (400 MHz, CDCl₃) δ 8.04 (bs, 1H), 7.35-7.32 (m, 2H), 7.26 (m, 3H), 7.18 (t, J=2.8 Hz, 1H), 7.11 (d, J=2.3 Hz, 1H), 6.87 (dd, J=2.4, 8.8 Hz, 1H), 6.46 (m, 1H), 4.23 (t, J=7.2 Hz, 2H), 3.13 (t, J=7.2 Hz, 2H).

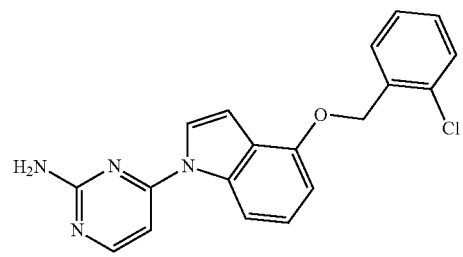 [SMILES: Nc1nccc(-n2ccc3c(OCc4ccccc4Cl)cccc32)n1]

4-(4-(2-chlorobenzyloxy)-1H-indol-1-yl)pyrimidin-2-amine (21h) A mixture of 20b (0.068 g, 0.264 mmol) and 2-amino-4-chloropyrimidine (0.041 g, 0.317 mmol) in anhydrous 1-Methyl-2-pyrrolidinone (0.42 mL) and cesium carbonate (0.328 g, 1.00 mmol), was heated in the microwave at 150° C. for 30 minutes. After cooling to room temperature, the solvent was removed under reduced pressure. Chromatography on silica gel, performed using the Flash Master 3 purification station (AcOEt/Hexane), afforded a yellow oil. Water was added and the solid precipitate was filtered, washed with water and dried under vacuum. Pure 21h was obtained as an off white solid (0.017 g, 0.0486 mmol, 18%). ¹H NMR (400 MHz, CDCl₃) δ 8.27 (bs, 1H), 7.97 (d, J=8.5 Hz, 1H), 7.58-7.56 (m, 2H), 7.35 (dd, J=1.7, 7.2 Hz, 1H), 7.25-7.14 (m, 3H), 6.86 (d, J=3.6 Hz, 1H), 6.74 (d, J=4.9 Hz, 1H), 6.66 (d, J=7.9 Hz, 1H), 5.27 (s, 2H), 5.21 (bs, 2H); HPLC purity 99.87% {t_R=5.047 min, Flow 1 ml/min, [(MeOH/(0.1% TFA in H₂O):70/30]}; HRMS (ESI+ve) m/z calculated for C₁₉H₁₆N₄OCl (M+H)⁺ 351.1007, found 351.1000.

4-(4-(3-chlorobenzyloxy)-1H-indol-1-yl)pyrimidin-2-amine (21g). This was prepared from 20c (0.100 g, 0.382 mmol) and 2-amino-4-chloropyrimidine (0.060 g, 0.458 mmol) in a similar manner as described for 12 h. Chromatography on silica gel, performed using the Flash Master 3 purification station (AcOEt/Hexane), afforded a yellow oil. Water was added and the solid precipitate was filtered, washed with water, dried under vacuum, triturated with a solution of hexane/ethyl acetate (8/2), filtered and dried under vacuum. Pure 21g was obtained as an off white solid (0.020 g, 0.056 mmol, 15%). ¹H NMR (400 MHz, CDCl₃) δ 8.31 (d, J=5.9 Hz, 1H), 8.04 (d, J=8.4 Hz, 1H), 7.64 (d, J=3.6 Hz, 1H), 7.51 (s, 1H), 7.34 (m, 3H), 7.22 (m, 1H), 6.90 (d, J=3.6 Hz, 1H), 6.80 (d, J=5.7 Hz, 1H), 6.69 (d, J=7.8 Hz, 1H), 5.21 (s, 2H), 5.11 (s, 2H); HPLC purity 99.40% {t_R=5.047 min, Flow 1 ml/min, [(MeOH/(0.1% TFA in H₂O):70/30]}; HRMS (ESI+ve) m/z calculated for C₁₉H₁₆N₄OCl (M+H)⁺ 351.1007, found 351.0997.

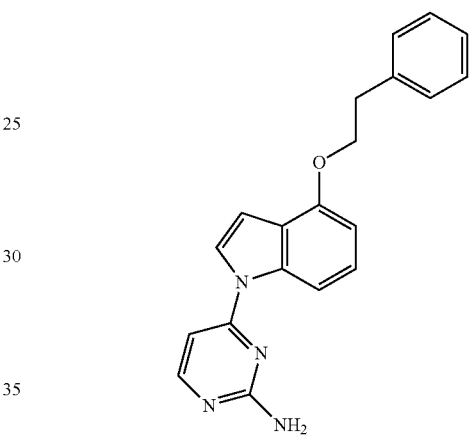

4-(4-phenethoxy-1H-indol-1-yl)pyrimidin-2-amine (21c). This was prepared from 20a (0.211 g, 0.890 mmol) and 2-amino-4-chloropyrimidine (0.115 g, 0.890 mmol) in a similar manner as described for 12 h. Chromatography on silica gel, performed using the Flash Master 3 purification station, afforded a yellow oil. Water was added and the solid precipitate was filtered, washed with water, dried under vacuum. Pure 21c was obtained as an off white solid (0.071 g, 0.212 mmol, 24%). ¹H NMR (400 MHz, DMSO-d₆) δ 8.32 (d, J=8.4 Hz, 1H), 8.23 (d, J=5.7 Hz, 1H), 7.91 (d, J=3.7 Hz, 1H), 7.37 (d, J=7.3 Hz, 2H), 7.31 (t, J=7.5 Hz, 2H), 7.23-7.18 (m, 1H), 7.15 (t, J=8.2 Hz, 1H), 6.91 (s, OH), 6.86 (s, 2H), 6.74 (d, J=8.0 Hz, 1H), 6.67 (d, J=3.6 Hz, 1H), 4.29 (t, J=6.7 Hz, 2H), 3.10 (t, J=6.6 Hz, 2H). HPLC purity 99.14% {t_R=5.780 min, Flow 1 ml/min, [(MeOH/(0.1% TFA in H₂O):60/40]}; HRMS (ESI+ve) m/z calculated for C₂₀H₁₉N₄O (M+H)⁺ 331.1553, found 331.1551.

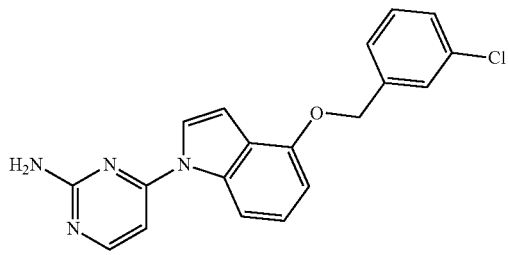 [SMILES: Nc1nccc(-n2ccc3c(OCc4cccc(Cl)c4)cccc32)n1]

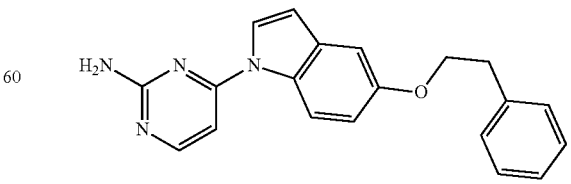

4-(5-phenethoxy-1H-indol-1-yl)pyrimidin-2-amine (21f). This was prepared from 20f (0.100 g, 0.420 mmol) and 2-amino-4-chloropyrimidine (0.065 g, 0.504 mmol) in a similar manner as described for 12 h. Chromatography on silica gel, performed using the Flash Master 3 purification station, afforded a yellow oil. Water was added and the solid precipitate was filtered, washed with water, dried under vacuum. Pure 21f was obtained as an off white solid (0.038 g, 0.115 mmol, 27%). $^1$H NMR (400 MHz, CDCl$_3$) δ 8.37 (d, J=9.1 Hz, 1H), 8.27 (d, J=5.8 Hz, 1H), 7.66 (d, J=3.6 Hz, 1H), 7.35-7.31 (m, 3H), 7.27-7.23 (m, 2H), 7.08 (d, J=2.5 Hz, 1H), 6.94 (dd, J=2.5, 9.1 Hz, 1H), 6.73 (d, J=5.7 Hz, 1H), 6.62 (d, J=3.6 Hz, 1H), 5.09 (s, 2H), 4.24 (t, J=7.2 Hz, 2H), 3.14 (t, J=7.2 Hz, 2H); HPLC purity 99.05% {t$_R$=16.960 min, Flow 1 ml/min, [(MeOH/(0.1% TFA in H$_2$O):60/40]}; HRMS (ESI+ve) m/z calculated for C$_{20}$H$_{19}$N$_4$O (M+H)$^+$ 331.1553, found 331.1545.

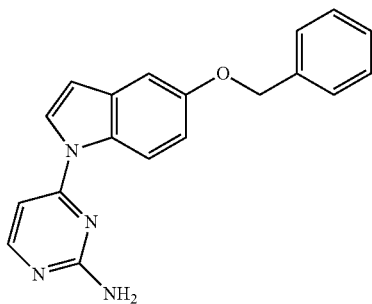 [SMILES: Nc1nccc(-n2ccc3cc(OCc4ccccc4)ccc32)n1]

4-(5-(benzyloxy)-1H-indol-1-yl)pyrimidin-2-amine (21b)
A mixture of 5-benzyloxyindole (0.207 g, 0.926 mmol), 2-amino-4-chloropyrimidine (0.080 g, 0.617 mmol), and cesium carbonate (0.600 g, 0.59 mmol) in NMP (0.65 mL) was stirred, at 150° C. for 30 minutes in a microwave. After cooling to room temperature, water was added and the reaction mixture was extracted with DCM. The organic extract was dried over Na$_2$SO$_4$, the solvent removed under reduced pressure. Chromatography on silica gel, performed using the Flash Master 3 purification station (AcOEt/Hexane), afforded a yellow oil. Water was added and the solid precipitate was filtered, washed with water, dried under vacuum. Pure 21b was obtained as an off white solid (0.058 g, 0.183 mmol, 30%). $^1$H NMR (400 MHz, DMSO-d$_6$) δ 8.71 (d, J=9.1 Hz, 1H), 8.20 (d, J=5.7, 1H), 8.01 (d, J=3.6 Hz, 1H), 7.47 (d, J=7.0, 2H), 7.38 (t, J=7.4 Hz, 2H), 7.31 (t, J=7.9 Hz, 1H), 7.20 (d, J=2.4 Hz, 1H), 6.92-6.88 (m, 2H), 6.84 (bs, 2H), 6.67 (d, J=3.6 Hz, 1H), 5.13 (s, 2H); HPLC purity 97.28% {t$_R$=10.960 min, Flow 1 ml/min, [(MeOH/(0.1% TFA in H$_2$O):60/40]}; HRMS (ESI+ve) m/z calculated for C$_{18}$H$_{17}$N$_4$O (M+H)$^+$ 317.1396, found 317.1396.

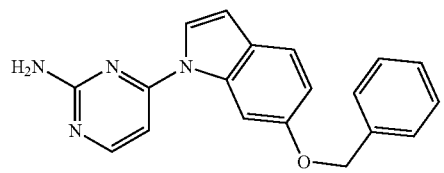 [SMILES: Nc1nccc(-n2ccc3ccc(OCc4ccccc4)cc32)n1]

4-(6-(benzyloxy)-1H-indol-1-yl)pyrimidin-2-amine (21i)
This was prepared from 6-(benzyloxy)-1H-indole (0.145 g, 0.643 mmol) and 2-amino-4-chloropyrimidine (0.100 g, 0.772 mmol) in a similar manner as described for 12 h.-Chromatography on silica gel, performed using the Flash Master 3 purification station (AcOEt/Hexane), afforded a yellow oil. Water was added and the solid precipitate was filtered, washed with water, dried under vacuum. Pure 21i was obtained as a pink solid (0.069 g, 0.219 mmol, 34. $^1$H NMR (400 MHz, CDCl$_3$) δ 8.19 (d, J=5.8 Hz, 1H), 8.06 (d, J=2.2 Hz, 1H), 7.47 (d, J=3.6 Hz, 1H), 7.43-/7.41 (m, 1H), 7.36-7.32 (m, 2H), 7.29-7.26 (d, J=7.3 Hz, 1H), 6.91 (dd, J=8.6, 2.3 Hz, 1H), 6.61 (d, J=5.8 Hz, 1H), 6.57 (d, J=3.5 Hz, 1H), 5.12 (s, 2H), 4.99 (s, 1H).); HPLC purity 99.87% {t$_R$=3.733 min, Flow 1 ml/min, [(MeOH/(0.1% TFA in H$_2$O):70/30]}; HRMS (ESI+ve) m/z calculated for C$_{19}$H$_{17}$N$_4$O (M+H)$^+$ 317.1396, found 317.1387.

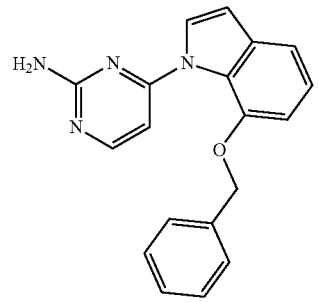 [SMILES: Nc1nccc(-n2ccc3cccc(OCc4ccccc4)c32)n1]

4-(6-(benzyloxy)-1H-indol-1-yl)pyrimidin-2-amine (21j)
This was prepared from 7-(benzyloxy)-1H-indole (0.145 g, 0.643 mmol) and 2-amino-4-chloropyrimidine (0.100 g, 0.772 mmol) in a similar manner as described for 12 h.-Chromatography on silica gel, performed using the Flash Master 3 purification station (AcOEt/Hexane), afforded a yellow oil. Water was added and the solid precipitate was filtered, washed with water, dried under vacuum. Pure 21j was obtained as a pink solid (0.016 g, 0.051 mmol, 7%). $^1$H NMR (400 MHz, DMSO-d$_6$) δ 8.04 (d, J=5.4 Hz, 1H), 7.63 (d, J=3.5 Hz, 1H), 7.35-7.28 (m, 5H), 7.24 (d, J=7.7 Hz, 1H), 7.11 (t, J=7.8 Hz, 1H), 6.95 (d, J=7.9 Hz, 1H), 6.72 (s, 2H), 6.67 (d, J=3.3 Hz, 1H), 6.58 (d, J=5.4 Hz, 1H), 5.15 (s, 2H). HPLC purity 98.79% {t$_R$=3.360 min, Flow 1 ml/min, [(MeOH/(0.1% TFA in H$_2$O):70/30]}; HRMS (ESI+ve) m/z calculated for C$_{19}$H$_{17}$N$_4$O (M+H)$^+$ 317.1396, found 317.1406.

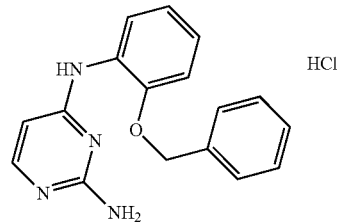 [SMILES: Nc1nccc(Nc2ccccc2OCc2ccccc2)n1 ; Cl]

N4-(2-(benzyloxy)phenyl)pyrimidine-2,4-diamine (1ah)
A mixture of 2-(benzyloxy)aniline (0.154 g, 0.772 mmol) and 2-amino-4-chloropyrimidine (0.100 g, 0.77 2 mmol) in anhydrous ethanol (0.700 mL) was stirred, at 150° C. for 20 minutes in a microwave. After cooling to room temperature, the solvent was removed under reduced pressure. Ethyl acetate was added and the mixture was stirred under refluxed for 2 h. The solid precipitated was filtered, dried under vacuum. Pure 1ah was obtained as an off white solid (0.135 g, 0.462 mmol, 60%). $^1$H NMR (400 MHz, CD$_3$OD) δ 7.79 (s, 1H), 7.66 (s, 1H), 7.4-7.13 (m, 6H), 7.00 (s, 1H), 6.40 (s, 1H), 5.17 (s, 2H); purity 97.96% {t$_R$=7.327 min, Flow 1 ml/min, [(MeOH/(0.1% TFA in H₂O):50/50]}; HRMS (ESI+ve) m/z calculated for $C_{17}H_{17}N_4O$ (M+H—Cl)⁺ 293.1396, found 293.1392.

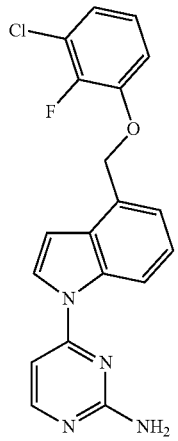 [SMILES: Nc1nccc(-n2ccc3c(COc4cccc(Cl)c4F)cccc32)n1]

4-(4-(3-chloro-2-fluorobenzyloxy)-1H-indol-1-yl)pyrimidin-2-amine (21d). This was obtained from 2-amino-4-chloropyrimidine (0.062 g, 0.478 mmol), and 20e (0.088 g, 0.319 mmol) in a similar manner as described for 15c. After cooling to room temperature, the reaction mixture diluted with water and extracted with DCM. The organic extract was dried over Na₂SO₄ and the solvent removed under reduced pressure. Chromatography on silica gel using the FlashMaster 3 purification station (AcOEt/Hexane) afforded 21d as an off white solid. The obtained solid was slurried with ether, filtered, and dried in vacuo. Pure 21d was obtained (0.025 g, 0.067 mmol, 21%) as an off-white solid. ¹H NMR (400 MHz, DMSO-d₆) δ 8.39 (d, J=8.5 Hz, 1H), 8.24 (d, J=5.6 Hz, 1H), 7.95 (d, J=3.7 Hz, 1H), 7.62-7.56 (m, 2H), 7.27 (t, J=8.4 Hz, 1H), 7.19 (t, J=8.2 Hz, 1H), 6.93 (d, J=5.7 Hz, 1H), 6.87-6.85 (m, 3H), 6.77 (d, J=3.6 Hz, 1H), 5.33 (s, 2H). HPLC: Purity 99.72%, MeOH 70%, (0.1% TFA in H₂O) 30%, 20 min, Flow 1 ml/min, $R_t$ 7.233 min. HRMS (ESI–ve) calculated for $C_{19}H_{15}N_5OClF$ (M+H)⁺ 369.0912, found 369.0912

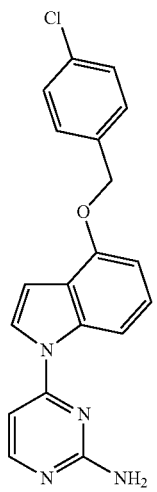 [SMILES: Nc1nccc(-n2ccc3c(OCc4ccc(Cl)cc4)cccc32)n1]

4-(4-(4-chlorobenzyloxy)-1H-indol-1-yl)pyrimidin-2-amine (21e) This was obtained from 2-amino-4-chloropyrimidine (0.109 g, 0.843 mmol), and 20d (0.144 g, 0.562 mmol) in a similar manner as described for 15c. After cooling to room temperature, the reaction mixture diluted with water and extracted with DCM. The organic extract was dried over Na₂SO₄ and the solvent removed under reduced pressure. Chromatography on silica gel using the FlashMaster 3 purification station (AcOEt/Hexane) afforded 21e as an off white solid. Water was added to the obtained solid and the solid precipitate was filtered, washed with water, slurried with a solution CH₃CN/Ether, filtered, and dried in vacuo. Pure 21e was obtained (0.035 g, 0.099 mmol, 18%) as an off-white solid. ¹H NMR (400 MHz, DMSO-d₆) δ 8.36 (d, J=8.5 Hz, 1H), 8.24 (d, J=5.7 Hz, 1H), 7.95 (d, J=3.7 Hz, 1H), 7.53 (d, J=8.5 Hz, 2H), 7.45 (d, J=8.5 Hz, 2H), 7.17 (t, J=8.2 Hz, 1H), 6.92 (d, J=5.7 Hz, 1H), 6.87 (s, 2H), 6.80-6.78 (m, 2H), 5.24 (s, 2H). HPLC: Purity 99.77%, MeOH 70%, (0.1% TFA in H₂O) 30%, 20 min, Flow 1 ml/min, $R_t$ 6.827 min. HRMS (ESI–ve) calculated for $C_{19}H_{16}N_5OCl$ (M+H)⁺ 351.1007, found 351.1009

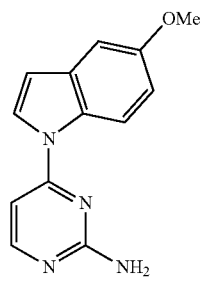 [SMILES: COc1ccc2c(ccn2-c2ccnc(N)n2)c1]

4-(5-methoxy-1H-indol-1-yl)pyrimidin-2-amine (15f). This was obtained from 2-amino-4-chloropyrimidine (0.103 g, 0.795 mmol), and 5-methoxyyindole (0.175 g, 1.19 mmol) in a similar manner as described for 15c. After cooling to room temperature, the reaction mixture diluted with water and extracted with DCM. The organic extract was dried over Na₂SO₄ and the solvent removed under reduced pressure. Chromatography on silica gel using the FlashMaster 3 purification station (AcOEt/Hexane) afforded 15f as an off white solid. Water was added to the obtained solid and the solid precipitate was filtered, washed with water and dried in vacuo. Pure 15f was obtained (0.084 g, 0.348 mmol, 44%) as an off-white solid. ¹H NMR (400 MHz, DMSO-d₆) δ 8.70 (d, J=9.1 Hz, 1H), 8.20 (d, J=5.7 Hz, 1H), 8.01 (d, J=3.6 Hz, 1H), 7.11 (d, J=2.5 Hz, 1H), 6.89 (d, J=5.7 Hz, 1H), 6.85-6.82 (m, 2H), 6.67 (d, J=3.5 Hz, 1H), 3.77 (s, 3H); HPLC: Purity 98.73%, CH₃CN 30%, (0.1% TFA in H₂O) 70%, 20 min, Flow 1 ml/min: $R_t$ 4.760 min; Purity 99.68%, MeOH 40%, (0.1% TFA in H₂O) 60%, 20 min, Flow 1 ml/min, $R_t$ 14.147 min, HRMS (ESI–ve) calculated for $C_{13}H_{13}ON_4$ (M+H)⁺ 241.1083, found 241.1086.

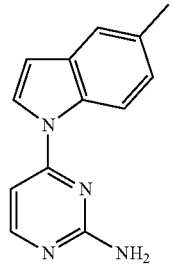 [SMILES: Cc1ccc2c(ccn2-c2ccnc(N)n2)c1]

4-(5-methyl-1H-indol-1-yl)pyrimidin-2-amine (15g). This was obtained from 2-amino-4-chloropyrimidine (0.096 g, 0.741 mmol), and 5-methylindole (0.194 g, 1.482 mmol) in a similar manner as described for 15c. After cooling to room temperature, the reaction mixture diluted with water and extracted with DCM. The organic extract was dried over $Na_2SO_4$ and the solvent removed under reduced pressure. Chromatography on silica gel using the FlashMaster 3 purification station (AcOEt/Hexane) afforded 15g as an off white solid. Water was added to the obtained solid and the solid precipitate was filtered, washed with water and dried in vacuo. Pure 15g was obtained (0.056 g, 0.249 mmol, 37%) as an off-white solid. $^1$H NMR (400 MHz, DMSO-$d_6$) δ 8.65 (d, J=8.5 Hz, 1H), 8.21 (d, J=5.7 Hz, 1H), 7.99 (d, J=3.7 Hz, 1H), 7.37 (s, 1H), 7.07 (dd, J=8.6, 1.8 Hz, 1H), 6.90 (d, J=5.7 Hz, 1H), 6.84 (s, 2H), 6.66 (d, J=3.6 Hz, 1H), 2.38 (s, 3H). HPLC: Purity 99.52%, $CH_3CN$ 30%, (0.1% TFA in $H_2O$) 70%, 20 min, Flow 1 ml/min, $R_t$ 7.873 min. HRMS (ESI–ve) calculated for $C_{13}H_{13}N_4$ (M+H)$^+$ 225.1134, found 225.1134

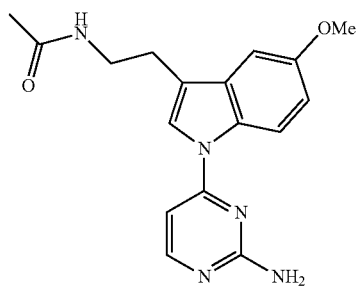 [SMILES: COc1ccc2c(c1)c(CCNC(C)=O)cn2-c1ccnc(N)n1]

N-(2-(1-(2-aminopyrimidin-4-yl)-5-methoxy-1H-indol-3-yl)ethyl)acetamide (15h). This was obtained from 2-amino-4-chloropyrimidine (0.043 g, 0.333 mmol), and melatonine (0.155 g, 0.667 mmol) in a similar manner as described for 15c. After cooling to room temperature, the reaction mixture diluted with water and extracted with DCM. The organic extract was dried over $Na_2SO_4$ and the solvent removed under reduced pressure. Chromatography on silica gel using the FlashMaster 3 purification station (AcOEt/MeOH) afforded 15h as an off white solid. Water was added to the obtained solid and the solid precipitate was filtered, washed with water and dried in vacuo. Pure 15h was obtained (0.028 g, 0.086 mmol, 13%) as an off-white solid. $^1$H NMR (400 MHz, DMSO-$d_6$) δ 8.70 (d, J=9.0 Hz, 1H), 8.17 (d, J=5.7 Hz, 1H), 8.02 (t, J=4.6 Hz, 1H), 7.83 (s, 1H), 7.10 (d, J=2.5 Hz, 1H), 6.85-6.83 (m, 2H), 6.78 (s, 2H), 3.79 (s, 3H), 2.79 (t, J=7.1 Hz, 2H), 1.79 (s, 3H). HPLC: Purity 91.11%, MeOH 50%, (0.1% TFA in $H_2O$) 50%, 20 min, Flow 1 ml/min, $R_t$ 4.153 min. HRMS (ESI–ve) calculated for $C_{17}H_{20}N_5O_2$ (M+H)$^+$ [M+H]+326.1611, found 326.1620

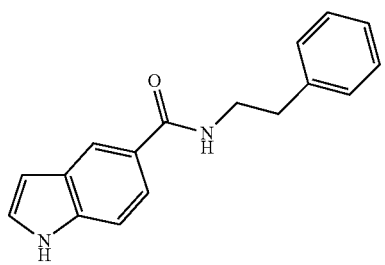 [SMILES: O=C(NCCc1ccccc1)c1ccc2[nH]ccc2c1]

N-phenethyl-1H-indole-5-carboxamide (23a) A mixture of indole-5-carboxylic acid (0.173 g, 1.073 mmol) and 2-phenylethanamine (0.143 g, 1.180 mmol), EDC-HCl (0.226 g g, 1.178 mmol), cat. 4-dimethylaminopyridine in DCM (1.1 mL) was heated in the Biotage Microwave for 15 min at 60° C. The solution was washed with aq. 1N HCl, extracted with DCM. The organic phase was separated, washed with aq. $NaHCO_3$ (sat. solution), separated, dried over $Na_2SO_4$, filtered, and the solvent removed under reduced pressure to provide 23a (0.160 g, 0.606 mmol, 56%) as an off white solid. The crude material was used as obtained in the next step. $^1$H NMR (400 MHz, CDCl$_3$) δ 8.54 (s, 1H), 8.02 (d, J=1.6 Hz, 1H), 7.58 (dd, J=8.5, 1.7 Hz, 1H), 7.39 (d, J=8.5 Hz, 1H), 7.36-7.30 (m, 2H), 7.28-7.24 (m, 4H), 6.62-6.58 (m, 1H), 6.21 (s, 1H), 3.76 (q, J=6.8 Hz, 2H), 2.96 (t, J=6.9 Hz, 2H).

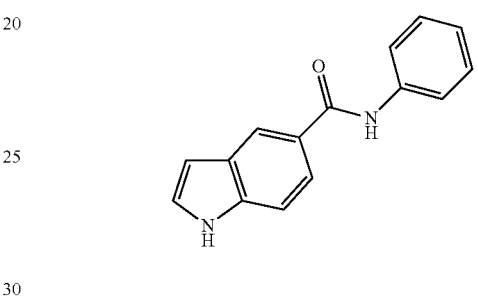

N-phenyl-1H-indole-5-carboxamide (23b) This was obtained as an off white solid (0.145 g, 0.614 mmol, 55%) from indole-5-carboxylic acid (0.182 g, 1.129 mmol) and aniline (0.115 g, 1.242 mmol) in a similar manner as described for 23a. The crude material was used as obtained in the next step. $^1$H NMR (400 MHz, CDCl$_3$) δ 8.49 (s, 1H), 8.21 (s, 1H), 7.91 (s, 1H), 7.75 (dd, J=8.5, 1.6 Hz, 1H), 7.68 (d, J=8.0 Hz, 2H), 7.47 (d, J=8.6 Hz, 1H), 7.38 (t, J=7.9 Hz, 2H), 7.32-7.30 (m, 1H), 7.15 (t, J=7.4 Hz, 1H), 6.67-6.66 (m, 1H).

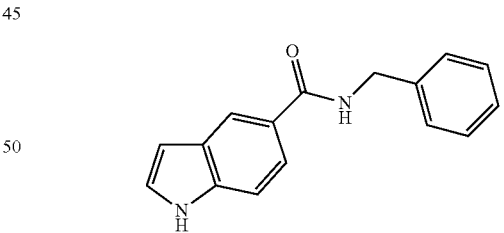

N-benzyl-1H-indole-5-carboxamide (23c) This was obtained as an off white solid (0.179 g, 0.716 mmol, 73%) from indole-5-carboxylic acid (0.158 g, 0.980 mmol) and benzylamine (0.115 g, 1.078 mmol) in a similar manner as described for 23a. The crude material was used as obtained in the next step. $^1$H NMR (400 MHz, CDCl$_3$) δ 9.32 (s, 1H), 8.13 (s, 1H), 7.63 (dd, J=8.5, 1.6 Hz, 1H), 7.36-7.25 (m, 6H), 7.21-7.14 (t, J=2.7 Hz, 1H), 6.72 (t, J=5.6 Hz, 1H), 6.54-6.53 (m, 1H), 4.66 (d, J=5.7 Hz, 2H).

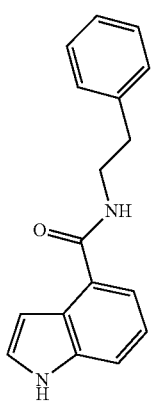 [SMILES: O=C(NCCc1ccccc1)c1cccc2[nH]ccc12]

N-phenethyl-1H-indole-4-carboxamide (23d) This was obtained as an off white solid (0.206 g, 0.780 mmol, 67%) from indole-4-carboxylic acid (0.189 g, 1.172 mmol) and 2-phenylethanamine (0.56 g, 1.290 mmol) in a similar manner as described for 23a. The crude material was used as obtained in the next step. $^1$H NMR (400 MHz, CDCl$_3$) δ 9.22 (s, 1H), 7.45 (s, J=6.4 Hz, 2H), 7.34-7.31 (m, 2H), 7.27-7.25 (m, 3H), 7.21 (t, J=2.7 Hz, 1H), 7.15 (t, J=7.8 Hz, 1H), 6.69 (s, 1H), 6.36-6.34 (m, 1H), 3.81 (q, J=6.8 Hz, 2H), 2.99 (t, J=6.9 Hz, 2H).

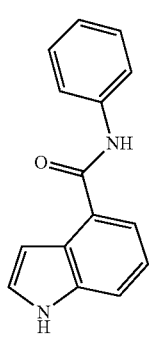 [SMILES: O=C(Nc1ccccc1)c1cccc2[nH]ccc12]

N-phenyl-1H-indole-4-carboxamide (23e) This was obtained as an off white solid (0.265 g, 1.12 mmol, 77%) from indole-4-carboxylic acid (0.235 g, 1.450 mmol) and aniline (0.149 g, 1.603 mmol) in a similar manner as described for 23a. The crude material was used as obtained in the next step. $^1$H NMR (400 MHz, CDCl$_3$) δ 9.16 (s, 1H), 8.10 (s, 1H), 7.70 (d, J=9.5 Hz, 1H), 7.60 (d, J=7.4 Hz, 1H), 7.50 (d, J=8.2 Hz, 1H), 7.40-7.36 (m, 2H), 7.27-=7.26 (m, 1H), 7.22 (d, J=7.9 Hz, 1H), 7.18-7.13 (m, 1H), 6.95-6.94 (m, 1H).

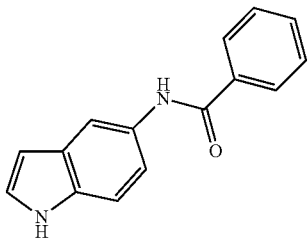 [SMILES: O=C(Nc1ccc2[nH]ccc2c1)c1ccccc1]

N-(1H-indol-5-yl)benzamide (26a) This was obtained from 5-aminoindole (0.235 g, 1.450 mmol) and benzoic acid (0.149 g, 1.603 mmol) in a similar manner as described for 21a. Chromatography on silica gel using the FlashMaster 3 purification station (AcOEt/hexane) afforded pure 26a (0.137 g, 0.580 mmol, 40%). $^1$H NMR (400 MHz, CDCl$_3$) δ 8.22 (s, 1H), 7.98 (s, 1H), 7.91 (d, J=7.0 Hz, 2H), 7.86 (s, 1H), 7.57-7.48 (m, 3H), 7.39-7.37 (m, 2H), 7.24 (t, J=3.0 Hz, 1H), 6.55 (t, J=2.5 Hz, 1H)

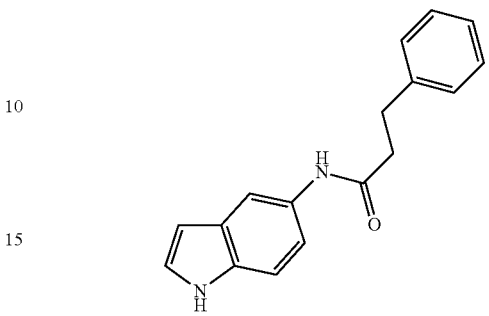

N-(1H-indol-5-yl)-3-phenylpropanamide (26b) This was obtained as an off white solid (0.343 g, 0.972 mmol, 74%) from 5-aminoindole (0.174 g, 1.316 mmol) and 3-phenylpropanoic acid (0.237 g, 1.579 mmol) in a similar manner as described for 21a. The crude material was used as obtained in the next step. $^1$H NMR (400 MHz, CDCl$_3$) δ 8.47 (s, 1H), 7.64 (d, J=1.7 Hz, 1H), 7.30 (s, 1H), 7.23-7.11 (m, 6H), 7.07-7.04 (d, J=2.8 Hz, 1H), 7.03 (dd, J=8.7, 1.9 Hz, 1H), 6.38 (s, 1H), 2.98 (t, J=7.7 Hz, 2H), 2.57 (t, J=7.7 Hz, 2H).

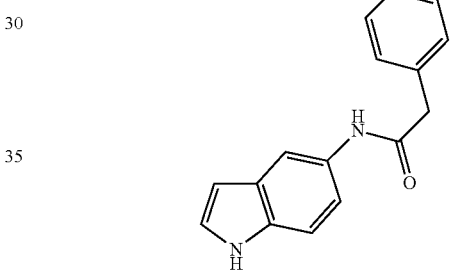

N-(1H-indol-5-yl)-2-phenylacetamide (26c). This was obtained as an off white solid (0.629 g, 2.50 mmol, 92%) from 5-aminoindole (0.357 g, 2.70 mmol) and 2-phenylacetic acid (0.478 g, 3.5 mmol) in a similar manner as described for 21a. The crude material was used as obtained in the next step. $^1$H NMR (400 MHz, CDCl$_3$) δ 8.22 (s, 1H), 7.74 (d, J=1.8 Hz, 1H), 7.46-7.31 (m, 4H), 7.28-7.26 (m, 2H), 7.18 (d, J=2.6 Hz, 1H), 7.12 (d, J=2.0 Hz, 1H), 7.10 (d, J=2.0 Hz, 1H), 6.48-6.46 (m, 1H), 3.77 (s, 2H).

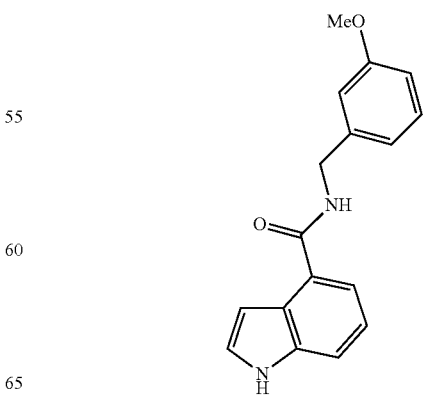

N-(3-methoxybenzyl)-1H-indole-4-carboxamide (29a) A mixture of indole-5-carboxylic acid (0.258 g, 1.60 mmol) and 3-methoxybenzylamine (0.263 g, 1.92 mmol), EDC-HCl (0.432 g g, 2.26 mmol), cat. 4-dimethylaminopyridine (0.007 g) in CH₃CN (1.1 mL) was heated in the Biotage Microwave for 30 min at 80° C. The solution was washed with aq. 1N HCl, extracted with DCM. The organic phase was separated, washed with aq. NaHCO₃ (sat. solution), separated, dried over Na₂SO₄, filtered, and the solvent removed under reduced pressure to provide 29a (0.311 g, 1.11 mmol, 69%) as an off white solid. The crude material was used as obtained in the next step. ¹H NMR (400 MHz, CDCl₃) δ 8.48 (s, 1H), 7.53-7.50 (m, 2H), 7.34-7.27 (m, 2H), 7.24-7.19 (d, J=7.8 Hz, 1H), 6.99 (d, J=7.7 Hz, 1H), 6.95-6.93 (m, 2H), 6.84 (dd, J=8.1, 2.7 Hz, 1H), 6.51 (s, 1H), 4.71 (d, J=5.8 Hz, 2H), 3.80 (s, 3H).

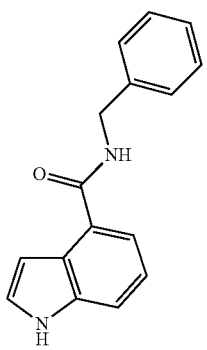 [SMILES: O=C(NCc1ccccc1)c1cccc2[nH]ccc12]

N-benzyl-1H-indole-4-carboxamide (23f) This was obtained as an off white solid (0.229 g, 0.916 mmol, 66%) from indole-4-carboxylic acid (0.225 g, 1.396 mmol) and benzylamine (0.165 g, 1.535 mmol) in a similar manner as described for 29a. The crude material was used as obtained in the next step. ¹H NMR (400 MHz, CDCl₃) δ 8.86 (s, 1H), 7.51 (d, J=4.3 Hz, 1H), 7.49 (d, J=5.1 Hz, 1H), 7.40-7.33 (m, 4H), 7.31-7.25 (m, 2H), 7.17 (t, J=8 Hz, 1H), 6.89 (s, 1H), 6.60 (s, 1H), 4.73 (d, J=5.6 Hz, 2H).

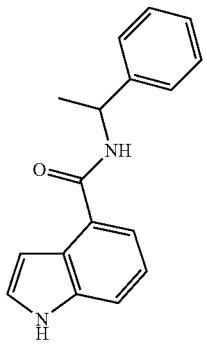 [SMILES: CC(NC(=O)c1cccc2[nH]ccc12)c1ccccc1]

N-(1-phenylethyl)-1H-indole-4-carboxamide (29b) This was obtained as an off white solid (0.218 g, 0825 mmol, 52%) from indole-4-carboxylic acid (0.256 g, 1.588 mmol) and 1-phenylethanamine (0.230 g, 1.98 mmol) in a similar manner as described for 29a. The crude material was used as obtained in the next step. ¹H NMR (400 MHz, CDCl₃) δ 8.67 (s, 1H), 7.45-7.35 (m, 4H), 7.27 (t, J=7.5 Hz, 2H), 7.20-7.14 (m, 2H), 7.12 (t, J=7.8 Hz, 1H), 6.81 (s, 1H), 6.42 (d, J=7.9 Hz, 1H), 5.37 (quin, J=7.0 Hz, 1H), 1.57 (d, J=6.8 Hz, 3H).

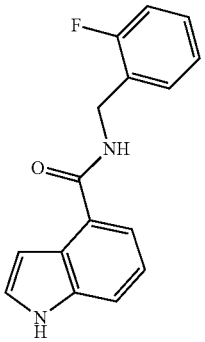 [SMILES: O=C(NCc1ccccc1F)c1cccc2[nH]ccc12]

N-(2-fluorobenzyl)-1H-indole-4-carboxamide (29c) This was obtained as an off white solid (0.354 g, 1.32 mmol, 66%) from indole-4-carboxylic acid (0.322 g, 1.99 mmol) and 2-fluorobenzylamine (0.300 g, 2.39 mmol) in a similar manner as described for 29a. The crude material was used as obtained in the next step. ¹H NMR (400 MHz, CDCl₃) δ 8.52 (s, 1H), 7.53-7.39 (m, 3H), 7.32-7.21 (m, 3H), 7.14-7.05 (m, 2H), 6.93 (s, 1H), 6.62 (s, 1H), 4.78 (d, J=5.9 Hz, 2H).

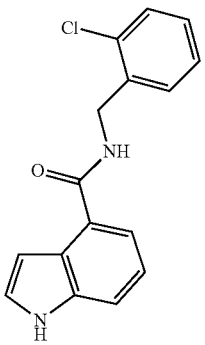 [SMILES: O=C(NCc1ccccc1Cl)c1cccc2[nH]ccc12]

N-(2-chlorobenzyl)-1H-indole-4-carboxamide (29d) This was obtained as an off white solid (0.373 g, 1.31 mmol, 71%) from indole-4-carboxylic acid (0.296 g, 1.83 mmol) and 2-chlorobenzylamine (0.312 g, 2.20 mmol) in a similar manner as described for 29a. The crude material was used as obtained in the next step. ¹H NMR (400 MHz, CDCl₃) δ 8.53 (s, 1H), 7.58-7.49 (m, 3H), 7.42-7.38 (m, 1H), 7.32 (t, J=3.0 Hz, 1H), 7.26-7.19 (m, 3H), 6.95 (m, 1H), 6.72 (s, 1H), 4.81 (d, J=6.0 Hz, 2H).

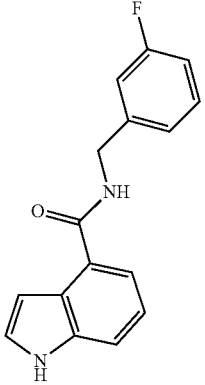 [SMILES: O=C(NCc1cccc(F)c1)c1cccc2[nH]ccc12]

N-(3-fluorobenzyl)-1H-indole-4-carboxamide (29e) This was obtained as an off white solid (0.221 g, 0.824 mmol, 52%) from indole-4-carboxylic acid (0.257 g, 1.59 mmol) and 3-fluorobenzylamine (0.238 g, 1.90 mmol) in a similar manner as described for 29a. The crude material was used as obtained in the next step. $^1$H NMR (400 MHz, CDCl$_3$) δ 8.53 (s, 1H), 7.54-7.51 (m, 2H), 7.29-7.32 (m, 2H), 7.25-7.17 (m, 2H), 7.12 (d, J=7.9 Hz, 1H), 7.05-6.93 (m, 2H), 6.59 (s, 1H), 4.72 (d, J=6.0 Hz, 2H).

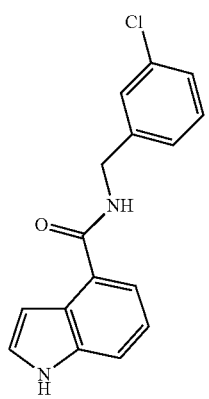 [SMILES: O=C(NCc1cccc(Cl)c1)c1cccc2[nH]ccc12]

N-(3-chlorobenzyl)-1H-indole-4-carboxamide (29f) This was obtained as an off white solid (0.244 g, 0.859 mmol, 55%) from indole-4-carboxylic acid (0.252 g, 1.56 mmol) and 3-chlorobenzylamine (0.264 g, 1.87 mmol) in a similar manner as described for 29a. The crude material was used as obtained in the next step. $^1$H NMR (400 MHz, CDCl$_3$) δ 8.58 (s, 1H), 7.56-7.50 (m, 2H), 7.39 (d, J=1.9 Hz, 1H), 7.32 (t, J=2.9 Hz, 1H), 7.30-7.17 (m, 4H), 6.93 (t, J=2.6 Hz, 1H), 6.58 (s, 1H), 4.71 (d, J=6.0 Hz, 2H).

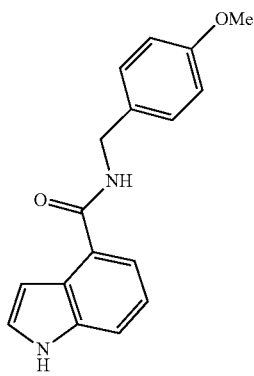 [SMILES: COc1ccc(CNC(=O)c2cccc3[nH]ccc23)cc1]

N-(4-methoxybenzyl)-1H-indole-4-carboxamide (29g) This was obtained as an off white solid (0.304 g, 1.085 mmol, 66%) from indole-4-carboxylic acid (0.266 g, 1.65 mmol) and 4-methoxybenzylamine (0.270 g, 1.96 mmol) in a similar manner as described for 29a. The crude material was used as obtained in the next step. $^1$H NMR (400 MHz, CDCl$_3$) δ 9.06 (s, 1H), 7.50 (d, J=7.3 Hz, 1H), 7.47 (d, J=8.2 Hz, 1H), 7.31 (d, J=8.7 Hz, 2H), 7.26-7.21 (m, 1H), 7.16 (t, J=7.8 Hz, 1H), 6.92-6.85 (m, 3H), 6.54 (t, J=5.8 Hz, 1H), 4.65 (d, J=5.6 Hz, 2H), 3.79 (s, 3H).

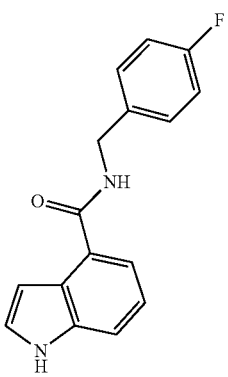 [SMILES: O=C(NCc1ccc(F)cc1)c1cccc2[nH]ccc12]

N-(4-fluorobenzyl)-1H-indole-4-carboxamide (29h) This was obtained as an off white solid (0.240 g, 0.895 mmol, 56%) from indole-4-carboxylic acid (0.257 g, 1.59 mmol) and 4-fluorobenzylamine (0.234 g, 1.86 mmol) in a similar manner as described for 29a. The crude material was used as obtained in the next step. $^1$H NMR (400 MHz, CDCl$_3$) δ 8.62 (s, 1H), 7.52 (d, J=7.5 Hz, 2H), 7.38-7.35 (m, 2H), 7.31 (t, J=2.9 Hz, 1H), 7.21 (t, J=7.8 Hz, 1H), 7.07-7.00 (m, 2H), 6.91-6.90 (m, 1H), 6.54 (s, 1H), 4.69 (d, J=5.8 Hz, 2H).

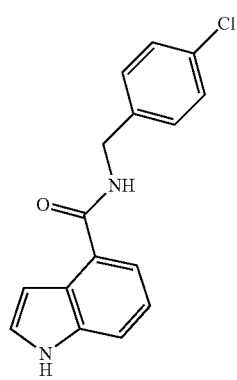 [SMILES: O=C(NCc1ccc(Cl)cc1)c1cccc2[nH]ccc12]

N-(4-chlorobenzyl)-1H-indole-4-carboxamide (29i) This was obtained as an off white solid (0.289 g, 1.017 mmol, 56%) from indole-4-carboxylic acid (0.290 g, 1.79 mmol) and 4-chlorobenzylamine (0.287 g, 2.05 mmol) in a similar manner as described for 29a. The crude material was used as obtained in the next step. $^1$H NMR (400 MHz, CDCl$_3$) δ 8.54 (s, 1H), 7.56-7.52. (m, 2H), 7.36-7.32 (m, 5H), 7.23 (t, J=7.6 Hz, 1H), 6.92 (s, 1H), 6.54 (s, 1H), 4.68 (d, J=5.6 Hz, 2H).

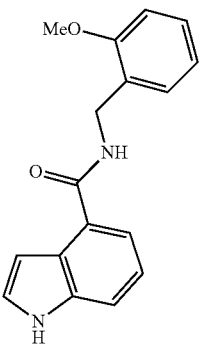 [SMILES: COc1ccccc1CNC(=O)c1cccc2[nH]ccc12]

N-(2-methoxybenzyl)-1H-indole-4-carboxamide (20j) This was obtained as an off white solid (0.360 g, 1.44 mmol, 91%) from indole-4-carboxylic acid (0.251 g, 1.55 mmol) and 2-methoxybenzylamine (0.262 g, 1.96 mmol) in a similar manner as described for 29a. The crude material was used as obtained in the next step. $^1$H NMR (400 MHz, CDCl$_3$) δ 8.90 (s, 1H), 7.45 (d, J=7.4 Hz, 1H), 7.39 (d, J=8.1 Hz, 1H), 7.31 (d, J=7.3 Hz, 1H), 7.22-7.18 (m, 2H), 7.10 (t, J=7.8 Hz, 1H), 6.92-6.66 (m, 4H), 4.65 (d, J=5.8 Hz, 2H), 3.79 (s, 3H).

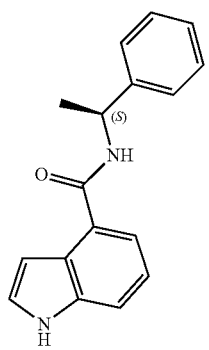

(S)—N-(1-phenylethyl)-1H-indole-4-carboxamide (29k) This was obtained as an off white solid (0.269 g, 1.01 mmol, 72%) from indole-4-carboxylic acid (0.230 g, 1.42 mmol) and (S)-1-phenylethanamine (0.190 g, 1.57 mmol) in a similar manner as described for 29a. The crude material was used as obtained in the next step. $^1$H NMR (400 MHz, CDCl$_3$) δ 8.87 (s, 1H), 7.52 (d, J=7.3 Hz, 1H), 7.47-7.42 (m, 3H), 7.36 (t, J=7.5 Hz, 2H), 7.29-7.21 (m, 2H), 7.18 (t, J=7.8 Hz, 1H), 6.88 (s, 1H), 6.53 (d, J=7.4 Hz, 1H), 5.44 (quin, J=7.0 Hz, 1H), 1.65 (d, J=6.9 Hz, 3H).

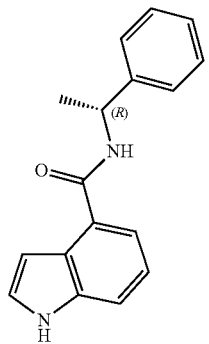

(R)—N-(1-phenylethyl)-1H-indole-4-carboxamide (29l) This was obtained as an off white solid (0.284 g, 1.07 mmol, 80%) from indole-4-carboxylic acid (0.217 g, 1.34 mmol) and (R)-1-phenylethanamine (0.190 g, 1.57 mmol) in a similar manner as described for 29a. The crude material was used as obtained in the next step. $^1$H NMR (400 MHz, CDCl$_3$) δ 9.03 (s, 1H), 7.51 (d, J=7.4 Hz, 1H), 7.47-7.42 (m, 3H), 7.36 (t, J=7.5 Hz, 2H), 7.29-7.21 (m, 2H), 7.18 (t, J=7.8 Hz, 1H), 6.86 (s, 1H), 6.55 (d, J=7.9 Hz, 1H), 5.45 (quin, J=7.1 Hz, 1H), 1.65 (d, J=6.9 Hz, 3H).

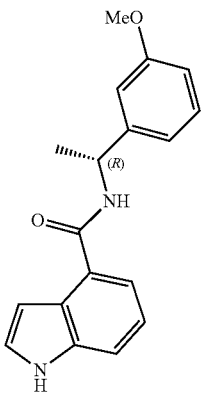

(R)—N-(1-(3-methoxyphenyl)ethyl)-1H-indole-4-carboxamide (29m) This was obtained as an off white solid (0.294 g, 1.05 mmol, 28%) from indole-4-carboxylic acid (0.608 g, 3.77 mmol) and (R)-1-(3-methoxyphenyl)ethanamine (0.613 g, 4.06 mmol) in a similar manner as described for 29a. The crude material was used as obtained in the next step. $^1$H NMR (400 MHz, CDCl$_3$) δ 8.66 (s, 1H), 7.50 (t, J=8.1 Hz, 2H), 7.31-7.24 (m, 2H), 7.19 (t, J=7.7 Hz, 1H), 7.02 (d, J=8.0 Hz, 1H), 6.98 (t, J=2.1 Hz, 1H), 6.90-6.88 (m, 1H), 6.82 (dd, J=8.2, 2.6 Hz, 1H), 6.47 (d, J=7.5 Hz, 1H), 5.41 (quin, J=7.0 Hz, 1H), 3.80 (s, 3H), 1.64 (d, J=6.8 Hz, 3H).

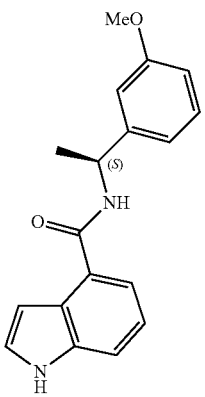

(S)—N-(1-(3-methoxyphenyl)ethyl)-1H-indole-4-carboxamide (29n) This was obtained as an off white solid (0.538 g, 1.83 mmol, 66%) from indole-4-carboxylic acid (0.451 g, 2.79 mmol) and (S)-1-(3-methoxyphenyl)ethanamine (0.511 g, 3.38 mmol) in a similar manner as described for 29a. The crude material was used as obtained in the next step. $^1$H NMR (400 MHz, CDCl$_3$) δ 8.61 (s, 1H), 7.50-7.48 (m, 2H), 7.33-7.28 (m, 2H), 7.19 (t, J=7.9 Hz, 1H), 7.02 (d, J=7.7 Hz, 1H), 66.97 (t, J=2.08 Hz, 1H), 6.90-6.89 (m, 1H), 6.82 (dd, J=7.9, 2.7 Hz, 1H), 6.47 (d, J=7.4 Hz, 1H), 5.41 (quin, J=7.0 Hz, 1H), 3.80 (s, 3H), 1.64 (d, J=6.8 Hz, 3H).

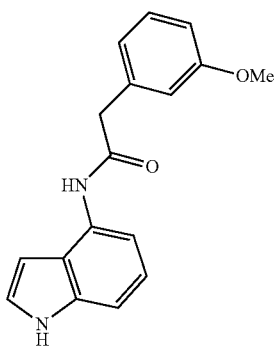 [SMILES: COc1cccc(CC(=O)Nc2cccc3[nH]ccc23)c1]

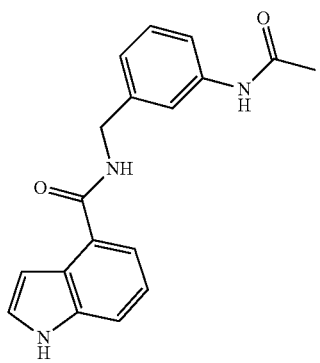

N-(3-acetamidobenzyl)-1H-indole-4-carboxamide ((29p). This was obtained as a brown oil (0.050 g, 0.163 mmol, 33%). from N-(3-(aminomethyl)phenyl)acetamide (0.110 g, 0.550 mmol) and indole-4-carboxylic acid (0.080 g, 0.495 mmol) in a similar manner as described for preparation of 29a. Reaction time: 1 hr. The crude material was used in the next step without purification. $^1$H NMR (400 MHz, CD$_3$OD) δ 7.58-7.53 (m, 2H), 7.48-7.44 (m, 2H), 7.35 (d, J=3.2 Hz, 1H), 7.29 (t, J=7.9 Hz, 1H), 7.20-7.13 (m, 2H), 6.85 (dd, J=3.1, 0.8 Hz, 1H), 4.62 (s, 2H), 2.10 (s, 3H).

N-(1H-indol-4-yl)-2-(3-methoxyphenyl)acetamide (26d) A mixture of 4-Aminoindole (0.150 g, 1.135 mmol), 3-methoxyphenyl acetic acid (260 g, 1.564 mmol), EDC hydrochloride (0.440 g, 2.26 mmol), 4-dimethylaminopyridine (0.050 g, 0.410 mmol) in acetonitrile (4 mL) was heated in the Biotage Microwave for 30 min at 80° C. The solution was then washed with 10 mL of 1N HCl, extracted with ethyl acetate, and then washed with 10 mL of a saturated NaHCO$_3$ solution. The organic phase was dried over Na$_2$SO$_4$ and filtered. The solution was concentrated under reduced pressure to afford 26d as a dark brown solid (0.312 g, 1.114 mmol, 99%). The crude material was used in the next step without purification. $^1$H NMR (400 MHz, CDCl$_3$) δ 8.22 (s, 1H), 7.79 (t, J=4.4 Hz, 1H), 7.47-7.29 (m, 1H), 7.17 (d, J=4.5 Hz, 2H), 7.11 (t, J=2.9 Hz, 1H), 7.01 (d, J=7.9 Hz, 1H), 6.94-6.92 (m, 1H), 5.99 (t, J=2.2 Hz, 1H), 3.84 (s, 3H), 3.82 (s, 2H).

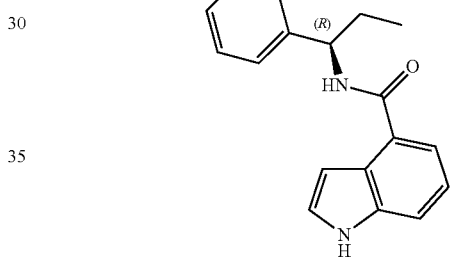

(R)—N-(1-phenylpropyl)-1H-indole-4-carboxamide (29q) This was obtained as an off-white solid (0.072 g, 0.259 mmol, 38%) from (R)-1-phenylpropan-1-amine (0.110 g, 0.818 mmol, 0.080 mL) and indole-4-carboxylic acid (0.110 g, 0.682 mmol) in a similar manner as described for preparation of 29a. Reaction time: 1 hr. The crude material was used as obtained in the next step. $^1$H NMR (400 MHz, CD$_3$OD) δ 7.53 (d, J=8.2 Hz, 1H), 7.44-7.89 (m, 3H), 7.37-7.31 (m, 3H), 7.26-7.27 (m, 1H), 7.16 (t, J=7.8 Hz, 1H), 6.75-6.72 (m, 1H), 5.04 (t, J=7.6 Hz, 1H), 1.94 (d, J=15.9 Hz, 2H), 1.02 (t, J=7.4 Hz, 3H).

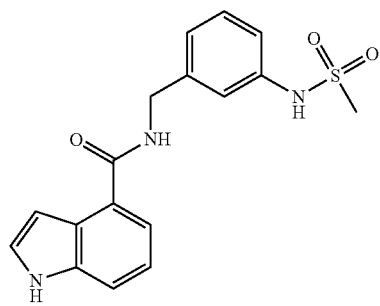 [SMILES: CS(=O)(=O)Nc1cccc(CNC(=O)c2cccc3[nH]ccc23)c1]

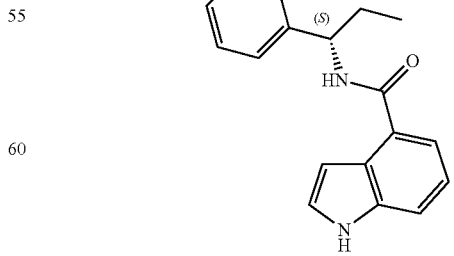

N-(3-(methylsulfonamido)benzyl)-1H-indole-4-carboxamide (29o) This was obtained as a green solid (0.056 g, 0.148 mmol, 59%) from N-(3 (aminomethyl)phenyl)methanesulfonamide (0.059 g, 0.249 mmol) and indole-4-carboxylic acid (0.036 g, 0.224 mmol) in a similar manner as described for preparation of 29a. Reaction time: 1 hr. The crude material; was used in the net step without further purification. $^1$H NMR (400 MHz, CD$_3$OD) δ 7.55 (d, J=8.1 Hz, 1H), 7.45 (d, J=7.4 Hz, 1H), 7.37-7.28 (m, 3H), 7.20 (d, J=8.3 Hz, 1H), 7.16 (d, J=7.7 Hz, 2H), 6.84 (d, J=3.1 Hz, 1H), 4.62 (s, 2H), 2.94 (s, 3H).

(S)—N-(1-phenylpropyl)-1H-indole-4-carboxamide (29r) This was obtained as an of-white solid (0.370 g, 1.329 mmol, 39%) from (S)-1-phenylpropan-1-amine (0.605 g, 4.478 mmol) and indole-4-carboxylic acid (0.603 g, 3.731 mmol) in a similar manner as described for preparation of 29a. The crude material was used as obtained in the next step. ¹H NMR (400 MHz, CD₃OD) δ 7.53 (d, J=8.2 Hz, 1H), 7.48-7.40 (m, 3H), 7.36-7.31 (m, 3H), 7.26-7.21 (m, 1H), 7.16 (t, J=7.8 Hz, 1H), 6.73 (dd, J=3.1, 0.9 Hz, 1H), 5.07-5.01 (m, 1H), 2.04-1.83 (m, 2H), 1.01 (t, J=7.4 Hz, 3H).

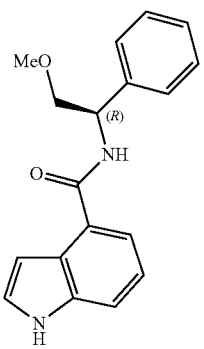

(R)—N-(2-methoxy-1-phenylethyl)-1H-indole-4-carboxamide (29s) This was obtained a brown oil (0.035 g, 0.119 mmol, 30%). from (R)-2-methoxy-1-phenylethanamine (0.060 g, 0.397 mmol) and indole-4-carboxylic acid (0.64 g, 0.397 mmol) in a similar manner as described for preparation of 29a. Reaction time: 1 hr. The crude material was used as obtained in the next step. ¹H NMR (400 MHz, CD₃OD) δ 7.55 (d, J=8.2 Hz, 1H), 7.45 (d, J=7.4 Hz, 3H), 7.38-7.30 (m, 3H), 7.27 (t, J=7.8 Hz, 1H), 7.18 (t, J=7.8 Hz, 1H), 6.80 (d, J=3.1 Hz, 1H), 5.46-5.28 (m, 1H), 3.90-3.65 (m, 2H), 3.42 (s, 3H).

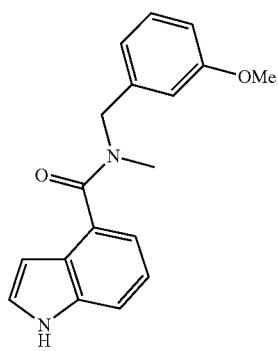 [SMILES: COc1cccc(CN(C)C(=O)c2cccc3[nH]ccc23)c1]

N-(3-methoxybenzyl)-N-methyl-1H-indole-4-carboxamide (29t) This was obtained as a brown oil (0.062 g, 0.211 mmol, 34%) from 1-(3-methoxyphenyl)-N-methylmethanamine (0.114 g, 0.745 mmol, 0.11 mL) and indole-4-carboxylic acid (0.100 g, 0.621 mmol) in a similar manner as described for preparation of 29a. Reaction time: 1 hr. The crude material was used as obtained in the next step. MS (M+H)⁺ 295.14.

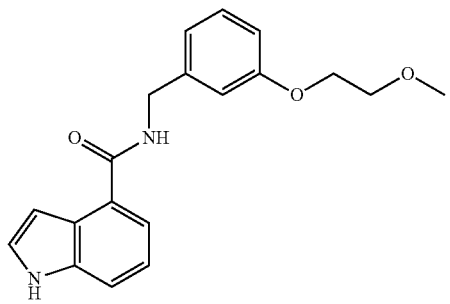 [SMILES: COCCOc1cccc(CNC(=O)c2cccc3[nH]ccc23)c1]

N-(3-(2-methoxyethoxy)benzyl)-1H-indole-4-carboxamide (29u) This was obtained as a green oil (0.128 g, 0.395 mmol, 34%) from (3-(2-methoxyethoxy)phenyl)methanamine (0.256 g, 1.414 mmol, 0.15 mL) and indole-4-carboxylic acid (0.190 g, 1.178 mmol) in a similar manner as described for preparation of 29a. Reaction time: 1 hr. The crude material was used as obtained in the next step. ¹H NMR (400 MHz, CD₃OD) δ 7.55 (dt, J=8.1, 0.9 Hz, 1H), 7.43 (dd, J=7.4, 0.9 Hz, 1H), 7.35 (d, J=3.2 Hz, 1H), 7.25 (t, J=7.9 Hz, 1H), 7.16 (t, J=7.9 Hz, 1H), 7.00-6.98 (m, 2H), 6.85-6.82 (m, 2H), 4.61 (s, 2H), 4.12-4.07 (m, 2H), 3.75-3.65 (m, 2H), 3.40 (s, 3H).

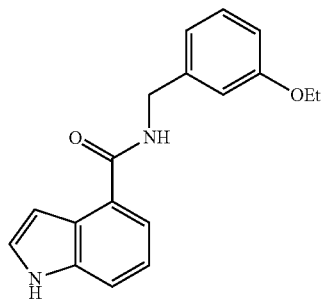 [SMILES: CCOc1cccc(CNC(=O)c2cccc3[nH]ccc23)c1]

N-(3-ethoxybenzyl)-1H-indole-4-carboxamide (29v) This was obtained as a red oil (0.304 g, 1.033 mmol, 83%) from (3-ethoxyphenyl)methanamine (0.225 g, 1.490 mmol, 0.22 mL) and indole-4-carboxylic acid (0.200 g, 1.241 mmol) in a similar manner as described for preparation of 29a. Reaction time: 1 hr. The crude material was used as obtained in the next step. ¹H NMR (400 MHz, DMSO-d₆) δ 11.26 (s, 1H), 8.72 (t, J=5.8 Hz, 1H), 7.53 (d, J=8.0 Hz, 1H), 7.45 (d, J=7.3 Hz, 1H), 7.40 (t, J=2.9 Hz, 1H). 7.21 (t, J=8.1 Hz, 1H), 7.13 (t, J=7.7 Hz, 1H), 6.9-6.82 (m, 3H), 6.78-6.76 (m, 1H), 4.46 (d, J=6.0 Hz, 2H), 3.98 (q, J=6.9 Hz, 2H), 1.29 (t, J=6.9 Hz, 3H).

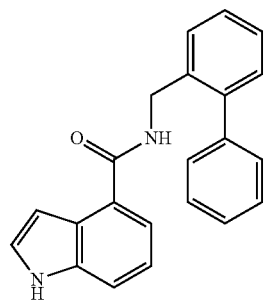 [SMILES: O=C(NCc1ccccc1-c1ccccc1)c1cccc2[nH]ccc12]

N-(biphenyl-2-ylmethyl)-1H-indole-4-carboxamide (29w) This was obtained as a white solid (0.207 g, 0.634 mmol, 51%). from biphenyl-2-ylmethanamine (0.274 g, 1.495 mmol, 0.26 mL) and indole-4-carboxylic acid (0.200 g, 1.241 mmol) in a similar manner as described for preparation of 29a. Reaction time: 1 hr. The crude material was used as obtained in the next step. $^1$H NMR (400 MHz, DMSO-d$_6$) δ 11.25 (s, 1H), 8.64 (t, J=5.8 Hz, 1H), 7.55-7.29 (m, 11H), 7.23 (dd, J=7.2, 1.5 Hz, 1H), 7.12 (t, J=7.7 Hz, 1H), 6.81 (s, 1H), 4.45 (d, J=5.8 Hz, 2H).

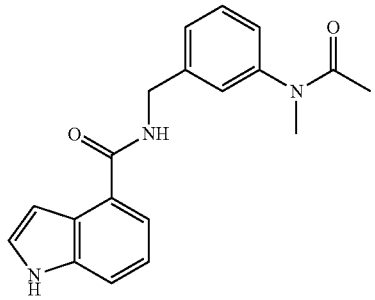 [SMILES: CC(=O)N(C)c1cccc(CNC(=O)c2cccc3[nH]ccc23)c1]

N-(3-(N-methylacetamido)benzyl)-1H-indole-4-carboxamide (29x) This was obtained as a brown oil (0.075 g, 0.210 mmol, 17%) from N-(3-(aminomethyl)phenyl)-N-methylacetamide (0.320 g, 1.495 mmol) and indole-4-carboxylic acid (0.200 g, 1.241 mmol) in a similar manner as described for preparation of 29a. Reaction time: 1 hr. The crude material was used as obtained in the next step. $^1$H NMR (400 MHz, DMSO-d$_6$) δ 11.27 (s, 1H), 8.78 (t, J=6.0 Hz, 1H), 7.54 (d, J=8.1 Hz, 1H), 7.45 (d, J=6.8 Hz, 1H), 7.42 (t, J=2.7 Hz, 1H), 7.39 (d, J=7.9 Hz, 1H), 7.30-2.27 (m, 2H), 7.19 (d, J=6.9 Hz, 1H), 7.13 (t, J=7.8 Hz, 1H), 6.82 (s, 1H), 4.52 (d, J=6.0 Hz, 2H), 3.13 (s, 3H), 1.76 (s, 3H).

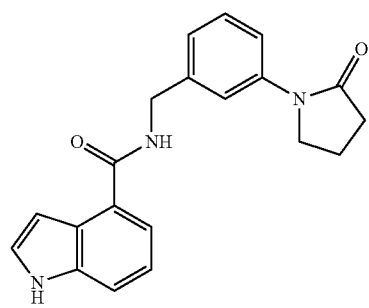 [SMILES: O=C(NCc1cccc(N2CCCC2=O)c1)c1cccc2[nH]ccc12]

N-(3-(2-oxopyrrolidin-1-yl)benzyl)-1H-indole-4-carboxamide (29y) This was obtained as a brown oil (0.086 g, 0.258 mmol, 35%) from 1-(3-(aminomethyl)phenyl)pyrrolidin-2-one (0.170 g, 0.894 mmol) and indole-4-carboxylic acid (0.120 g, 0.745 mmol) in a similar manner as described for preparation of 29a. Reaction time: 1 hr. The crude material was used as obtained in the next step. $^1$H NMR (400 MHz, DMSO-d$_6$) δ 11.27 (s, 1H), 8.78 (t, J=5.9 Hz, 1H), 7.66 (s, 1H), 7.53 (t, J=8.5 Hz, 2H), 7.47 (d, J=7.3 Hz, 1H), 7.43-7.39 (m, 1H), 7.32 (t, J=7.8 Hz, 1H), 7.15-7.11 (m, 2H), 6.85 (s, 1H), 4.50 (d, J=5.8 Hz, 2H), 3.81 (t, J=7.0 Hz, 2H), 2.13-1.96 (m, 2H).

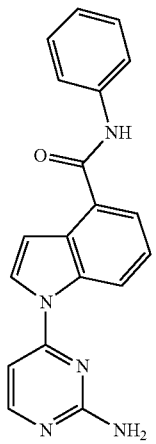 [SMILES: Nc1nccc(-n2ccc3c(C(=O)Nc4ccccc4)cccc32)n1]

1-(2-aminopyrimidin-4-yl)-N-phenyl-1H-indole-4-carboxamide (24a) This was obtained from 2-amino-4-chloropyrimidine (0.065 g, 0.501 mmol), and 23e (0.155 g, 0.667 mmol) in a similar manner as described for 15c. After cooling to room temperature, the reaction mixture diluted with water. The solid precipitated was filtered. Chromatography on silica gel using the FlashMaster 3 purification station (AcOEt/hexane) afforded pure 24a (0.032 g, 0.097 mmol, 19%) as an off white solid. $^1$H NMR (400 MHz, DMSO-d$_6$) δ 10.33 (s, 1H), 9.03 (d, J=8.5 Hz, 1H), 8.27 (d, J=5.6 Hz, 1H), 8.18 (d, J=3.7 Hz, 1H), 7.84-7.72 (m, 2H), 7.68 (d, J=7.1 Hz, 1H), 7.41-7.32 (m, 3H), 7.10-7.05 (m, 2H), 6.97 (d, J=5.8 Hz, 1H), 6.95 (s, 2H). HPLC: Purity 97.51%, MeOH 60%, (0.1% TFA in H$_2$O) 40%, 20 min, Flow 1 ml/min, R$_t$ 3.600 min. HRMS (ESI–ve) calculated for C$_{19}$H$_{16}$N$_5$O (M+H)$^+$ 330.1349, found 330.1359

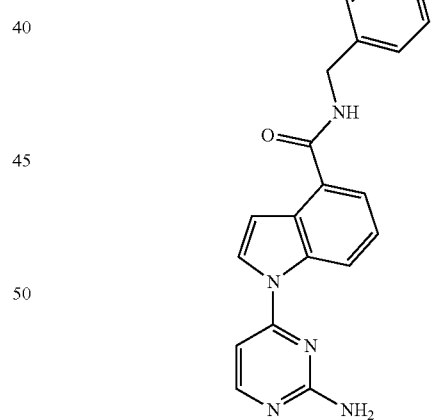

1-(2-aminopyrimidin-4-yl)-N-benzyl-1H-indole-4-carboxamide (24b). This was obtained from 2-amino-4-chloropyrimidine (0.072 g, 0.555 mmol), and 23f (0.203 g, 0.812 mmol) in a similar manner as described for 15c. After cooling to room temperature, the reaction mixture was diluted with water. The solid precipitated was filtered, slurried with CH$_3$CN, filtered and dried under vacuum. Pure 24b (0.081 g, 0.235 mmol, 42%) was obtained as an off white solid. $^1$H NMR (400 MHz, DMSO-d$_6$) δ 9.00-8.93 (m, 2H), 8.26 (d, J=5.6 Hz, 1H), 8.12 (d, J=3.6 Hz, 1H), 7.62 (d, J=7.5 Hz, 1H), 7.36-7.30 (m, 5H), 7.25-7.21 (m, 1H), 7.15 (d, J=3.6 Hz, 1H), 6.94 (d, J=5.8 Hz, 1H), 6.92 (s, 2H), 4.51 (d, J=6.0 Hz, 2H). MeOH 50%, (0.1% TFA in H$_2$O) 50%, 20 min, Flow 1 ml/min: R$_t$ 7.113 min, Purity 97.99%. HRMS (ESI–ve) calculated for C$_{20}$H$_{18}$N$_5$O (M+H)$^+$ 344.1505. found 344.1514

The solid precipitated was filtered. Chromatography on silica gel using the FlashMaster 3 purification station (AcOEt/hexane) afforded pure 27b (0.060 g, 0.182 mmol, 51%) as an off white solid. $^1$H NMR (400 MHz, DMSO-d$_6$) δ 10.25 (s, 1H), 8.78 (d, J=9.1 Hz, 1H), 8.23 (d, J=5.7 Hz, 1H), 8.15 (s, 1H), 8.06 (d, J=3.7 Hz, 1H), 7.97-7.95 (m, 1H), 7.58-7.52 (m, 4H), 6.93 (d, J=5.8 Hz, 1H), 6.88 (s, 2H), 6.76 (d, 1H, J=3.7 Hz, 1H). HPLC: Purity 98.93%, MeOH 50%, (0.1% TFA in H$_2$O) 50%, 20 min, Flow 1 ml/min, R$_t$ 8.007 min, HRMS (ESI–ve) calculated for C$_{19}$H$_{16}$N$_5$O (M+H)$^+$ 330.1349, found 330.1349

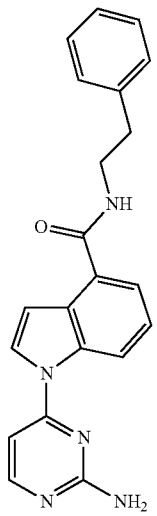 [SMILES: Nc1nccc(-n2ccc3c(C(=O)NCCc4ccccc4)cccc32)n1]

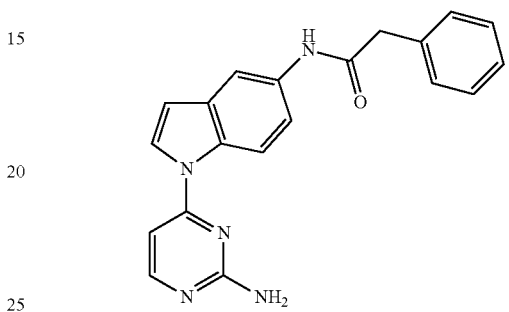

1-(2-aminopyrimidin-4-yl)-N-phenethyl-1H-indole-4-carboxamide (24c) This was obtained from 2-amino-4-chloropyrimidine (0.672 g, 0.517 mmol), and 23d (0.187 g, 0.708 mmol) in a similar manner as described for 15c. After cooling to room temperature, the reaction mixture was diluted with water. The solid precipitated was filtered, slurried with CH$_3$CN, filtered and dried under vacuum. Pure 24c (0.144 g, 0.402 mmol, 72%) was obtained as an off white solid. $^1$H NMR (400 MHz, DMSO-d$_6$) 8.94 (d, J=8.4 Hz, 1H), 8.47 (t, J=5.6 Hz, 1H), 8.25 (d, J=5.7 Hz, 1H), 8.11 (d, J=3.7 Hz, 1H), 7.49 (d, J=7.3 Hz, 1H), 7.31-7.25 (m, 5H), 7.21-7.18 (m, 1H), 7.06 (d, J=3.6 Hz, 1H), 6.95 (d, J=5.8 Hz, 1H), 6.91 (s, 2H), 3.52 (q, J=6.0 Hz, 1H), 2.88 (t, J=7.4 Hz, 2H). MeOH 60%, (0.1% TFA in H$_2$O) 40%, 20 min, Flow 1 ml/min: R$_t$ 4.087 min, Purity 92.23%. HRMS (ESI–ve) calculated for C$_{21}$H$_{20}$N$_5$O (M+H)$^+$ 358.1662, found 358.1670

N-(1-(2-aminopyrimidin-4-yl)-1H-indol-5-yl)-2-phenylacetamide (27a). This was obtained from 2-amino-4-chloropyrimidine (0.104 g, 0.802 mmol), and 26c (0.301 g, 1.20 mmol) in a similar manner as described for 15c. After cooling to room temperature, the reaction mixture was diluted with water. The solid precipitated was filtered. Chromatography on silica gel using the FlashMaster 3 purification station (AcOEt/hexane) afforded 27a as an off white solid. CH$_3$CN was added to the obtained solid and the solid precipitate was filtered, washed with water and dried in vacuo. Pure 27a was obtained (0.040 g, 0.116 mmol, 15%) as an off-white solid. $^1$H NMR (400 MHz, DMSO-d$_6$) δ 10.15 (s, 1H), 8.72 (d, J=8.9 Hz, 1H), 8.21 (d, J=5.7 Hz, 1H), 8.02 (d, J=3.6 Hz, 1H), 7.98 (d, J=2.1 Hz, 1H), 7.37-7.29 (m, 4H), 7.25-7.21 (m, 1H), 6.90 (d, J=5.8 Hz, 1H), 6.85 (s, 2H), 6.71 (d, J=3.6 Hz, 1H), 3.64 (s, 2H). HPLC: Purity 95.87%, MeOH 60%, (0.1% TFA in H$_2$O) 40%, 20 min, Flow 1 ml/min, R$_t$ 3.963 min, HRMS (ESI–ve) calculated for C$_{20}$H$_{18}$N$_5$O (M+H)$^+$ 344.1505, found 344.1516

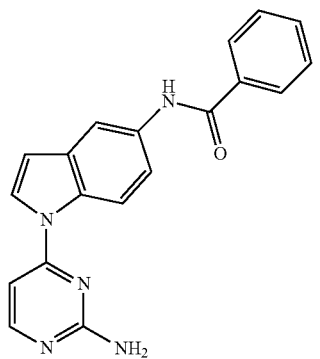 [SMILES: Nc1nccc(-n2ccc3cc(NC(=O)c4ccccc4)ccc32)n1]

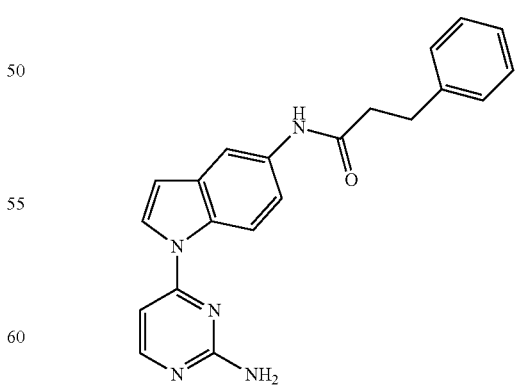

N-(1-(2-aminopyrimidin-4-yl)-1H-indol-5-yl)benzamide (27b) This was obtained from 2-amino-4-chloropyrimidine (0.046 g, 0.355 mmol), and 26a (0.123 g, 0.521 mmol) in a similar manner as described for 15c. After cooling to room temperature, the reaction mixture was diluted with water.

N-(1-(2-aminopyrimidin-4-yl)-1H-indol-5-yl)-3-phenylpropanamide (27c) This was obtained from 2-amino-4-chloropyrimidine (0.072 g, 0.555 mmol), and 26a (0.219 g, 0.829 mmol) in a similar manner as described for 15c. After cooling to room temperature, the reaction mixture was diluted with water. The solid precipitated was filtered. Chromatography on silica gel using the FlashMaster 3 purification station (AcOEt/MeOH) afforded 27c as an off white solid. Water was added to the obtained solid and the solid precipitate was filtered, washed with water and dried in vacuo. Pure 27c was obtained (0.058 g, 0.162 mmol, 29%) as an off-white solid. $^1$H NMR (400 MHz, DMSO-d$_6$) δ 9.89 (s, 1H), 8.71 (d, J=4.5 Hz, 1H), 8.21 (d, J=5.7 Hz, 1H), 8.02 (d, J=3.7 Hz, 1H), 7.99 (d, J=1.8 Hz, 1H), 7.32-7.19 (m, 4H), 7.19-7.14 (m, 1H), 6.90 (d, J=5.8 Hz, 1H), 6.84 (s, 2H), 6.72 (d, J=3.5 Hz, 1H), 2.92 (t, J=7.6 Hz, 2H), 2.62 (t, J=7.8 Hz, 2H). HRMS (ESI-ve) calculated for $C_{21}H_{20}N_5O$ (M+H)$^+$ 358.1662, found 358.1664.

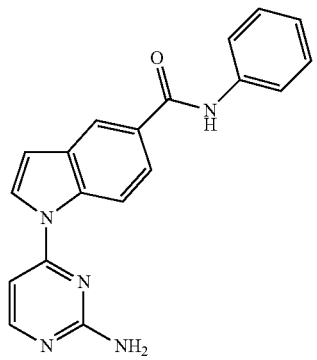 [SMILES: Nc1nccc(-n2ccc3cc(C(=O)Nc4ccccc4)ccc32)n1]

1-(2-aminopyrimidin-4-yl)-N-phenyl-1H-indole-5-carboxamide (24f) This was obtained from 2-amino-4-chloropyrimidine (0.052 g, 0.401 mmol), and 23b (0.114 g, 0.483 mmol) in a similar manner as described for 15c. After cooling to room temperature, the reaction mixture was diluted with water. The solid precipitated was filtered. Chromatography on silica gel using the FlashMaster 3 purification station (AcOEt/hexane) afforded pure 24f (0.014 g, 0.042 mmol, 11%) as an off-white solid. $^1$H NMR (400 MHz, DMSO-d$_6$) δ 10.26 (s, 2H), 8.89 (d, J=8.8 Hz, 1H), 8.29-7.27 (m, 2H), 8.18 (d, J=3.8 Hz, 1H), 7.86 (dd, J=1.8, 8.7 Hz, 1H), 7.80-7.78 (m, 1H), 7.36-7.32 (m, 2H), 7.09-7.05 (m, 1H), 6.99 (d, J=5.8 Hz, 1H), 6.96 (s, 2H), 6.92 (d, J=3.5 Hz, 1H). HPLC: Purity 96.46%, MeOH 50%, (0.1% TFA in H$_2$O) 50%, 20 min, Flow 1 ml/min, R$_t$ 9.440 min. HRMS (ESI-ve) calculated for $C_{19}H_{16}N_5O$ (M+H)$^+$ 330.1349, found 330.1343

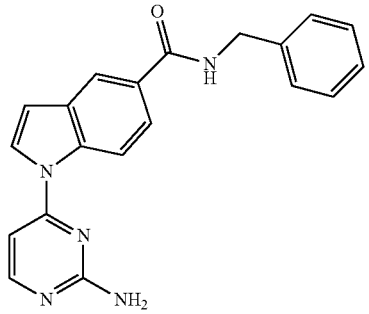 [SMILES: Nc1nccc(-n2ccc3cc(C(=O)NCc4ccccc4)ccc32)n1]

1-(2-aminopyrimidin-4-yl)-N-benzyl-1H-indole-5-carboxamide (24e) This was obtained from 2-amino-4-chloropyrimidine (0.042 g, 0.416 mmol), and 23c (0.124 g, 0.486 mmol) in a similar manner as described for 15c. After cooling to room temperature, the reaction mixture was diluted with water. The solid precipitated was filtered, slurried with CH$_3$CN, filtered and dried under vacuum. Pure 24e (0.083 g, 0.241 mmol, 58%) was obtained as an off white solid. $^1$H NMR (400 MHz, DMSO-d$_6$) δ 9.05 (t, J=6.0 Hz, 1H), 8.82 (d, J=8.9 Hz, 1H), 8.27 (d, J=5.7 Hz, 1H), 8.20 (d, J=1.5 Hz, 1H), 8.14 (d, J=3.7 Hz, 1H), 7.81 (dd, J=1.8, 8.8 Hz, 1H), 7.32-7.29 (m, 4H), 7.25-7.20 (m, 1H), 6.97 (d, J=5.8 Hz, 1H), 6.94 (s, 2H), 6.86 (d, J=3.2 Hz, 1H), 4.50 (d, J=6.0 Hz, 1H). HRMS (ESI-ve) calculated for $C_{20}H_{18}N_5O$ (M+H)$^+$ 344.1505, found 344.1515

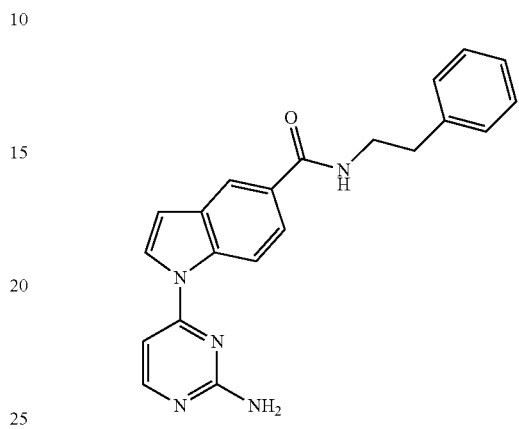

1-(2-aminopyrimidin-4-yl)-N-phenethyl-1H-indole-5-carboxamide (24d) This was obtained from 2-amino-4-chloropyrimidine (0.051 g, 0.393 mmol), and 23a (0.146 g, 0.553 mmol) in a similar manner as described for 15c. After cooling to room temperature, the reaction mixture diluted with water and extracted with AcOEt. The organic extract was dried over Na$_2$SO$_4$ and the solvent removed under reduced pressure. Chromatography on silica gel using the FlashMaster 3 purification station (AcOEt/hexane) afforded 24d as an off white solid. Water was added to the obtained solid and the solid precipitate was filtered, washed with water and dried in vacuo. Pure 24d was obtained (0.025 g, 0.070 mmol, 19%) as an off-white solid. $^1$H NMR (400 MHz, DMSO-d$_6$) δ 8.81 (d, J=8.8 Hz, 1H), 8.56 (t, J=5.9 Hz, 1H), 8.27 (d, J=5.7 Hz, 1H), 8.13 (d, J=3.7 Hz, 1H), 8.11 (d, J=1.5 Hz, 1H), 7.74 (dd, J=1.7, 8.9 Hz, 1H), 7.30-7.23 (m, 4H), 7.20-7.16 (m, 1H), 6.96 (d, J=5.7 Hz, 1H), 6.94 (s, 2H), 6.85 (d, J=3.7 Hz, 1H), 3.51-3.46 (m, 2H), 2.85 (t, J=7.2 Hz, 2H). HPLC: Purity 85.18% MeOH 60%, (0.1% TFA in H$_2$O) 40%, 20 min, Flow 1 ml/min, R$_t$ 4.687 min, HRMS (ESI-ve) calculated for $C_{21}H_{20}N_5O$ (M+H)$^+$ 358.1662, found 358.1674.

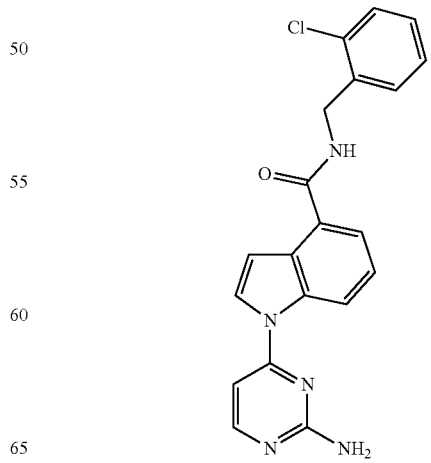

1-(2-aminopyrimidin-4-yl)-N-(2-chlorobenzyl)-1H-indole-4-carboxamide (30a) A mixture of 2-amino-4-chloropyrimidine (0.037 g, 0.285 mmol), 29d (0.121 g, 0.424 mmol) and $Cs_2CO_3$ (0.308 g) in anhydrous DMF (0.4 ml) was stirred in a Biotage microwave reactor for 30 min at 150° C. After cooling to room temperature, the reaction mixture was diluted with water. The solid precipitated was filtered, slurried with methanol, filtered, washed with methanol and dried under vacuum. Pure 30a (0.072 g, 0.190 mmol, 69%) was obtained as an off white solid. $^1$H NMR (400 MHz, DMSO-$d_6$) δ 9.02-8.98 (m, 2H), 8.26 (d, J=5.7 Hz, 1H), 8.14 (d, J=3.7 Hz, 1H), 7.68 (d, J=7.5 Hz, 1H), 7.46 (dd, J=1.6, 7.6 Hz, 1H), 7.41 (dd, J=1.6, 7.1 Hz, 1H), 7.36-7.26 (m, 3H), 7.16 (d, J=3.8 Hz, 1H), 6.95 (d, J=5.7 Hz, 1H), 6.94 (s, 2H), 4.57 (d, J=5.7 Hz, 2H). HPLC: Purity 97.81%, MeOH 50%, (0.1% TFA in $H_2O$) 50%, 20 min, Flow 1 ml/min, $R_t$ 12.807 min, Purity 97.91%, $CH_3CN$ 30%, (0.1% TFA in $H_2O$) 70%, 20 min, Flow 1 ml/min, $R_t$ 13.007 min, HRMS (ESI-ve) calculated for $C_{20}H_{17}N_5OCl$ (M+H)$^+$ 378.1116, found 378.1115.

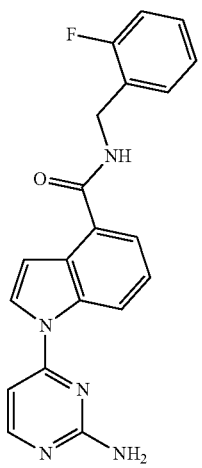 [SMILES: Nc1nccc(-n2ccc3c(C(=O)NCc4ccccc4F)cccc32)n1]

1-(2-aminopyrimidin-4-yl)-N-(2-fluorobenzyl)-1H-indole-4-carboxamide (30k) This was obtained from 2-amino-4-chloropyrimidine (0.057 g, 0.439 mmol), and 29c (0.171 g, 0.638 mmol) in a similar manner as described for 30a. After cooling to room temperature, the reaction mixture was diluted with water. The solid precipitated was filtered, slurried with methanol, filtered, washed with methanol and dried under vacuum. Pure 30k (0.113 g, 0.312 mmol, 71%) was obtained as an off white solid. $^1$H NMR (400 MHz, DMSO-$d_6$) δ 8.98-8.95 (m, 2H), 8.26 (d, J=5.7 Hz, 1H), 8.13 (d, J=3.7 Hz, 1H), 7.63 (d, J=6.7 Hz, 1H), 7.42-7.39 (m, 1H), 7.35-7.26 (m, 2H), 7.20-7.13 (m, 3H), 6.94 (d, J=5.8 Hz, 1H), 6.92 (s, 2H), 4.54 (d, J=6.0 Hz, 2H). HPLC: Purity 98.68%, MeOH 50%, (0.1% TFA in $H_2O$) 50%, 20 min, Flow 1 ml/min: $R_t$ 7.573 min, Purity 99.00%, $CH_3CN$ 30%, (0.1% TFA in $H_2O$) 70%, 20 min, Flow 1 ml/min, $R_t$ 7.933 min, HRMS (ESI-ve) calculated for $C_{20}H_{17}N_5OF$ (M+H)$^+$ 362.1411, found 362.1407.

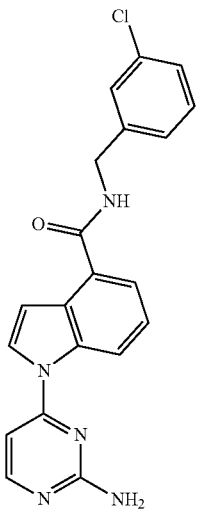 [SMILES: Nc1nccc(-n2ccc3c(C(=O)NCc4cccc(Cl)c4)cccc32)n1]

1-(2-aminopyrimidin-4-yl)-N-(3-chlorobenzyl)-1H-indole-4-carboxamide (30c) This was obtained from 2-amino-4-chloropyrimidine (0.036 g, 0.277 mmol), and 29f (0.114 g, 0.400 mmol) in a similar manner as described for 30a. After cooling to room temperature, the reaction mixture was diluted with water. The solid precipitated was filtered, slurried with methanol, filtered, washed with methanol and dried under vacuum. Pure 30c (0.048 g, 0.127 mmol, 46%) was obtained as an off white solid. $^1$H NMR (400 MHz, DMSO-$d_6$) δ 9.04 (t, J=5.7 Hz, 1H), 8.99 (d, J=8.4 Hz, 1H), 8.26 (d, J=5.7 Hz, 1H), 8.14 (d, J=3.7 Hz, 1H), 7.63 (d, J=7.5 Hz, 1H), 7.40-7.27 (m, 4H), 7.15 (d, J=3.2 Hz, 1H), 6.95 (d, J=5.7 Hz, 1H), 6.93 (s, 2H), 4.50 (d, J=6.1 Hz, 2H). HPLC: Purity 98.68%, MeOH 50%, (0.1% TFA in $H_2O$) 50%, 20 min, Flow 1 ml/min, $R_t$ 15.520 min, Purity 99.13%, $CH_3CN$ 30%, (0.1% TFA in $H_2O$) 70%, 20 min, Flow 1 ml/min, $R_t$ 15.227 min, HRMS (ESI-ve) calculated for $C_{20}H_{17}N_5OCl$ (M+H)$^+$ 378.1116, found 378.1113.

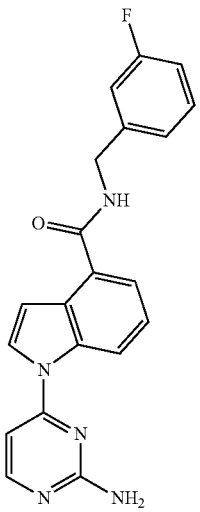 [SMILES: Nc1nccc(-n2ccc3c(C(=O)NCc4cccc(F)c4)cccc32)n1]

1-(2-aminopyrimidin-4-yl)-N-(3-fluorobenzyl)-1H-indole-4-carboxamide (30d) This was obtained from 2-amino-4-chloropyrimidine (0.039 g, 0.301 mmol), and 29e (0.118 g, 0.439 mmol) in a similar manner as described for 30a. After cooling to room temperature, the reaction mixture was diluted with water. The solid precipitated was filtered, slurried with methanol, filtered, washed with methanol and dried under vacuum. Pure 30d (0.066 g, 0.182 mmol, 60%) was obtained as an off white solid. $^1$H NMR (400 MHz, DMSO-$d_6$) δ 9.03 (t, J=6.1 Hz, 1H), 8.98 (d, J=8.4 Hz, 1H), 8.26 (d, J=5.7 Hz, 1H), 8.14 (d, J=3.7 Hz, 1H), 7.63 (d, J=7.2 Hz, 1H), 7.42-7.31 (m, 2H), 7.20-7.13 (m, 3H), 7.06 (td, J=8.6, 2.7 Hz, 1H), 6.95 (d, J=5.7 Hz, 1H), 6.92 (s, 2H), 4.52 (d, J=6.0 Hz, 2H). HPLC: Purity 98.78%, MeOH 50%, (0.1% TFA in H$_2$O) 50%, 20 min, Flow 1 ml/min: R$_t$ 8.333 min, Purity 99.24%, CH$_3$CN 30%, (0.1% TFA in H$_2$O) 70%, 20 min, Flow 1 ml/min, R$_t$ 8.620 min, HRMS (ESI-ve) calculated for C$_{20}$H$_{17}$N$_5$OF (M+H)$^+$ 362.1411, found 362.1411.

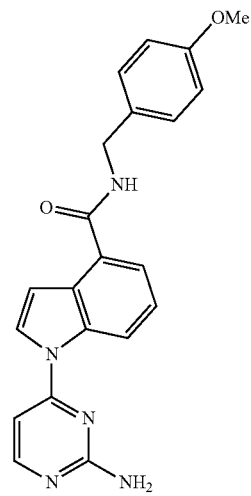

1-(2-aminopyrimidin-4-yl)-N-(4-methoxybenzyl)-1H-indole-4-carboxamide (30l) This was obtained from 2-amino-4-chloropyrimidine (0.039 g, 0.301 mmol), and 29g (0.118 g, 0.449 mmol) in a similar manner as described for 30a. After cooling to room temperature, the reaction mixture was diluted with water. The solid precipitated was filtered, slurried with methanol, filtered, washed with CH$_3$CN and dried under vacuum. Pure 30l (0.055 g, 0.147 mmol, 49%) was obtained as an off white solid. $^1$H NMR (400 MHz, DMSO-$d_6$) δ 8.96 (d, J=8.4 Hz, 1H), 8.91 (t, J=6.1 Hz, 1H), 8.25 (d, J=5.7 Hz, 1H), 8.12 (d, J=3.7 Hz, 1H), 7.59 (d, J=7.0 Hz, 1H), 7.32 (d, J=8.2 Hz, 1H), 7.28 (d, J=8.7 Hz, 2H), 7.14 (d, J=3.6 Hz, 1H), 6.94 (d, J=5.8 Hz, 1H), 6.92 (s, 2H), 6.89 (d, J=8.7 Hz, 2H), 4.43 (d, J=6.0 Hz, 2H), 3.71 (s, 3H). HPLC: Purity 98.32%, MeOH 50%, (0.1% TFA in H$_2$O) 50%, 20 min, Flow 1 ml/min, R$_t$ 6.807 min, Purity 97.77%, CH$_3$CN 30%, (0.1% TFA in H$_2$O) 70%, 20 min, Flow 1 ml/min: R$_t$ 6.987 min, HRMS (ESI-ve) calculated for C$_{21}$H$_{20}$N$_5$O$_2$(M+H)$^+$ 374.1611, found 374.1601

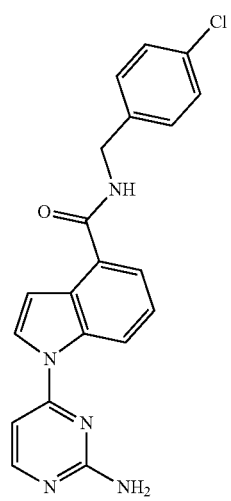 [SMILES: Nc1nccc(-n2ccc3c(C(=O)NCc4ccc(Cl)cc4)cccc32)n1]

1-(2-aminopyrimidin-4-yl)-N-(4-chlorobenzyl)-1H-indole-4-carboxamide (30e) This was obtained from 2-amino-4-chloropyrimidine (0.035 g, 0.270 mmol), and 29i (0.113 g, 0.396 mmol) in a similar manner as described for 30a. After cooling to room temperature, the reaction mixture was diluted with water. The solid precipitated was filtered, slurried with methanol, filtered, washed with methanol and dried under vacuum. Pure 30e (0.079 g, 0.209 mmol, 77%) was obtained as an off white solid. $^1$H NMR (400 MHz, DMSO-$d_6$) δ 9.02 (t, J=4.8 Hz, 1H), 8.98 (d, J=8.4 Hz, 1H), 8.26 (d, J=5.7 Hz, 1H), 8.13 (d, J=3.7 Hz, 1H), 7.62 (d, J=7.4 Hz, 1H), 7.40 (d, J=8.9 Hz, 2H), 7.37 (d, J=9.1 Hz, 2H), 7.33 (t, J=7.9 Hz, 1H), 7.15 (d, J=3.6 Hz, 1H), 6.95 (d, J=5.8 Hz, 1H), 6.92 (s, 2H), 4.48 (d, J=6.0 Hz, 2H). HPLC: Purity 99.73%, MeOH 50%, (0.1% TFA in H$_2$O) 50%, 20 min, Flow 1 ml/min, R$_t$ 16.340 min; Purity 99.91%, CH$_3$CN 30%, (0.1% TFA in H$_2$O) 70%, 20 min, Flow 1 ml/min, R$_t$ 15.560 min. HRMS (ESI-ve) calculated for C$_{20}$H$_{17}$N$_5$OCl (M+H)$^+$ 378.1116, found 378.1116

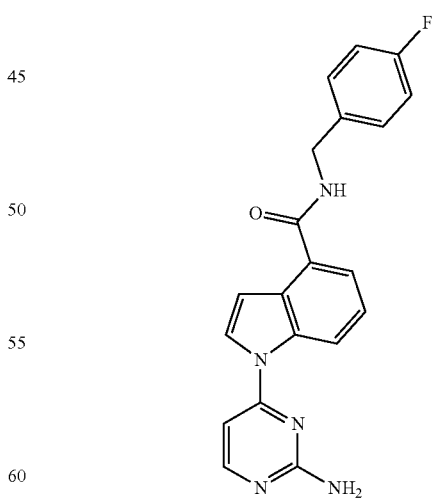

1-(2-aminopyrimidin-4-yl)-N-(4-fluorobenzyl)-1H-indole-4-carboxamide (30f) This was obtained from 2-amino-4-chloropyrimidine (0.035 g, 0.270 mmol), and 29h (0.109 g, 0.406 mmol) in a similar manner as described for 30a. After cooling to room temperature, the reaction mixture was diluted with water. The solid precipitated was filtered, slurried with methanol, filtered, washed with methanol and dried under vacuum. Pure 30f (0.063 g, 0.174 mmol, 65%) was obtained as an off white solid. $^1$H NMR (400 MHz, DMSO-$d_6$) δ 9.10-8.96 (m, 2H), 8.26 (d, J=5.7 Hz, 1H), 8.13 (d, J=3.7 Hz, 1H), 7.61 (d, J=7.2 Hz, 1H), 7.40-7.37 (m, 2H), 7.32 (t, J=7.7 Hz, 1H), 7.17-7.13 (m, 3H,), 6.95 (d, J=5.7 Hz, 1H), 6.92 (s, 2H), 4.48 (d, J=6.0 Hz, 2H). HPLC: Purity 98.37%, MeOH 50%, (0.1% TFA in H$_2$O) 50%, 20 min, Flow 1 ml/min, R$_t$ 8.407 min; Purity 99.08%, CH$_3$CN 30%, (0.1% TFA in H$_2$O) 70%, 20 min, Flow 1 ml/min, R$_t$ 8.580 min, HRMS (ESI-ve) calculated for C$_{21}$H$_{17}$N$_5$O$_2$F (M+H)$^+$ 362.1411, found 362.1412

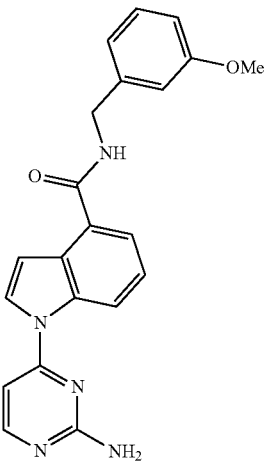

1-(2-aminopyrimidin-4-yl)-N-(3-methoxybenzyl)-1H-indole-4-carboxamide (30b). This was obtained from 2-amino-4-chloropyrimidine (0.079 g, 0.609 mmol), and 29a (0.202 g, 0.720 mmol) in a similar manner as described for 30a. After cooling to room temperature, the reaction mixture was diluted with water. The solid precipitated was filtered, slurried with methanol, filtered, washed with methanol and dried under vacuum. Pure 30b (0.079 g, 0.212 mmol, 35%) was obtained as an off white solid. $^1$H NMR (400 MHz, DMSO-$d_6$) δ 8.98-8.95 (m, 2H), 8.26 (d, J=5.7 Hz, 1H), 8.13 (d, J=3.7 Hz, 1H), 7.62 (d, J=7.4 Hz, 1H), 7.33 (t, J=7.9 Hz, 1H), 7.24 (t, J=8.1 Hz, 1H), 7.15 (d, J=3.6 Hz, 1H), 6.95-6.91 (m, 5H), 6.81-6.79 (m, 1H), 4.48 (d, J=6.0 Hz, 2H), 3.72 (s, 3H). HPLC: Purity 98.10%, MeOH 50%, (0.1% TFA in H$_2$O) 50%, 20 min, Flow 1 ml/min: R$_t$ 7.153 min; Purity 97.57%, CH$_3$CN 30%, (0.1% TFA in H$_2$O) 70%, 20 min, Flow 1 ml/min: R$_t$ 7.687 min, HRMS (ESI-ve) calculated for C$_{21}$H$_{20}$N$_5$O$_2$ (M+H)$^+$ 374.1601. found 374.1601

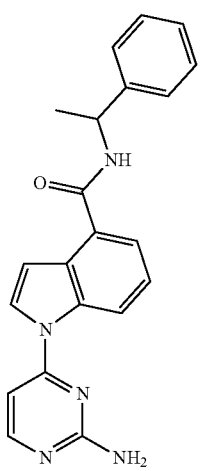 [SMILES: CC(NC(=O)c1cccc2c1ccn2-c1ccnc(N)n1)c1ccccc1]

1-(2-aminopyrimidin-4-yl)-N-(1-phenylethyl)-1H-indole-4-carboxamide (30g) This was obtained from 2-amino-4-chloropyrimidine (0.040 g, 0.308 mmol), and 29b (0.115 g, 0.435 mmol) in a similar manner as described for 30a. After cooling to room temperature, the reaction mixture was diluted with water. The solid precipitated was filtered, slurried with methanol, filtered, washed with methanol and dried under vacuum. Pure 30g (0.074 g, 0.207 mmol, 67%) was obtained as an off white solid. $^1$H NMR (400 MHz, DMSO-$d_6$) δ 8.96 (d, J=8.4 Hz, 1H), 8.81 (d, J=8.2 Hz, 1H), 8.25 (d, J=5.7 Hz, 1H), 8.11 (d, J=3.7 Hz, 1H), 7.63 (d, J=7.1 Hz, 1H), 7.42 (d, J=7.3 Hz, 2H), 7.32 (t, J=7.8 Hz, 3H), 7.21 (t, J=6.7 Hz, 1H), 7.06 (d, J=3.6 Hz, 1H), 6.94 (d, J=5.7 Hz, 1H), 6.92 (s, 2H), 5.20 (quin, J=6.7 Hz, 1H), 1.48 (d, J=7.1 Hz, 3H). HPLC: Purity 99.95%, MeOH 50%, (0.1% TFA in H$_2$O) 50%, 20 min, Flow 1 ml/min, R$_t$ 9.053 min, Purity 99.68%, CH$_3$CN 30%, (0.1% TFA in H$_2$O) 70%, 20 min, Flow 1 ml/min: R$_t$ 9.867 min; HRMS (ESI-ve) calculated for C$_{21}$H$_{20}$N$_5$O (M+H)$^+$ 358.1662, found 358.1687

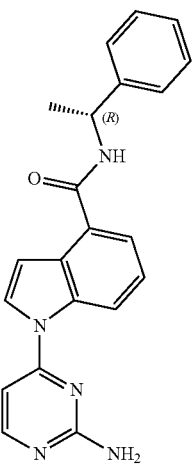

(R)-1-(2-aminopyrimidin-4-yl)-N-(1-phenylethyl)-1H-indole-4-carboxamide (30h). This was obtained from 2-amino-4-chloropyrimidine (0.051 g, 0.393 mmol), and 29l (0.120 g, 0.454 mmol) in a similar manner as described for 30a. After cooling to room temperature, the reaction mixture was diluted with water. The solid precipitated was filtered, slurried with methanol, filtered, washed with methanol and dried under vacuum. Pure 30h (0.059 g, 0.165 mmol, 42%) was obtained as an off white solid $^1$H NMR (400 MHz, DMSO-$d_6$) δ 8.96 (d, J=8.4 Hz, 1H), 8.82 (d, J=8.2 Hz, 1H), 8.25 (d, J=5.7 Hz, 1H), 8.11 (d, J=3.7 Hz, 1H), 7.62 (d, J=7.4 Hz, 1H), 7.42 (d, J=7.7 Hz, 2H), 7.32 (t, J=7.8 Hz, 3H), 7.23-7.19 (m, 1H), 7.06 (d, J=3.7 Hz, 1H), 6.94 (d, J=5.8 Hz, 1H), 6.92 (s, 2H), 5.19 (quin, J=7.3 Hz, 1H), 1.48 (d, J=7.1 Hz, 3H). HRMS (ESI–ve) calculated for $C_{21}H_{20}N_5O$ (M+H)$^+$ 358.1662, found 358.1654.

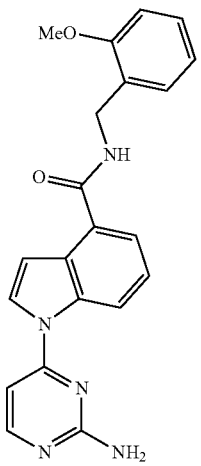 [SMILES: COc1ccccc1CNC(=O)c1cccc2c1ccn2-c1ccnc(N)n1]

1-(2-aminopyrimidin-4-yl)-N-(2-methoxybenzyl)-1H-indole-4-carboxamide. (30i) This was obtained from 2-amino-4-chloropyrimidine (0.050 g, 0.385 mmol), and 20j (0.126 g, 0.449 mmol) in a similar manner as described for 30a. After cooling to room temperature, the reaction mixture was diluted with water. The solid precipitated was filtered, slurried with methanol, filtered, washed with methanol and dried under vacuum. Pure 30i (0.077 g, 0.206 mmol, 54%) was obtained as an off white solid $^1$H NMR (400 MHz, DMSO-$d_6$) δ 8.98 (d, J=8.4 Hz, 1H), 8.79 (t, J=6.0 Hz, 1H), 8.26 (d, J=5.7 Hz, 1H), 8.13 (d, J=3.7 Hz, 1H), 7.66 (d, J=6.8 Hz, 1H) 7.33 (t, J=7.7 Hz, 1H), 7.25-7.21 (m, 2H), 7.15 (d, 1H, J=3.3 Hz, 1H), 7.00-6.88 (m, 5H), 4.48 (d, J=5.9 Hz, 2H), 3.83 (s, 3H). HRMS (ESI–ve) calculated for $C_{21}H_{20}N_5O_2$ (M+H)$^+$ 374.1611, found 374.1603

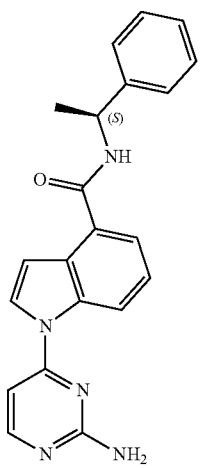

(S)-1-(2-aminopyrimidin-4-yl)-N-(1-phenylethyl)-1H-indole-4-carboxamide (30j). This was obtained from 2-amino-4-chloropyrimidine (0.048 g, 0.370 mmol), and 29k (0.130 g, 0.492 mmol) in a similar manner as described for 30a. After cooling to room temperature, the reaction mixture was diluted with water. The solid precipitated was filtered, slurried with methanol, filtered, washed with methanol and dried under vacuum. Pure 30j (0.080 g, 0.224 mmol, 60%) was obtained as an off white solid $^1$H NMR (400 MHz, DMSO-$d_6$) δ 8.97 (d, J=8.3 Hz, 1H), 8.82 (d, J=8.0 Hz, 1H), 8.26 (d, 1H, J=5.7 Hz, 1H), 8.11 (d, J=3.7 Hz, 1H), 7.63 (d, J=7.3 Hz, 1H), 7.43 (d, J=7.3 Hz, 2H), 7.33 (t, J=7.8 Hz, 3H), 7.23-7.19 (m, 1H), 7.07 (d, J=3.6 Hz, 1H), 6.94 (d, J=5.8 Hz, 1H), 6.93 (s, 2H), 5.21 (quin, J=7.3 Hz, 1H), 1.48 (d, J=7.1 Hz, 3H). HRMS (ESI–ve) calculated for $C_{21}H_{20}N_5O$ (M+H)$^+$ 358.1662, found 358.1653.

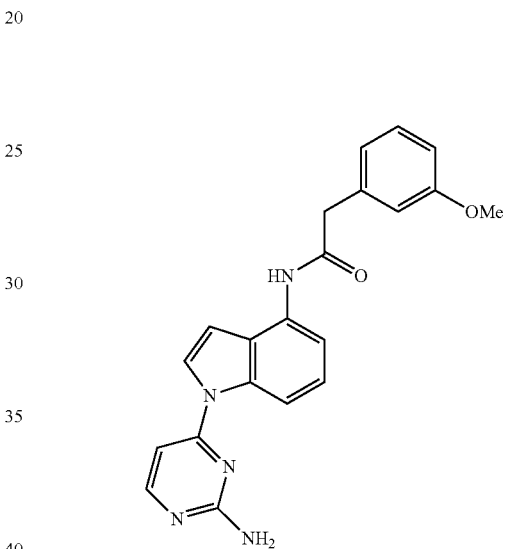

N-(1-(2-aminopyrimidin-4-yl)-1H-indol-4-yl)-2-(3-methoxyphenyl)acetamide (27d). A mixture of 26d (0.32 g, 0.245 mmol) and 2-amino-4-chloropyrimidine (0.080 g, 0.215 mmol) in anhydrous DMF (0.50 mL) and $Cs_2CO_3$ (0.195 g, 0.602 mmol), was heated in the microwave at 150° C. for 30 minutes. After cooling to room temperature, water (3 mL) was added and the solution was filtered. The obtained solid was slurried with acetonitrile, filtered, dried under vacuum to afford pure 27d as an orange solid (0.050 g, 0.134 mmol, 55%), which was dried under vacuum. $^1$H NMR (400 MHz, DMSO-$d_6$) δ 9.91 (s, 1H), 8.52 (d, J=8.4 Hz, 1H), 8.24 (d, J=5.7 Hz, 1H), 8.02 (d, J=3.8 Hz, 1H), 7.68 (d, J=7.8 Hz, 1H), 7.24 (t, J=7.9 Hz, 1H), 7.18 (t, J=8.1 Hz, 1H), 7.00-6.85 (m, 6H), 6.82 (dd, J=8.6, 2.2 Hz, 1H), 3.74 (s, 5H), 2.07 (s, 2H); HPLC purity 97.38% {$t_R$=7.787 min, Flow 1 ml/min, [(CH$_3$CN/(0.1% TFA in H$_2$O):30/70]}; HRMS (ESI+ve) m/z calculated for $C_{21}H_{19}N_5O_2$ (M+H)$^+$ 374.1615, found 374.1605.

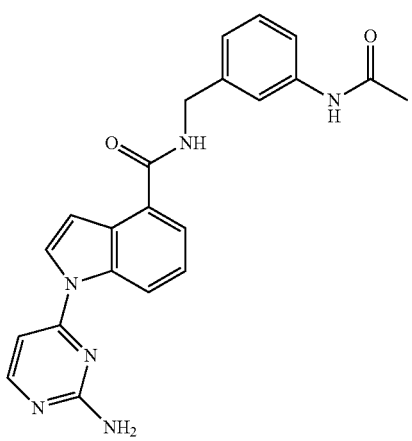 [SMILES: CC(=O)Nc1cccc(CNC(=O)c2cccc3c2ccn3-c2ccnc(N)n2)c1]

N-(3-acetamidobenzyl)-1-(2-aminopyrimidin-4-yl)-1H-indole-4-carboxamide (30n). A mixture of 29p (0.085 g, 0.235 mmol) and 2-amino-4-chloropyrimidine (0.037 g, 0.282 mmol) in anhydrous DMF (0.4 mL) and Cs$_2$CO$_3$ (0.245 g, 0.752 mmol), was heated in the microwave at 150° C. for 45 minutes. After cooling to room temperature. MeOH (5 mL) was added and the solution was filtered. The filtrate was concentrated under reduced pressure. The obtained solid was then washed with water and filtered. Slurry with acetonitrile afforded a brown solid 30n (0.035 g, 0.087 mmol, 37%). $^1$H NMR (400 MHz, CD$_3$OD) δ 8.90 (d, J=8.5 Hz, 1H), 8.23 (d, J=5.8 Hz, 1H), 7.96 (d, J=3.9 Hz, 1H), 7.69-7.52 (m, 2H), 7.45 (d, J=8.1 Hz, 1H), 7.36 (t, J=7.9 Hz, 1H), 7.29 (t, J=7.8 Hz, 1H), 7.15 (s, 1H), 6.90 (d, J=5.9 Hz, 1H), 2.10 (s, 3H). HPLC purity 96.99% {t$_R$=5.883 min, Flow 1 ml/min, [(MeOH/(0.1% TFA in H$_2$O):50/50]}; HRMS (ESI+ve) m/z calculated for C$_{22}$H$_{21}$N$_6$O$_2$ (M+H)$^+$ 401.1720, found 401.1722.

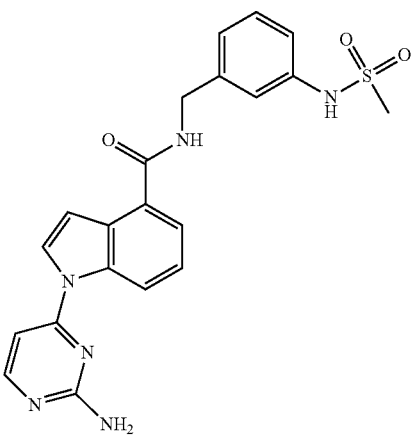 [SMILES: CS(=O)(=O)Nc1cccc(CNC(=O)c2cccc3c2ccn3-c2ccnc(N)n2)c1]

1-(2-aminopyrimidin-4-yl)-N-(3-(methylsulfonamido)benzyl)-1H-indole-4-carboxamide (30m). This was prepared from 29o (0.035 g, 0.097 mmol) and 2-amino-4-chloropyrimidine (0.014 g, 0.111 mmol) in a similar manner as described for preparation of 30n. After cooling to room temperature, water (10 mL) was added and the solid precipitate filtered and dried under vacuum. The obtained solid was slurried with MeOH, filtered, dried under vacuum to afford pure 30m (0.014 g, 0.030 mmol, 32%) as a brown solid. $^1$H NMR (400 MHz, DMSO-d$_6$) δ 9.72 (s, 1H), 8.97 (d, J=6.9 Hz, 2H), 8.26 (d, J=4.7 Hz, 1H), 8.13 (d, J=3.6 Hz, 1H), 7.63 (d, J=7.6 Hz, 1H), 7.37-7.25 (m, 3H), 7.23 (s, 1H), 7.16 (d, J=2.7 Hz, 1H), 7.09 (d, J=7.1 Hz, 2H), 6.95 (d, J=5.8 Hz, 1H), 6.90 (s, 2H), 4.48 (d, J=5.0 Hz, 2H), 2.97 (s, 4H). HPLC purity 96.92% {t$_R$=4.200 min, Flow 1 ml/min, [(MeOH/(0.1% TFA in H$_2$O):40/60]}; HRMS (ESI+ve) m/z calculated for C$_{21}$H$_{21}$N$_6$O$_3$S (M+H)$^+$ 437.1390, found 437.1391.

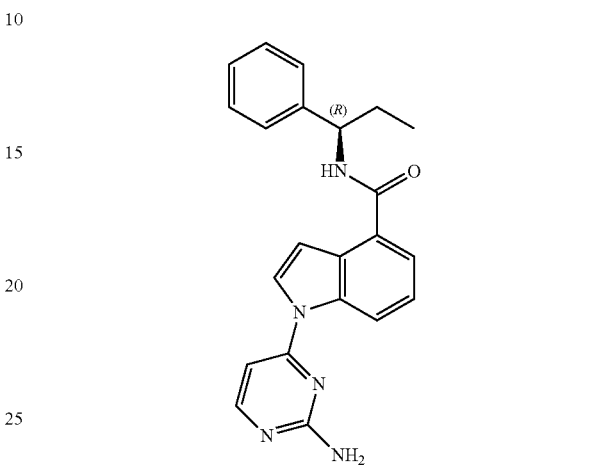

(R)-1-(2-aminopyrimidin-4-yl)-N-(1-phenylpropyl)-1H-indole-4-carboxamide (30o) This was prepared from 29q (0.036 g, 0.129 mmol) and 2-amino-4-chloropyrimidine (0.020 g, 0.154 mmol) in a similar manner as described for preparation of 30n. After the reaction, water (5 mL) was added and the mixture extracted with ethyl acetate. The organic phase was washed with NaHCO$_3$ (aq., sat.), separated dried (Na$_2$SO$_4$), filtered and concentrated under reduced pressure. Slurry with methanol afforded 30o (0.012 g, 0.032 mmol, 25%) as a white solid. $^1$H NMR (400 MHz, CD$_3$OD) δ 8.90 (d, J=8.4 Hz, 1H), 8.23 (d, J=5.7 Hz, 1H), 7.95 (d, J=3.4 Hz, 1H), 7.55 (d, J=7.5 Hz, 1H), 7.43 (d, J=7.6 Hz, 2H), 7.38-7.33 (m, 3H), 7.25 (t, J=8.0 Hz, 1H), 7.02 (d, J=3.5 Hz, 1H), 6.90 (d, J=5.9 Hz, 1H), 5.05-5.01 (m, 1H), 1.98-1.89 (m, 1H), 1.02 (t, J=7.3 Hz, 3H). HPLC purity 99.98% {t$_R$=17.167 min, Flow 1 ml/min, [(CH$_3$CN/(0.1% TFA in H$_2$O):30/70]}; HRMS (ESI+ve) m/z calculated for C$_{22}$H$_{22}$N$_5$O (M+H)$^+$ 372.1818, found 372.1819.

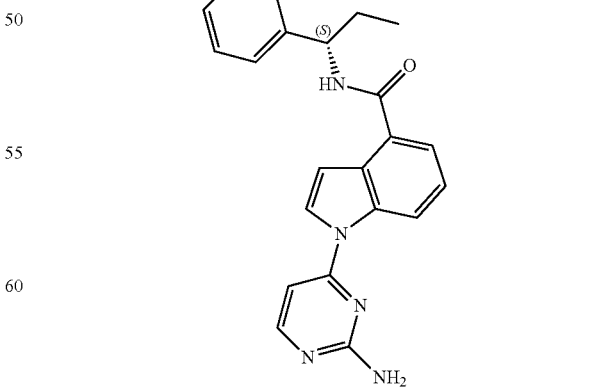

(S)-1-(2-aminopyrimidin-4-yl)-N-(1-phenylpropyl)-1H-indole-4-carboxamide (3aa) This was prepared from 29r (0.036 g, 0.129 mmol) and 2-amino-4-chloropyrimidine (0.020 g, 0.154 mmol) in a similar manner as described for preparation of 30n. After the reaction, water (5 mL) was added and the mixture extracted with ethyl acetate. The organic phase was washed with NaHCO$_3$ (aq., sat.), separated dried (Na$_2$SO$_4$), filtered and concentrated under reduced pressure. Slurry with methanol afforded 30aa (0.012 g, 0.032 mmol, 25%) as a white solid. $^1$H NMR (400 MHz, DMSO-d$_6$) δ 8.96 (d, J=8.5 Hz, 1H), 8.76 (d, J=7.9 Hz, 1H), 8.25 (d, J=4.1 Hz, 1H), 8.10 (s, 1H), 7.61 (d, J=7.4 Hz, 1H), 7.41 (d, J=6.8 Hz, 2H), 7.32 (t, J=7.3 Hz, 3H), 7.21 (t, J=7.3 Hz, 1H), 7.03 (s, 1H), 6.92 (s, 3H), 5.1-4.75 (m, 1H), 1.86-1.75 (m 2H), 0.91 (t, J=6.4 Hz, 3H). HPLC purity 97.30% {t$_R$=8.967 min, Flow 1 ml/min, [(MeOH/(0.1% TFA in H$_2$O):60/40]}; HRMS (ESI+ve) m/z calculated for C$_{22}$H$_{22}$N$_5$O (M+H)$^+$ 372.1818, found 372.1816.

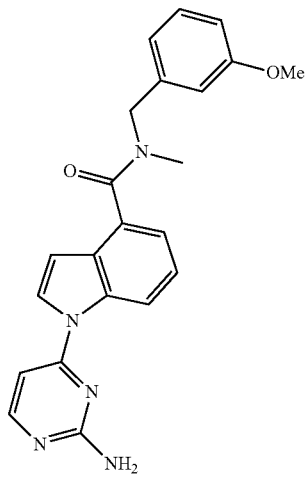

1-(2-aminopyrimidin-4-yl)-N-(3-methoxybenzyl)-N-methyl-1H-indole-4-carboxamide (30q) A mixture of 29t (0.062 g, 0.211 mmol), 2-amino-4-chloropyrimidine (0.033 g, 0.253 mmol), and Cs$_2$CO$_3$ (0.206 g, 0.633 mmol) in DMF (0.5 mL) was heated in the Biotage Microwave for 45 min at 150° C. The solvent was then removed under reduced pressure. Chromatography on silica gel, performed using a FlashMaster 3 purification station afforded 30q (0.028 g, 0.074 mmol, 34%) as a tan solid. HRMS (ESI+ve) m/z calculated for C$_{22}$H$_{21}$N$_5$O$_2$ (M+H)$^+$ 388.17680, found 388.17691

$^1$H NMR (400 MHz, DMSO-d6, 25° C., two rotamers present) δ 8.88 (d, J=8.0 Hz, 1H), 8.27 (d, J=5.6 Hz, 1H), 8.16 (d, J=3.6 Hz, 1H), 7.37-7.28 (m, 2H), 7.23 (d, J=7.1 Hz, 1H), 6.95 (d, J=6.1 Hz, 3H), 6.89 (d, J=6.4 Hz, 1H), 6.80 (d, J=8.0 Hz, 1H), 6.71 (d, J=14.7 Hz, 1H), 6.59 (d, J=19.5 Hz, 2H), 4.72 (s, 2H), 4.41 (s, 1H), 3.77 (s, 2H), 3.68 (s, 1H), 2.95 (s, 1H), 2.74 (s, 1H), 1.90 (s, 2H).

$^1$H NMR (400 MHz, DMSO-d6, 80° C.) δ 8.75 (d, J=7.7 Hz, 1H), 8.27 (d, J=5.5 Hz, 1H), 8.06 (d, J=3.7 Hz, 1H), 7.30 (q, J=17.0, 8.7 Hz, 2H), 7.21 (d, J=7.4 Hz, 1H), 6.91 (d, J=5.7 Hz, 1H), 6.84 (d, J=8.2 Hz, 2H), 6.66-6.57 (m, 3H), 3.75 (s, 3H), 2.86 (s, 2H), 1.90 (s, 3H).

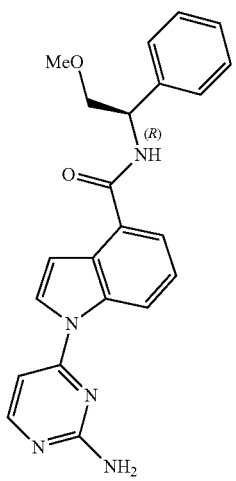

(R)-1-(2-aminopyrimidin-4-yl)-N-(2-methoxy-1-phenylethyl)-1H-indole-4-carboxamide (30p) This was prepared from 29s (0.035 g, 0.119 mmol) and 2-amino-4-chloropyrimidine (0.020 g, 0.154 mmol) in a similar manner as described for preparation of 30n. After the reaction, water (5 mL) was added and the mixture extracted with ethyl acetate. The organic phase was washed with NaHCO$_3$ (aq., sat.), separated dried (Na$_2$SO$_4$), filtered and concentrated under reduced pressure. Slurry with acetonitrile afforded 30p (0.012 g, 0.032 mmol, 25%) as a white solid. $^1$H NMR (400 MHz, DMSO-d$_6$) δ 8.98 (d, J=8.1 Hz, 1H), 8.85 (d, J=8.6 Hz, 1H), 8.26 (d, J=5.4 Hz, 1H), 8.13 (d, J=3.6 Hz, 1H), 7.62 (d, J=7.6 Hz, 1H), 7.45 (d, J=7.6 Hz, 2H), 7.34 (t, J=7.7 Hz, 2H), 7.30-7.21 (m, 1H), 7.08 (d, J=3.3 Hz, 1H), 6.95-6.93 (m, 3H) 5.32-5.27 (m, 1H), 3.70 (t, J=8.8 Hz, 1H), 3.55 (dd, J=10.1, 5.4 Hz, 2H). HPLC purity 96.86% {t$_R$=15,600 min, Flow 1 ml/min, [(MeOH/(0.1% TFA in H$_2$O):40/60]}; HRMS (ESI+ve) m/z calculated for C$_{22}$H$_{21}$N$_5$O$_2$ (M+H)$^+$ 388.1768, found 388.1766.

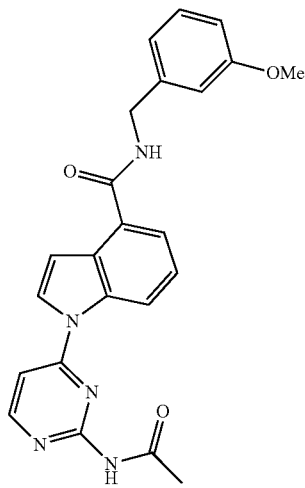 [SMILES: COc1cccc(CNC(=O)c2cccc3c2ccn3-c2ccnc(NC(C)=O)n2)c1]

1-(2-acetamidopyrimidin-4-yl)-N-(3-methoxybenzyl)-1H-indole-4-carboxamide (36) A mixture of acetic anhydride (1.75 mL) and 30b (0.100 g, 0.270 mmol) was refluxed under Argon for 2 hours. The mixture was then cooled to room temperature. The solid precipitate was filtered and washed with ethyl ether, dried under vacuum to afford 36 (0.044 g, 0.106 mmol, 39%) as a white solid. $^1$H NMR (400 MHz, DMSO-d6) δ 10.83 (s, 1H), 9.56 (d, J=7.6 Hz, 1H), 9.01 (t, J=5.5 Hz, 1H), 8.63 (d, J=5.7 Hz, 1H), 8.28 (d, J=4.3 Hz, 1H), 7.66 (d, J=8.2 Hz, 1H), 7.56 (d, J=6.1 Hz, 1H), 7.37 (t, J=8.0 Hz, 1H), 7.28-7.20 (m, 2H), 6.98-6.89 (m, 2H), 6.82 (d, J=9.3 Hz, 1H), 4.49 (d, J=5.3 Hz, 1H), 3.74 (s, 2H), 2.21 (s, 2H). HPLC purity 97.88% {$t_R$=15.300 min, Flow 1 ml/min, [(MeOH/(0.1% TFA in H$_2$O):40/60]}; HRMS (ESI+ve) m/z calculated for $C_{23}H_{22}N_5O_3$ (M+H)$^+$ 416.1717, found 416.1712.

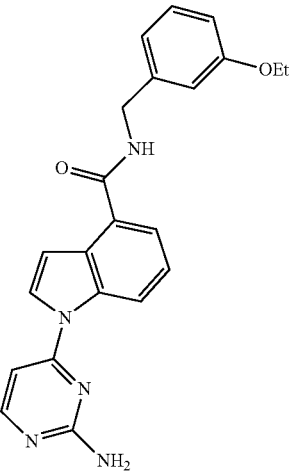

1-(2-aminopyrimidin-4-yl)-N-(3-ethoxybenzyl)-1H-indole-4-carboxamide (30s) This was prepared from 29v (0.283 g, 0.963 mmol) and 2-amino-4-chloropyrimidine (0.150 g, 1.155 mmol) in a similar manner as described for preparation of 27d. After cooling to room temperature, water (5 mL) added and the solid precipitated was filtered and dried under vacuum. The obtained solid was slurried with methanol, filtered dried under vacuum to a white solid 30s (0.212 g, 0.548 mmol, 57% yield). $^1$H NMR (400 MHz, DMSO-d$_6$) δ 8.96-8.91 (m, 2H), 8.25 (d, J=5.6 Hz, 1H), 8.11 (d, J=3.6 Hz, 1H), 7.61 (d, J=7.3 Hz, 1H), 7.32 (t, J=7.9 Hz, 1H), 7.22 (t, J=8.0 Hz, 1H), 6.96-6.85 (m, 3H), 6.78 (d, J=8.9 Hz, 1H), 4.46 (d, J=5.9 Hz, 3H), 3.98 (q, J=7.0 Hz, 2H), 1.29 (t, J=6.9 Hz, 2H). HPLC purity 96.39% {$t_R$=3.583 min, Flow 1 ml/min, [(MeOH/(0.1% TFA in H$_2$O):40/60]}; HRMS (ESI+ve) m/z calculated for $C_{22}H_{22}N_5O_2$ (M+H)$^+$ 388.1768. found 388.1771.

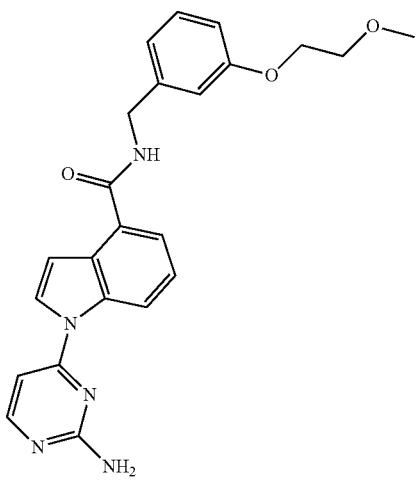 [SMILES: COCCOc1cccc(CNC(=O)c2cccc3c2ccn3-c2ccnc(N)n2)c1]

1-(2-aminopyrimidin-4-yl)-N-(3-(2-methoxyethoxy)benzyl)-1H-indole-4-carboxamide (30r) This was prepared from 29u (0.128 g, 0.395 mmol) and 2-amino-4-chloropyrimidine (0.061 g, 0.474 mmol) in a similar manner as described for preparation of 27d. After cooling to room temperature, the solvent was removed under reduced pressure. Water (5 mL) added and the solid precipitated was filtered and dried under vacuum. The obtained solid was slurried with acetonitrile, filtered, slurried with and methanol, filtered dried under vacuum to 30r (0.082 g, 0.197 mmol, 50%) as an off-white solid. $^1$H NMR (400 MHz, DMSO-d6) δ 8.98-8.92 (m, 2H), 8.26 (d, J=5.7 Hz, 1H), 8.12 (d, J=3.7 Hz, 1H), 7.62 (d, J=7.4 Hz, 1H), 7.34 (d, J=8.2 Hz, 1H), 7.23 (t, J=8.1 Hz, 1H), 7.15 (d, J=3.7 Hz, 1H), 6.97-6.87 (m, 5H), 6.81 (dd, J=7.8, 2.0 Hz, 1H), 4.48 (d, J=6.0 Hz, 2H), 4.08-4.03 (m, 2H), 3.65-3.60 (m, 2H), 3.27 (s, 3H). HPLC purity 99.15% {$t_R$=9.253 min, Flow 1 ml/min, [(MeOH/(0.1% TFA in H$_2$O):50/50]}; HRMS (ESI+ve) m/z calculated for $C_{23}H_{24}N_5O_3$ (M+H)$^+$ 418.1873, found 418.1874.

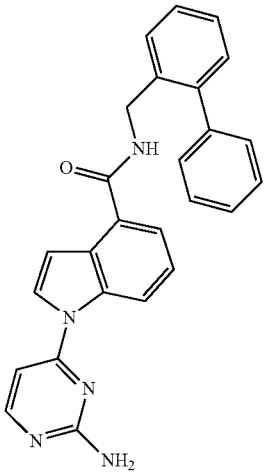 [SMILES: Nc1nccc(-n2ccc3c(C(=O)NCc4ccccc4-c4ccccc4)cccc32)n1]

1-(2-aminopyrimidin-4-yl)-N-(biphenyl-2-ylmethyl)-1H-indole-4-carboxamide (30t) This was prepared from 29w (0.207 g, 0.634 mmol) and 2-amino-4-chloropyrimidine (0.099 g, 0.764 mmol) in a similar manner as described for preparation of 27d. Reaction time: 55 min. After cooling to room temperature, water (10 mL) added and the solid precipitated was filtered and dried under vacuum. The obtained solid was slurried with methanol to afford 30t (0.160 g, 0.381 mmol, 60%) as a white solid. $^1$H NMR (400 MHz, DMSO-$d_6$) δ 8.96 (d, J=8.3 Hz, 1H), 8.85 (t, J=5.6 Hz, 1H), 8.26 (d, J=5.6 Hz, 1H), 8.11 (d, J=3.6 Hz, 1H), 7.60 (d, J=7.5 Hz, 1H), 7.52-7.28 (m, 10H), 7.23 (d, J=7.3 Hz, 1H), 7.12 (d, J=3.5 Hz, 1H), 6.94 (d, J=5.7 Hz, 1H), 6.90 (s, 2H), 4.46 (d, J=5.6 Hz, 2H). HPLC purity 96.23% {$t_R$=8.950 min, Flow 1 ml/min, [(MeOH/(0.1% TFA in H$_2$O):40/60]}; HRMS (ESI+ve) m/z calculated for $C_{26}H_{22}N_5O$ (M+H)$^+$ 420.1818, found 420.1824.

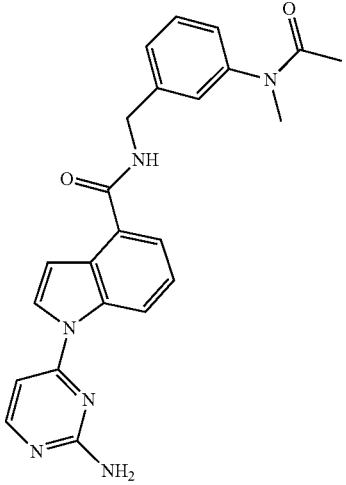 [SMILES: CC(=O)N(C)c1cccc(CNC(=O)c2cccc3c2ccn3-c2ccnc(N)n2)c1]

1-(2-aminopyrimidin-4-yl)-N-(3-(N-methylacetamido) benzyl)-1H-indole-4-carboxamide (30u) This was prepared from 29x (0.075 g, 0.210 mmol) and 2-amino-4-chloropyrimidine (0.0333 g, 0.252 mmol) in a similar manner as described for preparation of 27d. After cooling to room temperature, the solvents was removed under reduced pressure and the obtained solid was slurried with 10 mL of water (10 mL), filtered and dried under vacuum. The obtained solid was slurried with acetonitrile, filtered, dried under vacuum to afford 30u (0.015 g, 0.036 mmol, 17%) as an off white solid. $^1$H NMR (400 MHz, DMSO-$d_6$) δ 8.99-8.95 (m, 2H), 8.25 (d, J=5.6 Hz, 1H), 8.12 (d, J=3.7 Hz, 1H), 7.62 (d, J=7.1 Hz, 1H), 7.41-7.27 (m, 4H), 7.19 (d, J=7.6 Hz, 1H), 7.13 (d, J=3.6 Hz, 1H), 6.94 (d, J=5.7 Hz, 1H), 6.90 (s, 2H), 4.53 (d, J=6.0 Hz, 2H), 3.11 (s, 3H), 1.75 (s, 3H). HPLC purity 98.11% {$t_R$=8.033 min, Flow 1 ml/min, [(MeOH/(0.1% TFA in H$_2$O):40/60]}; HRMS (ESI+ve) m/z calculated for $C_{23}H_{21}N_6O_2$ (M+H)$^+$ 415.1877, found 415.1872.

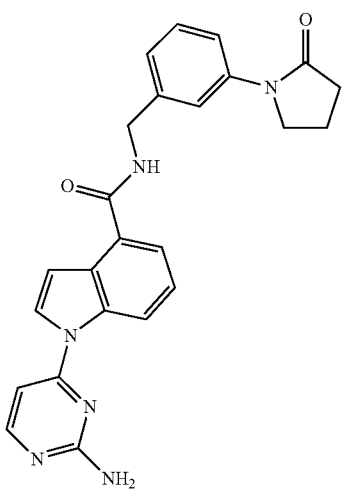 [SMILES: Nc1nccc(-n2ccc3c(C(=O)NCc4cccc(N5CCCC5=O)c4)cccc32)n1]

1-(2-aminopyrimidin-4-yl)-N-(3-(2-oxopyrrolidin-1-yl) benzyl)-1H-indole-4-carboxamide (30v) This was prepared from 29y (0.086 g, 0.258 mmol) and 2-amino-4-chloropyrimidine (0.040 g, 0.310 mmol) in a similar manner as described for preparation of 27d. After cooling to room temperature, water (10 mL) added and the solid precipitated was filtered and dried under vacuum. The obtained solid was slurried with ethyl acetate afforded an off white solid 30v (0.054 g, 0.127 mmol, 49%). $^1$H NMR (400 MHz, DMSO-$d_6$) δ 8.98-8.94 (m, 2H), 8.25 (d, J=5.6 Hz, 1H), 8.12 (d, J=3.7 Hz, 1H), 7.68 (s, 1H), 7.62 (d, J=7.4 Hz, 1H), 7.49 (d, J=8.2 Hz, 1H), 7.32 (td, J=8.0, 3.1 Hz, 2H), 7.16 (d, J=3.4 Hz, 1H), 7.12 (d, J=7.2 Hz, 1H), 6.94 (d, J=5.7 Hz, 1H), 6.89 (s, 2H), 4.50 (d, J=5.9 Hz, 2H), 3.80 (t, J=7.0 Hz, 2H), 2.03 (quin, J=7.6 Hz, 2H). HPLC purity 98.11% {$t_R$=9.317 min, Flow 1 ml/min, [(MeOH/(0.1% TFA in H$_2$O):40/60]}; HRMS (ESI+ve) m/z calculated for $C_{24}H_{23}N_6O_2$ (M+H)$^+$ 427.1877, found 427.1887.

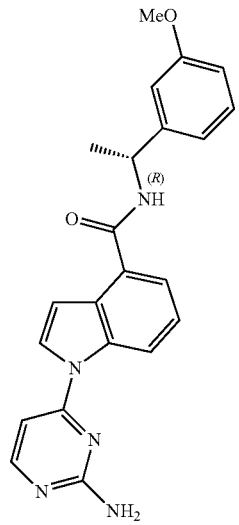

(R)-1-(2-aminopyrimidin-4-yl)-N-(1-(3-methoxyphenyl) ethyl)-1H-indole-4-carboxamide (30w) This was prepared from 29m (0.131 g, 0.445 mmol) and 2-amino-4-chloropyrimidine (0.051 g, 0.393 mmol) in a similar manner as described for preparation of 30a. After cooling to room temperature, the reaction mixture diluted with water (10 ml) and extracted with ethyl acetate (2×10 ml). The combined organic extracts were dried over Na$_2$SO$_4$ and the solvent removed under reduced pressure to provide an off white solid. The obtained solid was slurried with methanol (3 ml), filtered, washed with methanol and dried under vacuum to afford pure 30w as a white solid (0.063 g, 0.162 mmol, 41%). $^1$H NMR (400 MHz, DMSO-$d_6$) δ 8.95 (d, J=8.4 Hz, 1H), 8.77 (d, J=8.2 Hz, 1H), 8.25 (d, J=5.7 Hz, 1H), 8.10 (d, J=3.7 Hz, 1H), 7.61 (d, J=7.6 Hz, 1H), 7.23 (t, J=8.1 Hz, 1H), 7.23 (t, J=8.1 Hz, 1H), 7.06 (d, J=3.6 Hz, 1H), 7.02-6.98 (m, 2H), 6.93 (d, J=5.7 Hz, 1H), 6.90 (s, 1H), 6.79 (m, 1H), 5.16 (quin, J=7.5 Hz, 1H), 3.71 (s, 3H), 1.46 (d, J=7.0 Hz, 2H). HPLC purity 98.33% {$t_R$=6.750 min, Flow 1 ml/min, [(MeOH/(0.1% TFA in H$_2$O):50/50]}; HRMS (ESI+ve) m/z calculated for $C_{22}H_{22}N_5O_2$ (M+H)$^+$ 388.1768, found 388.1769.

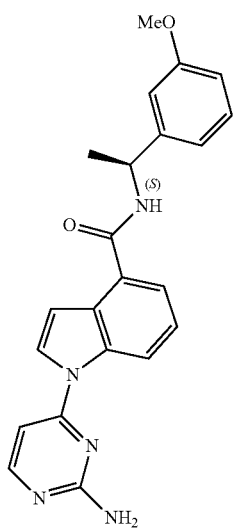

(S)-1-(2-aminopyrimidin-4-yl)-N-(1-(3-methoxyphenyl)ethyl)-1H-indole-4-carboxamide (30z) This was prepared from 29n (0.151 g, 0.513 mmol) and 2-amino-4-chloropyrimidine (0.058 g, 0.447 mmol) in a similar manner as described for preparation of 30a. After cooling to room temperature, the reaction mixture diluted with water (10 ml) and extracted with ethyl acetate (2×10 ml). The combined organic extracts were dried over $Na_2SO_4$ and the solvent removed under reduced pressure to provide an off white solid. The obtained solid was slurried with methanol (3 ml), filtered, washed with methanol and dried under vacuum to afford pure 30z as a white solid (0.087 g, 0.224 mmol, 50%). $^1$H NMR (400 MHz, DMSO-$d_6$) δ 8.96 (d, J=8.5 Hz, 1H), 8.79 (d, J=8.0 Hz, 1H), 8.25 (d, J=5.6 Hz, 1H), 8.11 (d, J=3.8 Hz, 1H), 7.61 (d, J=7.5 Hz, 1H),), 7.23 (t, J=7.8 Hz, 1H), 7.25-7.21 (m, 1H), 7.06 (d, J=3.8 Hz, 1H), 7.01-6.97 (m, 2H), 6.94 (d, J=5.7 Hz, 1H), 6.92 (s, 2H), 6.82-6.76 (m, 1H), 5.34-5.08 (m, 1H), 3.72 (s, 3H), 1.46 (d, J=7.0 Hz, 3H). HPLC purity 97.92% {$t_R$=6.700 min, Flow 1 ml/min, [(MeOH/(0.1% TFA in $H_2O$):50/50]}; HRMS (ESI+ve) m/z calculated for $C_{22}H_{22}N_5O_2$ (M+H)$^+$ 388.1768, found 388.1765.

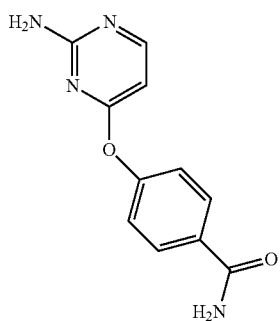 [SMILES: NC(=O)c1ccc(Oc2ccnc(N)n2)cc1]

4-(2-aminopyrimidin-4-yloxy)benzamide (10c). A mixture of 2-amino-4-chloropyrimidine (0.092 g, 0.715 mmol), 4-hydroxybenzamide (0.108 g, 0.787 mmol) in water (2.5 ml) was stirred in a Biotage microwave reactor for 10 min at 165° C. in presence of aq. KOH (2M, 0.392 ml). After cooling to room temperature, the precipitate was filtered, washed with cold water, and dried under vacuum. Pure 10c (0.062 g, 0.269 mmol, 38%) as an a white solid. $^1$H NMR (400 MHz, DMSO-$d_6$) δ 8.11 (d, J=5.5 Hz, 1H), 7.97 (s, 1H), 7.90 (d, J=8.4 Hz, 2H), 7.36 (s, 1H), 7.21 (d, J=8.5 Hz, 2H), 6.64 (s, 2H), 6.15 (d, J=5.5 Hz, 1H). HRMS (ESI+ve) calculated for $C_{11}H_{11}N_4O_2$ (M+H)$^+$ 231.0876, found 231.0877.

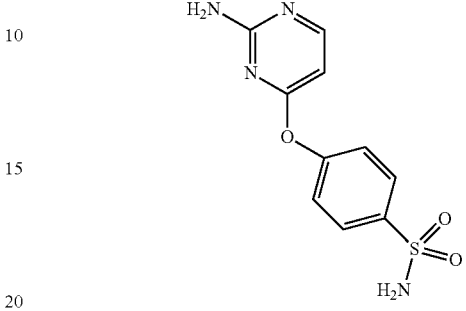

4-(2-aminopyrimidin-4-yloxy)benzenesulfonamide (10b). This was obtained from 2-amino-4-chloropyrimidine (0.069 g, 0.535 mmol), 4-hydroxybenzenesulfonamide (0.102 g, 0.588 mmol), in a similar manner as described for 10c. After cooling to room temperature, the solid precipitate was filtered, washed with water, further slurried with a solution methanol/water (50/50), filtered and dried under vacuum (0.018 g). The methanolic solution was concentrated to dryness. The obtained solid was slurried with water filtered and dried under vacuum (0.025 g). The two batches were combined to provide pure 10b (0.043 g, 0.141 mmol, 30%) as a white solid. $^1$H NMR (400 MHz, $CD_3OD$) δ 8.11 (d, J=6.3 Hz, 1H), 7.95 (d, J=8.9 Hz, 2H), 7.31 (d, J=7.3 Hz, 2H), 6.26 (d, J=5.1 Hz, 1H), HRMS (ESI+ve) calculated for $C_{01}H_{11}N_4O_2S$ (M+H)$^+$ 267.0546. found 267.0550

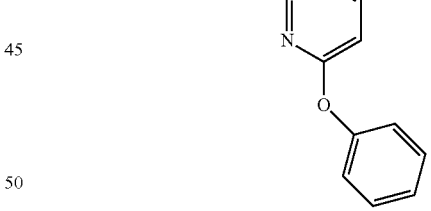

4-phenoxypyrimidin-2-amine (10a). This was obtained from 2-amino-4-chloropyrimidine (0.161 g, 1.71 mmol), phenol (0.201 g, 1.55 mmol), in a similar manner as described for 10c. After cooling to room temperature, the precipitate was filtered, washed with cold water, further slurried with a solution methanol/ether (50/50), filtered and dried under vacuum. Pure 10a (0.136 g, 0.724 mmol, 47%) as an white solid. $^1$H NMR (400 MHz, DMSO-$d_6$) δ 8.08 (d, 1H, J=5.6 Hz, 1H), 7.40 (t, J=7.6 Hz, 2H), 7.22 (t, J=7.9 Hz, 1H), 7.13 (d, J=8.5 Hz, 2H), 6.60 (s, 2H), 6.06 (d, J=5.6 Hz, 1H). HRMS (ESI+ve) calculated for $C_{10}H_{10}N_3O$ (M+H)$^+$ 188.0818, found 188.0839

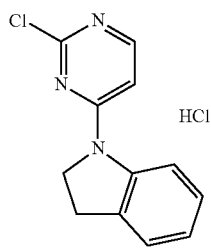 [SMILES: Clc1nccc(N2CCc3ccccc32)n1 ; Cl]

1-(2-chloropyrimidin-4-yl)indoline hydrochloride (32). A mixture of 2,4-dichloropyrimidine (0.165 g, 1.10 mmol), indoline (0.131 g, 1.10 mmol) in aq. HCl (0.1M, 3 ml) was stirred in a Biotage microwave reactor for 30 min at 100° C. After cooling to room temperature, the precipitate was filtered, washed with water, ether, and dried under vacuum. The obtained solid was slurried with methanol, filtered and dried under vacuum (0.029 g). The methanolic solution was concentrated to dryness. Chromatography on silica gel using the FlashMaster 3 purification station (AcOEt/Hexane) afforded 32 (0.055 g). The two batches were combined to afford pure 32 (0.085 g, 0.313 mmol, 28%) as an off white solid. $^1$H NMR (400 MHz, DMSO-$d_6$) δ 8.29 (d, J=6.7 Hz, 1H), 8.26 (d, J=7.3 Hz, 1H), 7.28 (d, J=7.5 Hz, 1H), 7.23 (t, J=8.1 Hz, 1H), 7.01 (t, J=7.4 Hz, 1H), 6.84 (d, J=6.0 Hz, 1H), 4.05 (t, J=8.5 Hz, 2H), 3.21 (t, J=8.5 Hz, 2H), HRMS (ESI+ve) calculated for $C_{12}H_{11}N_3Cl$ (M+H)$^+$ 232.0636, found 232.0645

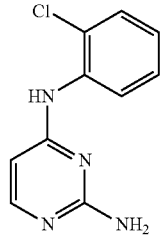

$N^4$-(2-chlorophenyl)pyrimidine-2,4-diamine (1bi). A mixture of 2-amino-4-chloropyrimidine (0.460 g, 3.55 mmol), 2-chloroaniline (0.544 g, 4.26 mmol) EtOH (3.5 ml) was stirred in a Biotage microwave reactor for 20 min at 150° C. After cooling to room temperature, the solvent was removed under reduced pressure and the crude material was diluted with MeOH (10 mL), followed by the addition of $Et_3N$ (1.5 ml). The solvent was then removed under reduced pressure. Water (10 mL) was added and the solid precipitated was filtered, washed with water (10 mL), dried under vacuum to provide 1bi (0.640 g, 2.89 mmol, 82%) as an off-white solid. $^1$H NMR (400 MHz, DMSO-$d_6$) δ 8.51 (s, 1H), 7.87 (d, J=8.2 Hz, 1H), 7.79 (d, J=5.6 Hz, 1H), 7.45 (d, J=8.0 Hz, 1H), 7.29 (t, J=7.8 Hz, 1H), 7.10 (t, J=7.7 Hz, 1H), 6.12 (s, 2H), 6.03 (d, J=5.7 Hz, 1H); HPLC: Purity 98.37%, MeOH 40%, (0.1% TFA in $H_2O$) 60%, 20 min, Flow 1 ml/min: $R_t$ 4.467 min. HRMS (ESI–ve) calculated for $C_{10}H_{10}N_4$ (M+H)$^+$ 221.0588, found 221.0587.

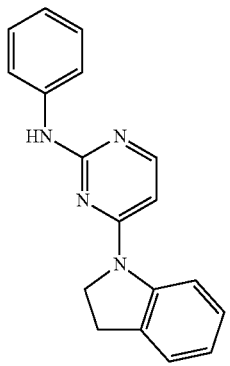 [SMILES: c1ccc(Nc2nccc(N3CCc4ccccc43)n2)cc1]

4-(indolin-1-yl)-N-phenylpyrimidin-2-amine (33). A mixture of 32 (0.044 g, 0.164 mmol), aniline (0.015 g, 0.164 mmol) in aq. HCl (0.1M, 0.7 ml) was stirred in a Biotage microwave reactor for 15 min at 160° C. After cooling to room temperature, DIPEA (1.5 ml) was added. The solvent was removed under reduced pressure. The obtained solid was slurried with water, filtered, dried under vacuum, washed with a solution hexane/DCM (11/2), dried under vacuum. Pure 33 (0.027 g, 0.093 mmol, 57%) was obtained as a yellow solid. $^1$H NMR (400 MHz, DMSO-$d_6$) δ 9.22 (s, 1H), 8.44 (d, J=8.9 Hz, 1H), 8.14 (d, J=5.9 Hz, 1H), 7.72 (d, J=8.1 Hz, 2H), 7.26 (t, J=7.8Hz, 2H), 7.21 (d, J=6.8 Hz, 1H), 7.11 (t, J=7.6 Hz, 1H), 6.94-6.89 (m, 2H), 6.27 (d, J=5.9 Hz, 1H), 4.01 (t, J=8.6 Hz, 2H), 3.18 (t, J=8. Hz, 2H), HRMS (ESI+ve) calculated for $C_{18}H_{17}N_4$ (M+H)$^+$ 289.1447, found 289.1449.

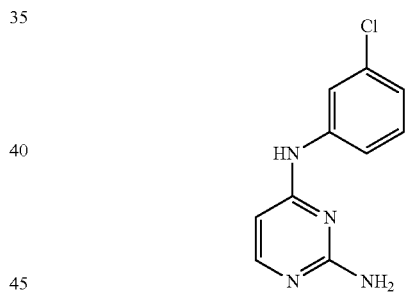

N4-(3-chlorophenyl)pyrimidine-2,4-diamine (1bj). This was obtained from 2-amino-4-chloropyrimidine (0.495 g, 3.82 mmol), 3-chloroaniline (0.625 g, 3.82 mmol), in a similar manner as described for 1bi. After cooling to room temperature, the solvent was removed under reduced pressure and the obtained solid was triturated with AcOEt (15 mL), filtered, washed with AcOEt (5 mL×2), dried, suspended in a saturated solution of aq. sat. $NaHCO_3$ (15 mL). The mixture was sonicated at room temperature, filtered, washed with aq. sat. $NaHCO_3$ (15 mL), water (10 mL), dried under vacuum to provide 1bj (0.692 g, 3.13 mmol, 82%) as an off-white solid. $^1$H NMR (400 MHz, DMSO-d6) δ 9.28 (s, 1H), 7.90 (t, J=2.0 Hz, 1H), 7.82 (d, J=5.7 Hz, 1H), 7.61 (dd, J=8.3, 1.2 Hz, 1H), 7.25 (t, J=8.1 Hz, 1H), 6.95 (dd, J=7.7, 1.7 Hz, 1H), 6.30 (s, 2H), 5.98 (d, J=5.6 Hz, 1H). HPLC: Purity 98.84%, MeOH 50%, (0.1% TFA in $H_2O$) 50%, 20 min, Flow 1 ml/min: $R_t$ 4.347 min. HRMS (ESI–ve) calculated for $C_{10}H_{10}N_4$ (M+H)$^+$ 221.0588. found 221.0587.

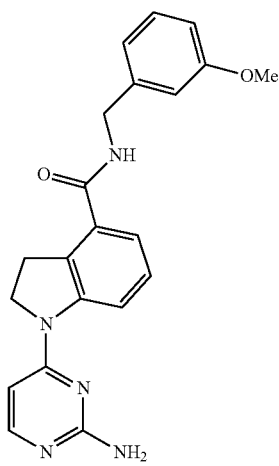 [SMILES: COc1cccc(CNC(=O)c2cccc3c2CCN3c2ccnc(N)n2)c1]

1-(2-aminopyrimidin-4-yl)-N-(3-methoxybenzyl)indoline-4-carboxamide (13r) A mixture of 2-amino-4-chloropyrimidine (0.033 g, 0.254 mmol), 12f (0.115 g, 0.403 mmol) in EtOH (0.7 ml) was stirred in a Biotage microwave reactor for 30 min at 120° C. After cooling to room temperature, the solvent was removed under reduced pressure. Acetone was added and the solid precipitated was filtered, washed with acetone (3 ml×2), hexane (3 ml×2), dried under vacuum. The obtained solid was then suspended in an aq. sat. solution of NaHCO$_3$ (3 ml). The solid precipitate was filtered, washed with water (3 ml×2), acetone (1.5 ml×2), hexane (5 ml×2), dried under vacuum to provide 13r (0.054 g, 0.143 mmol, 56%) as an off-white solid. $^1$H NMR (400 MHz, DMSO-d$_6$) δ 8.83 (t, J=6.0 Hz, 1H), 8.68 (quin, J=3.9 Hz, 1H), 7.95 (d, J=5.8 Hz, 1H), 7.25-7.20 (m, 3H), 6.89-6.87 (m, 2H), 6.80-6.78 (m, 1H), 6.37 (s, 2H), 6.00 (d, J=5.9 Hz, 1H), 4.41 (d, J=6.0 Hz, 2H), 3.94 (t, J=8.7 Hz, 2H), 3.72 (s, 2H), 3.36 (t, J=8.7 Hz, 2H). HRMS (ESI−ve) calculated for C$_{21}$H$_{22}$N$_5$O$_2$(M+H)$^+$ 376.1768, found 376.1765.

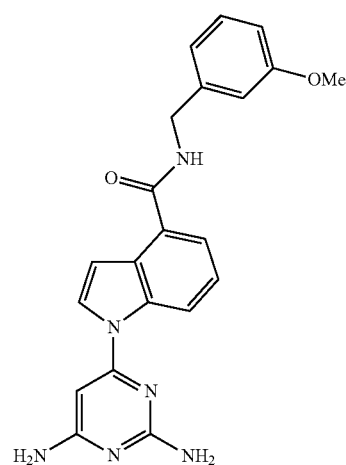 [SMILES: COc1cccc(CNC(=O)c2cccc3c2ccn3-c2cc(N)nc(N)n2)c1]

1-(2,6-diaminopyrimidin-4-yl)-N-(3-methoxybenzyl)-1H-indole-4-carboxamide (38) This was prepared from 29a (0.171 g, 0.610 mmol) and 6-chloropyrimidine-2,4-diamine (0.070 g, 0.484 mmol) in a similar manner as described for preparation of 30a. After cooling to room temperature, the solvent was removed under reduced pressure. Chromatography on silica gel using the FlashMaster 3 purification station (AcOEt/Hexane) afforded 38 as an off white solid. The obtained solid was slurried with ether, filtered, and dried in vacuo. Pure 38 was obtained (0.008 g, 0.020 mmol, 4%) as an off-white solid.[1] $^1$H NMR (400 MHz, DMSO-d$_6$) δ 8.92 (t, J=6.1 Hz, 1H), 8.59 (d, J=8.4 Hz, 1H), 7.86 (d, J=3.5 Hz, 1H), 7.56 (d, J=7.1 Hz, 1H), 7.29-7.21 (m, 2H), 7.07 (d, J=3.6 Hz, 1H), 6.92-6.91 (m, 2H), 6.83-6.78 (m, 1H), 6.45 (s, 2H), 6.24 (s, 2H), 5.92 (s, 1H), 4.47 (d, J=6.1 Hz, 2H), 3.72 (s, 2H).

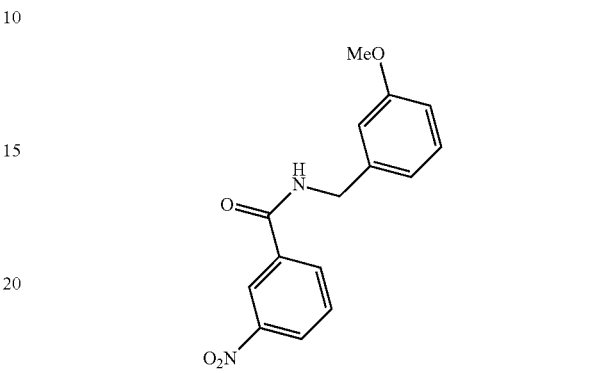

3-Nitro-N-(3-methoxybenzyl)benzamide (41). A solution of 3-nitrobenzoyl chloride (2.27 g, 12.238 mmol) and 3-methoxybenzylamine (2.015 g, 14.686 mmol) in anhydrous DCM (12 mL) was stirred at room temperature for 1 h in presence of Et$_3$N (1.9 mL). DCM (10 mL) was then added followed by aq. HCl (1M, 15 mL). The mixture was filtered. The filtrate was recovered, the organic phase separated, washed with aq. sat NaHCO$_3$, water, dried (Na2SO$_4$), filtered and the solvent removed under reduced pressure to provide a white solid (3.443 g, 12.026 mmol, 98%). The crude material was used in the next step without further purification. $^1$H NMR (400 MHz, DMSO-d6) δ 9.40 (s, 1H), 8.71 (d, J=1.6 Hz, 1H), 8.37 (d, J=8.1 Hz, 1H), 8.32 (d, J=8.4 Hz, 1H), 7.78 (t, J=8.9 Hz, 1H), 7.23 (t, J=7.0 Hz, 1H), 6.88-6.76 (m, 3H), 4.47 (d, J=5.7 Hz, 2H), 3.72 (s, 3H).

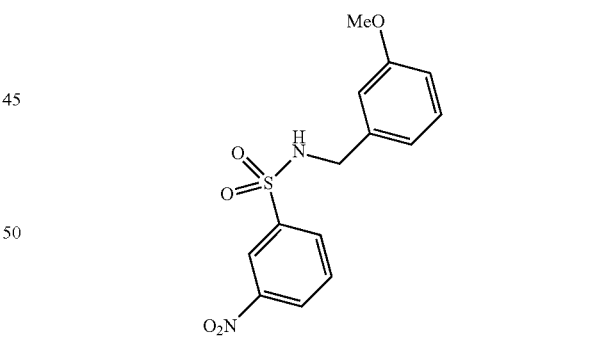

N-(3-methoxybenzyl)-3-nitrobenzenesulfonamide This was obtained from 3-nitrosulfonyl chloride (2.207 g, 9.958 mmol) and 3-methoxybenzylamine (1.639 g, 11.950 mmol) in a similar manner as described for preparation of 41. Chromatography on silica gel using the FlashMaster 3 purification station (AcOEt/Hexane) afforded 44 (0.770 g, 2.39 mmol, 24%) as a yellow oil. $^1$H NMR (400 MHz, DMSO-d6) δ 8.52 (t, J=6.3 Hz, 1H), 8.38-8.30 (m, 2H), 8.10 (d, J=7.7 Hz, 1H), 7.78 (t, J=8.0 Hz, 1H), 7.07 (t, J=7.7 Hz, 1H), 6.75-6.52 (m, 3H), 4.05 (d, J=6.3 Hz, 2H), 3.62 (s, 3H). HRMS (ESI+ve) m/z calculated for C$_{14}$H$_{14}$N$_2$O$_5$SNa (M+Na)$^+$ 345.0515, found 345.0522.

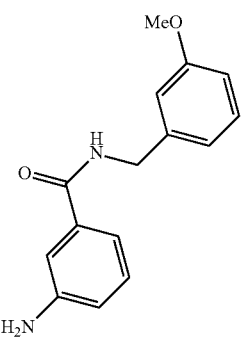 [SMILES: COc1cccc(CNC(=O)c2cccc([N+](=O)[O-])c2)c1]

3-amino-N-(3-methoxybenzyl)benzamide 42. A solution of 41 (0.300 g, 1.048 mmol) in AcOEt (4 mL) was refluxed for 3 h in presence of 5 nCl₂.H₂O (1.182 g, 5.240 mmol). After cooling to room temperature, AcOEt and aq. sat NaHCO₃ were added. The mixture was filtered. The filtrate was collected, the organic phase separated, dried (Na₂SO₄) and the solvent removed under reduced pressure to provide a brown oil (0.233 g, 0.917 mmol, 88%). The crude material was used in the next step without further purification. ¹H NMR (400 MHz, DMSO-d₆) δ 8.73 (t, J=5.9 Hz, 1H), 7.19 (t, J=8.1 Hz, 1H), 7.07-7.00 (m, 2H), 6.95 (d, J=7.7 Hz, 1H), 6.83-6.82 (m, 2H), 6.77-6.75 (m, 1H), 6.65 (dd, J=8.2, 1.6 Hz, 1H), 5.18 (s, 2H), 4.36 (d, J=6.0 Hz, 2H), 3.69 (s, 3H).

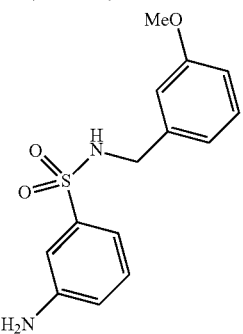 [SMILES: COc1cccc(CNS(=O)(=O)c2cccc([N+](=O)[O-])c2)c1]

3-amino-N-(3-methoxybenzyl)benzenesulfonamide (45). This was obtained as a yellow oil (0.204 g, 0.698 mmol, 75%) from 44 (0.300 g, 0.931 mmol) in a similar manner as described for preparation of 42. The crude material was used in the next step without further purification. ¹H NMR (400 MHz, DMSO-d₆) δ 7.86 (t, J=6.2 Hz, 1H), 7.15-7.10 (m, 2H), 6.96 (s, 1H), 6.85 (d, J=7.6 Hz, 1H), 6.80-6.62 (m, 4H), 5.49 (s, 2H), 3.85 (d, J=6.1 Hz, 1H), 3.64 (s, 3H).

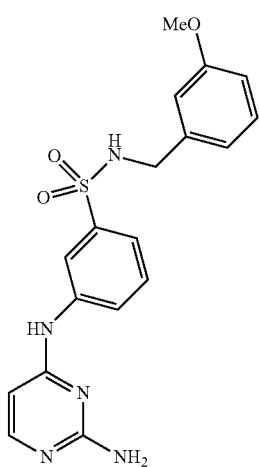 [SMILES: COc1cccc(CNS(=O)(=O)c2cccc(Nc3ccnc(N)n3)c2)c1]

3-(2-aminopyrimidin-4-ylamino)-N-(3-methoxybenzyl)benzenesulfonamide (47) This was prepared from 45 (0.204 g, 0.698 mmol) and 2-amino-4-chloropyrimidine (0.091 g, 0.698 mmol) in a similar manner as described for preparation of 1ae. After cooling to room temperature the solid precipitate was filtered, washed with methanol, and dried under vacuum. The obtained solid was dissolved in ethyl acetate the mixture was then washed with an aq. sat. solution of NaHCO₃. The organic phase was separated, dried (Na₂SO₄), filtered and the solvent removed under reduced pressure. The obtained solid was slurried with methanol, filtered, dried under vacuum to provide pure 47 as an white solid (0.026 g, 0.063 mmol, 10%). ¹H NMR (400 MHz, DMSO-d₆) δ 9.41 (s, 1H), 8.13 (s, 2H), 8.02 (d, J=7.8 Hz, 1H), 7.83 (d, J=5.3 Hz, 1H), 7.42 (t, J=7.8 Hz, 1H), 7.31 (d, J=7.2 Hz, 1H), 7.15 (t, J=7.6 Hz, 1H), 6.81-6.73 (m, 3H), 6.25 (s, 2H), 6.00 (d, J=5.3 Hz, 1H), 3.95 (d, J=5.6 Hz, 3H), 3.65 (s, 3H). HPLC purity 98.01% {$t_R$=12.000 min, Flow 1 ml/min, [(MeOH/(0.1% TFA in H₂O):50/60]}; HRMS (ESI+ve) m/z calculated for $C_{18}H_{20}N_5O_3S$ (M+H)⁺ 386.1281, found 386.1280.

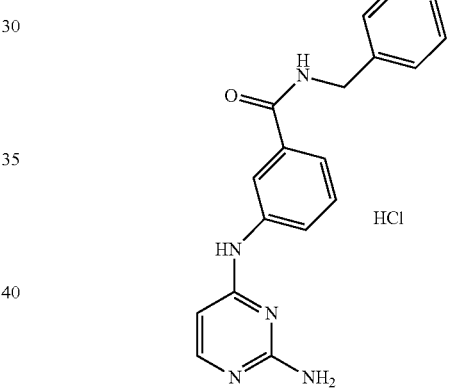

3-(2-aminopyrimidin-4-ylamino)-N-(3-methoxybenzyl)benzamide hydrochloride (46) This was prepared from 42 (0.233 g, 0.917 mmol) and 2-amino-4-chloropyrimidine (0.120 g, 0.917 mmol) in a similar manner as described for preparation of 1ae. After cooling to room temperature, ethyl acetate was added and the solid precipitated was filtered, washed with water and dried under vacuum. Pure 46 was obtained as a white solid (0.134 g, 0.386 mmol, 42%). ¹H NMR (400 MHz, DMSO-d₆) δ 12.29 (s, 1H), 10.82 (s, 1H), 9.06 (t, J=5.2 Hz, 1H), 8.07 (s, 2H), 7.98 (s, 1H), 7.84 (d, J=7.2 Hz, 1H), 7.67 (d, J=8.0 Hz, 1H), 7.47 (t, J=7.9 Hz, 2H), 7.22 (t, J=8.0 Hz, 1H), 6.87-6.86 (m 2H), 6.79 (d, J=8.7 Hz, 1H), 6.34 (d, J=7.0 Hz, 1H), 4.43 (d, J=5.9 Hz, 2H), 3.70 (s, 3H). HPLC purity 99.32% {$t_R$=5.317 min, Flow 1 ml/min, [(MeOH/(0.1% TFA in H₂O):50/50]}; HRMS (ESI+ve) m/z calculated for $C_{19}H_{19}N_5O_3$ (M+H)⁺ 350.16.11. found 350.1608

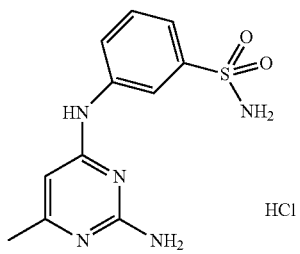

(6)

3-(2-amino-6-methylpyrimidin-4-ylamino)benzenesulfonamide hydrochloride (6). A mixture of 2-amino-6-methyl-4-chloropyrimidine (0.095 g, 0.660 mmol), and 4-aminobenzenesulfonamide (0.113 g, 0.660 mmol) in anhydrous ethanol (0.7 ml) was stirred in a Biotage microwave reactor for 15 min at 160° C. After cooling to room temperature, the solid precipitate was filtered, slurried with methanol and dried under vacuum to afford 6 (0.033 g, 0.105 mmol, 16%) as an off-white solid. $^1$H NMR (400 MHz, CD$_3$OD) δ δ8.39 (s, 1H), 7.84 (s, 1H), 7.70 (d, J=8.2 Hz, 1H), 7.55 (t, J=7.9 Hz, 1H), 6.16 (s, 1H), 2.34 (s, 3H). HRMS (ESI+ve) calculated for $C_{11}H_{15}N_5O_2S$ (M+H—Cl)$^+$ 280.0862, found 280.0867.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

EXAMPLE

Crystal Structure of Human Rock1 with RPM1510

Figure 6:
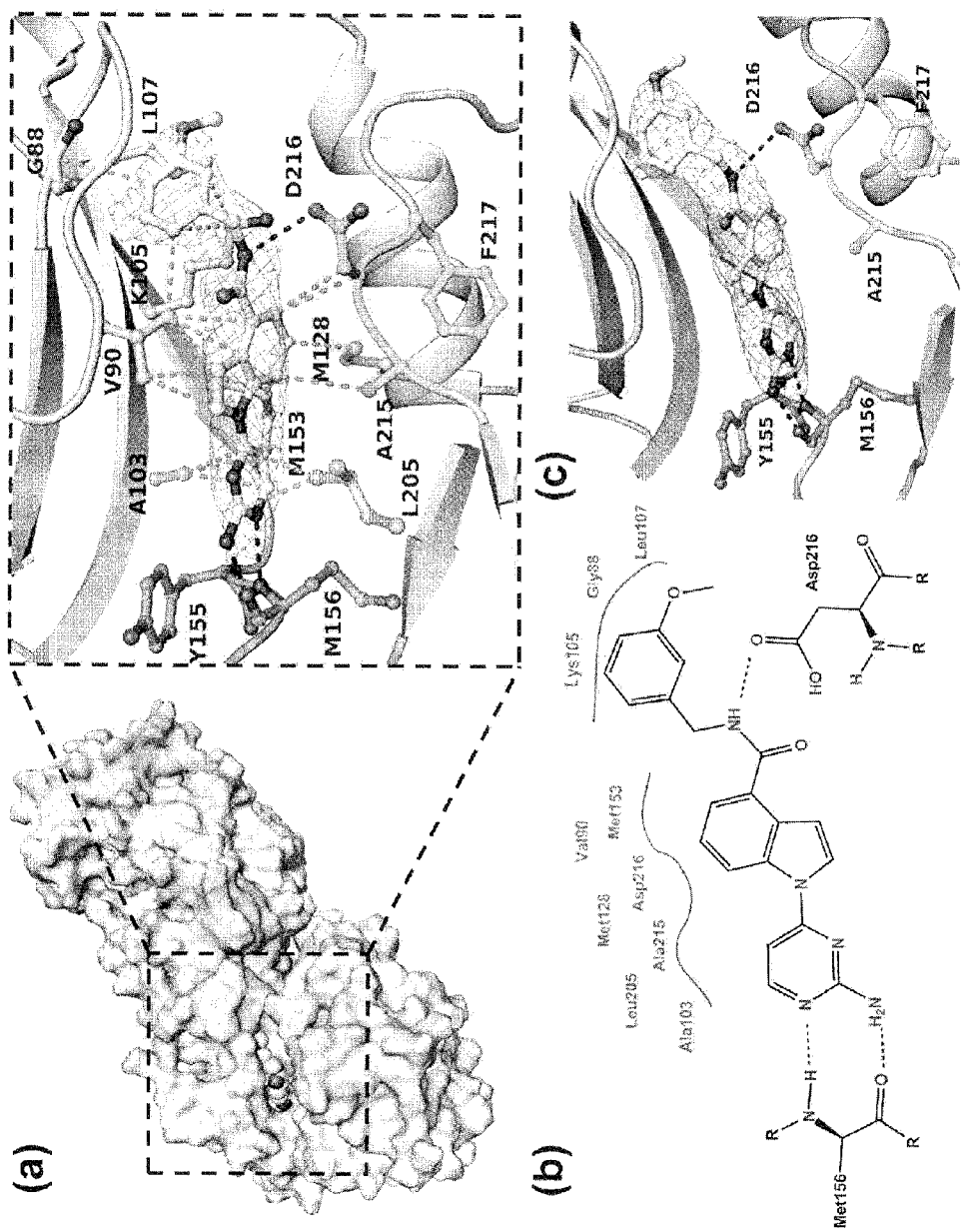
FIGS. 6a-6c: Molecular mode of action of compound 18.

To experimentally determine the mode of action of the aminopyrimidineindole containing ROCK1 inhibitor series, we co-crystallized RPM1510 (also shown as compound 30b herein) with the kinase domain of human ROCK1 (residues 6-415). The ROCK1-RPM1510 complex crystallized in space group C222$_1$ with two dimers per asymmetric unit. The structure was refined to 3.25 Å resolution with current $R_{cryst}$ and $R_{free}$ values of 22.5% and 29.1%, respectively (Table 3). The inhibitor binds to the ATP site of ROCK1 through hydrogen bonding interactions between the aminopyrimidne moiety and the main chain of residue Met156 of the hinge region (FIG. 6). In addition, the amide functionality adjacent to the indole ring establishes a single hydrogen bond with Asp216 of the DFG motif. The m-methoxyphenyl ring is sandwiched between the P-loop (Arg84-Gly88) of the upper N-terminal lobe and the side chain of the catalytic residue Lys 105. RPM 1510 is further stabilized through a series of van der Waals (hydrophobic) interactions with Gly88, Val90, Ala103, Lys105, Leu107, Met128, Met153, Leu205, Ala215, and Asp216.

TABLE 3

Summary of data collection and structure refinement

| Structure | ROCK1-RPM1510 |
|---|---|
| Data Collection | |
| Wavelength (Å) | 1.54 |
| Space group | C222$_1$ |
| Unit cell dimensions (Å) | a = 147.39 |
| | b = 153.27 |
| | c = 205.24 |
| Resolution range | 20-3.25 (3.3-3.25) |
| Unique reflections | 36456 (1629) |
| Completeness (%) | 98.7 (99.3) |
| I/σI | 21.3 (3.9) |
| $R_{merge}$$^a$ (%) | 7.8 (42.3) |
| Structure refinement | |
| Protein atoms | 12888 (2 dimers) |
| Average B-factor (Å$^2$) | 95 |
| Ligand atoms | 56 |
| Average B-factor (Å$^2$) | 98 |
| Solvent molecules | 14 |
| Average B-factor (Å$^2$) | 39 |
| r.m.s.d.$^b$ bonds (Å) | 0.011 |
| r.m.s.d.angles (°) | 1.4 |
| $R_{cryst}$$^c$ (%) | 22.5 |
| $R_{free}$$^d$ (%) | 29.1 |
| $R_{free}$ reflection set size | 1094 (3.0%) |
| Coordinate error (Å) | 0.47 |

$^a$$R_{merge}$ = quality of amplitudes (F) in the scaled data set (Diederichs & Karplus (1997), Nature Struct. Biol. 4, 269-275).
$^b$r.m.s.d. = root mean square deviation from ideal values.
$^c$$R_{cryst}$ = 100 × Σ | $F_{obs}$ − $F_{model}$ |/$F_{obs}$ where $F_{obs}$ and $F_{model}$ are observed and calculated structure factor amplitudes, respectively.
$^d$$R_{free}$ is $R_{cryst}$ calculated for randomly chosen unique reflections, which were excluded from the refinement.

MATERIALS AND METHODS

Reagents and compounds. Reagents and compounds were purchased from Sigma-Aldrich (St. Louis, Mo.) and Hampton Research unless otherwise indicated. The concentration of crystallization grade proteins was determined by A280 molar absorbance using a nanodrop ND-1000 spectrophotometer (Nanodrop Technologies).

Cloning and expression. The gene for human ROCK1 (comprising residues 6-415) was custom-synthesized, cloned into the pFB-Dual-PBL bacmid to provide an N-terminal His-Puritin-tag, and over-expressed in SF9 insect cells after 72 h infection (BlueSky, Worcester, Mass.).

Enzyme purification. Harvested cells were resuspended in 100 mM Na/K phosphate buffer (pH 7.4) containing 300 mM NaCl, 10 mM MgCl$_2$, 10 mM imidazole, and 0.01% Triton X-100 at 4° C. for 1 h. After sonication and centrifugation (1 h at 29000×g), the supernatant was purified by Ni$^{2+}$ affinity column chromatography (GE LifeSciences, Piscataway, N.J.). Following incubation of peak fractions with TEV protease (20:1) at 4° C., the cleaved His-Puritin-tag was separated using a Superdex 75 26/60 column (GE LifeSciences), and eluted with 50 mM HEPES buffer (pH 7.4) containing 150 mM NaCl, 10 mM MgCl$_2$, and 1 mM DTT. Purified ROCK1 was exchanged into 50 mM HEPES buffer (pH 7.4) containing 1 mM DTT and concentrated to 20 mg mL$^{-1}$ prior to crystallization.

Protein crystallography. Crystallization was performed at 18° C. using the sitting drop vapor-diffusion method. Crystals of the ROCK1-RPM1510 complex were grown from 0.1 M HEPES (pH 7.4), 5% tacsimate (pH 7.0), and 10% PEG 5000 MME, in the presence of 1 mM inhibitor. Crystals were harvested in cryo-protectant mixture (reservoir solution including 25% (v/v) ethylene glycol and 1 mM inhibitor) and a complete data set was recorded at −180° C. using CuKa radiation generated by a Rigaku Micro-Max 007-HF rotating anode (MSC, The Woodlands, Tex.) using a CCD Saturn 944+ in the Moffitt Structural Biology Core facility. Data were reduced with XDS (Kabsch, 1993), the structure was solved by molecular replacement using the MolRep program from CCP4 (Acta Crystallogr D Biol Crystallogr, 1994) with pdb 3TWJ as a starting model. PHENIX (Adams et al., 2010) was employed for refinement, and model building was performed using Coot (Emsley et al., 2004). Figures were prepared using PyMol (Schrödinger, LLC).

Introduction

Rho associated protein kinase (ROCK) is a Ser/Thr kinase, activated by small GTPases of the Rho family,[1] which phosphorylates signaling proteins involved with tumor cell invasion,[2,3] angiogenesis,[4] and migration.[5] Although small molecule inhibition of Rho kinase is an established approach for the treatment of cardiovascular disease and CNS disorders, ROCK has only recently received attention for its role in cancer. ROCK activity affects the morphology, adhesion and invasion of cells, which are three important steps in the process of tumor growth and metastasis.[6] Overexpression of Rho and ROCK has been reported in a number of cancers including bladder, ovarian, pancreatic, and testicular, implicating the possible benefits of ROCK inhibition.[7,8] Our group focused on identification and optimization of ROCK1 inhibitors. Using *in vitro* assays, crystallography and molecular modeling we have developed a number of small molecules that inhibit ROCK1 activity at nanomolar concentrations.

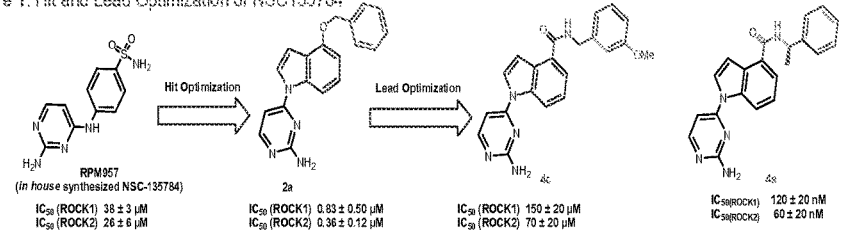

Figure 1. Hit and Lead Optimization of NSC135784

Hit Optimization

We describe the identification of potent ROCK inhibitors from the NCI Diversity set.

- From initial screening, NSC135784 (Figure1) was found to inhibit ROCK1 enzymatic activity, $IC_{50}$ 92 ± 6 µM (FRET-based Z'-Lyte assay).[9,10] *In house* synthesized analogs of NSC135784 [RPM957] led to the identification of compound 2a (ROCK1 $IC_{50}$ 0.83 ± 0.50 µM, ROCK2 $IC_{50}$ 0.36 ± 0.12 µM) as a promising scaffold for further development.

Lead Optimization

- In effort to optimize the potency and selectivity of 2a, we identified a number of amide analogs, including 4c and 4e (Figure 1) as potent inhibitors of ROCK1 and ROCK2.
- SAR studies from the hit optimization process, crystallography and molecular modeling assisted in the development of the pyrimidine-indole analogs.

Library synthesis

Figure 4:
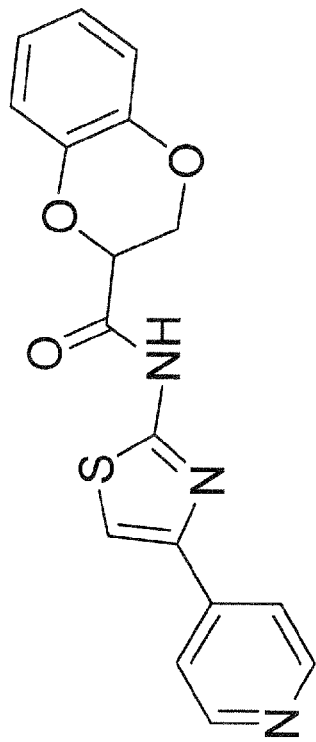
FIG. 4 shows the structure of the compound CID5056270.
Figure 5:
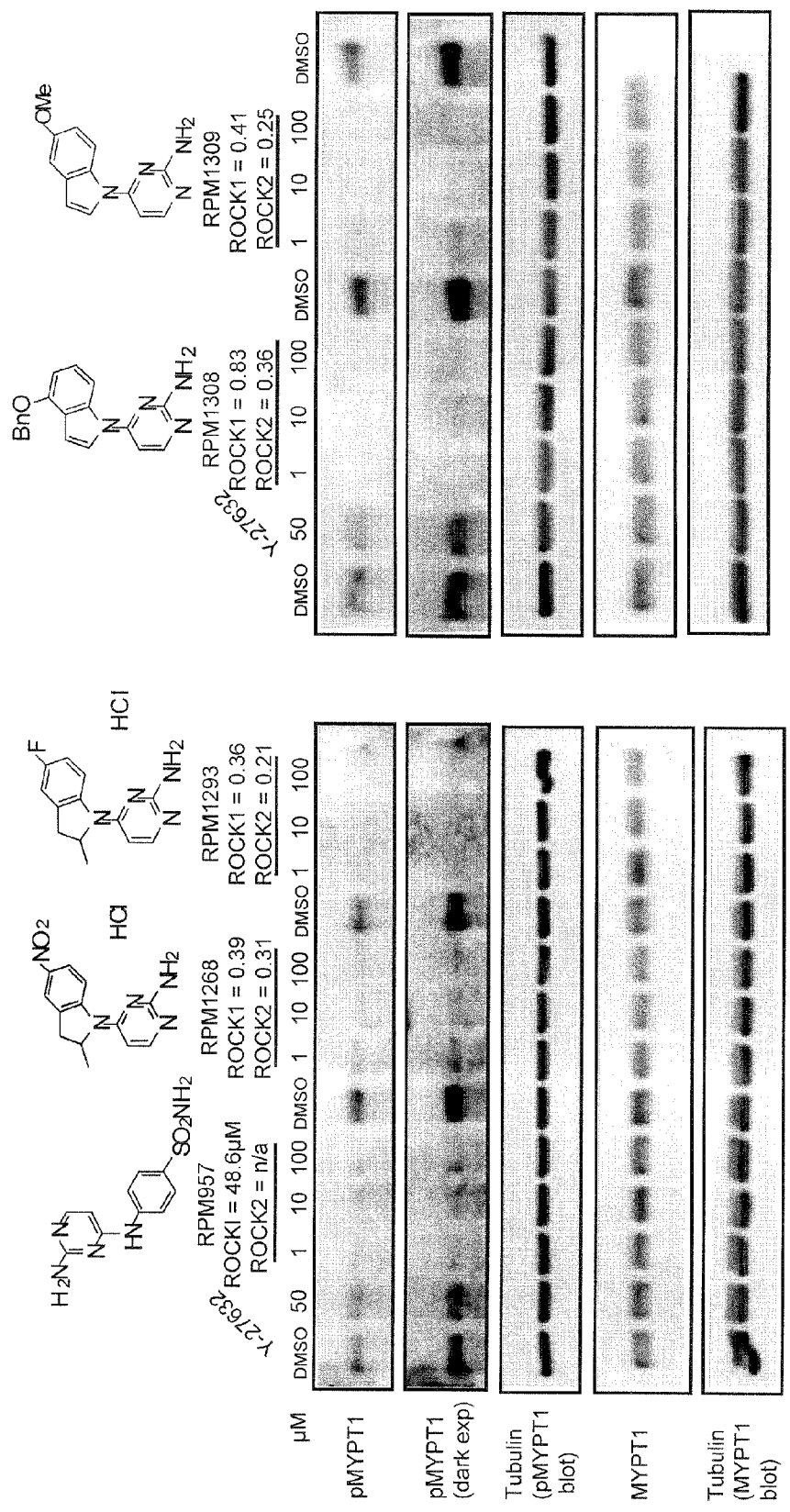
FIG. 5 shows activity of ROCK inhibitors of the invention.

- Libraries of compounds have been designed to aid the hit-to-lead process and probe structure activity relationships.
- Scheme 1 illustrates the synthetic routes followed for the synthesis of our molecular library.
- All compounds were first assessed for *in vitro* ROCK1 inhibition, using a Z'-Lyte kinase assay.[9,10] Only selected compounds were then screened for activity against the ROCK2 isoform.
- 4c and ROCK1 were co-crystalized (Figure 4) to aid in the development of more potent ROCK inhibitors.

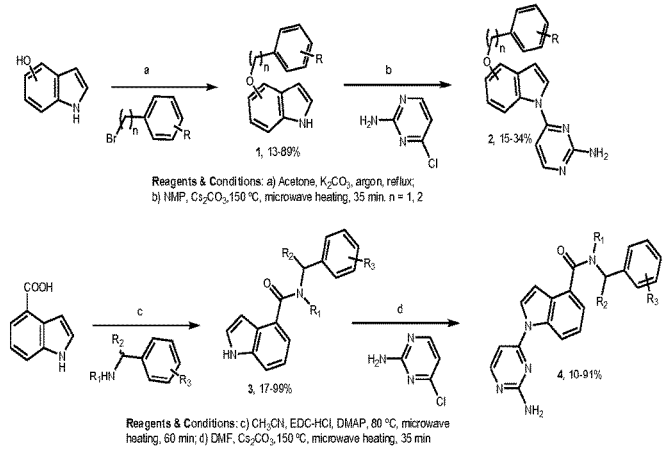

Scheme 1. Synthesis of Library 1

Reagents & Conditions: a) Acetone, $K_2CO_3$, argon, reflux; b) NMP, $Cs_2CO_3$, 150 °C, microwave heating, 35 min. n = 1, 2

Figure 3:
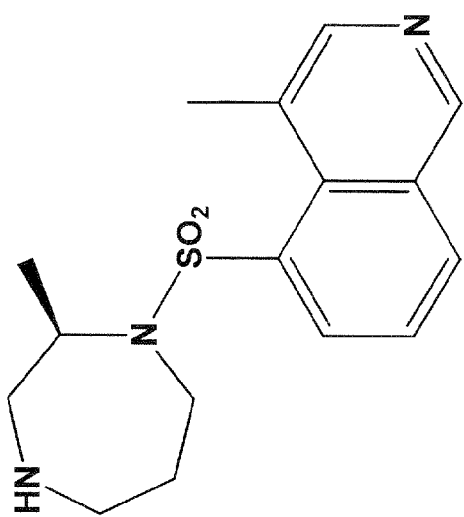
FIG. 3 shows the structure of the compound H-1152P.

Reagents & Conditions: c) $CH_3CN$, EDC-HCl, DMAP, 80 °C, microwave heating, 60 min; d) DMF, $Cs_2CO_3$, 150 °C, microwave heating, 35 min Figure 3. In vitro SAR around scaffold of 4c

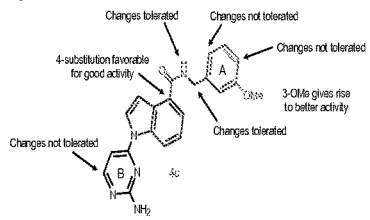

Results and Discussion

- Hit to Lead Optimization of NSC135784 and 2a aided in the development of analogs containing the amide-linker, similar to 4c and 4e.
- Analogs of 2a, 4c, and 4e were synthesized and evaluated for their inhibition of ROCK1 and ROCK2 enzymatic activity.
- Compound 4c and 4e displayed ROCK1 $IC_{50}$ values of 150 nM and 120 nM, respectively (Table 2).
- The ability ROCK1 and ROCK2 to discriminate between an enantiomeric pair of small molecules has been established (Table 2).
- Through initial hit and lead optimization we determined:
  - The indole scaffold acts as a spacer
  - Substitution on the indole's C4 position is optimal for ROCK inhibition
  - Meta substitution of the A ring is optimal for ROCK inhibition
  - (R) stereoisomer, 4e, is preferred over the (S) stereoisomer, 4f, in the amide linker

Crystallography

- X-Ray crystallography has provided new information regarding ROCK1 and 4c binding.
  - Ring A is buried in a hydrophobic pocket created by the Glycine Rich Loop
  - Pyrimidine moiety B acts as the hinge binder
  - 3-OMe may be interacting with ROCK1 via hydrogen bonding
- Guided by the crystallography data, a new set of pyrimidine-indole analogs were created, 4h-s, and will be tested.

Summary and Conclusions

- In search of novel ROCK1 selective inhibitors, 2a was chosen as a starting point for the synthesis of a focused library of pyridines. Structure activity relationship studies led to the identification of potent in vitro inhibitors of ROCK1 and ROCK2, showing nanomolar potency, as exemplified by compound 4c and 4e. Crystallography has provided new information regarding molecular binding and orientation. These tools will be used to further develop potent ROCK inhibitors and elucidate the role of Rho kinase in cancer.

Acknowledgements

All the members of the Drug Discovery Department for help and cooperation, and the H. Lee Moffitt Cancer Center and Research Institute and NIH (U19CA67771-14) for funding, are gratefully acknowledged.

Table 2. In vitro SAR of 4c and analogs

| Name | Entry | R$^1$ | R$^2$ | R$^3$ | ROCK1 $IC_{50}$ (μM)$^a$ | ROCK2 $IC_{50}$ (μM)$^a$ |
|---|---|---|---|---|---|---|
| RPM1418 | 4a | H | H | H | 1.03±0.47 | 0.23±0.08 |
| RPM1532 | 4b | H | H | o-OMe | 5.99±1.98 | 1.80±0.68 |
| RPM1510 | 4c | H | H | m-OMe | 0.15±0.02 | 0.07±0.02 |
| RPM1503 | 4d | H | H | p-OMe | - | - |
| RPM1533 | 4e | H | (R)-Me | H | 0.12±0.02 | 0.06±0.02 |
| RPM1536 | 4f | H | (S)-Me | H | 3.43±0.44 | 1.20±0.32 |
| BA1-081B | 4h | H | H | m-NHSO$_2$CH$_3$ | To be tested | To be tested |
| BA1-085A | 4i | H | (R)-Me | m-OMe | To be tested | To be tested |
| BA1-085B | 4j | H | H | m-NHCOCH$_3$ | To be tested | To be tested |
| BA1-085D | 4k | H | (R)-Et | H | To be tested | To be tested |
| BA1-085E | 4l | H | (R)-CH$_2$OMe | H | To be tested | To be tested |
| BA1-090 | 4m | Me | H | m-OMe | To be tested | To be tested |
| BA1-093 | 4n | H | H | m-OH | To be tested | To be tested |
| BA1-109 | 4o | H | H | m-OCH$_2$CH$_2$OCH$_3$ | To be tested | To be tested |
| BA1-110 | 4p | H | H | m-OEt | To be tested | To be tested |
| BA1-114 | 4q | H | H | o-Ph | To be tested | To be tested |
| BA1-116A | 4r | H | H | m-NCH$_3$COCH$_3$ | To be tested | To be tested |
| BA1-116B | 4s | H | H | m-pyrrolidin-2-one | To be tested | To be tested |

Figure 2:
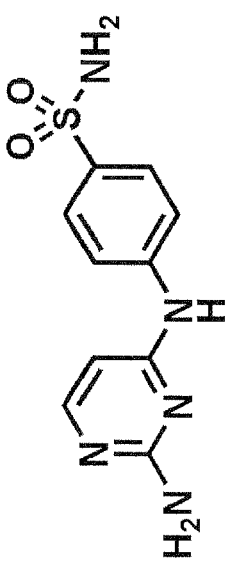
FIG. 2 shows the structure of the compound NSC 135784 (1aa).

Key: a) (FRET)-based Z'-Lyte assay. Y27632: positive control, 90% inhibition @ 2.5 μM Figure 2. X-Ray Crystal structure of 4c bound to the ATP binding site of ROCK1

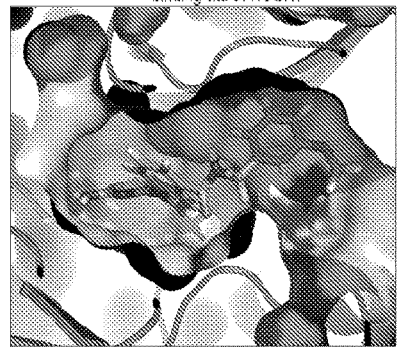

References

1) Fritz, G.; Kaina B., *Curr. Cancer Drug Target.* 2006, 6, 1-14
2) Schmitz, A. A. P.; Govek, E. E.; Böttner, P.; VanAelst, L. *Exp. cell res.* 2000, 261, 1-12 17
3) Imamura, F.; Mujai, M.; Ayaki, M.; Akedo, H. *Jpn. J. Cancer Res.* 2000, 91, 811-816
4) Uchida, S.; Watanabe, G.; Shimada, Y.; Maeda, M.; Kawabe, A.; Mori, A.; Arii, S.; Uehata, M.; Kishimoto, T.; Oikawa, T.; Imamura, M. *Biochem. Biophys. Res. Commn.* 2000, 269, 633-640
5) Somlyo, A. V.; Bradshaw, D.; Ramos, S.; Murphy, C.; Myers, C. E.; Andrew P. Somlyo, A. P. *Biochem. Biophys. Res. Commn.* 2000, 269, 652-659
6) Matsui, T.; Amano, M.; Yamamoto, T.; Chihara, K.; Nakafuku, M.; Ito, M.; Nakano, T.; Okawa, K.; Iwamatsu, A.; Kaibuchi, K. *EMBO J.* 1996, 15, 2208-2216
7) Suwa, H.; Ohshio, G.; Imamura, T.; Watanabe, G.; Arii, S.; Imamura, M.; Narumyia, S.; Hiai, H.; Fukumoto, M. *Br. J. Cancer* 1998, 77, 147-152
8) Kamai, T.; Yamanishi, T.; Shirataki, H.; Takagi, K.; Asami, H.; Ito, Y.; Yoshida, K. I.; *Clin. Cancer. Res.* 2004, 10, 4799-4805
9) Kang, N. S.; Lee, G. N.; Kim, C. H.; Bae, M. A.; Kim, I.; Cho, Y. S., *Bioorg. Med. Chem. Lett.* 2009, 19, 533-537
10) Koresawa, M.; Okabe, T., *Assay Drug Dev. Technol.* 2004, 2, 153-160

REFERENCES

U.S. Pat. No. 6,960,648
U.S. Pat. No. 5,167,649
U.S. Pat. No. 4,992,478
U.S. Pat. No. 4,938,949
U.S. Pat. No. 4,820,508
U.S. Pat. No. 4,608,392
U.S. Pat. No. 4,559,157
Published U.S. patent application No. 20030032594
Published U.S. patent application No. 20020120100
Published U.S. patent application No. 20020035243
Lu, Q.; Longo, F. M.; Zhou, H.; Massa, S. M.; Chen, Y.-H. Signaling through Rho GTPase pathway as viable drug target. Current Medicinal Chemistry 2009, 16, 1355-1365.
Shimokawa, H.; Rashid, M. Development of Rho-kinase inhibitors for cardiovascular medicine. Trends in Pharmacological Sciences 2007, 28, 296-302.
Xing, X.-q.; Gan, Y.; Wu, S.-J.; Chen, P.; Zhou, R.; Xiang, X.-d. Rho-kinase as a potential therapeutic target for the treatment of pulmonary hypertension. Drug News & Perspectives 2006, 19, 517-522.
Liao, J. K.; Seto, M.; Noma, K. Rho kinase (ROCK) inhibitors. Journal of Cardiovascular Pharmacology 2007, 50, 17-24.
Shimokawa, H.; Takeshita, A. Rho-Kinase Is an Important Therapeutic Target in Cardiovascular Medicine. Arteriosclerosis, Thrombosis, and Vascular Biology 2005, 25, 1767-1775.
Dong, M.; Yan, B. P.; Yu, C.-M. Current status of Rho-associated kinases (ROCKs) in coronary atherosclerosis and vasospasm. Cardiovascular & Hematological Agents in Medicinal Chemistry 2009, 7, 322-330.
Hu, E.; Lee, D. Rho kinase as potential therapeutic target for cardiovascular diseases: opportunities and challenges. Expert Opinion on Therapeutic Targets 2005, 9, 715-736.
Kubo, T.; Yamaguchi, A.; Iwata, N.; Yamashita, T. The therapeutic effects of Rho-ROCK inhibitors on CNS disorders. Therapeutics and Clinical Risk Management 2008, 4, 605-615.
Kubo, T.; Yamashita, T. Rho-ROCK inhibitors for the treatment of CNS injury. Recent patents on CNS drug discovery 2007, 2, 173-9.
LoGrasso Philip, V.; Feng, Y. Rho kinase (ROCK) inhibitors and their application to inflammatory disorders. Current topics in medicinal chemistry 2009, 9, 704-23.
Suwa, H.; Ohshio, G.; Imamura, T.; Watanabe, G.; Arii, S.; Imamura, M.; Narumiya, S.; Hiai, H.; Fukumoto, M. Overexpression of the rhoC gene correlates with progression of ductal adenocarcinoma of the pancreas. British Journal of Cancer 1998, 77, 147-152.
Kamai, T.; Yamanishi, T.; Shirataki, H.; Takagi, K.; Asami, H.; Ito, Y.; Yoshida, K.-I. Overexpression of RhoA, Rac1, and Cdc42 GTPases Is Associated with Progression in Testicular Cancer. Clinical Cancer Research 2004, 10, 4799-4805.
Schmitz, A. A. P.; Govek, E.-E.; Bottner, B.; Van Aelst, L. Rho GTPases: Signaling, Migration, and Invasion. Experimental Cell Research 2000, 261, 1-12.
Imamura, F.; Mukai, M.; Ayaki, M.; Akedo, H. Y-27632, an inhibitor of rho-associated protein kinase, suppresses tumor cell invasion via regulation of focal adhesion and focal adhesion kinase. Japanese Journal of Cancer Research 2000, 91, 811-816.
Somlyo, A. V.; Bradshaw, D.; Ramos, S.; Murphy, C.; Myers, C. E.; Somlyo, A. P. Rho-kinase inhibitor retards migration and in vivo dissemination of human prostate cancer cells. Biochemical and Biophysical Research Communications 2000, 269, 652-659.
Uchida, S.; Watanabe, G.; Shimada, Y.; Maeda, M.; Kawabe, A.; Mori, A.; Arii, S.; Uehata, M.; Kishimoto, T.; Oikawa, T.; Imamura, M. The Suppression of Small GTPase Rho Signal Transduction Pathway Inhibits Angiogenesis in Vitro and in Vivo. Biochemical and Biophysical Research Communications 2000, 269, 633-640.
Itoh, K.; Yoshioka, K.; Akedo, H.; Uehata, M.; Ishizaki, T.; Narumiya, S. An essential part for Rho-associated kinase in the transcellular invasion of tumor cells. Nature Medicine (New York) 1999, 5, 221-225.
Uehata, M.; Ishizaki, T.; Satoh, H.; Ono, T.; Kawahara, T.; Morishita, T.; Tamakawa, H.; Yamagami, K.; Inui, J.; Maekawa, M.; Narumiya, S. Calcium sensitization of smooth muscle mediated by a Rho-associated protein kinase in hypertension. Nature 1997, 389, 990-4.
Ishizaki, T.; Uehata, M.; Tamechika, I.; Keel, J.; Nonomura, K.; Maekawa, M.; Narumiya, S. Pharmacological properties of Y-27632, a specific inhibitor of Rho-associated kinases. Molecular Pharmacology 2000, 57, 976-983.
Narumiya, S.; Ishizaki, T.; Uehata, M. Use and properties of ROCK-specific inhibitor Y-27632. Methods in enzymology 2000, 325, 273-84.
Nakajima, M.; Hayashi, K.; Egi, Y.; Katayama, K.-i.; Amano, Y.; Uehata, M.; Ohtsuki, M.; Fujii, A.; Oshita, K.-i.; Kataoka, H.; Chiba, K.; Goto, N.; Kondo, T. Effect of Wf-536, a novel ROCK inhibitor, against metastasis of B16 melanoma. Cancer chemotherapy and pharmacology 2003a, 52, 319-24.
Nakajima, M.; Hayashi, K.; Katayama, K.-i.; Amano, Y.; Egi, Y.; Uehata, M.; Goto, N.; Kondo, T. Wf-536 prevents tumor metastasis by inhibiting both tumor motility and angiogenic actions. European journal of pharmacology 2003b, 459, 113-20.
Ying, H.; Biroc, S. L.; Li, W.-w.; Alicke, B.; Xuan, J.-A.; Pagila, R.; Ohashi, Y.; Okada, T.; Kamata, Y.; Dinter, H. The Rho kinase inhibitor fasudil inhibits tumor progression in human and rat tumor models. Molecular Cancer Therapeutics 2006, 5, 2158-2164.
Somlyo, A. V.; Phelps, C.; Dipierro, C.; Eto, M.; Read, P.; Barrett, M.; Gibson, J. J.; Burnitz, M. C.; Myers, C.; Somlyo, A. P. Rho kinase and matrix metalloproteinase inhibitors cooperate to inhibit angiogenesis and growth of human prostate cancer xenotransplants. FASEB Journal 2003, 17, 223-234.
Hampson, L.; He, X. T.; Oliver, A. W.; Hadfield, J. A.; Kemp, T.; Butler, J.; McGown, A.; Kitchener, H. C.; Hampson, I. N. Analogues of Y27632 increase gap junction communication and suppress the formation of transformed NIH3T3 colonies. British Journal of Cancer 2009, 101, 829-839.
Igishi, T.; Mikami, M.; Murakami, K.; Matsumoto, S.; Shigeoka, Y.; Nakanishi, H.; Yasuda, K.; Gutkind, J. S.; Hitsuda, Y.; Shimizu, E. Enhancement of cisplatin-induced cytotoxicity by ROCK inhibitor through suppression of focal adhesion kinase-independent mechanism in lung carcinoma cells. International Journal of Oncology 2003, 23, 1079-1085.
Liu, S.; Goldstein, R. H.; Scepansky, E. M.; Rosenblatt, M Inhibition of Rho-Associated Kinase Signaling Prevents Breast Cancer Metastasis to Human Bone. Cancer Research 2009, 69, 8742-8751.
Ogata, S.; Morishige, K.-I.; Sawada, K.; Hashimoto, K.; Mabuchi, S.; Kawase, C.; Ooyagi, C.; Sakata, M.; Kimura, T. Fasudil inhibits lysophosphatidic acid-induced invasiveness of human ovarian cancer cells. International Journal of Gynecological Cancer 2009, 19, 1473-80.

Zohrabian, V. M.; Forzani, B.; Chau, Z.; Murali, R.; Jhanwar-Uniyal, M. Rho/ROCK and MAPK signaling pathways are involved in glioblastoma cell migration and proliferation. Anticancer Research 2009, 29, 119-123.

Micuda, S.; Rosel, D.; Ryska, A.; Brabek, J. ROCK inhibitors as emerging therapeutic candidates for sarcomas. Curr. Cancer Drug Targets 2010, 10, 127-134.

Belgiovine, C.; Frapolli, R.; Bonezzi, K.; Chiodi, I.; Favero, F.; Mello-Grand, M.; Dei Tos, A. P.; Giulotto, E.; Taraboletti, G.; D'Incalci, M.; Mondello, C. Reduced expression of the ROCK inhibitor Rnd3 is associated with increased invasiveness and metastatic potential in mesenchymal tumor cells. PLoS One 2010, 5, e14154.

Nakabayashi, H.; Shimizu, K. HA1077, a Rho kinase inhibitor, suppresses glioma-induced angiogenesis by targeting the Rho-ROCK and the mitogen-activated protein kinase kinase/extracellular signal-regulated kinase (MEK/ERK) signal pathways. Cancer Sci. 2011, 102, 393-399.

Yin, L.; Morishige, K.-i.; Takahashi, T.; Hashimoto, K.; Ogata, S.; Tsutsumi, S.; Takata, K.; Ohta, T.; Kawagoe, J.; Takahashi, K.; Kurachi, H. Fasudil inhibits vascular endothelial growth factor-induced angiogenesis in vitro and in vivo. Mol. Cancer. Ther. 2007, 6, 1517-1525.

Kang, N. S.; Lee, G. N.; Kim, C. H.; Bae, M. A.; Kim, I.; Cho, Y. S. Identification of small molecules that inhibit GSK-3b through virtual screening. Bioorg. Med. Chem. Lett. 2009, 19, 533-537.

Wu, J.; Zhang, B.; Wu, M.; Li, H.; Niu, R.; Ying, G.; Zhang, N. Screening of a PKC z-specific kinase inhibitor PKCzI257.3 which inhibits EGF-induced breast cancer cell chemotaxis. Invest. New Drugs 2010, 28, 268-275.

de Suto-Nagy, G.; Johnson, T. B. Pyrimidines. CLXXV. (p-Sulfamylphenylamino)pyrimidines. J. Am. Chem. Soc. 1941, 63, 3234-5.

Huryn, D. M.; Cosford, N. D. P. The molecular libraries screening center network (MLSCN): identifying chemical probes of biological systems. Annu Rep. Med. Chem. 2007, 42, 401-416.

Huryn, D. M. Medicinal chemistry in the pilot phase of the Molecular Libraries Screening Center Network. Current Topics in Medicinal Chemistry 2009, 9, 1158-9.

Toyoizumi T, Mick R, Abbas A E, Kang E H, Kaiser L R, Molnar-Kimber K L (1999) "Combined therapy with chemotherapeutic agents and herpes simplex virus type IICP34.5 mutant (HSV-1716) in human non-small cell lung cancer" Human Gene Therapy, 10(18):17.

Kabsch, W., *Automatic processing of rotation diffraction data from crystals of initially unknown symmetry and cell constants*. Journal of Applied Crystallography, 1993. 26 (6): p. 795-800.

*The CCP4 suite: programs for protein crystallography*. Acta Crystallogr D Biol Crystallogr, 1994. 50 (Pt 5): p. 760-3.

Adams, P. D., et al., *PHENIX: a comprehensive Python-based system for macromolecular structure solution*. Acta Crystallogr D Biol Crystallogr, 2010. 66 (Pt 2): p. 213-21.

Emsley, P. and K. Cowtan, *Coot: model-building tools for molecular graphics*. Acta. Crystallogr. D Biol. Crystallogr., 2004. 60 (Pt 12 Pt 1): p. 2126-32.

We claim:

1. A compound having the chemical structure shown in formula I, formula IIa, formula IIb, formula III, or formula IV:

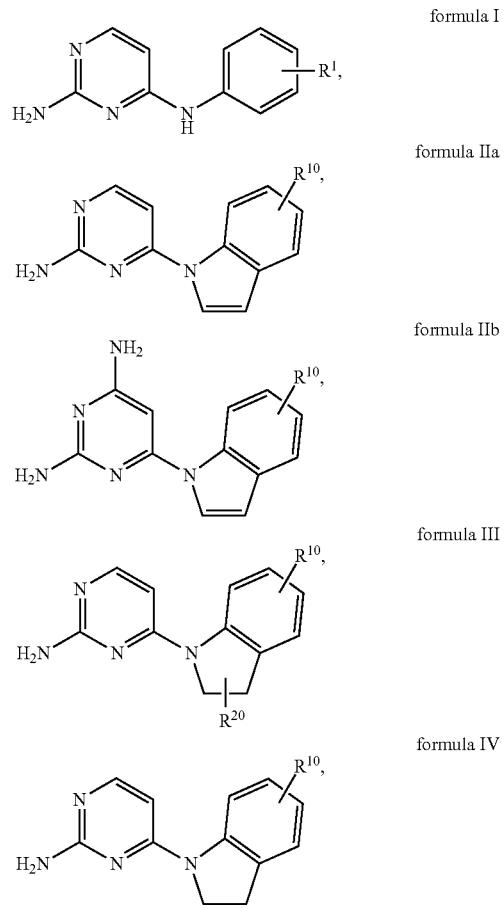

wherein $R^1$ in formula I is H, OH, S-alkyl, $SO_2NR^2R^3$, $NO_2$, $CONH_2$, $SO_2$-alkyl, NHC(O)-alkyl, $CO_2H$, alkyl, cycloalkyl, alkoxy, cycloalkoxy, heterocycloalkyl, alkoxycarbonyl, heteroaryl, or aryl;

$R^2$ is H, CO, alkoxy, alkyl, aryl, heteroalkyl, heteroaryl, heterocycloalkyl, alkylcarbonyl, arylcarbonyl, or alkoxycarbonyl;

$R^3$ is H, CO, alkoxy, alkyl, aryl, heteroalkyl, heteroaryl, heterocycloalkyl, alkylcarbonyl, arylcarbonyl, or alkoxycarbonyl;

any of which of $R^1$, $R^2$, and $R^3$ can be optionally substituted with one or more of halogen, alkyl, alkoxy or aryl optionally substituted with alkoxy;

$R^{10}$ in formula IIb is H, $NO_2$, halogen, $—CH_3$, $—SO_2$-alkyl, $—OCH_3$, alkoxy, —C(O)NH-alkyl, —C(O)NH-aryl, —NHC(O)-alkyl, —NHC(O)-aryl, or aryloxy, any of which can be substituted with one or more of aryl or alkoxy, any of which can be optionally substituted with halogen, —OH, alkoxy, or aryl optionally substituted with alkoxy;

$R^{10}$ in formula III is H, $NO_2$, —F, —Cl, —I, $—CH_3$, $—SO_2$-alkyl, $—OCH_3$, alkoxy, —C(O)NH-alkyl, —C(O)NH-aryl, —NHC(O)-alkyl, —NHC(O)-aryl, or aryloxy, any of which can be substituted with one or more of aryl or alkoxy, any of which can be optionally substituted with halogen, —OH, alkoxy, or aryl optionally substituted with alkoxy;

$R^{10}$ in formula IIa and formula IV is H, $NO_2$, —F, —Cl, —I, $—CH_3$, $—SO_2$-alkyl, $—OCH_3$, alkoxy, —C(O)

NH-alkyl, —C(O)NH-aryl, —NHC(O)-alkyl, —NHC(O)-aryl, or aryloxy, any of which can be substituted with one or more of aryl or alkoxy, any of which can be optionally substituted with halogen, —OH, alkoxy, or aryl optionally substituted with alkoxy;

$R^{20}$ in formula III is —CH$_3$, —CO$_2$H, heteroalkyl, aryl, or alkyl;

or a pharmaceutically acceptable salt or hydrate thereof; wherein said compound of formula I comprises one or more $R^1$, wherein said compound of formula IIa, IIb, III, or IV comprises one or more $R^{10}$, and wherein said compound of formula III comprises one or more $R^{20}$; or said compound having the chemical structure selected from:

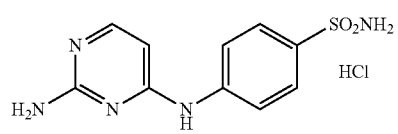

(1aa)

C$_{10}$H$_{12}$ClN$_5$O$_2$S; MW, 301.75

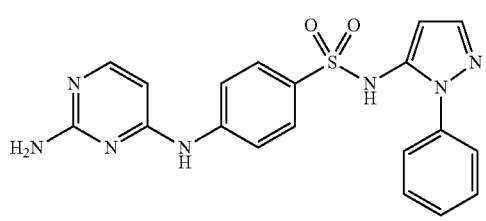

(1ab)

C$_{19}$H$_{17}$N$_7$O$_2$S; MW, 407.45

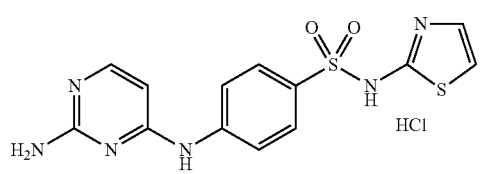

(1ac)

C$_{13}$H$_{13}$ClN$_6$O$_2$S$_2$; MW, 384.86

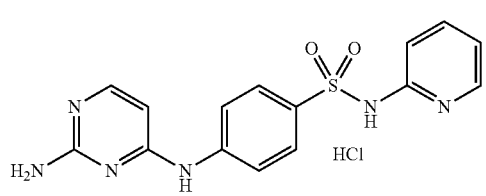

(1ad)

C$_{15}$H$_{15}$ClN$_6$O$_2$S; MW, 378.84

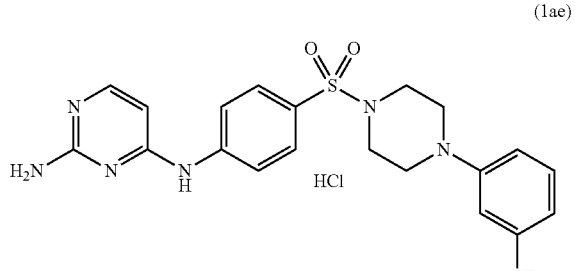

(1ae)

C$_{21}$H$_{22}$ClF$_3$N$_6$O$_2$; MW, 514.95

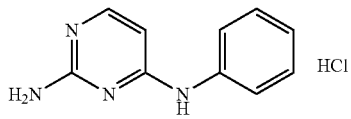

(1af)

C$_{10}$H$_{11}$ClN$_4$; MW, 222.67

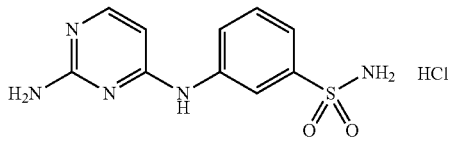

(1ag)

C$_{10}$H$_{12}$ClN$_5$O$_2$S; MW, 301.75

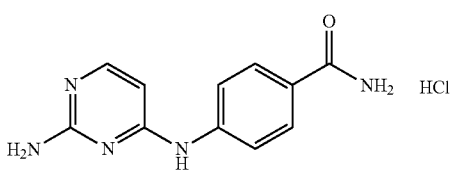

(1ah)

C$_{11}$H$_{12}$ClN$_5$O; MW, 265.70

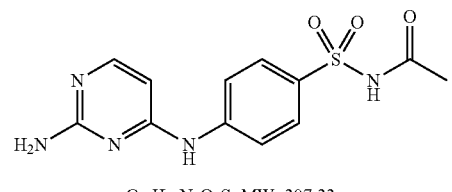

(1ai)

C$_{12}$H$_{13}$N$_5$O$_3$S; MW, 307.33

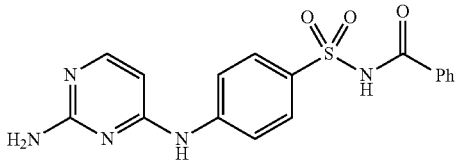

(1aj)

C$_{17}$H$_{15}$N$_5$O$_3$S; MW, 369.40

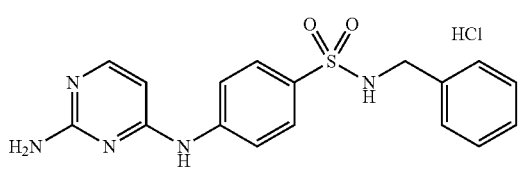

(1ak)

C$_{17}$H$_{18}$ClN$_5$O$_2$S; MW, 391.88

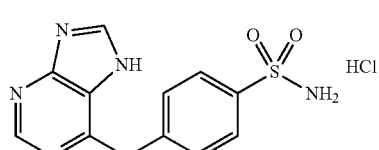

(8)

C$_{11}$H$_{11}$ClN$_6$O$_2$S; MW, 326.76

171
-continued
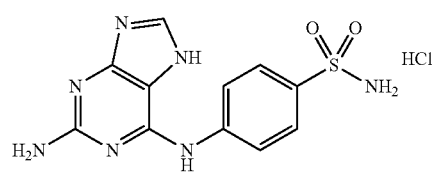
(7)
C₁₁H₁₂ClN₇O₂S; MW, 341.78
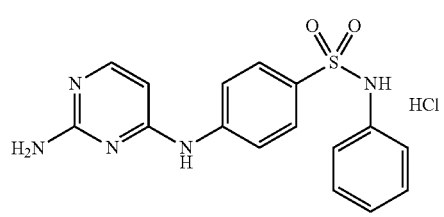
(1al)
C₁₆H₁₆ClN₅O₂S; MW, 377.85
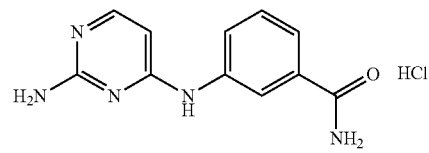
(1am)
C₁₁H₁₂ClN₅O; MW, 265.70
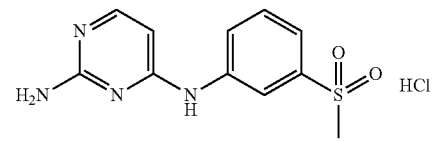
(1an)
C₁₁H₁₃ClN₄O₂S; MW, 300.76
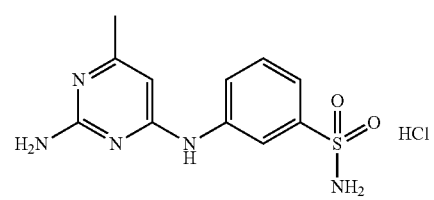
(6)
C₁₁H₁₄ClN₅O₂S; MW, 315.78
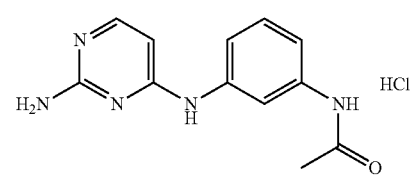
(1ao)
C₁₂H₁₄ClN₅O; MW, 279.73
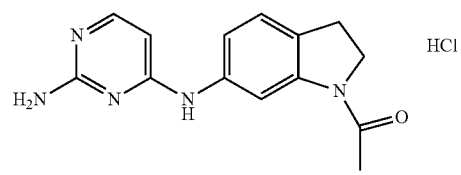
(1ap)
C₁₄H₁₆ClN₅O; MW, 305.76
172
-continued
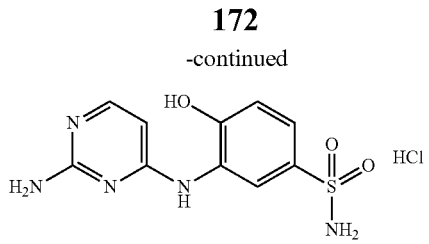
(1aq)
C₁₀H₁₂ClN₅O₂S; MW, 317.75
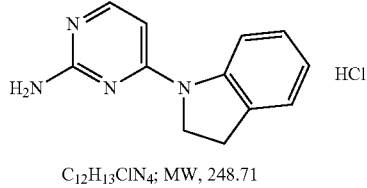
(13a)
C₁₂H₁₃ClN₄; MW, 248.71
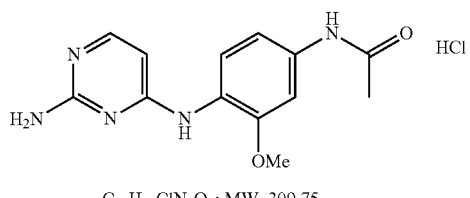
(1ar)
C₁₃H₁₆ClN₅O₂; MW, 309.75
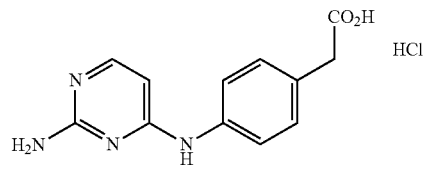
(1as)
C₁₂H₁₃ClN₄O₂
MW, 280.71
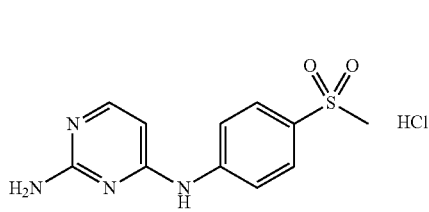
(1at)
C₁₁H₁₃ClN₄O₂S; MW, 300.76
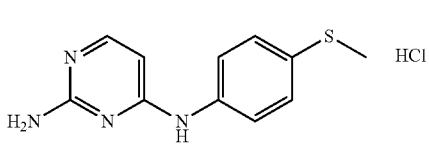
(1au)
C₁₁H₁₃ClN₄S; MW, 268.77
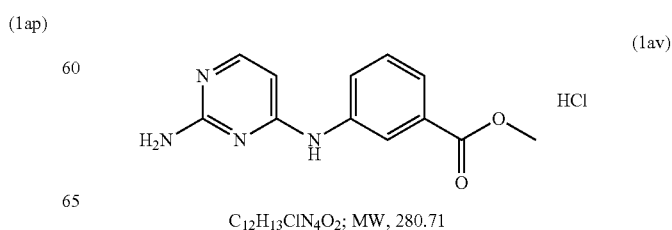
(1av)
C₁₂H₁₃ClN₄O₂; MW, 280.71

(1aw) Chemical Formula: $C_{12}H_{13}ClN_4O_2$; MW, 280.71 · HCl (1az) $C_{12}H_{12}ClN_5$; MW, 261.71 · HCl (1ba) $C_{12}H_{12}ClN_5$; MW, 261.71 · HCl

(16) $C_{13}H_{14}N_4$; MW, 226.28

(13b) $C_{13}H_{14}N_4$; MW, 226.28

(1bb) $C_{10}H_{10}ClN_5O_2$; MW, 267.67 · HCl (1bc) $C_{10}H_{10}ClN_5O_2$; MW, 267.67 · HCl (1bd) $C_{12}H_{14}N_4$; MW, 214.27

(1be) $C_{11}H_{13}ClN_4O$; MW, 252.70 · HCl (1bf) $C_{12}H_{14}N_4O$; MW, 230.27

(1bg) $C_{11}H_{10}F_2N_4O$; MW, 252.22

(13c) $C_{12}H_{12}Cl_2N_4$; MW, 283.16 · HCl (10a) $C_{10}H_9N_3O$; MW, 187.20

(10b) $C_{10}H_{10}N_4O_3S$; MW, 266.28

(10c) $C_{11}H_{10}N_4O_2$; MW, 230.22

-continued
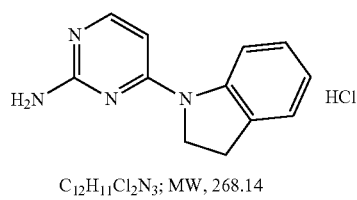
(32)
C₁₂H₁₁Cl₂N₃; MW, 268.14
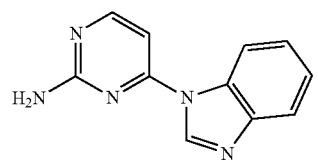
(18)
C₁₁H₉N₅; MW, 211.22
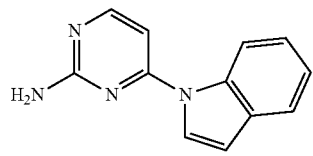
(15a)
C₁₂H₁₀N₄; MW, 210.23
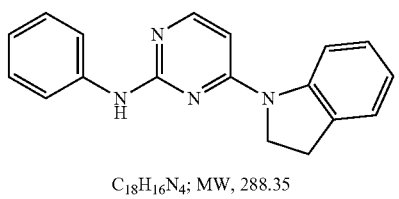
(33)
C₁₈H₁₆N₄; MW, 288.35
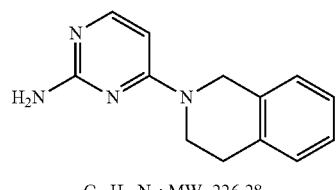
(17)
C₁₃H₁₄N₄; MW, 226.28
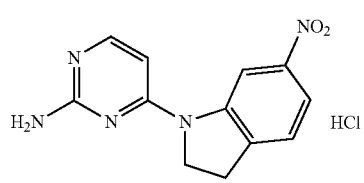
(13d)
C₁₂H₁₂ClN₅O₂; MW, 293.71
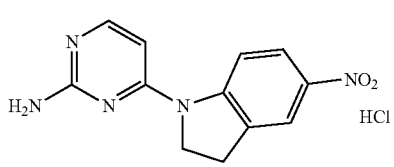
(13e)
C₁₂H₁₂ClN₅O₂; MW, 293.71
-continued
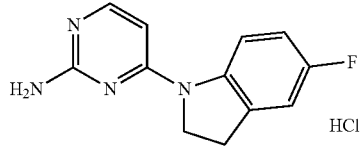
(13f)
C₁₂H₁₂ClFN₄; MW, 266.70
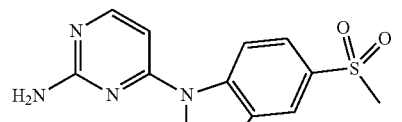
(13g)
C₁₃H₁₅ClN₄O₂S; MW, 326.80
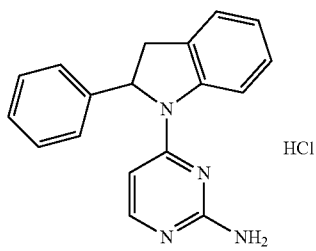
(13h)
C₁₈H₁₇ClN₄; MW, 324.81
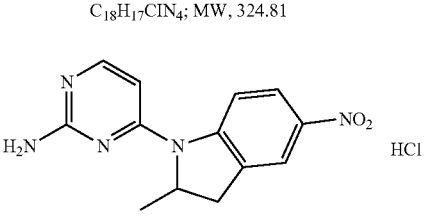
(13i)
C₁₃H₁₄ClN₅O₂; MW, 307.74
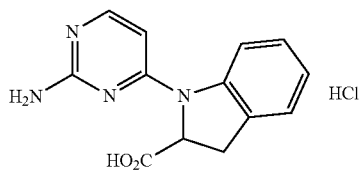
(13k)
C₁₃H₁₃ClN₄O₂; MW, 292.72
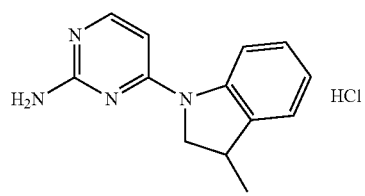
(13l)
C₁₃H₁₅ClN₄; MW, 262.74
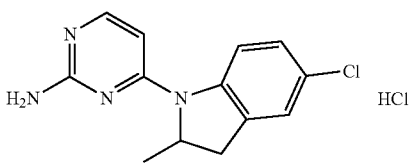
(13m)
C₁₃H₁₄Cl₂N₄; MW, 297.18

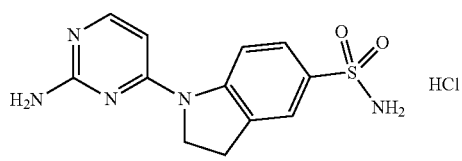
C₁₂H₁₄ClN₅O₂S; MW, 327.79 (13n)
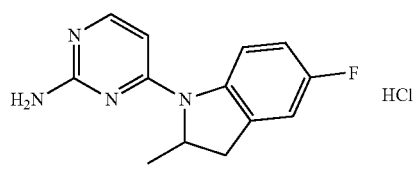
C₁₃H₁₄ClFN₄; MW, 280.73 (13o)
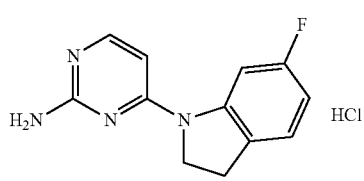
C₁₂H₁₂ClFN₄; MW, 266.70 (13p)
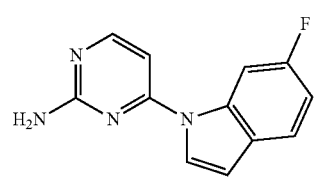
C₁₂H₉FN₄; MW, 228.23 (15b)
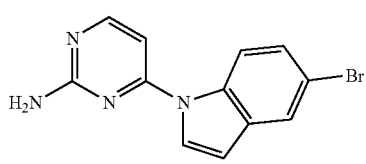
C₁₂H₉BrN₄; MW, 289.13 (15c)
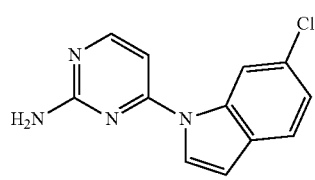
C₁₂H₉ClN₄; MW, 244.68 (15d)
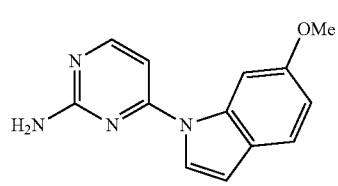
C₁₃H₁₂N₄O; MW, 240.26 (15e)
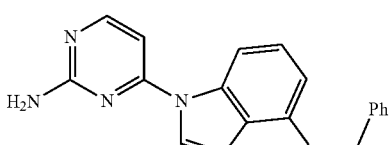
C₁₉H₁₆N₄O; MW, 316.36 (21a)
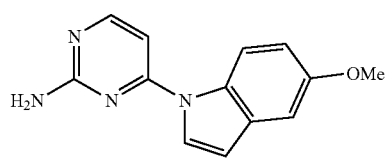
C₁₃H₁₂N₄O; MW, 240.26 (15f)
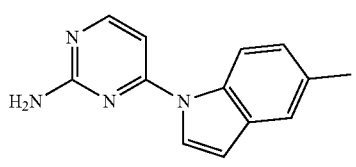
C₁₃H₁₂N₄; MW, 224.26 (15g)
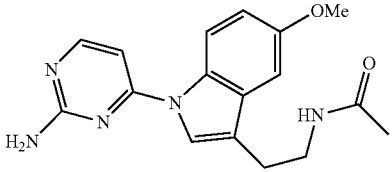
C₁₇H₁₉N₅O₂; MW, 335.37 (15h)
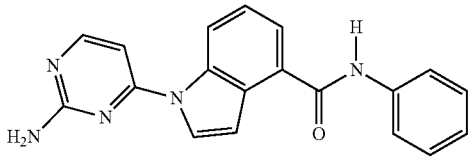
C₁₉H₁₅N₅O; MW, 329.36 (24a)
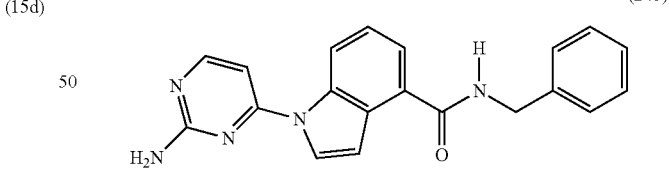
C₂₀H₁₇N₅O; MW, 343.38 (24b)
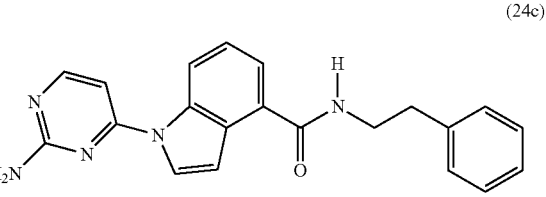
C₂₁H₁₉N₅O; MW, 357.41 (24c)

-continued (27a) C₂₀H₁₇N₅O; MW, 343.38

(27b) C₁₉H₁₅N₅O; MW, 329.36

(27c) C₂₁H₁₉N₅O; MW, 357.41

(24d) C₂₁H₁₉N₅O; MW, 357.41

(24e) C₂₀H₁₇N₅O; MW, 343.38

(24f) C₁₉H₁₅N₅O; MW, 329.36

-continued (13g) C₁₉H₁₉ClN₄O; MW, 354.83

(21b) C₁₉H₁₆N₄O; MW, 316.36

(21c) C₂₀H₁₈N₄O; MW, 330.38

(1ah)

(21d) C₁₉H₁₄ClN₄O; MW, 368.79

(21e) C₁₉H₁₅ClN₄O; MW, 350.80

-continued
(21f)
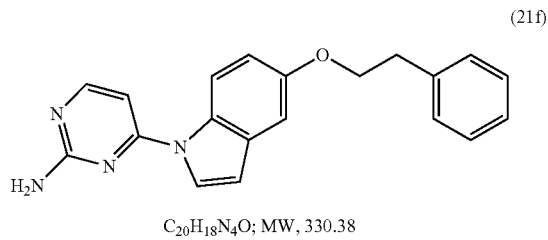
C₂₀H₁₈N₄O; MW, 330.38
(21g)
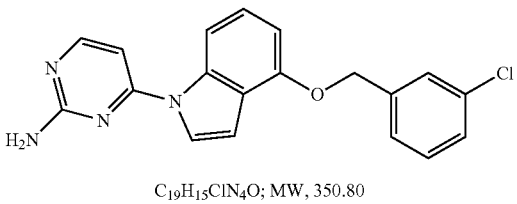
C₁₉H₁₅ClN₄O; MW, 350.80
(21h)
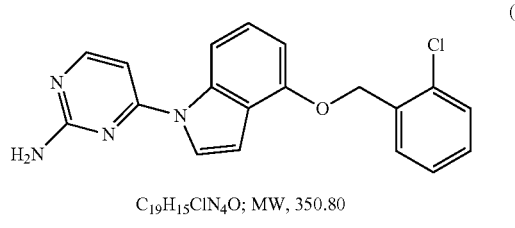
C₁₉H₁₅ClN₄O; MW, 350.80
(21i)
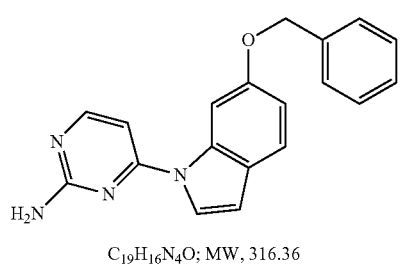
C₁₉H₁₆N₄O; MW, 316.36
(21j)
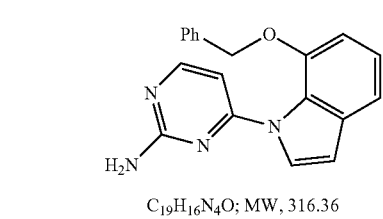
C₁₉H₁₆N₄O; MW, 316.36
(35)
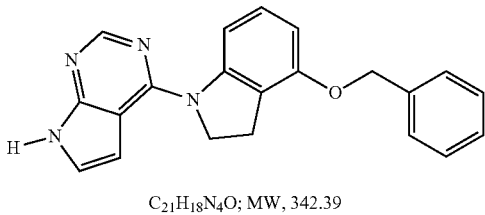
C₂₁H₁₈N₄O; MW, 342.39
(30a)
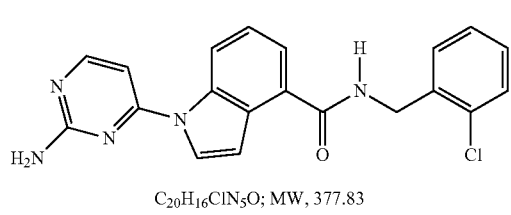
C₂₀H₁₆ClN₅O; MW, 377.83
-continued
(30b)
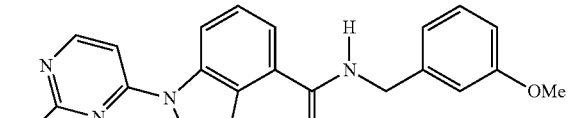
C₂₁H₁₉N₅O₂; MW, 373.41
(30c)
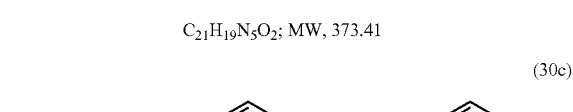
C₂₀H₁₆ClN₅O; MW, 377.83
(30d)
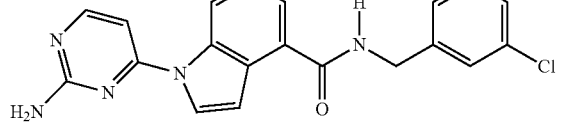
C₂₀H₁₆FN₅O; MW, 361.37
(30e)
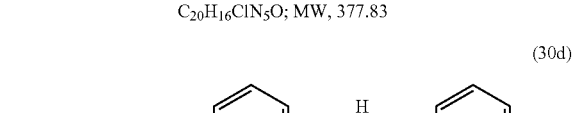
C₂₀H₁₆ClN₅O MW = 377.8269
(30f)
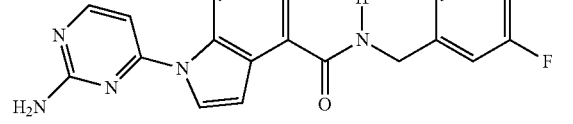
C₂₀H₁₆FN₅O; MW, 361.37
(30g)
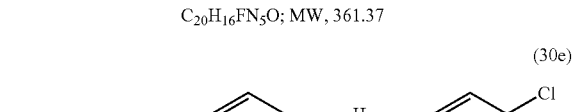
C₂₁H₁₉N₅O; MW, 357.41
(30h)
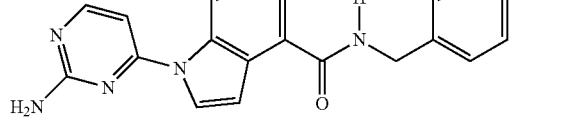
C₂₁H₁₉N₅O; MW, 357.41

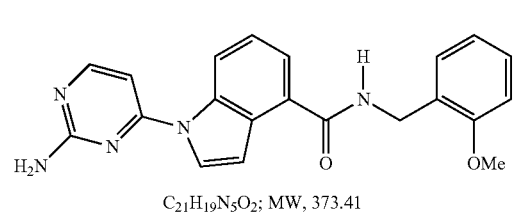
(30i)
C$_{21}$H$_{19}$N$_5$O$_2$; MW, 373.41
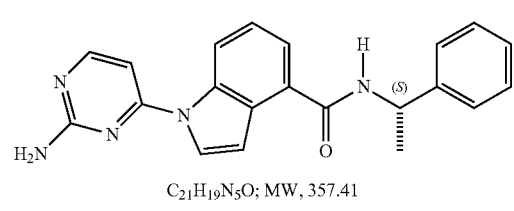
(30j)
C$_{21}$H$_{19}$N$_5$O; MW, 357.41
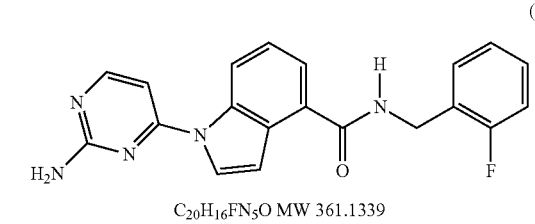
(30k)
C$_{20}$H$_{16}$FN$_5$O MW 361.1339
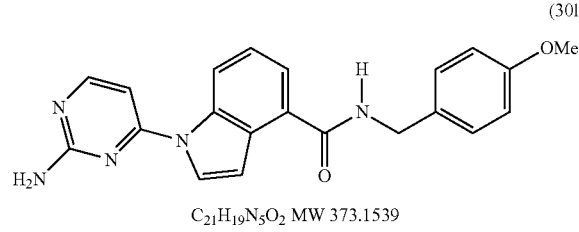
(30l)
C$_{21}$H$_{19}$N$_5$O$_2$ MW 373.1539
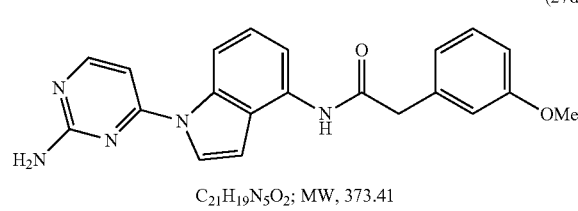
(27d)
C$_{21}$H$_{19}$N$_5$O$_2$; MW, 373.41
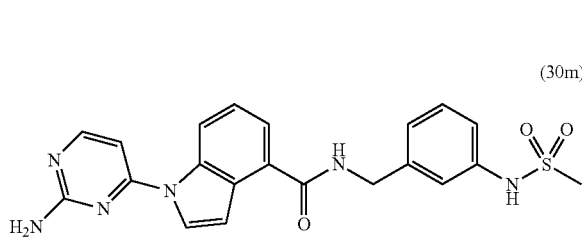
(30m)
C$_{21}$H$_{20}$N$_6$O$_3$S; MW, 436.49
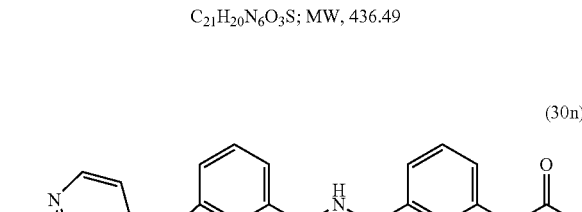
(30n)
C$_{22}$H$_{20}$N$_6$O$_2$; MW, 400.43
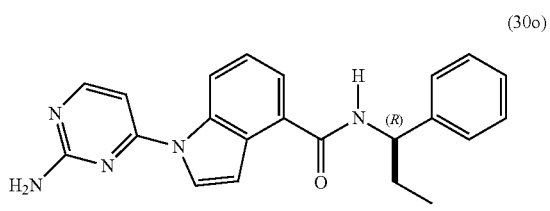
(30o)
C$_{22}$H$_{21}$N$_5$O; MW, 371.44
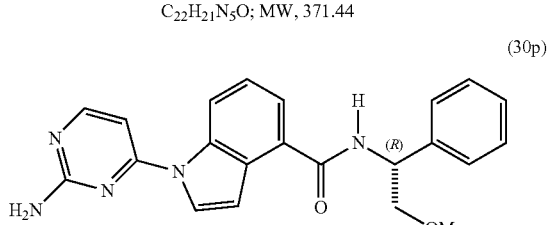
(30p)
C$_{22}$H$_{21}$N$_5$O$_2$; MW, 387.43
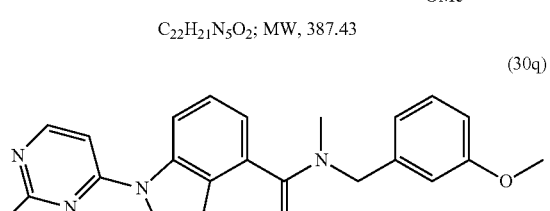
(30q)
C$_{22}$H$_{21}$N$_5$O$_2$; MW, 387.43
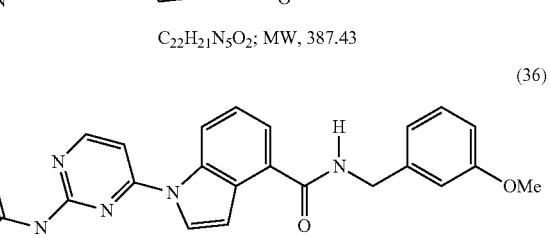
(36)
C$_{23}$H$_{21}$N$_5$O$_3$; MW, 415.44
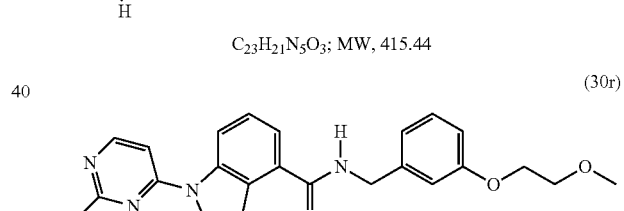
(30r)
C$_{23}$H$_{23}$N$_5$O$_3$; MW, 417.46
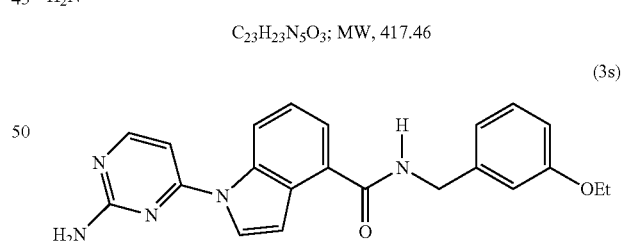
(3s)
C$_{22}$H$_{21}$N$_5$O$_2$; MW, 387.43
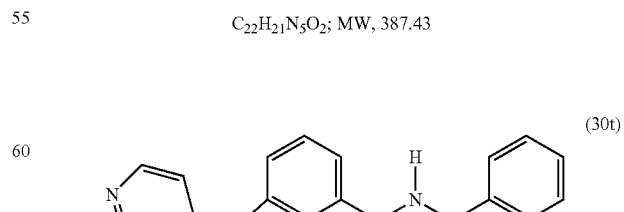
(30t)
C$_{26}$H$_{21}$N$_5$O; MW, 419.48

-continued
(30u)
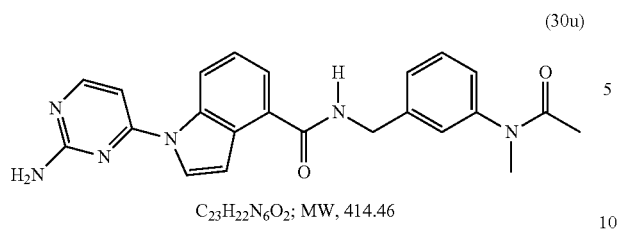
C₂₃H₂₂N₆O₂; MW, 414.46
(30v)
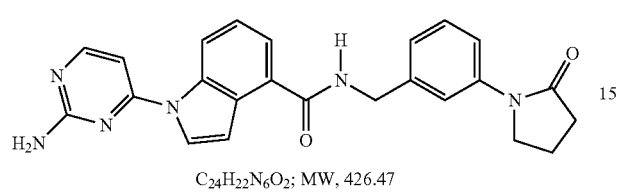
C₂₄H₂₂N₆O₂; MW, 426.47
(46)
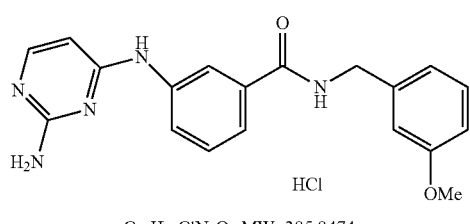
C₁₉H₂₀ClN₅O₂ MW: 385.8474
(47)
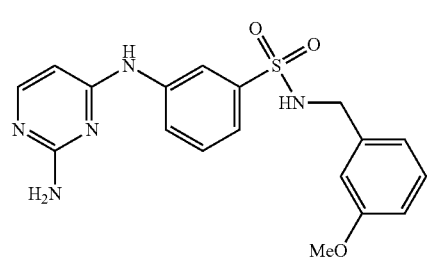
C₁₈H₁₉N₅O₃S MW: 385.4402
(30w)
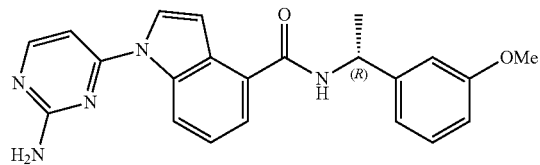
C₂₂H₂₁N₅O₂ MW 387.4344
(30z)
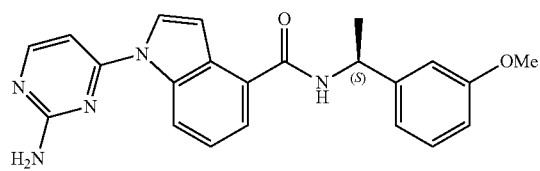
C₂₂H₂₁N₅O₂ MW 387.4344
-continued
(1bi)
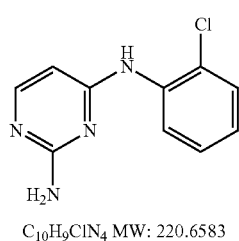
C₁₀H₉ClN₄ MW: 220.6583
(1bj)
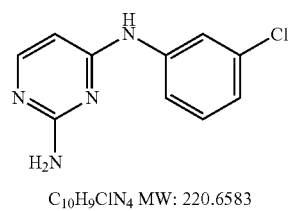
C₁₀H₉ClN₄ MW: 220.6583
(38)
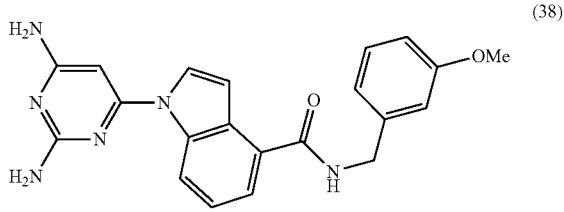
Molecular Weight: 388.4225
(13r)
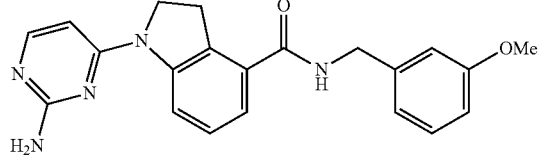
Molecular Weight: 375.4237
(30aa)
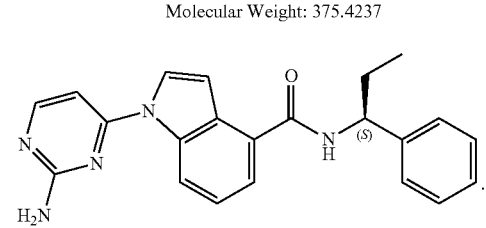
C₂₂H₂₁N₅O MW 371.4350
2. A composition comprising a compound, having the chemical structure shown in formula I, formula IIa, formula IIb, formula III, or formula IV:
formula I
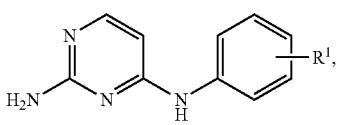
formula IIa
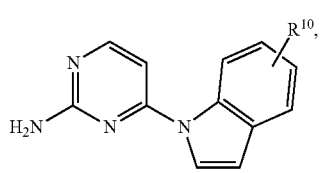

-continued

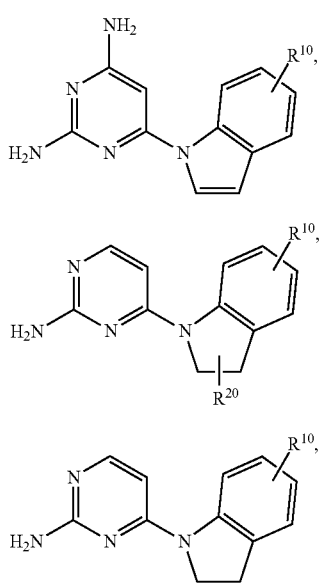

formula IIb formula III formula IV wherein
R¹ in formula I is H, OH, S-alkyl, SO₂NR²R³, NO₂, CONH₂, SO₂-alkyl, NHC(O)-alkyl, CO₂H, alkyl, cycloalkyl, alkoxy, cycloalkoxy, heterocycloalkyl, alkoxycarbonyl, heteroaryl, or aryl;
R² is H, CO, alkoxy, alkyl, aryl, heteroalkyl, heteroaryl, heterocycloalkyl, alkylcarbonyl, arylcarbonyl, or alkoxycarbonyl;
R³ is H, CO, alkoxy, alkyl, aryl, heteroalkyl, heteroaryl, heterocycloalkyl, alkylcarbonyl, arylcarbonyl, or alkoxycarbonyl;
any of which of R¹, R², and R³ can be optionally substituted with one or more of halogen, alkyl, alkoxy or aryl optionally substituted with alkoxy;
R¹⁰ in formula IIb is H, NO₂, halogen, —CH₃, —SO₂-alkyl, —OCH₃, alkoxy, —C(O)NH-alkyl, —C(O)NH-aryl, —NHC(O)-alkyl, —NHC(O)-aryl, or aryloxy, any of which can be substituted with one or more of aryl or alkoxy, any of which can be optionally substituted with halogen, —OH, alkoxy, or aryl optionally substituted with alkoxy;
R¹⁰ in formula III is H, NO₂, —F, —Cl, —I, —CH₃, —SO₂-alkyl, —OCH₃, alkoxy, —C(O)NH-alkyl, —C(O)NH-aryl, —NHC(O)-alkyl, —NHC(O)-aryl, or aryloxy, any of which can be substituted with one or more of aryl or alkoxy, any of which can be optionally substituted with halogen, —OH, alkoxy, or aryl optionally substituted with alkoxy;
R¹⁰ in formula IIa and formula IV is H, NO₂, —F, —Cl, —I, —CH₃, —SO₂-alkyl, —OCH₃, alkoxy, —C(O)NH-alkyl, —C(O)NH-aryl, —NHC(O)-alkyl, —NHC(O)-aryl, or aryloxy, any of which can be substituted with one or more of aryl or alkoxy, any of which can be optionally substituted with halogen, —OH, alkoxy, or aryl optionally substituted with alkoxy
R²⁰ in formula III is —CH₃, —CO₂H, heteroalkyl, aryl, or alkyl;
or a pharmaceutically acceptable salt or hydrate thereof;
wherein said compound of formula I comprises one or more R¹, wherein said compound of formula IIa, IIb, III, or IV comprises one or more R¹⁰, and wherein said compound of formula III comprises one or more R²⁰; or said compound having the chemical structure selected from:

(in house NSC135784)

(1aa)

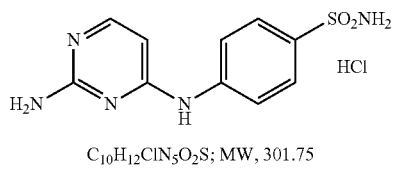

C₁₀H₁₂ClN₅O₂S; MW, 301.75

(1ab)

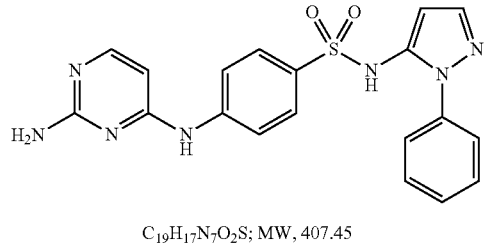

C₁₉H₁₇N₇O₂S; MW, 407.45

(1ac)

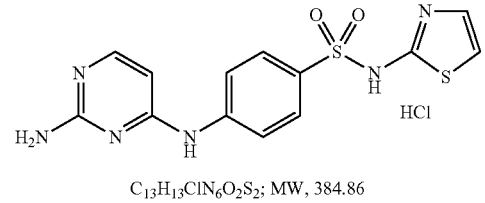

C₁₃H₁₃ClN₆O₂S₂; MW, 384.86

(1ad)

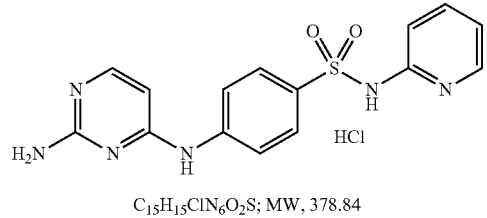

C₁₅H₁₅ClN₆O₂S; MW, 378.84

(1ae)

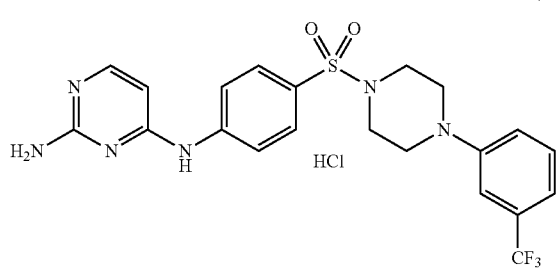

C₂₁H₂₂ClF₃N₆O₂; MW, 514.95

(1af)

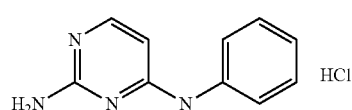

C₁₀H₁₁ClN₄; MW, 222.67

-continued
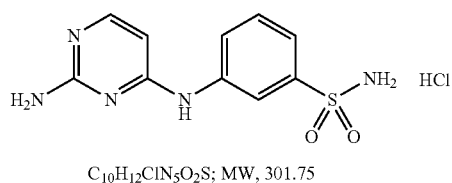
(1ag)
C₁₀H₁₂ClN₅O₂S; MW, 301.75
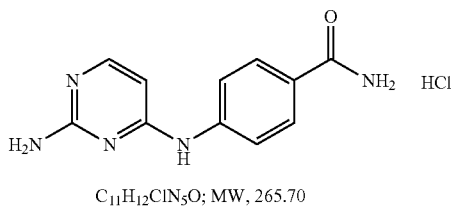
(1ah)
C₁₁H₁₂ClN₅O; MW, 265.70
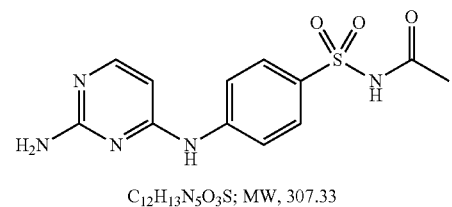
(1ai)
C₁₂H₁₃N₅O₃S; MW, 307.33
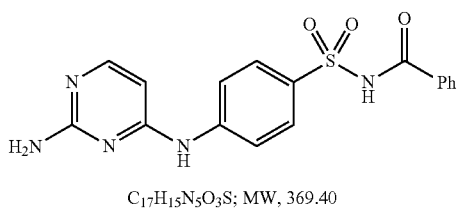
(1aj)
C₁₇H₁₅N₅O₃S; MW, 369.40
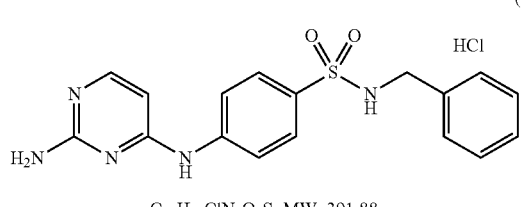
(1ak)
C₁₇H₁₈ClN₅O₂S; MW, 391.88
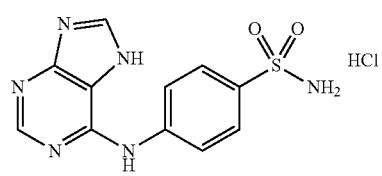
(8)
C₁₁H₁₁ClN₆O₂S; MW, 326.76
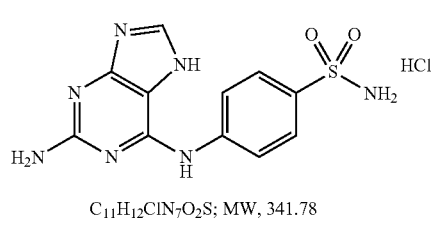
(7)
C₁₁H₁₂ClN₇O₂S; MW, 341.78
-continued
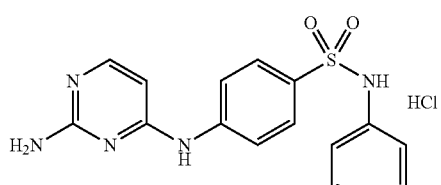
(1al)
C₁₆H₁₆ClN₅O₂S; MW, 377.85
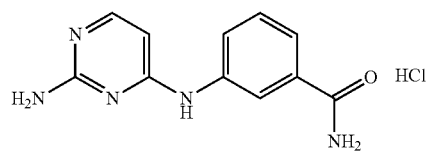
(1am)
C₁₁H₁₂ClN₅O; MW, 265.70
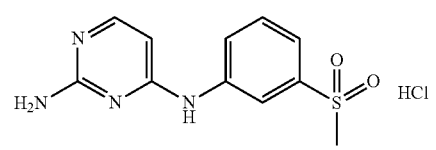
(1an)
C₁₁H₁₃ClN₄O₂S; MW, 300.76
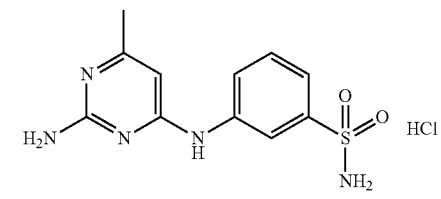
(6)
C₁₁H₁₄ClN₅O₂S; MW, 315.78
(1ao)
C₁₂H₁₄ClN₅O; MW, 279.73
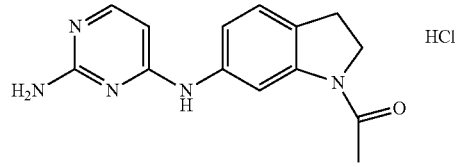
(1ap)
C₁₄H₁₆ClN₅O; MW, 305.76
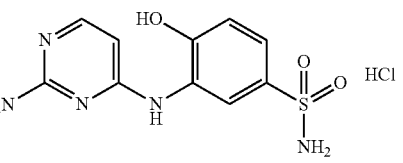
(1aq)
C₁₀H₁₂ClN₅O₂S; MW, 317.75

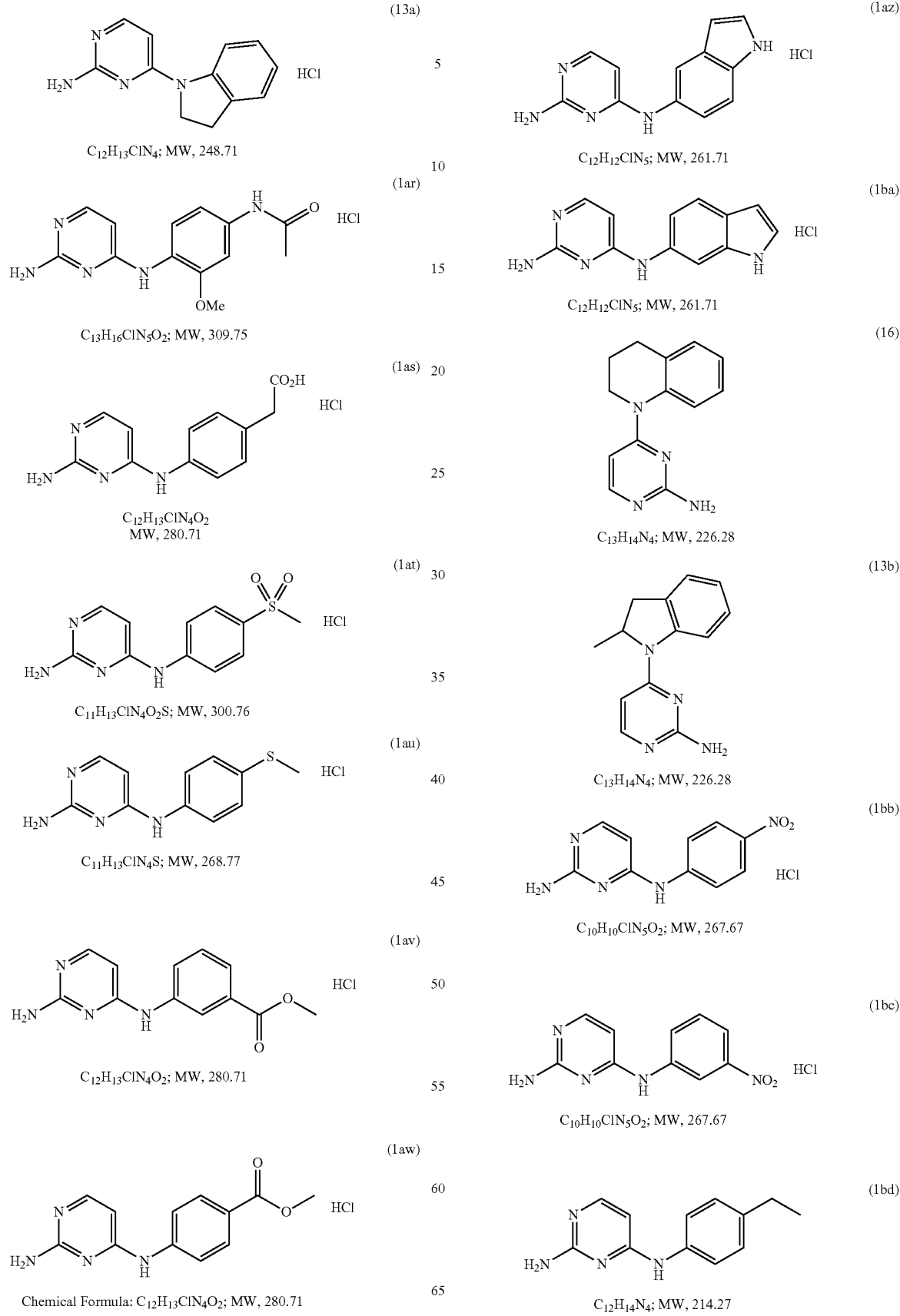

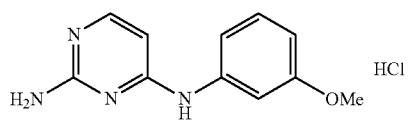
C₁₁H₁₃ClN₄O; MW, 252.70
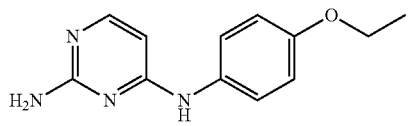
C₁₂H₁₄N₄O; MW, 230.27
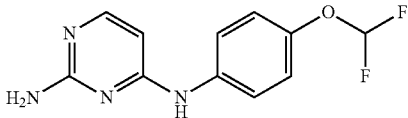
C₁₁H₁₀F₂N₄O; MW, 252.22
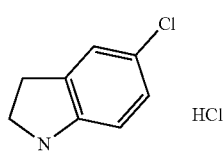
C₁₂H₁₂Cl₂N₄; MW, 283.16
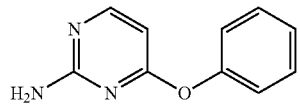
C₁₀H₉N₃O; MW, 187.20
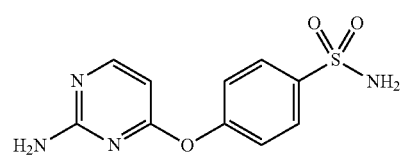
C₁₀H₁₀N₄O₃S; MW, 266.28
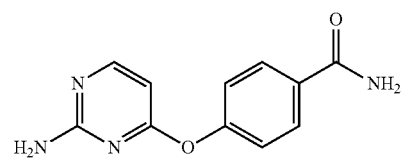
C₁₁H₁₀N₄O₂; MW, 230.22
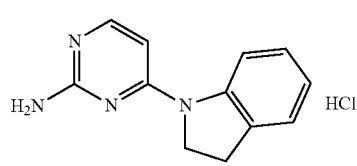
C₁₂H₁₁Cl₂N₃; MW, 268.14
(1be)
(1bf)
(1bg)
(13c)
(10a)
(10b)
(10c)
(32)
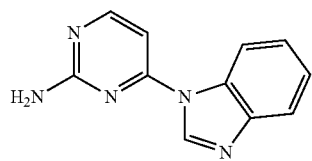
C₁₁H₉N₅; MW, 211.22
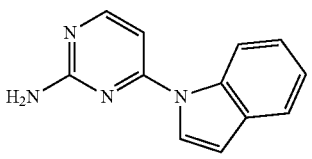
C₁₂H₁₀N₄; MW, 210.23
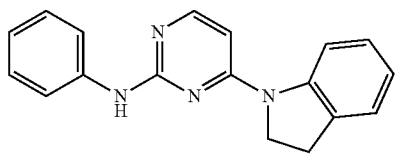
C₁₈H₁₆N₄; MW, 288.35
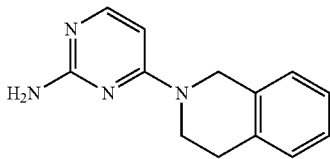
C₁₃H₁₄N₄; MW, 226.28
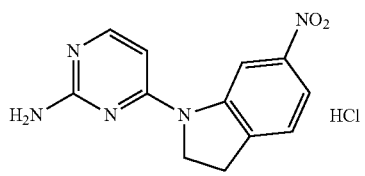
C₁₂H₁₂ClN₅O₂; MW, 293.71
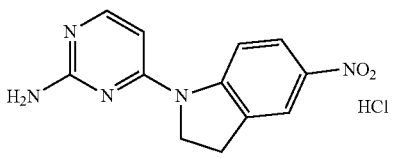
C₁₂H₁₂ClN₅O₂; MW, 293.71
C₁₂H₁₂ClFN₄; MW, 266.70
(18)
(15a)
(33)
(17)
(13d)
(13e)
(13f)

(13g)
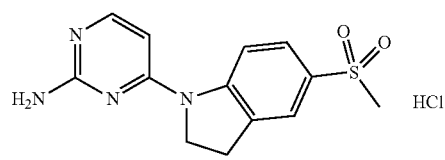
C₁₃H₁₅ClN₄O₂S; MW, 326.80
(13h)
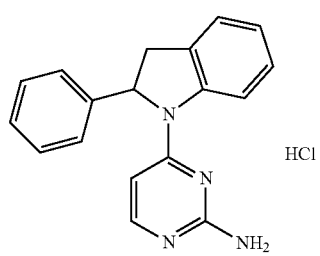
C₁₈H₁₇ClN₄; MW, 324.81
(13i)
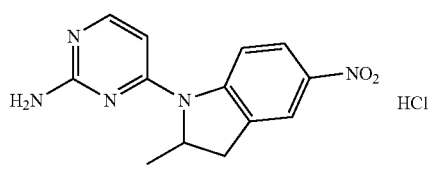
C₁₃H₁₄ClN₅O₂; MW, 307.74
(13k)
C₁₃H₁₃ClN₄O₂; MW, 292.72
(13l)
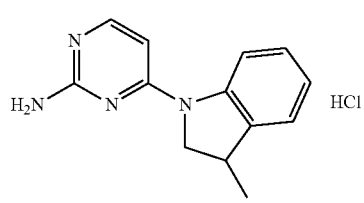
C₁₃H₁₅ClN₄; MW, 262.74
(13m)
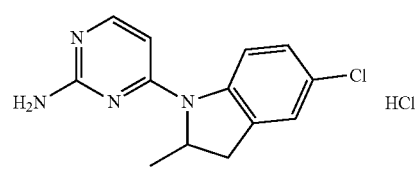
C₁₃H₁₄Cl₂N₄; MW, 297.18
(13n)
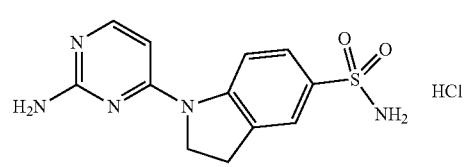
C₁₂H₁₄ClN₅O₂S; MW, 327.79
(13o)
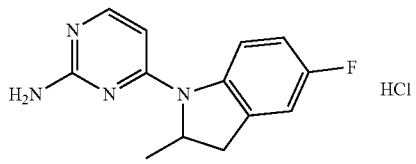
C₁₃H₁₄ClFN₄; MW, 280.73
(13p)
C₁₂H₁₂ClFN₄; MW, 266.70
(15b)
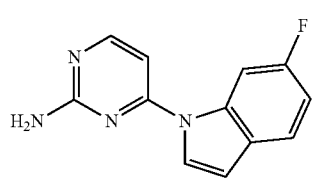
C₁₂H₉FN₄; MW, 228.23
(15c)
C₁₂H₉BrN₄; MW, 289.13
(15d)
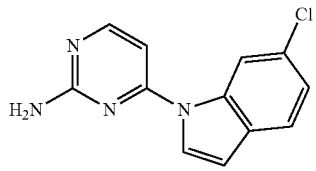
C₁₂H₉ClN₄; MW, 244.68
(15e)
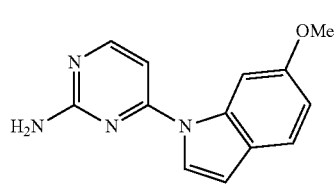
C₁₃H₁₂N₄O; MW, 240.26
(21a)
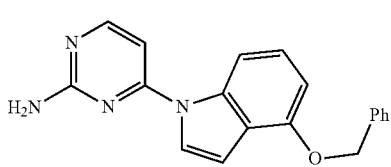
C₁₉H₁₆N₄O; MW, 316.36

-continued
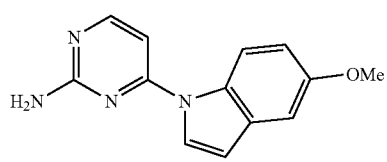
C₁₃H₁₂N₄O; MW, 240.26 (15f)
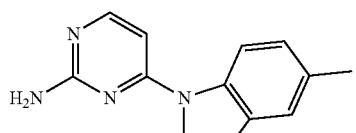
C₁₃H₁₂N₄; MW, 224.26 (15g)
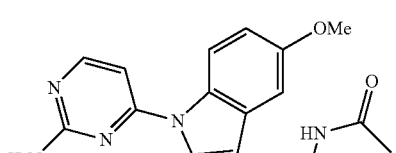
C₁₇H₁₉N₅O₂; MW, 325.37 (15h)
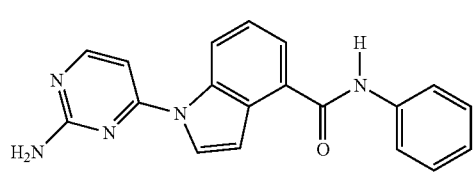
C₁₉H₁₅N₅O; MW, 329.36 (24a)
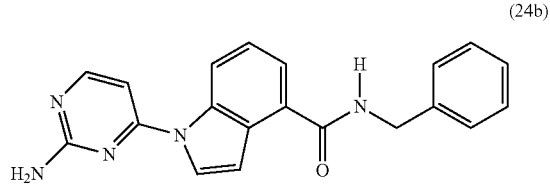
C₂₀H₁₇N₅O; MW, 343.38 (24b)
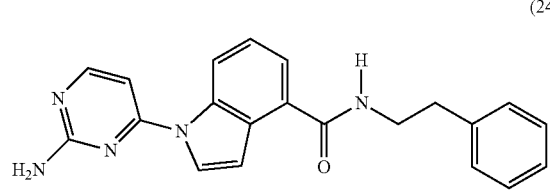
C₂₁H₁₉N₅O; MW, 357.41 (24c)
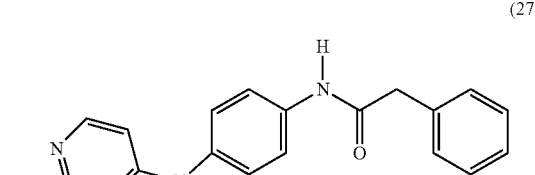
C₂₀H₁₇N₅O; MW, 343.38 (27a)
-continued
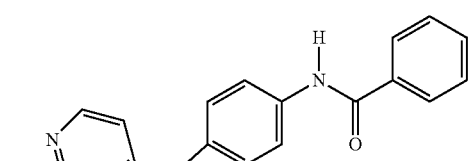
C₁₉H₁₅N₅O; MW, 329.36 (27b)
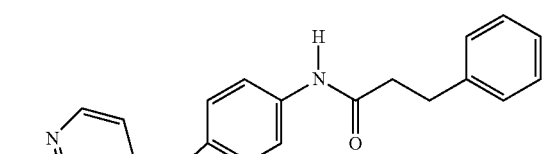
C₂₁H₁₉N₅O; MW, 357.41 (27c)
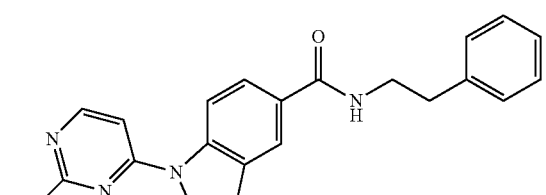
C₂₁H₁₉N₅O; MW, 357.41 (24d)
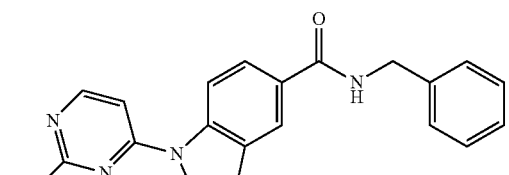
C₂₀H₁₇N₅O; MW, 343.38 (24e)
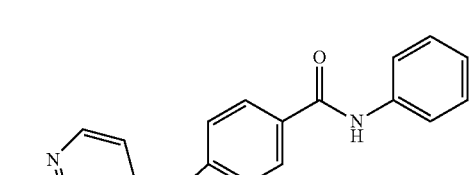
C₁₉H₁₅N₅O; MW, 329.36 (24f)
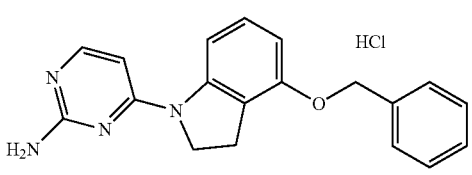
C₁₉H₁₉ClN₄O; MW, 354.83 (13q)

-continued
(21b)
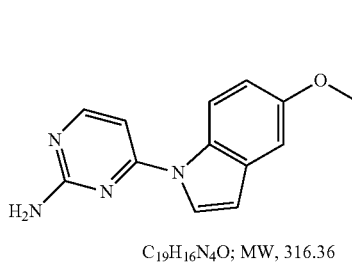
C₁₉H₁₆N₄O; MW, 316.36
(21c)
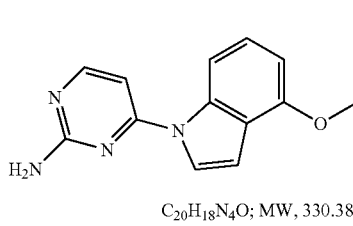
C₂₀H₁₈N₄O; MW, 330.38
(1ah)
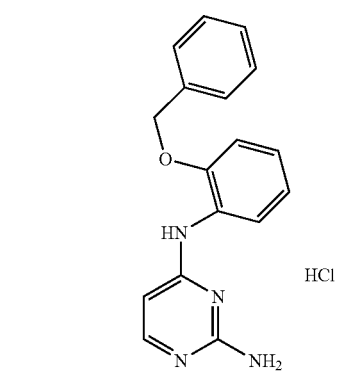
HCl
(21d)
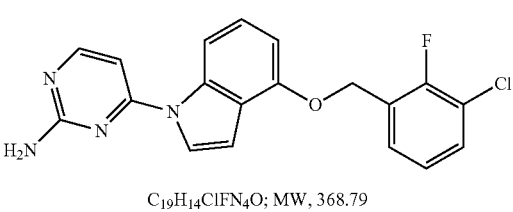
C₁₉H₁₄ClFN₄O; MW, 368.79
(21e)
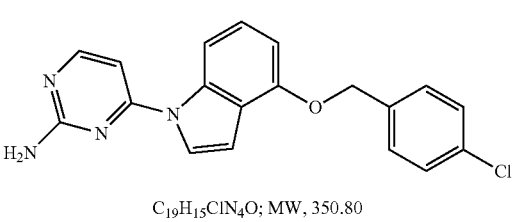
C₁₉H₁₅ClN₄O; MW, 350.80
(21f)
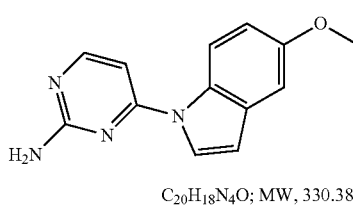
C₂₀H₁₈N₄O; MW, 330.38
-continued
(21g)
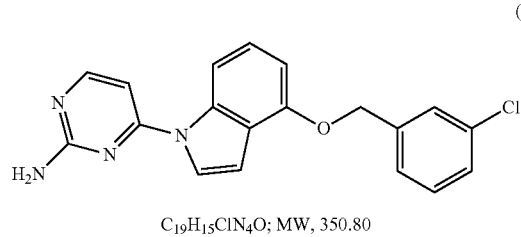
C₁₉H₁₅ClN₄O; MW, 350.80
(21h)
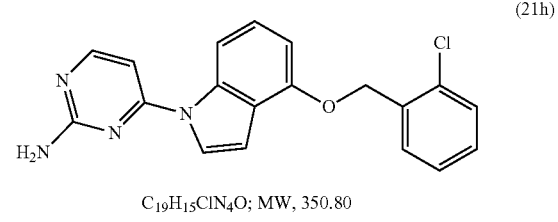
C₁₉H₁₅ClN₄O; MW, 350.80
(21i)
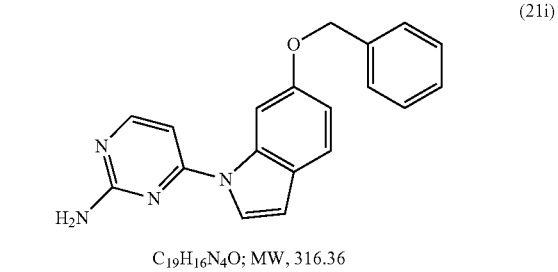
C₁₉H₁₆N₄O; MW, 316.36
(21j)
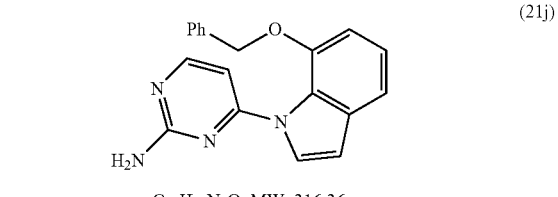
C₁₉H₁₆N₄O; MW, 316.36
(35)
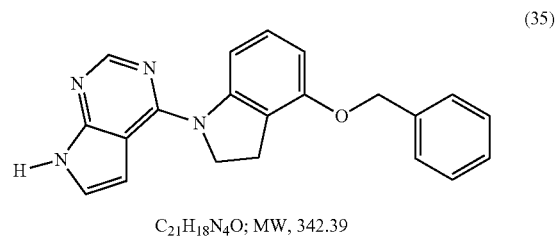
C₂₁H₁₈N₄O; MW, 342.39
(30a)
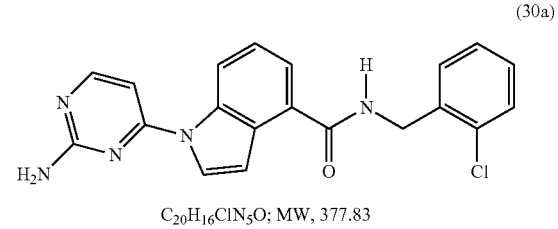
C₂₀H₁₆ClN₅O; MW, 377.83
(30b)
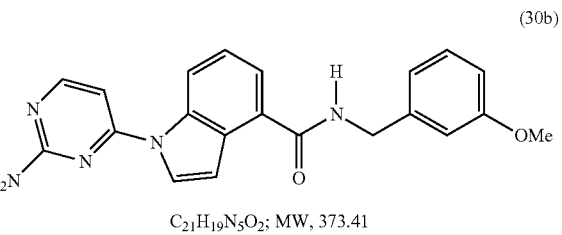
C₂₁H₁₉N₅O₂; MW, 373.41

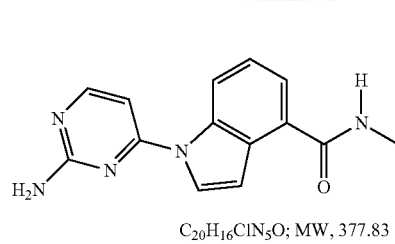
(30c)
$C_{20}H_{16}ClN_5O$; MW, 377.83
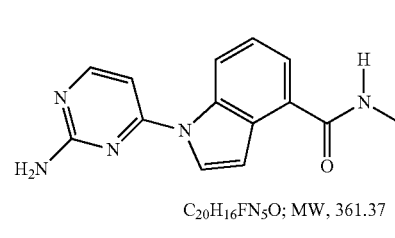
(30d)
$C_{20}H_{16}FN_5O$; MW, 361.37
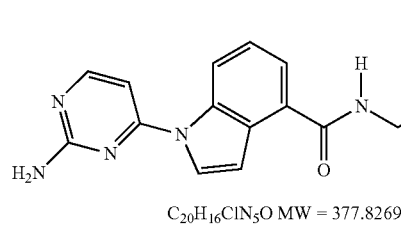
(30e)
$C_{20}H_{16}ClN_5O$ MW = 377.8269
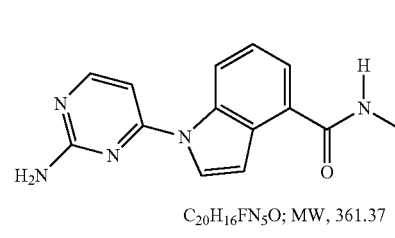
(30f)
$C_{20}H_{16}FN_5O$; MW, 361.37
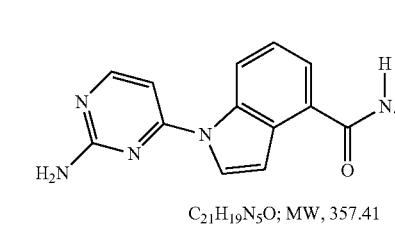
(30g)
$C_{21}H_{19}N_5O$; MW, 357.41
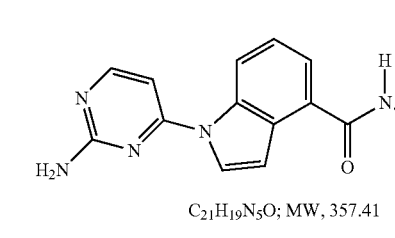
(30h)
$C_{21}H_{19}N_5O$; MW, 357.41
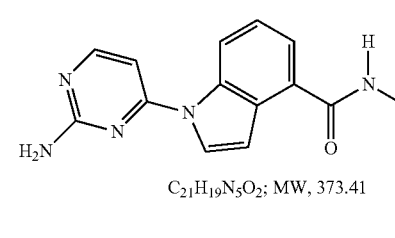
(30i)
$C_{21}H_{19}N_5O_2$; MW, 373.41
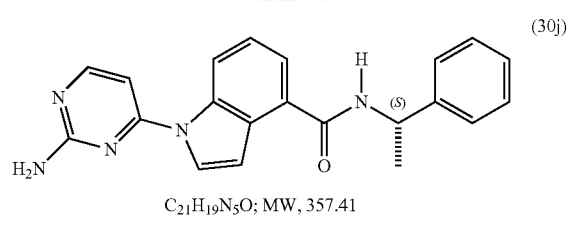
(30j)
$C_{21}H_{19}N_5O$; MW, 357.41
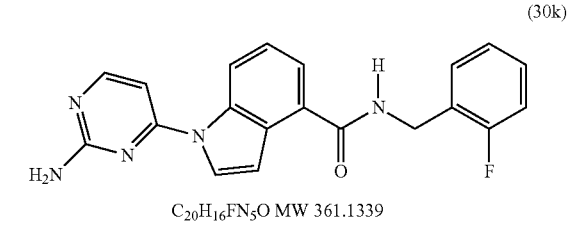
(30k)
$C_{20}H_{16}FN_5O$ MW 361.1339
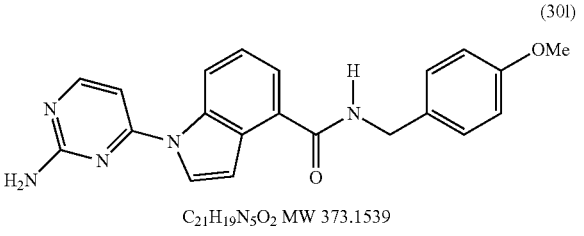
(30l)
$C_{21}H_{19}N_5O_2$ MW 373.1539
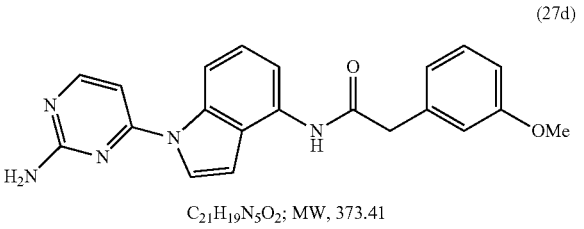
(27d)
$C_{21}H_{19}N_5O_2$; MW, 373.41
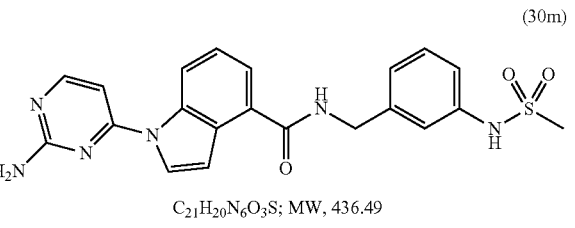
(30m)
$C_{21}H_{20}N_6O_3S$; MW, 436.49
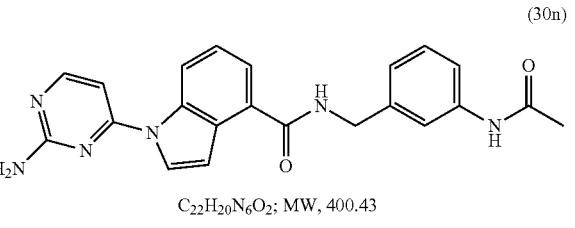
(30n)
$C_{22}H_{20}N_6O_2$; MW, 400.43
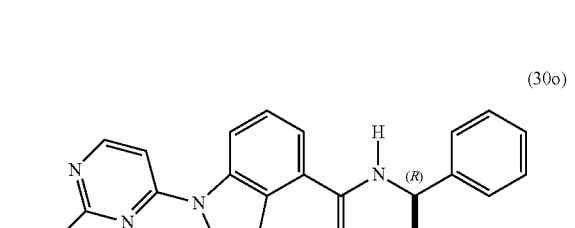
(30o)
$C_{22}H_{21}N_5O$; MW, 371.44

(30p)
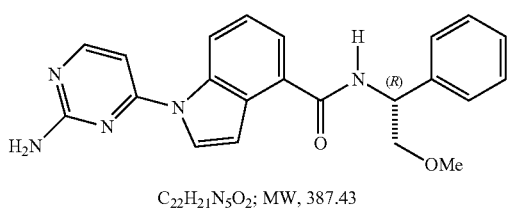
C₂₂H₂₁N₅O₂; MW, 387.43
(30q)
C₂₂H₂₁N₅O₂; MW, 387.43
(36)
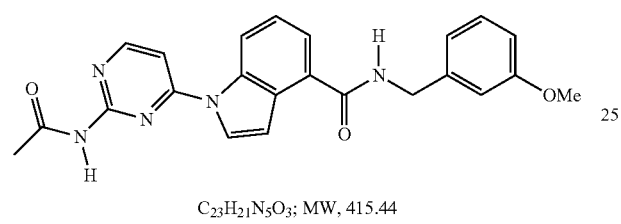
C₂₃H₂₁N₅O₃; MW, 415.44
(30r)
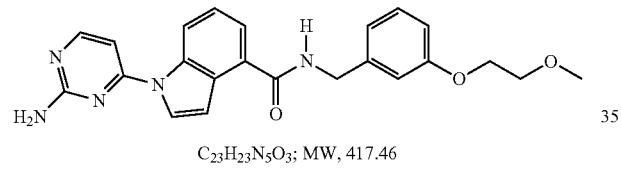
C₂₃H₂₃N₅O₃; MW, 417.46
(3s)
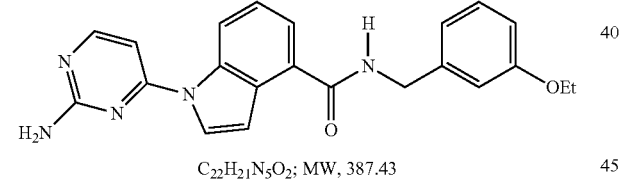
C₂₂H₂₁N₅O₂; MW, 387.43
(30t)
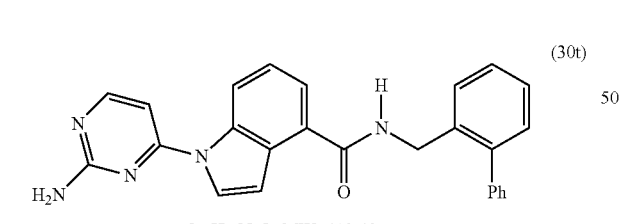
C₂₆H₂₁N₅O; MW, 419.48
(30u)
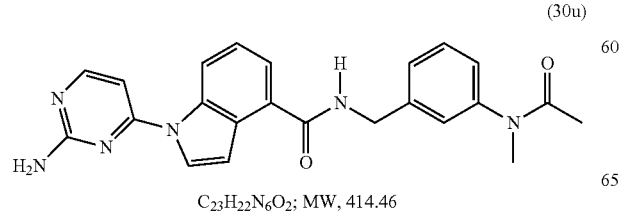
C₂₃H₂₂N₆O₂; MW, 414.46
(30v)
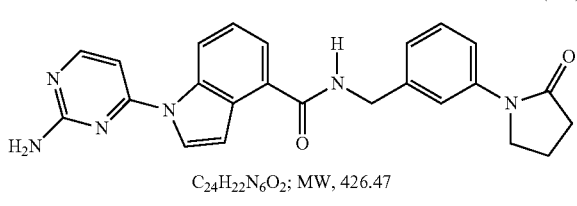
C₂₄H₂₂N₆O₂; MW, 426.47
(46)
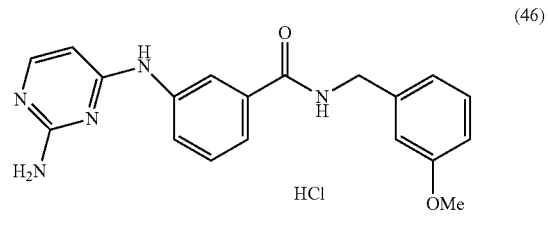
C₁₉H₂₀ClN₅O₂ MW: 385.8474
(47)
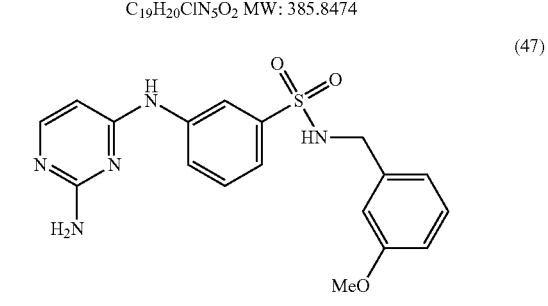
C₁₈H₁₉N₅O₃S MW: 385.4402
(30w)
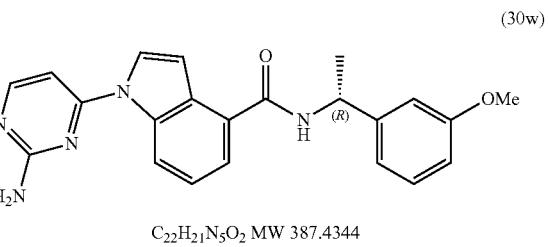
C₂₂H₂₁N₅O₂ MW 387.4344
(30z)
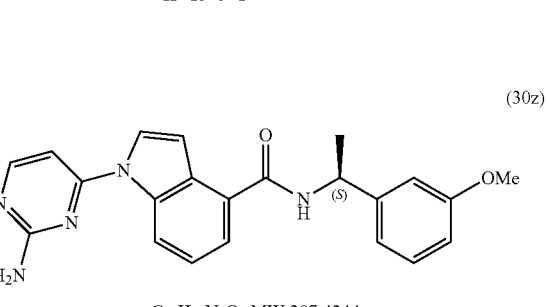
C₂₂H₂₁N₅O₂ MW 387.4344
(1bi)
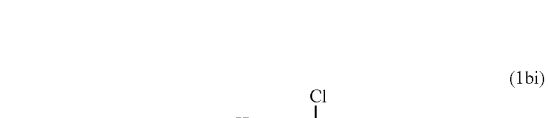
C₁₀H₉ClN₄ MW: 220.6583

-continued
(1bj)
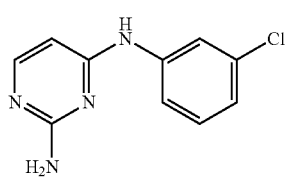
C₁₀H₉ClN₄ MW: 220.6583
(38)
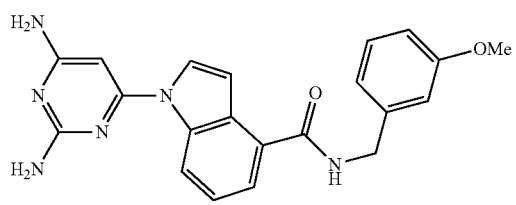
Molecular Weight: 388.4225
(13r)
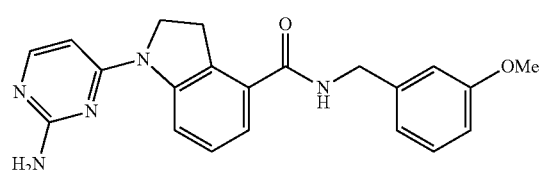
Molecular Weight: 375.4237
(30aa)
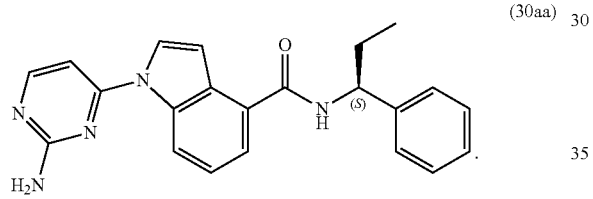
C₂₂H₂₁N₅O MW 371.4350
3. The compound according to claim 1, wherein R¹ is any of ( ⌇ =point of attachment):
| R¹ can be: |
|---|
| 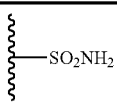 |
| 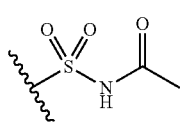 [SMILES: *S(=O)(=O)NC(C)=O] |
| 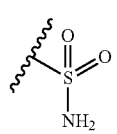 |
| 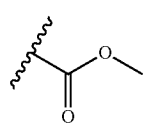 [SMILES: *C(=O)OC] |
-continued
| R¹ can be: |
|---|
| 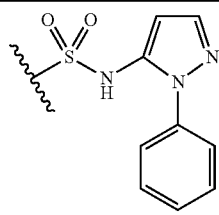 |
| 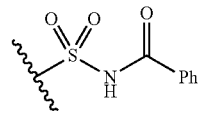 [SMILES: *S(=O)(=O)NC(=O)c1ccccc1] |
| 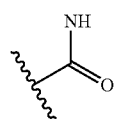 |
| 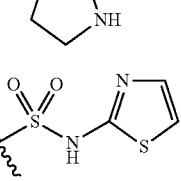 |
| 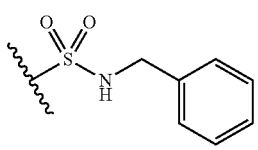 [SMILES: *S(=O)(=O)NCc1ccccc1] |
| 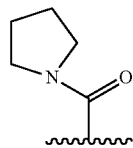 [SMILES: *C(=O)N1CCCC1] |
|  |
| 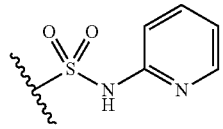 [SMILES: *S(=O)(=O)Nc1ccccn1] |
| 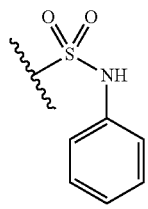 [SMILES: *S(=O)(=O)Nc1ccccc1] |
| 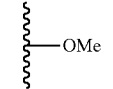 |

| $R^1$ can be: | $R^1$ can be: |
|---|---|
| 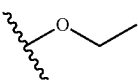 | 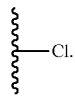 |
| 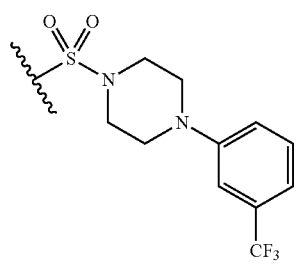 [SMILES: *S(=O)(=O)N1CCN(c2cccc(C(F)(F)F)c2)CC1] | |
4. The compound according to claim 1, wherein $R^{10}$ is any of (⌇=point of attachment):
| $R^{10}$ can be: |
|---|
| 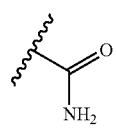 |
| 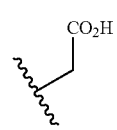 [SMILES: *CC(=O)O] |
| 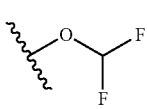 [SMILES: *OC(F)F] |
| 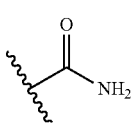 |
| 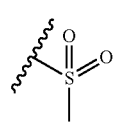 |
| 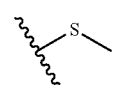 |
| 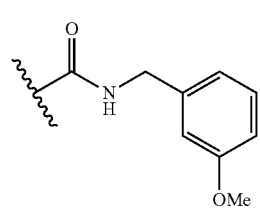 [SMILES: *C(=O)NCc1cccc(OC)c1] |
| 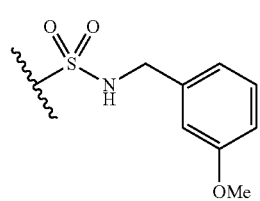 [SMILES: *S(=O)(=O)NCc1cccc(OC)c1] |
| $R^{10}$ can be: |
|---|
| 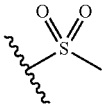 [SMILES: *S(C)(=O)=O] |
| 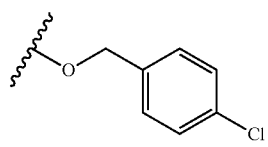 [SMILES: *OCc1ccc(Cl)cc1] |
| 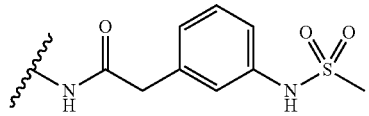 [SMILES: *NC(=O)Cc1cccc(NS(C)(=O)=O)c1] |
|  |
| 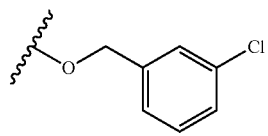 [SMILES: *OCc1cccc(Cl)c1] |
| 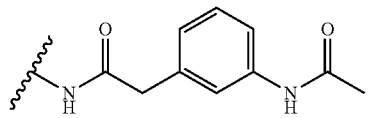 [SMILES: *NC(=O)Cc1cccc(NC(C)=O)c1] |
|  |
| 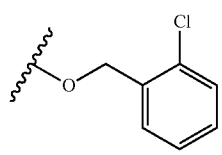 [SMILES: *OCc1ccccc1Cl] |
| 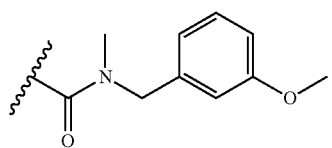 [SMILES: *C(=O)N(C)Cc1cccc(OC)c1] |

| 209 -continued | 210 -continued |
|---|---|
| R¹⁰ can be: | R¹⁰ can be: |
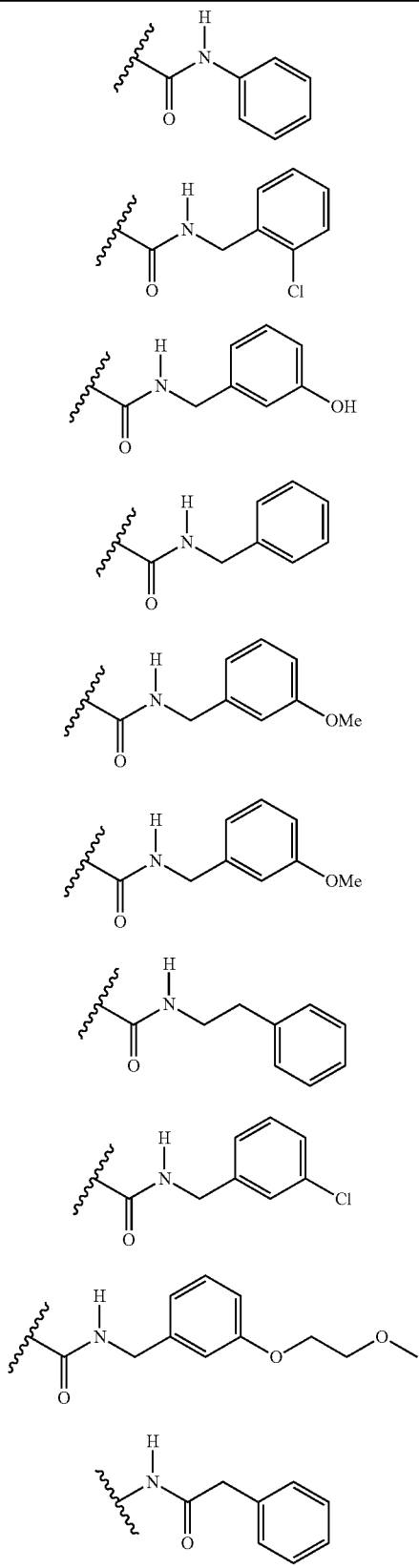
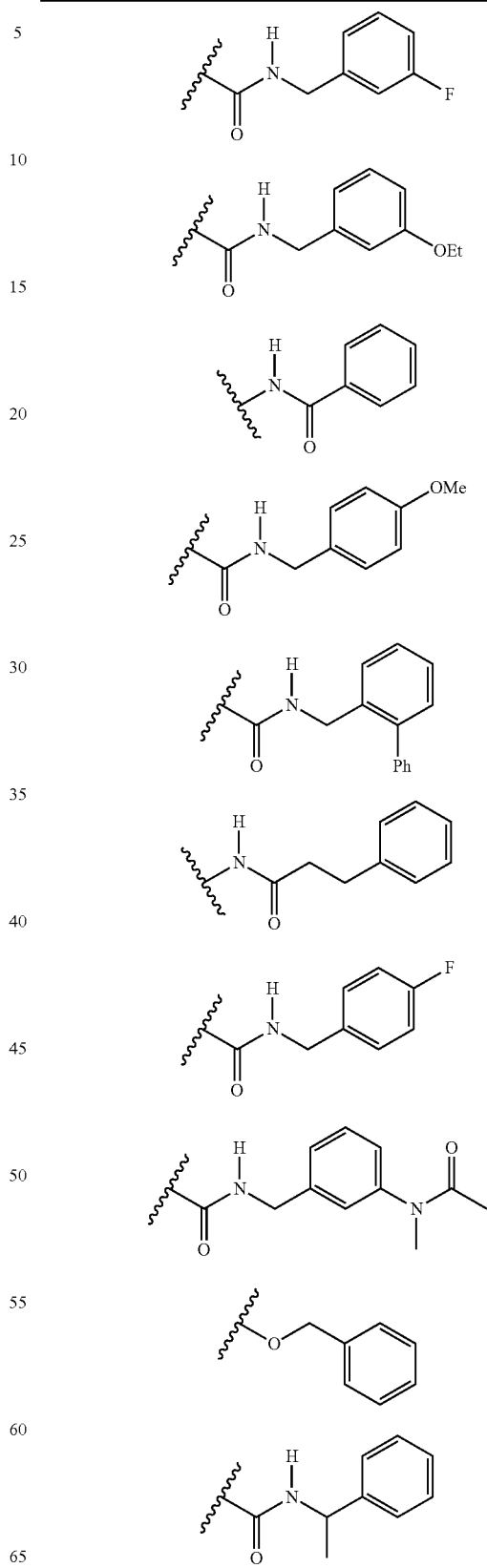

| 211 | 212 |
|---|---|
| -continued | -continued |
R[10] can be:
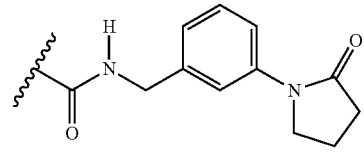 [SMILES: *C(=O)NCc1cccc(N2CCCC2=O)c1]
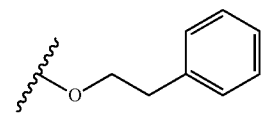 [SMILES: *OCCc1ccccc1]
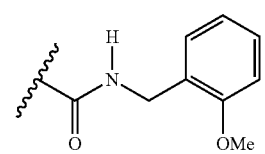 [SMILES: *C(=O)NCc1ccccc1OC]
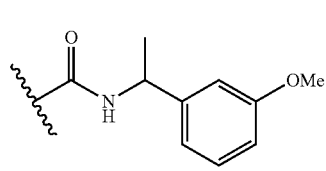 [SMILES: *C(=O)NC(C)c1cccc(OC)c1]
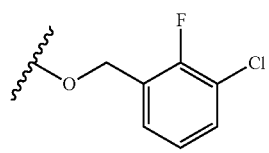 [SMILES: *OCc1cccc(Cl)c1F]
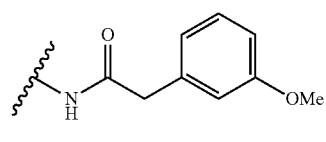 [SMILES: *NC(=O)Cc1cccc(OC)c1]
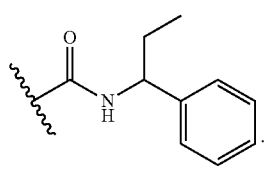 [SMILES: *C(=O)NC(CC)c1ccccc1]
5. The compound according to claim 1, wherein the compound has a chemical structure selected from:
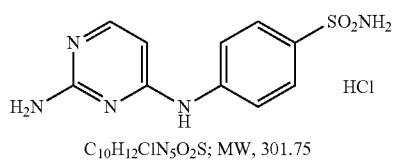
(1aa)
$C_{10}H_{12}ClN_5O_2S$; MW, 301.75
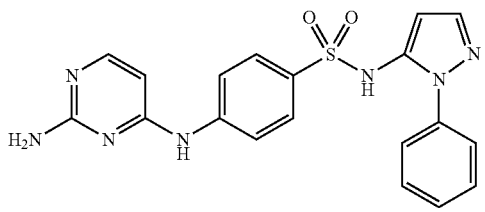
(1ab)
$C_{19}H_{17}N_7O_2S$; MW, 407.45
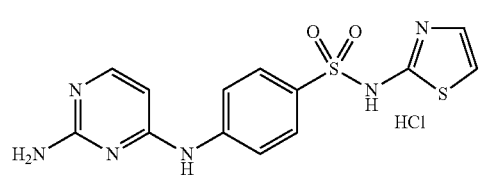
(1ac)
$C_{13}H_{13}ClN_6O_2S_2$; MW, 384.86
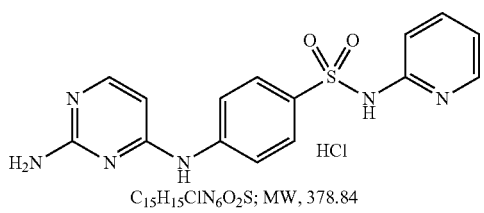
(1ad)
$C_{15}H_{15}ClN_6O_2S$; MW, 378.84
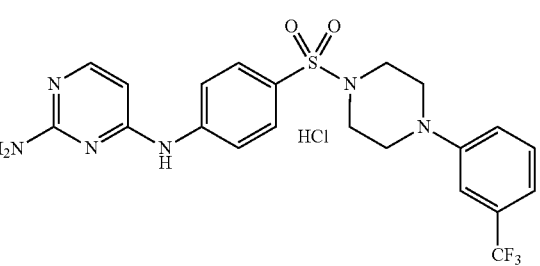
(1ae)
$C_{21}H_{22}ClF_3N_6O_2$; MW, 514.95
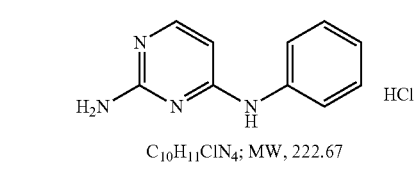
(1af)
$C_{10}H_{11}ClN_4$; MW, 222.67
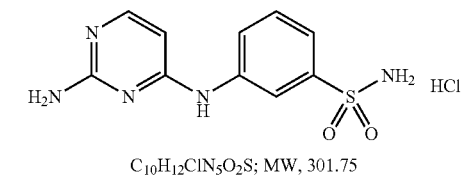
(1ag)
$C_{10}H_{12}ClN_5O_2S$; MW, 301.75
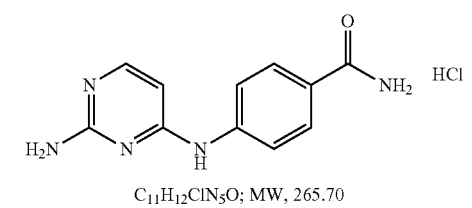
(1ah)
$C_{11}H_{12}ClN_5O$; MW, 265.70

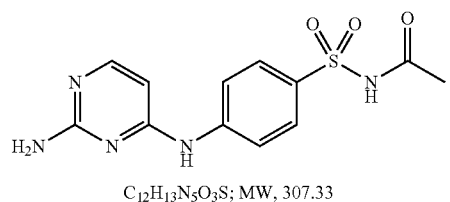
C₁₂H₁₃N₅O₃S; MW, 307.33 (1ai)
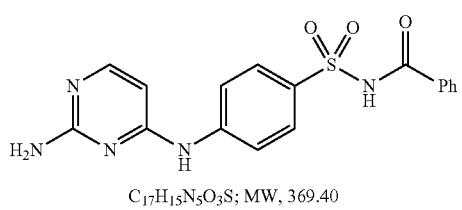
C₁₇H₁₅N₅O₃S; MW, 369.40 (1aj)
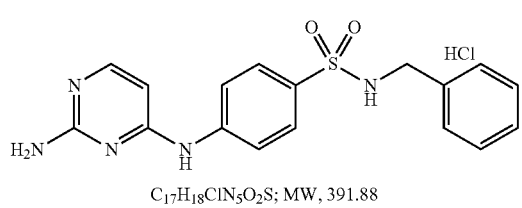
C₁₇H₁₈ClN₅O₂S; MW, 391.88 (1ak)
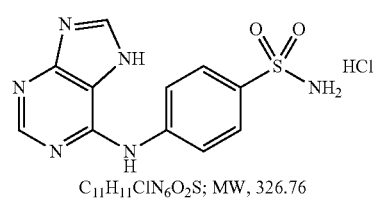
C₁₁H₁₁ClN₆O₂S; MW, 326.76 (8)
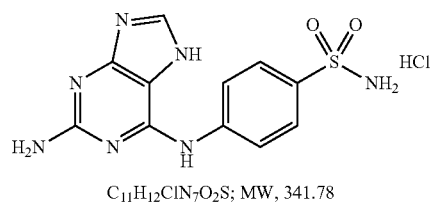
C₁₁H₁₂ClN₇O₂S; MW, 341.78 (7)
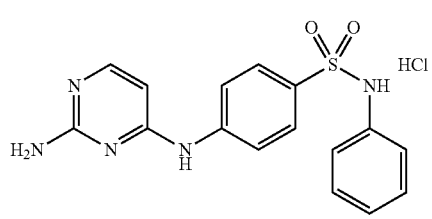
C₁₆H₁₆ClN₅O₂S; MW, 377.85 (1al)
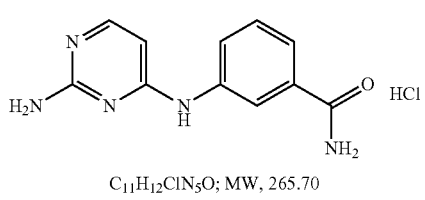
C₁₁H₁₂ClN₅O; MW, 265.70 (1am)
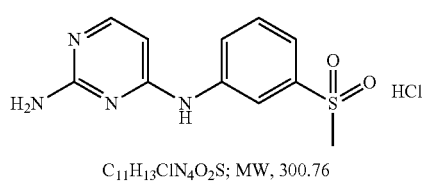
C₁₁H₁₃ClN₄O₂S; MW, 300.76 (1an)
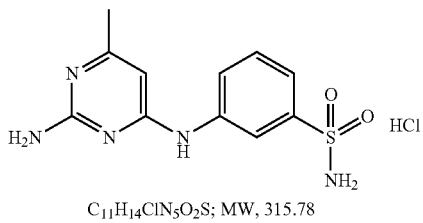
C₁₁H₁₄ClN₅O₂S; MW, 315.78 (6)
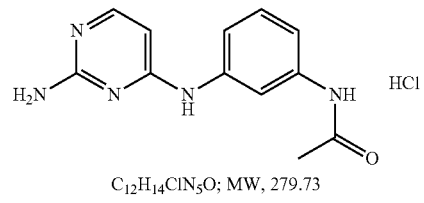
C₁₂H₁₄ClN₅O; MW, 279.73 (1ao)
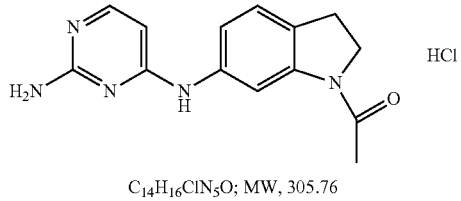
C₁₄H₁₆ClN₅O; MW, 305.76 (1ap)
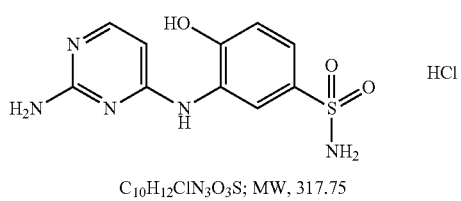
C₁₀H₁₂ClN₃O₃S; MW, 317.75 (1aq)
C₁₂H₁₃ClN₄; MW, 248.71 (13a)
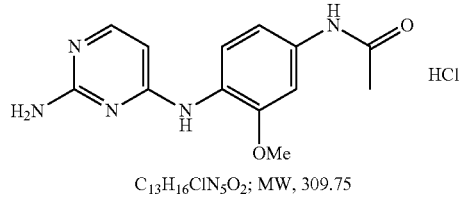
C₁₃H₁₆ClN₅O₂; MW, 309.75 (1ar)

-continued
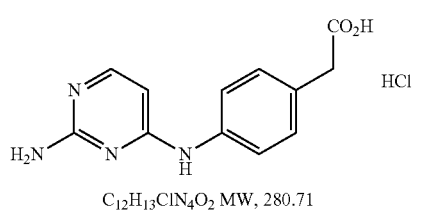 (1as)
C₁₂H₁₃ClN₄O₂ MW, 280.71
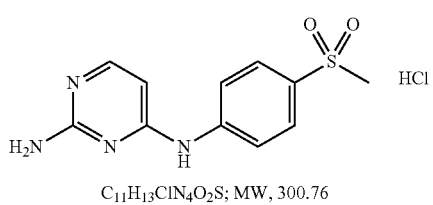 (1at)
C₁₁H₁₃ClN₄O₂S; MW, 300.76
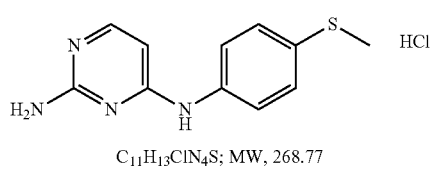 (1au)
C₁₁H₁₃ClN₄S; MW, 268.77
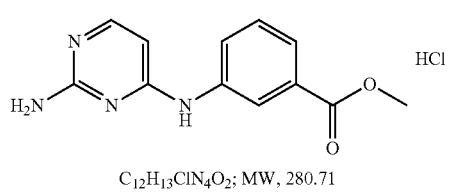 (1av)
C₁₂H₁₃ClN₄O₂; MW, 280.71
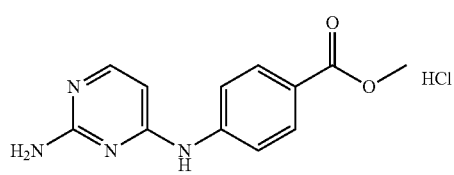 (1aw)
Chemical Formula: C₁₂H₁₃ClN₄O₂; MW, 280.71
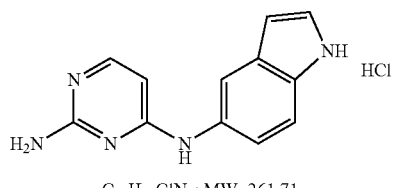 (1az)
C₁₂H₁₂ClN₅; MW, 261.71
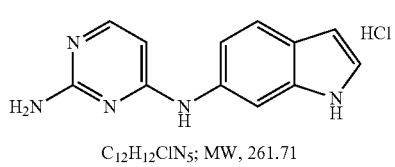 (1ba)
C₁₂H₁₂ClN₅; MW, 261.71
-continued
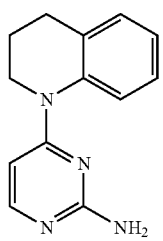 (16)
C₁₃H₁₄N₄; MW, 226.28
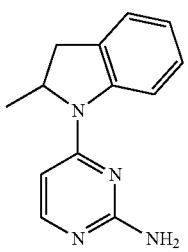 (13b)
C₁₃H₁₄N₄; MW, 226.28
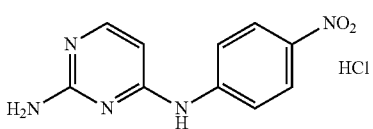 (1bb)
C₁₀H₁₀ClN₅O₂; MW, 267.67
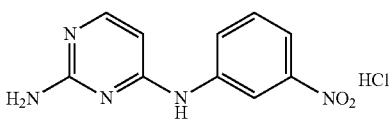 (1bc)
C₁₀H₁₀ClN₅O₂; MW, 267.67
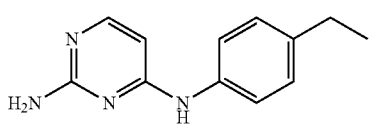 (1bd)
C₁₂H₁₄N₄; MW, 214.27
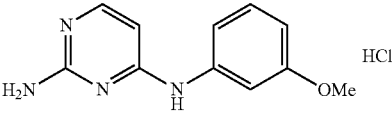 (1be)
C₁₁H₁₃ClN₄O; MW, 252.70
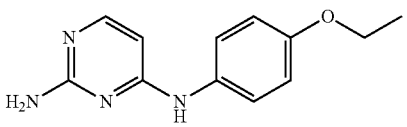 (1bf)
C₁₂H₁₄N₄O; MW, 230.27
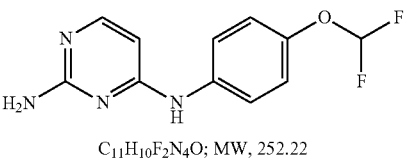 (1bg)
C₁₁H₁₀F₂N₄O; MW, 252.22

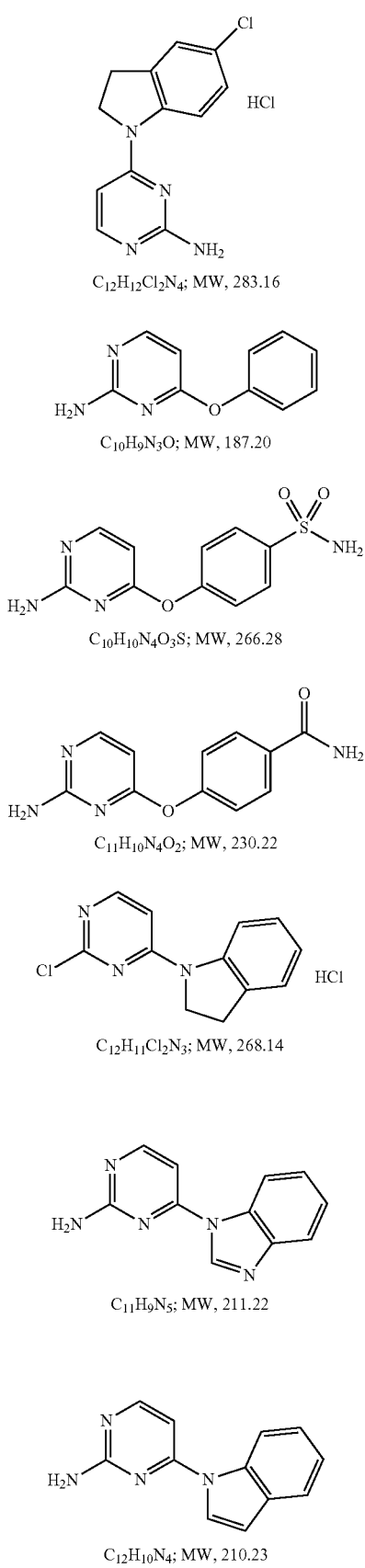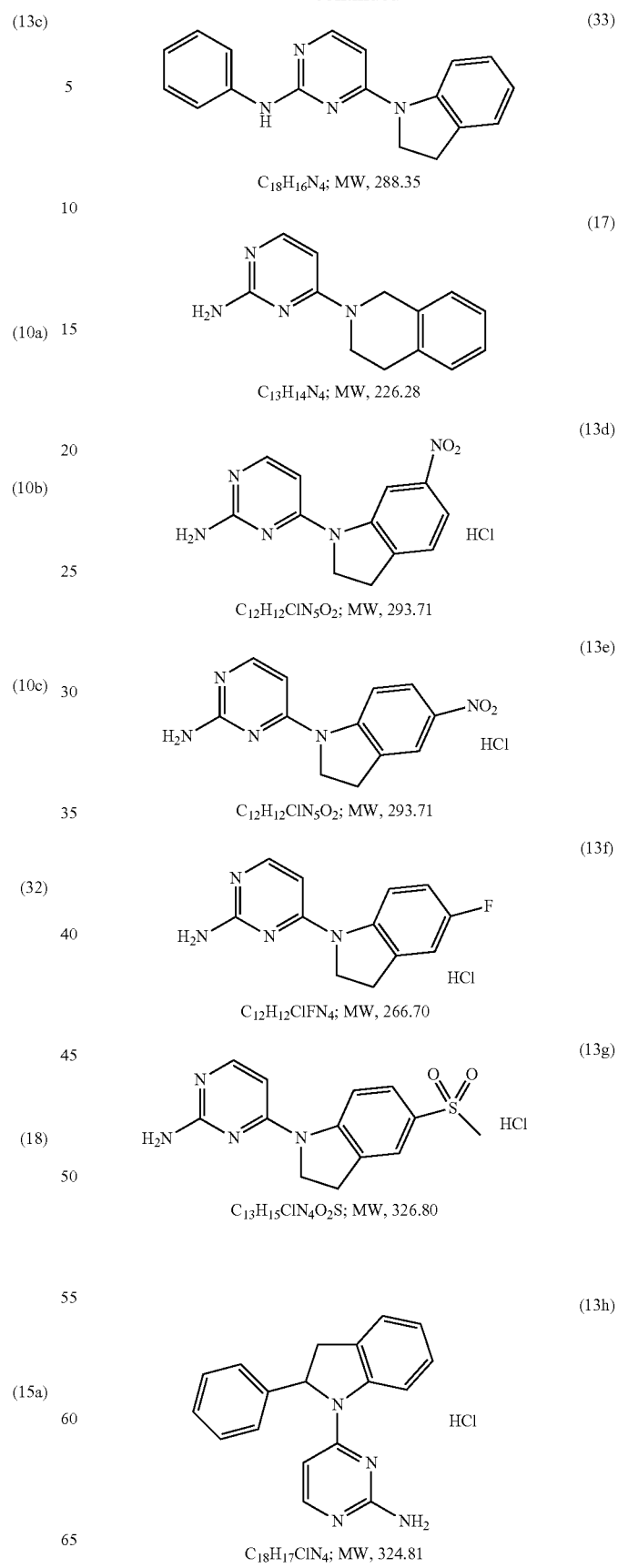

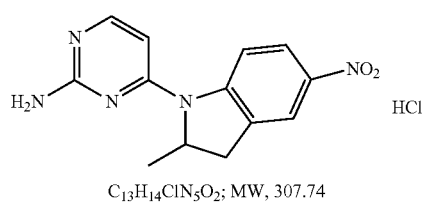
(13i)
C₁₃H₁₄ClN₅O₂; MW, 307.74   HCl
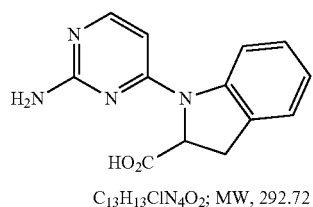
(13k)
C₁₃H₁₃ClN₄O₂; MW, 292.72   HCl
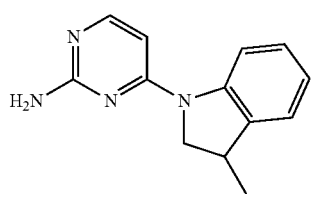
(13l)
C₁₃H₁₅ClN₄; MW, 262.74   HCl
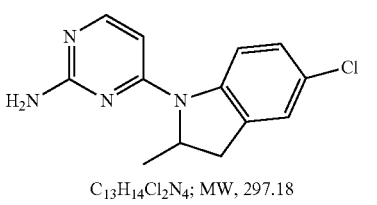
(13m)
C₁₃H₁₄Cl₂N₄; MW, 297.18   HCl
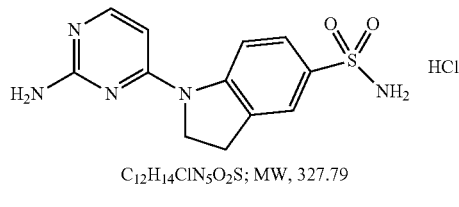
(13n)
C₁₂H₁₄ClN₅O₂S; MW, 327.79   HCl
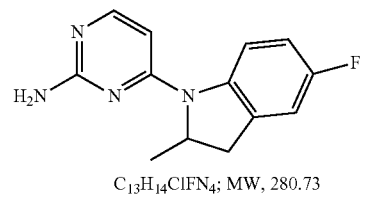
(13o)
C₁₃H₁₄ClFN₄; MW, 280.73   HCl
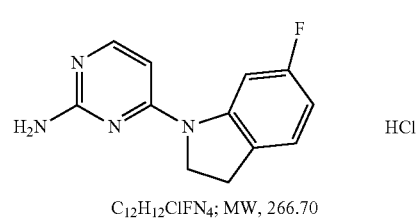
(13p)
C₁₂H₁₂ClFN₄; MW, 266.70   HCl
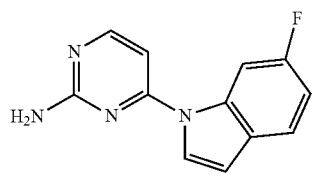
(15b)
C₁₂H₉FN₄; MW, 228.23
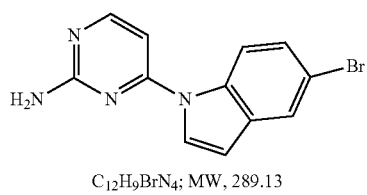
(15c)
C₁₂H₉BrN₄; MW, 289.13
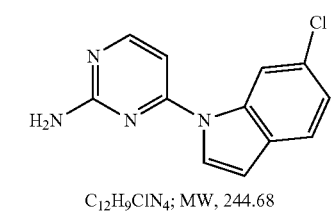
(15d)
C₁₂H₉ClN₄; MW, 244.68
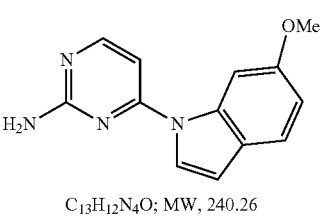
(15e)
C₁₃H₁₂N₄O; MW, 240.26
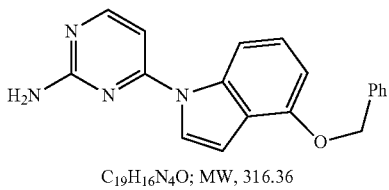
(21a)
C₁₉H₁₆N₄O; MW, 316.36
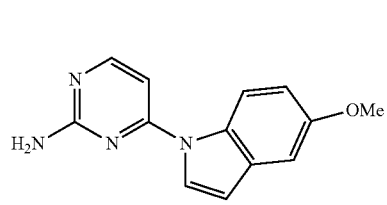
(15f)
C₁₃H₁₂N₄O; MW, 240.26
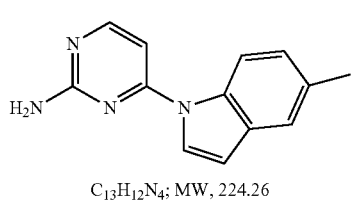
(15g)
C₁₃H₁₂N₄; MW, 224.26

(15h) C₁₇H₁₉N₅O₂; MW, 325.37

(24a) C₁₉H₁₅N₅O; MW, 329.36

(24b) C₂₀H₁₇N₅O; MW, 343.38

(24c) C₂₁H₁₉N₅O; MW, 357.41

(27a) C₂₀H₁₇N₅O; MW, 343.38

(27b) C₁₉H₁₅N₅O; MW, 329.36

(27c) C₂₁H₁₉N₅O; MW, 357.41

(24d) C₂₁H₁₉N₅O; MW, 357.41

(24e) C₂₀H₁₇N₅O; MW, 343.38

(24f) C₁₉H₁₅N₅O; MW, 329.36

(13q) C₁₉H₁₉ClN₄O; MW, 354.83

(21b) C₁₉H₁₆N₄O; MW, 316.36

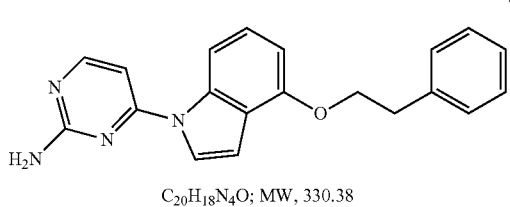
(21c)
$C_{20}H_{18}N_4O$; MW, 330.38
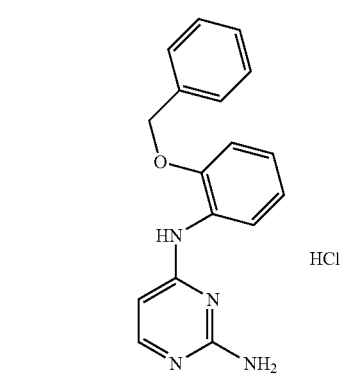
(1ah)
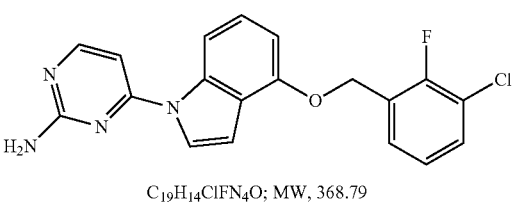
(21d)
$C_{19}H_{14}ClFN_4O$; MW, 368.79
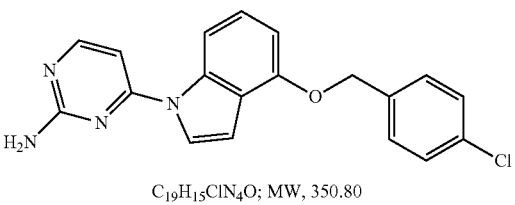
(21e)
$C_{19}H_{15}ClN_4O$; MW, 350.80
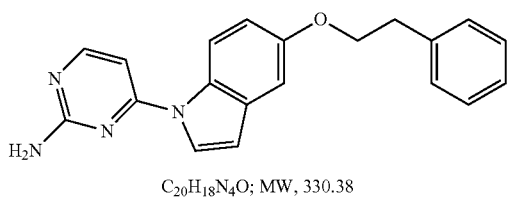
(21f)
$C_{20}H_{18}N_4O$; MW, 330.38
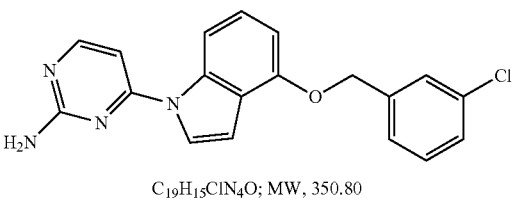
(21g)
$C_{19}H_{15}ClN_4O$; MW, 350.80
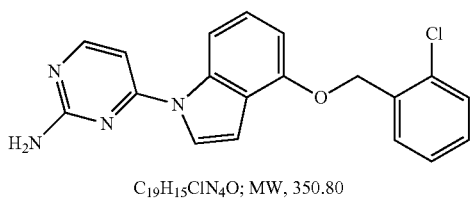
(21h)
$C_{19}H_{15}ClN_4O$; MW, 350.80
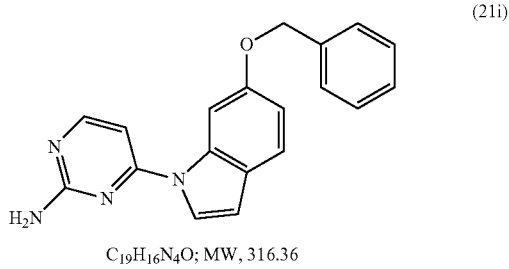
(21i)
$C_{19}H_{16}N_4O$; MW, 316.36
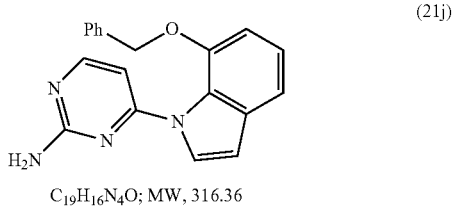
(21j)
$C_{19}H_{16}N_4O$; MW, 316.36
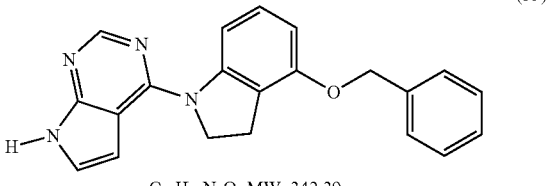
(35)
$C_{21}H_{18}N_4O$; MW, 342.39
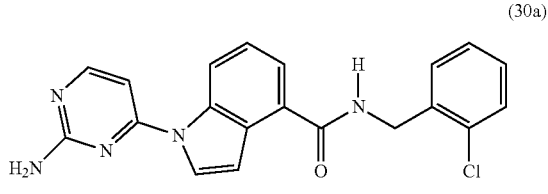
(30a)
$C_{20}H_{16}ClN_5O$; MW, 377.83
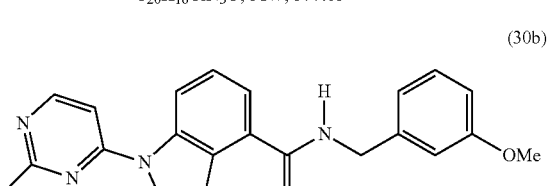
(30b)
$C_{21}H_{19}N_5O_2$; MW, 373.41
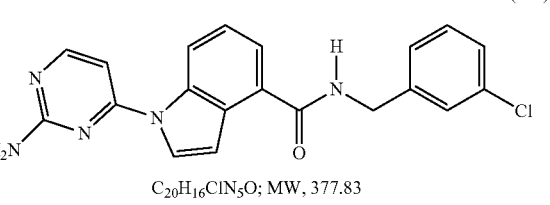
(30c)
$C_{20}H_{16}ClN_5O$; MW, 377.83

(30d)
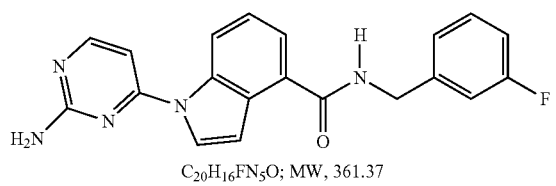
C20H16FN5O; MW, 361.37
(30e)
C20H16ClN5O; MW = 377.8269
(30f)
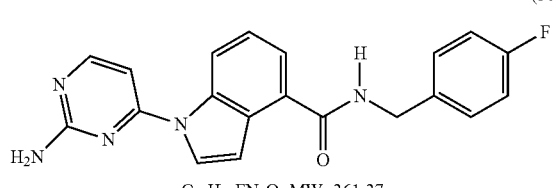
C20H16FN5O; MW, 361.37
(30g)
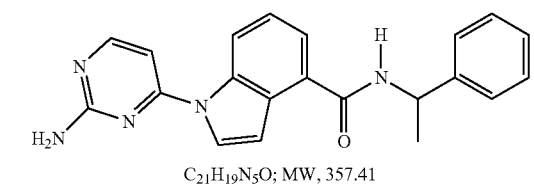
C21H19N5O; MW, 357.41
(30h)
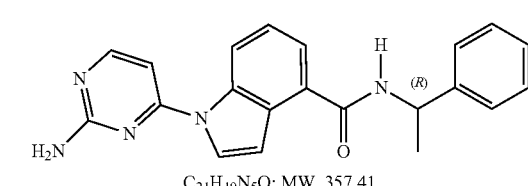
C21H19N5O; MW, 357.41
(30i)
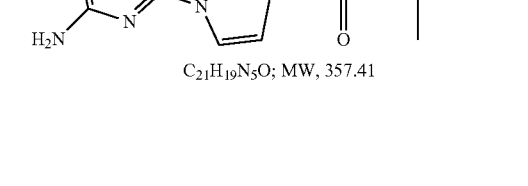
C21H19N5O; MW, 373.41
(30j)
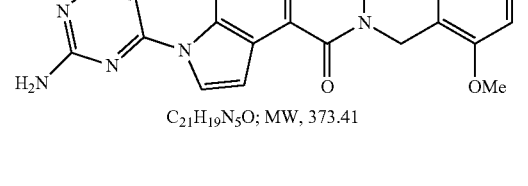
C21H19N5O; MW, 357.41
(30k)
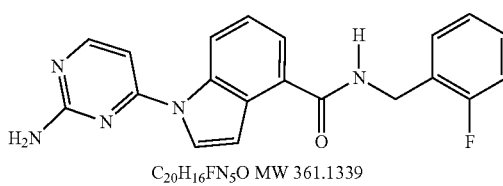
C20H16FN5O MW 361.1339
(30l)
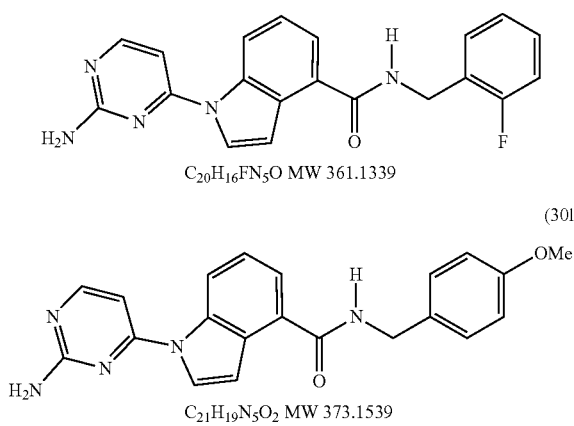
C21H19N5O2 MW 373.1539
(27d)
C21H19N5O2; MW, 373.41
(30m)
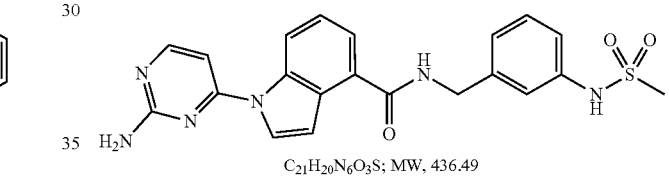
C21H20N6O3S; MW, 436.49
(30n)
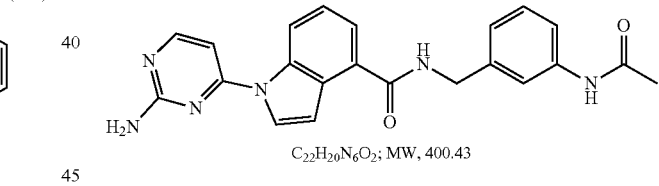
C22H20N6O2; MW, 400.43
(30o)
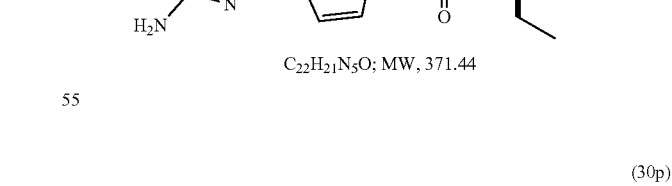
C22H21N5O; MW, 371.44
(30p)
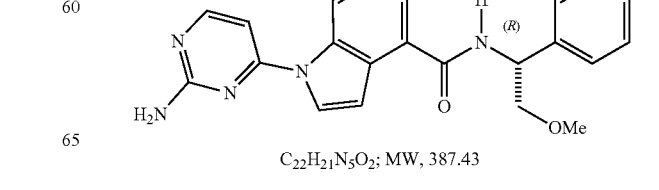
C22H21N5O2; MW, 387.43

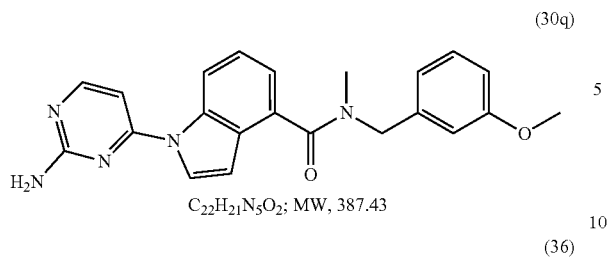
(30q)
C$_{22}$H$_{21}$N$_5$O$_2$; MW, 387.43
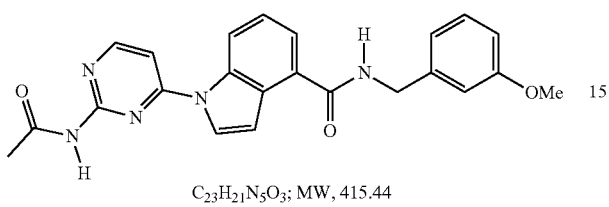
(36)
C$_{23}$H$_{21}$N$_5$O$_3$; MW, 415.44
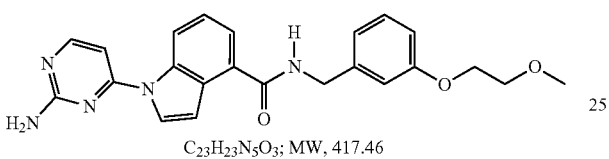
(30r)
C$_{23}$H$_{23}$N$_5$O$_3$; MW, 417.46
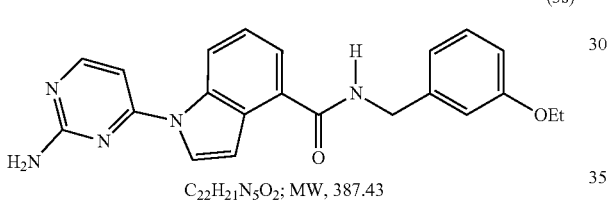
(3s)
C$_{22}$H$_{21}$N$_5$O$_2$; MW, 387.43
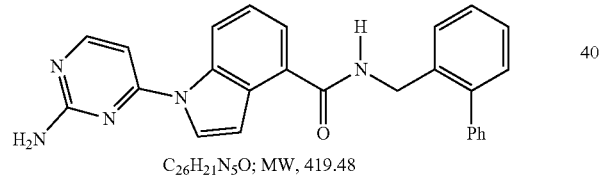
(30t)
C$_{26}$H$_{21}$N$_5$O; MW, 419.48
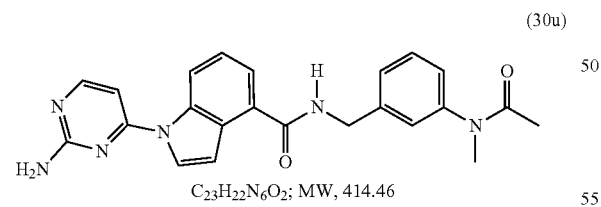
(30u)
C$_{23}$H$_{22}$N$_6$O$_2$; MW, 414.46
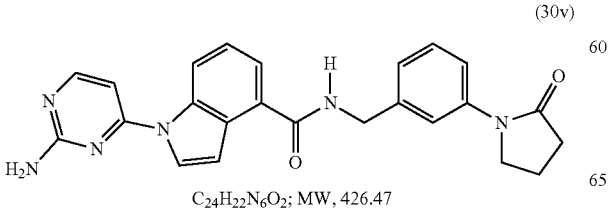
(30v)
C$_{24}$H$_{22}$N$_6$O$_2$; MW, 426.47
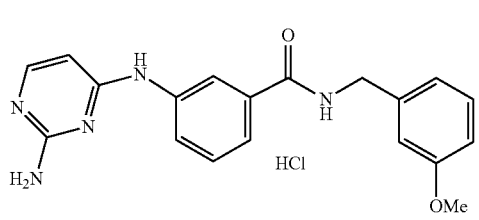
(46)
C$_{19}$H$_{20}$ClN$_5$O$_2$ MW: 385.8474
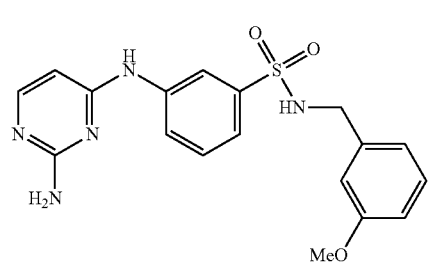
(47)
C$_{18}$H$_{19}$N$_5$O$_3$S MW: 385.4402
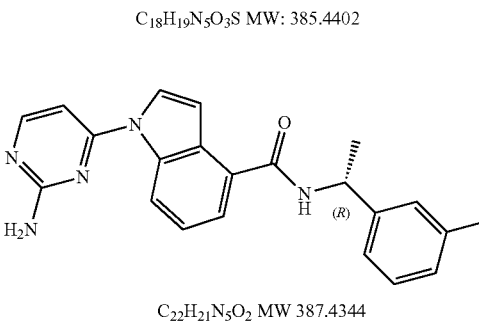
(30w)
C$_{22}$H$_{21}$N$_5$O$_2$ MW 387.4344
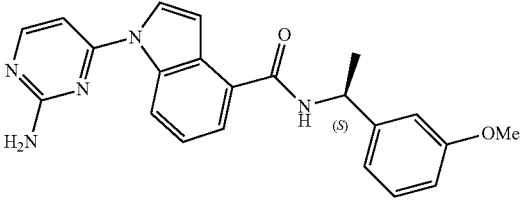
(30z)
C$_{22}$H$_{21}$N$_5$O$_2$ MW 387.4344
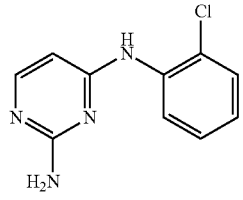
(1bi)
C$_{10}$H$_9$ClN$_4$ MW: 220.6583
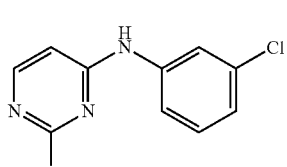
(1bj)
C$_{10}$H$_9$ClN$_4$ MW: 220.6583

-continued

(38)

Molecular Weight: 388.4225

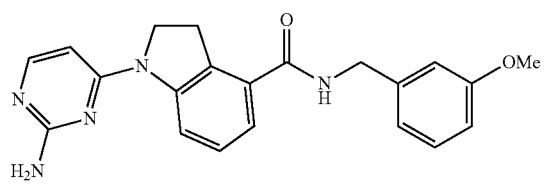

(-13r)

Molecular Weight 375.4237

-continued

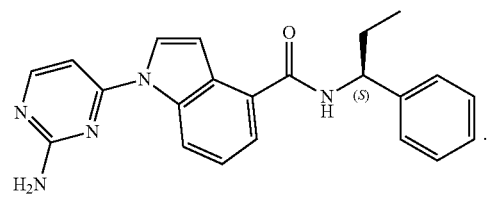

(30aa)

$C_{22}H_{21}N_5O$ MW 371.4350

6. The compound of claim 1, wherein $R^{10}$ in formula III is H, $NO_2$, —$CH_3$, —$SO_2$-alkyl, —$OCH_3$, alkoxy, —C(O)NH-alkyl, —C(O)NH-aryl, —NHC(O)-alkyl, —NHC(O)-aryl, or aryloxy, any of which can be substituted with one or more of aryl or alkoxy, any of which can be optionally substituted with halogen, —OH, alkoxy, or aryl optionally substituted with alkoxy.

7. The composition of claim 2, wherein $R^{10}$ in formula III is H, $NO_2$, —$CH_3$, —$SO_2$-alkyl, —$OCH_3$, alkoxy, —C(O)NH-alkyl, —C(O)NH-aryl, —NHC(O)-alkyl, —NHC(O)-aryl, or aryloxy, any of which can be substituted with one or more of aryl or alkoxy, any of which can be optionally substituted with halogen, —OH, alkoxy, or aryl optionally substituted with alkoxy.

8. The compound of claim 1, wherein $R^{20}$ in formula III is —$CO_2H$, heteroalkyl, or aryl.

9. The composition of claim 2, wherein $R^{20}$ in formula III is —$CO_2H$, heteroalkyl, or aryl.

\* \* \* \* \*

UNITED STATES PATENT AND TRADEMARK OFFICE
CERTIFICATE OF CORRECTION

PATENT NO. : 9,616,064 B2
APPLICATION NO. : 14/008678
DATED : April 11, 2017
INVENTOR(S) : Nicholas J. Lawrence, Said M. Sebti and Roberta Pireddu It is certified that error appears in the above-identified patent and that said Letters Patent is hereby corrected as shown below:

In the Specification

Column 2,
Line 53, "at 1a" should read --at 1σ--.

Column 28,
Line 46, " 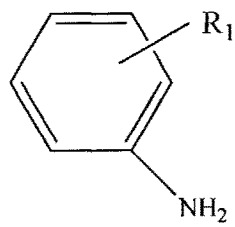 " should read -- 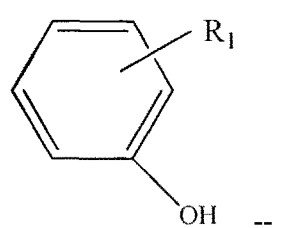 --.

Column 29,
Lines 25-28, " 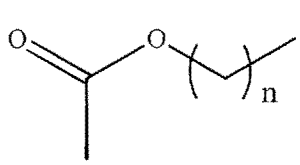 " should read -- 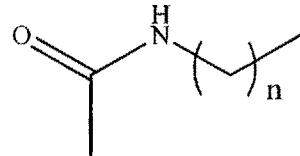 --.

Column 31,
Lines 30-31, " 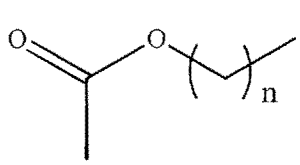 " should read -- 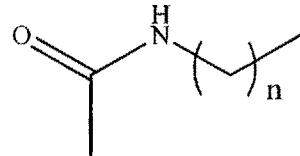 --.

Column 47,
Line 24, "(6)" should read --(1bc)--.

Signed and Sealed this
Ninth Day of October, 2018

Andrei Iancu
*Director of the United States Patent and Trademark Office*

Column 69,

Lines 18-24, " 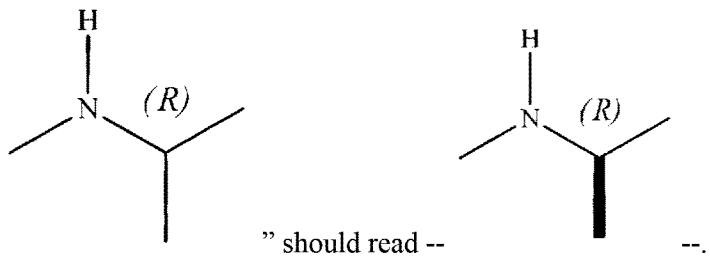 " should read -- --.

Column 75,
Line 64, "(ibi)" should read --(1bi)--.

Column 77,
Line 15, "(ibj)" should read --(1bj)--.

Column 88,
Lines 28-29, "hydrochloride (lay)" should read --hydrochloride (1av)--.
Line 35, "pure lay" should read --pure 1av--.

Column 89,
Line 24, "226.1087found" should read --226.1087, found--.

Column 95,
Line 28, "This w obtained" should read --This was obtained--.

Column 129,
Line 4, "344.1505." should read --344.1505,--.

Column 138,
Lines 38-39, "374.1601. found" should read --374.1601, found--.

Column 146,
Line 38, "388.1768. found" should read --388.1768, found--.

Column 147,
Line 45, "415.1877. found" should read --415.1877, found--.

Column 150,
Line 40, "267.0546. found" should read --267.0546, found--.

Column 152,
Line 13, "N$^4$-(2-chlorophenyl)pyrimidine-2,4-diamine" should read --N4-(2-chlorophenyl)pyrimidine-2,4-diamine--.
Line 25, "(400 MHz, DMSO-d$_6$)" should read --(400 MHz, DMSO-*d*6)--.
Line 67, "221.0588." should read --221.0588,--.

CERTIFICATE OF CORRECTION (continued)
U.S. Pat. No. 9,616,064 B2

Column 155,
Line 17, "5 nCl$_2$.H$_2$0" should read --SnCl$_2$.H20--.

In the Claims

Column 178,
Line 35, Claim 1 "C$_{17}$H$_{19}$N$_5$O$_2$; MW, 335.37" should read --C$_{17}$H$_{19}$N$_5$O$_2$; MW, 325.37--.

Column 180,
Line 1, Claim 1 "(13g)" should read --(13q)--.
Line 54, Claim 1 "C$_{19}$H$_{14}$ClN$_4$O; MW, 368.79" should read --C$_{19}$H$_{14}$ClFN$_4$O; MW, 368.79--.

Column 188,
Line 7, Claim 1 "(in house NSC135784)" should read --(blank)--.

Column 193,

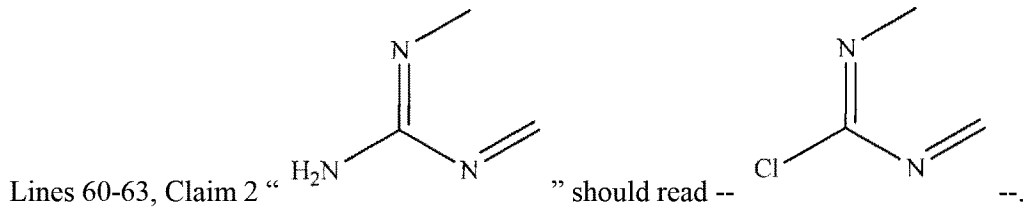

Lines 60-63, Claim 2 " " should read -- --.

Column 201,

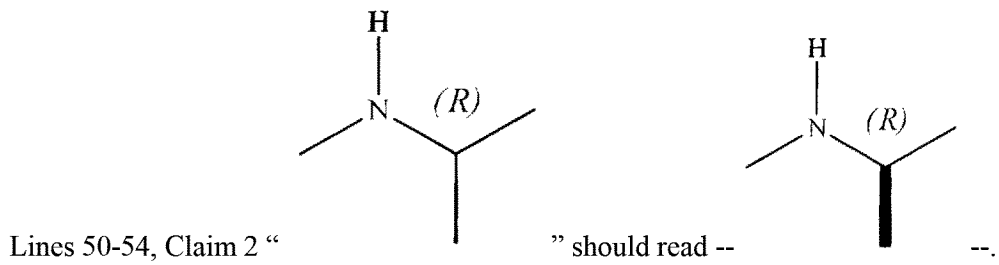

Lines 50-54, Claim 2 " " should read -- --.

Column 213,
Line 19, Claim 5 "(iak)" should read --(1ak)--.

Column 225,

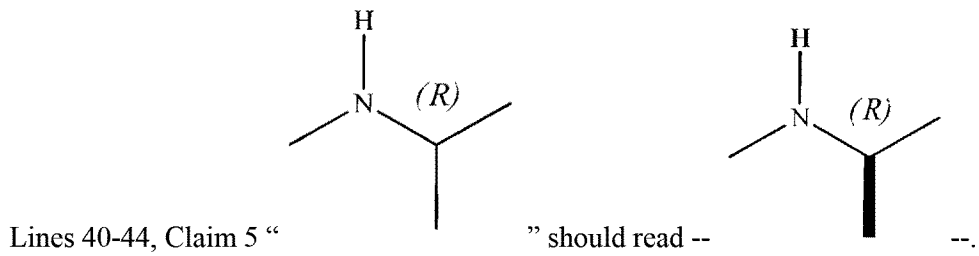

Lines 40-44, Claim 5 " " should read -- --.

Column 229,
Line 18, Claim 5 "(-13r)" should read --(13r)--.